United States Patent
Gu et al.

(10) Patent No.: US 11,434,303 B2
(45) Date of Patent: Sep. 6, 2022

(54) ANTI-LY6H ANTIBODIES AND ANTIBODY DRUG CONJUGATES

(71) Applicant: Bluefin BioMedicine, Inc., Beverly, MA (US)

(72) Inventors: Tinglei Gu, Andover, MA (US); Scott Michael Lonning, Westford, MA (US); Nels Eric Pederson, Mansfield, MA (US); Aleksandr Tkachev, Cambridge, MA (US); Klarisa Rikova, Reading, MA (US); Sean A. Beausoleil, Essex, MA (US)

(73) Assignee: Bluefin BioMedicine, Inc., Beverly, MA (US)

( * ) Notice: Subject to any disclaimer, the term of this patent is extended or adjusted under 35 U.S.C. 154(b) by 108 days.

(21) Appl. No.: 16/624,612

(22) PCT Filed: Jun. 28, 2018

(86) PCT No.: PCT/US2018/040085
§ 371 (c)(1),
(2) Date: Dec. 19, 2019

(87) PCT Pub. No.: WO2019/006162
PCT Pub. Date: Jan. 3, 2019

(65) Prior Publication Data
US 2020/0308298 A1     Oct. 1, 2020

Related U.S. Application Data

(60) Provisional application No. 62/588,520, filed on Nov. 20, 2017, provisional application No. 62/527,172, filed on Jun. 30, 2017, provisional application No. 62/526,297, filed on Jun. 28, 2017.

(51) Int. Cl.
| | |
|---|---|
| *C07K 16/28* | (2006.01) |
| *C07K 16/30* | (2006.01) |
| *A61K 39/395* | (2006.01) |
| *A61P 35/00* | (2006.01) |
| *A61K 33/243* | (2019.01) |
| *A61K 39/00* | (2006.01) |
| *A61K 33/244* | (2019.01) |

(52) U.S. Cl.
CPC ............ *C07K 16/30* (2013.01); *A61K 33/243* (2019.01); *A61P 35/00* (2018.01); *C07K 16/2818* (2013.01); *C07K 16/2827* (2013.01); *A61K 33/244* (2019.01); *A61K 2039/505* (2013.01); *C07K 2317/21* (2013.01); *C07K 2317/73* (2013.01); *C07K 2317/77* (2013.01); *C07K 2317/92* (2013.01)

(58) Field of Classification Search
CPC ............... C07K 16/28; C07K 16/2818; C07K 16/2827; C07K 16/30; C07K 2317/21; C07K 2317/73; C07K 2317/77; C07K 2317/92; A61K 39/39558; A61K 2039/505
See application file for complete search history.

(56) References Cited

U.S. PATENT DOCUMENTS

| | | |
|---|---|---|
| 2003/0198638 A1 | 10/2003 | Watkins |
| 2009/0111102 A1* | 4/2009 | Diehl ................... C12Q 1/6883 435/6.17 |
| 2011/0027286 A1 | 2/2011 | Thurston et al. |
| 2011/0159589 A1 | 6/2011 | Lewis et al. |
| 2016/0009800 A1 | 1/2016 | Corbin et al. |
| 2016/0176953 A1 | 6/2016 | Purcell Ngambo et al. |
| 2016/0220693 A1 | 8/2016 | Lewis et al. |
| 2017/0037124 A1 | 2/2017 | Gusarova et al. |

OTHER PUBLICATIONS

Paul, Fundamental Immunology, 3rd Edition, 1993, pp. 292-295.*
Rudikoff et al., Proc. Natl. Acad. Sci. USA, 1982, 79(6):1979-1983.*
Colman, Research in Immunology, 1994, 145:33-36.*
Bendig, Methods: A Companion to Methods in Enzymology, 1995; 8:83-93.*
Khantasup et al., Monoclonal Antibodies in Immunodiagnosis and Immunotherapy, 2015, 34(6): 404-417.*
Murphy et al. (Journal of Immunological Methods, vol. 463, p. 127-133, 2018.*
Padlan, Advances in Protein Chemistry, 1996, 49:57-133.*
Berglund et al., Protein Science, 2008, 17:606-613.*
Tzartos et al., Methods in Molecular Biology, 1996, 66:55-66.*
International Search Report and Written Opinion for Application No. PCT/US2018/040085, dated Oct. 2, 2018, 19 pages.
International Preliminary Report on Patentability for Application No. PCT/US2018/040085, dated Jan. 9, 2020, 17 pages.

* cited by examiner

*Primary Examiner* — Hong Sang
(74) *Attorney, Agent, or Firm* — McCarter & English, LLP; Marcie B. Clarke

(57) ABSTRACT

Disclosed herein are anti-lymphocyte antigen 6 complex, locus H (LY6H) antibodies and antibody drug conjugates (ADCs), including compositions and methods of using said antibodies and ADCs.

12 Claims, 32 Drawing Sheets
Specification includes a Sequence Listing.

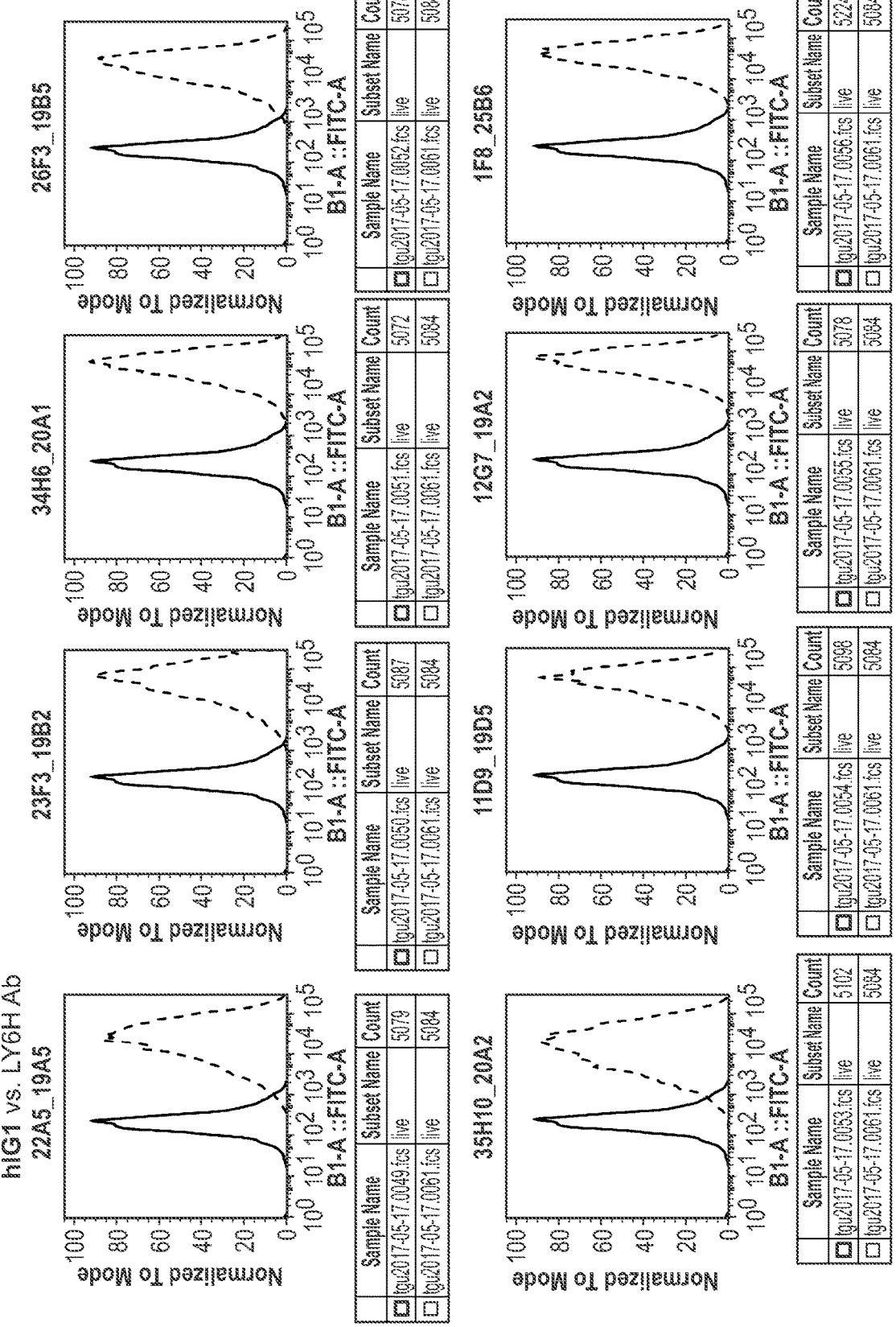

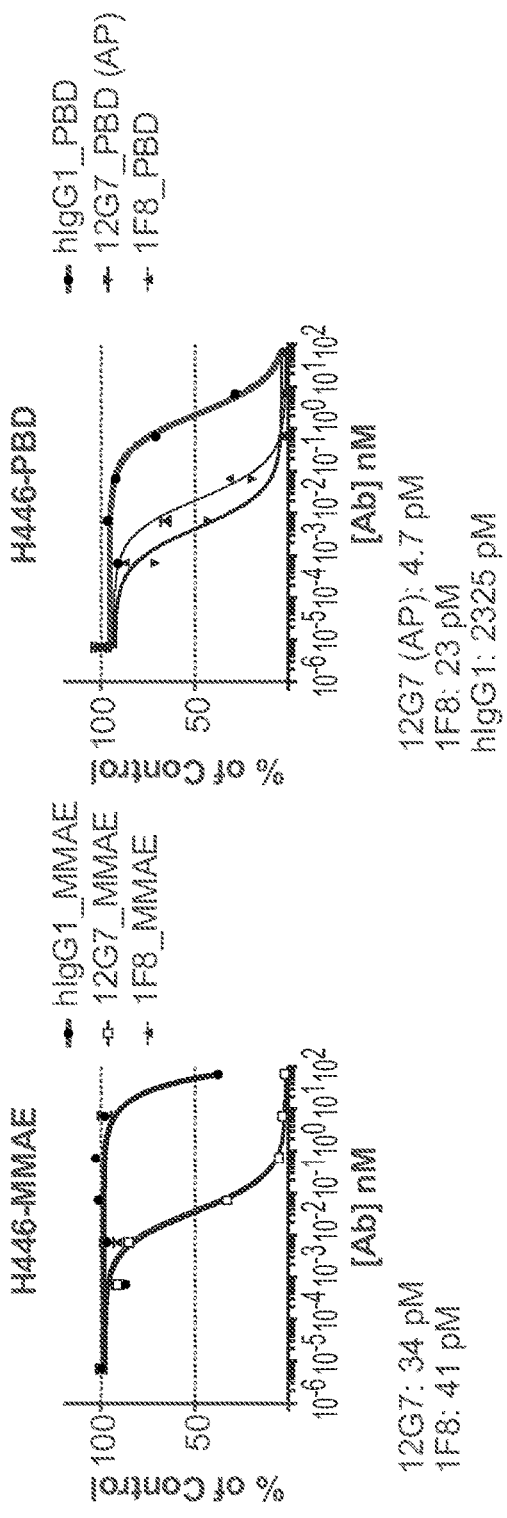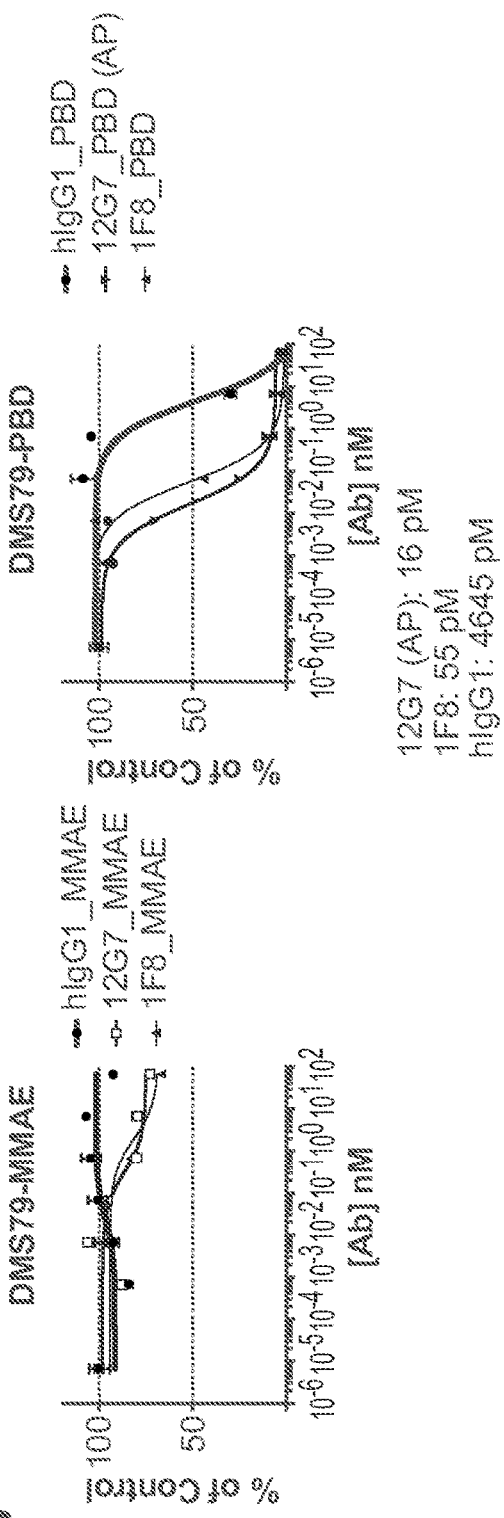
Fig. 8A
Fig. 8B

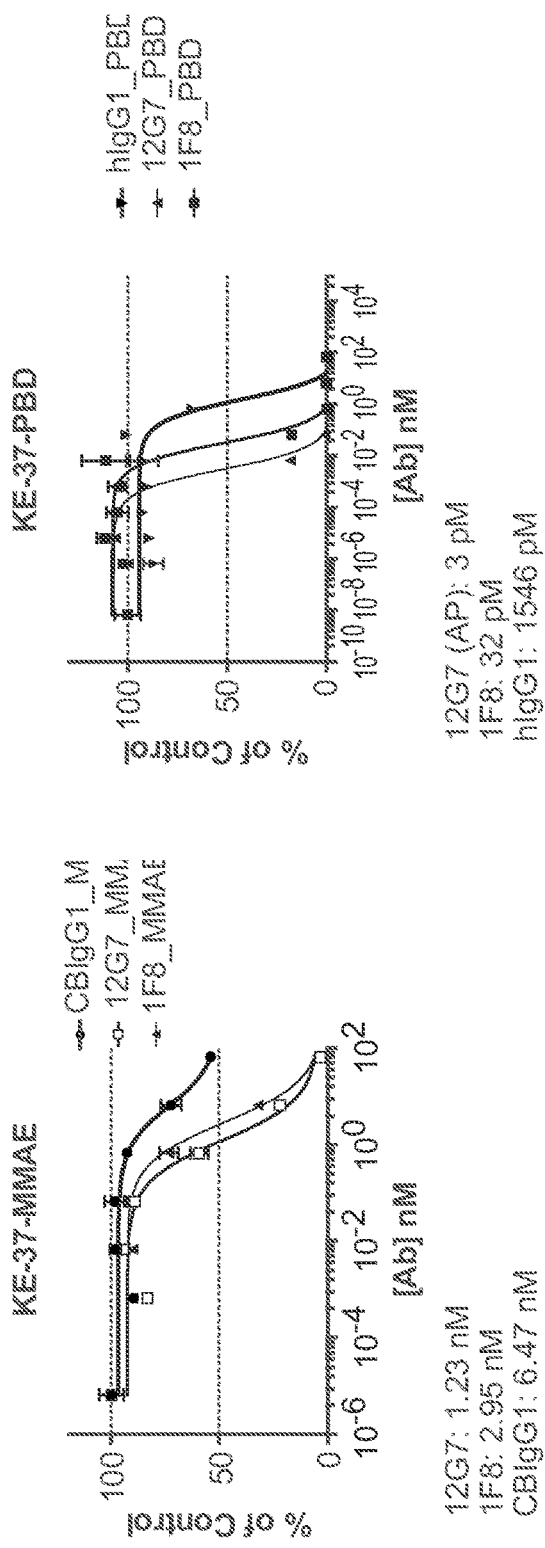
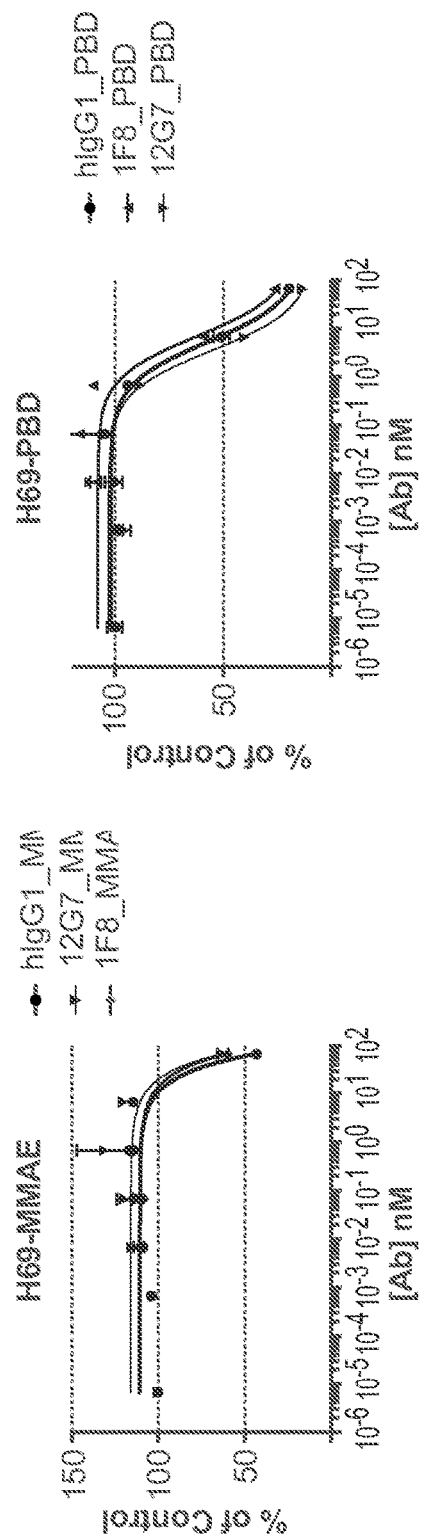
Fig. 8F
Fig. 8G

ANTI-LY6H ANTIBODIES AND ANTIBODY DRUG CONJUGATES

RELATED APPLICATIONS

The instant application is a 35 U.S.C. § 371 national stage filing of International Application No. PCT/US2018/040085, filed on Jun. 28, 2018, which in turn claims priority to U.S. Provisional Application No. 62/526,297, filed on Jun. 28, 2017, U.S. Provisional Application No. 62/527,172, filed on Jun. 30, 2017, and U.S. Provisional Application No. 62/588,520, filed on Nov. 20, 2017. The entire contents of each of the foregoing applications are expressly incorporated by reference herein in their entirety.

SEQUENCE LISTING

The instant application contains a Sequence Listing which has been filed electronically in ASCII format and is hereby incorporated by reference in its entirety. Said ASCII copy, created on Jun. 27, 2018, is named 127913-00420_SL.txt and is 67,506 bytes in size.

BACKGROUND

LY6H, also known as "lymphocyte antigen 6 complex, locus H," "Lymphocyte Antigen 6H," "Ly-6H," and "NMLY6," is a member of the LY6 family of glycosylphosphatidylinositol-anchored cell surface glycoproteins that are expressed on various types of cells. Isolation and characterization of LY6H was first reported in 1998 (Horie, M, et al. Genomics 53: 365-368, 1998).

Human LY6H is synthesized as a 140 amino acid precursor that contains a 25 amino acid signal sequence, 20 amino acid propeptide that is removed in the mature form, and a 90 amino acid mature chain. LY6H is highly expressed in brain (e.g., cerebral cortex, amygdala, hippocampus and subthalamic nucleus) and in acute lymphoblastic leukemia cells, such as MOLT-3 and MOLT-4. It is also found in lower levels in testis, pancreas, small intestine and colon. This suggests that LY6H may play a role in both the central nervous system and the immune system (Horie, M, et al. Genomics 53: 365-368, 1998). Intriguing patterns of expression of Ly6 genes on specific subpopulations of lymphoid and myeloid cells suggest that Ly6 molecules may be involved in the development and homeostasis of hematopoietic cells (Horie, M, et al. Genomics 53: 365-368, 1998). Further, increased expression of Ly6 family members in multiple cancer type indicate that Ly6 family members may be important targets in developing novel cancer therapeutics (Luo, L. et al. Oncotarget 7(10): 11165-11193, 2016).

Antibody drug conjugates (ADC) represent a new class of therapeutics comprising an antibody conjugated to a cytotoxic drug via a chemical linker. The therapeutic concept of ADCs is to combine binding capabilities of an antibody with a drug, where the antibody is used to deliver the drug to a tumor cell by means of binding to a target surface antigen.

Accordingly, there remains a need in the art for anti-LY6H antibodies and ADCs that can be used for therapeutic purposes in the treatment of cancer.

SUMMARY

In certain aspects, the present invention provides for anti-LY6H antibodies and antibody drug conjugates (ADCs). In certain embodiments of the invention, the antibodies, or antigen binding portions thereof, bind to LY6H (SEQ ID NO: 123) or the extracellular domain of LY6H.

In one embodiment, the antibodies, or antigen binding portions thereof, of the invention, bind to LY6H with a $K_d$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

In yet other embodiments of the invention, anti-LY6H antibody and antibody drug conjugates (ADCs) of the invention (e.g., the LY6H antibodies of the invention conjugated to a toxin) are capable of being internalized. In another embodiment, the anti-LY6H antibody and antibody drug conjugates (ADCs) of the invention are capable of inducing cell death of cells endogenously expressing LY6H.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 4 and a light chain variable region comprising a CDR3 having the amino acid sequence of SEQ ID NO: 8.

In some embodiments, the antibody, or antigen binding portion thereof, further comprises a heavy chain variable region comprising a CDR2 having one of the amino acid sequences selected from SEQ ID NO: 3 and SEQ ID NO: 69 and a light chain variable region comprising a CDR2 having the amino acid sequence of SEQ ID NO: 7. In other embodiments, the antibody, or antigen binding portion thereof, comprises a heavy chain variable region comprising a CDR1 having the amino acid sequence of SEQ ID NO: 2 and a light chain variable region comprising a CDR1 having the amino acid sequence of either SEQ ID NO: 6.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 12 and a light chain variable region comprising a CDR3 having the amino acid sequence of SEQ ID NO: 16.

In some embodiments, the antibody, or antigen binding portion thereof, further comprises a heavy chain variable region comprising a CDR2 having the amino acid sequence of SEQ ID NO: 11 and a light chain variable region comprising a CDR2 having the amino acid sequence of SEQ ID NO: 15. In other embodiments, the antibody, or antigen binding portion thereof, comprises a heavy chain variable region comprising a CDR1 having the amino acid sequence of SEQ ID NO: 10 and a light chain variable region comprising a CDR1 having the amino acid sequence of either SEQ ID NO: 14.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 19 and a light chain variable region comprising a CDR3 having the amino acid sequence of SEQ ID NO: 21.

In some embodiments, the antibody, or antigen binding portion thereof, comprises a heavy chain variable region comprising a CDR2 having the amino acid sequence of SEQ ID NO: 11 and a light chain variable region comprising a CDR2 having the amino acid sequence of SEQ ID NO: 15. In other embodiments, the antibody, or antigen binding portion thereof, comprises a heavy chain variable region comprising a CDR1 having the amino acid sequence of SEQ ID NO: 18 and a light chain variable region comprising a CDR1 having the amino acid sequence of either SEQ ID NO: 14.

In yet another aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 25 and a light chain variable region comprising a CDR3 having the amino acid sequence of SEQ ID NO: 8.

In some aspects, the antibody, or antigen binding portion thereof, comprises a heavy chain variable region comprising a CDR2 having one of the amino acid sequences selected from SEQ ID NO: 24, SEQ ID NO: 65, and SEQ ID NO: 67, and a light chain variable region comprising a CDR2 having the amino acid sequence of SEQ ID NO: 7. In other embodiments, the antibody, or antigen binding portion thereof, comprises a heavy chain variable region comprising a CDR1 having the amino acid sequence of SEQ ID NO: 23 and a light chain variable region comprising a CDR1 having the amino acid sequence of either SEQ ID NO: 6.

In another aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 30 and a light chain variable region comprising a CDR3 having the amino acid sequence of SEQ ID NO: 34.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 33. In other embodiments, the antibody, or antigen binding portion thereof, comprises a heavy chain variable region comprising a CDR1 having the amino acid sequence of SEQ ID NO: 28 and a light chain variable region comprising a CDR1 having the amino acid sequence of either SEQ ID NO: 32.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 36 and a light chain variable region comprising a CDR3 having the amino acid sequence of SEQ ID NO: 38.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 33. In other embodiments, the antibody, or antigen binding portion thereof, comprises a heavy chain variable region comprising a CDR1 having the amino acid sequence of SEQ ID NO: 28 and a light chain variable region comprising a CDR1 having the amino acid sequence of either SEQ ID NO: 32.

In another aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 40 and a light chain variable region comprising a CDR3 having the amino acid sequence of SEQ ID NO: 44.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 43. In other embodiments, the antibody, or antigen binding portion thereof, comprises a heavy chain variable region comprising a CDR1 having the amino acid sequence of SEQ ID NO: 28 and a light chain variable region comprising a CDR1 having the amino acid sequence of either SEQ ID NO: 42.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 48 and a light chain variable region comprising a CDR3 having the amino acid sequence of SEQ ID NO: 52.

In some aspects, the antibody, or antigen binding portion thereof, comprises a heavy chain variable region comprising a CDR2 having the amino acid sequence of SEQ ID NO: 47 and a light chain variable region comprising a CDR2 having the amino acid sequence of SEQ ID NO: 51. In other embodiments, the antibody, or antigen binding portion thereof, comprises a heavy chain variable region comprising a CDR1 having the amino acid sequence of SEQ ID NO: 46 and a light chain variable region comprising a CDR1 having the amino acid sequence of either SEQ ID NO: 50.

In another aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 48 and a light chain variable region comprising a CDR3 having the amino acid sequence of SEQ ID NO: 52.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 51. In other embodiments, the antibody, or antigen binding portion thereof, comprises a heavy chain variable region comprising a CDR1 having the amino acid sequence of SEQ ID NO: 46 and a light chain variable region comprising a CDR1 having the amino acid sequence of either SEQ ID NO: 50.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 55 and a light chain variable region comprising a CDR3 having the amino acid sequence of SEQ ID NO: 57.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 51. In other embodiments, the antibody, or antigen binding portion thereof, comprises a heavy chain variable region comprising a CDR1 having the amino acid sequence of SEQ ID NO: 28 and a light chain variable region comprising a CDR1 having the amino acid sequence of either SEQ ID NO: 50.

In another aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 59 and a light chain variable region comprising a CDR3 having the amino acid sequence of SEQ ID NO: 57.

In some aspects, the antibody, or antigen binding portion thereof, comprises a heavy chain variable region comprising a CDR2 having the amino acid sequence of SEQ ID NO: 29 and a light chain variable region comprising a CDR2 having the amino acid sequence of SEQ ID NO: 51. In other embodiments, the antibody, or antigen binding portion thereof, comprises a heavy chain variable region comprising a CDR1 having the amino acid sequence of SEQ ID NO: 28 and a light chain variable region comprising a CDR1 having the amino acid sequence of either SEQ ID NO: 50.

In one aspect of the invention, the present disclosure provides an isolated antibody, or antigen binding portion thereof, that binds to human LY6H, wherein the antibody, or antigen binding portion thereof, comprises a heavy chain variable region comprising a CDR3 having the amino acid sequence of SEQ ID NO: 63 and a light chain variable region comprising a CDR3 having the amino acid sequence of SEQ ID NO: 8.

In some embodiments, the antibody, or antigen binding portion thereof, comprises a heavy chain variable region comprising a CDR2 having one of the amino acid sequences selected from SEQ ID NO: 62 and SEQ ID NO: 71, and a light chain variable region comprising a CDR2 having the amino acid sequence of SEQ ID NO: 7. In some embodiments, the antibody, or antigen binding portion thereof, comprises a heavy chain variable region comprising a CDR1 having the amino acid sequence of SEQ ID NO: 61 and a light chain variable region comprising a CDR1 having the amino acid sequence of either SEQ ID NO: 6.

In some aspects, the antibody, or antigen binding portion thereof, is an IgG isotype.

In some aspects, the antibody, or antigen binding portion thereof, has a $K_D$ of 200 nM or less.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 4, a CDR2 domain comprising the amino acid sequence of SEQ ID NO: 3 or SEQ ID NO: 69, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 19, a CDR2 domain comprising the amino acid sequence of SEQ ID NO: 11, and a CDR1 domain comprising the amino acid sequence of SEQ ID NO: 18, and a light chain variable region comprising a CDR3 domain comprising the amino acid sequence of SEQ ID NO: 21, a CDR2 domain comprising the amino acid sequence of SEQ ID NO: 15, and a CDR1 domain comprising the amino acid sequence of SEQ ID NO: 14.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 25, a CDR2 domain comprising one of the amino acid sequences selected from SEQ ID NO: 24, SEQ ID NO: 65, and SEQ ID NO: 67, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 30, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 34, a CDR2 domain comprising the amino acid sequence of SEQ ID NO: 33, and a CDR1 domain comprising the amino acid sequence of SEQ ID NO: 32.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 36, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 38, a CDR2 domain comprising the amino acid sequence of SEQ ID NO: 33, and a CDR1 domain comprising the amino acid sequence of SEQ ID NO: 32.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 40, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 44, a CDR2 domain comprising the amino acid sequence of SEQ ID NO: 43, and a CDR1 domain comprising the amino acid sequence of SEQ ID NO: 42.

In one aspect of the invention, the present disclosure provides an anti-LY6H antibody, or antigen-binding portion thereof, comprising a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 48, a CDR2 domain comprising the amino acid sequence of SEQ ID NO: 29, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 55, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 59, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50.

In another aspect of the invention, the present disclosure provides an anti-LY6H antibody, or antigen-binding portion thereof, comprising a heavy chain variable region comprising a CDR3 domain comprising the amino acid sequence of SEQ ID NO: 63, a CDR2 domain comprising one of the amino acid sequence selected from SEQ ID NO: 62 and SEQ ID NO: 71, and a CDR1 domain comprising the amino acid sequence of SEQ ID NO: 61, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an anti-LY6H antibody, or antigen-binding portion thereof, comprising a heavy chain variable domain comprising an amino acid sequence set forth in SEQ ID NO: 1 or SEQ ID NO: 68 and a light chain variable domain comprising an amino acid sequence set forth in SEQ ID NO: 5.

In another aspect of the invention, the present disclosure provides an anti-LY6H antibody, or antigen-binding portion thereof, comprising a heavy chain comprising an amino acid sequence set forth in SEQ ID NO: 1 or SEQ ID NO: 68, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In another aspect of the invention, the present disclosure provides an anti-LY6H antibody, or antigen-binding portion thereof, comprising a heavy chain variable region comprising the amino acid sequence of SEQ ID NO: 9 and a light chain variable region comprising the amino acid sequence of SEQ ID NO: 13.

In another aspect of the invention, the present disclosure provides an anti-LY6H antibody, or antigen-binding portion thereof, comprising a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In another aspect of the invention, the present disclosure provides an anti-LY6H antibody, or antigen-binding portion thereof, comprising a heavy chain variable region comprising the amino acid sequence of SEQ ID NO: 17 and a light chain variable region comprising the amino acid sequence of SEQ ID NO: 20.

In another aspect of the invention, the present disclosure provides an anti-LY6H antibody, or antigen-binding portion thereof, comprising a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In another aspect of the invention, the present disclosure provides an anti-LY6H antibody, or antigen-binding portion thereof, comprising a heavy chain variable region comprising one of the amino acid sequences selected from SEQ ID NO: 22, SEQ ID NO: 64, and SEQ ID NO: 66, and a light chain variable region comprising the amino acid sequence of SEQ ID NO: 26.

In another aspect of the invention, the present disclosure provides an anti-LY6H antibody, or antigen-binding portion thereof, comprising a heavy chain comprising an amino acid sequence set forth in one of SEQ ID NO: 22, SEQ ID NO: 64, and SEQ ID NO: 66, or a sequence having at least 90%, 95%, 96%, 97%, 98%, or 99% identity to one of SEQ ID NO: 22, SEQ ID NO: 64, and SEQ ID NO: 66, and/or a light chain comprising an amino acid sequence set forth in SEQ ID NO: 29, or a sequence having at least 90%, 95%, 96%, 97%, 98%, or 99% identity to SEQ ID NO: 26.

In another aspect of the invention, the present disclosure provides an anti-LY6H antibody, or antigen-binding portion thereof, comprising a heavy chain variable region comprising the amino acid sequence of SEQ ID NO: 27 and a light chain variable region comprising the amino acid sequence of SEQ ID NO: 31.

In another aspect of the invention, the present disclosure provides an anti-LY6H antibody, or antigen-binding portion thereof, comprising a heavy chain comprising an amino acid sequence set forth in SEQ ID NO: 27, or a sequence having at least 90%, 95%, 96%, 97%, 98%, or 99% identity to SEQ ID NO: 27, and/or a light chain comprising an amino acid sequence set forth in SEQ ID NO: 31, or a sequence having at least 90%, 95%, 96%, 97%, 98%, or 99% identity to SEQ ID NO: 31.

In another aspect of the invention, the present disclosure provides an anti-LY6H antibody, or antigen-binding portion thereof, comprising a heavy chain variable region comprising the amino acid sequence of SEQ ID NO: 35 and a light chain variable region comprising the amino acid sequence of SEQ ID NO: 37.

In another aspect of the invention, the present disclosure provides an anti-LY6H antibody, or antigen-binding portion thereof, comprising a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 37, or a sequence having at least 90%, 95%, 96%, 97%, 98%, or 99% identity to SEQ ID NO: 37.

In another aspect of the invention, the present disclosure provides an anti-LY6H antibody, or antigen-binding portion thereof, comprising a heavy chain variable region comprising the amino acid sequence of SEQ ID NO: 39 and a light chain variable region comprising the amino acid sequence of SEQ ID NO: 41.

In another aspect of the invention, the present disclosure provides an anti-LY6H antibody, or antigen-binding portion thereof, comprising a heavy chain comprising an amino acid sequence set forth in SEQ ID NO: 39, or a sequence having at least 90%, 95%, 96%, 97%, 98%, or 99% identity to SEQ ID NO: 39, and/or a light chain comprising an amino acid sequence set forth in SEQ ID NO: 41, or a sequence having at least 90%, 95%, 96%, 97%, 98%, or 99% identity to SEQ ID NO: 41.

In another aspect of the invention, the present disclosure provides an anti-LY6H antibody, or antigen-binding portion thereof, comprising a heavy chain variable region comprising the amino acid sequence of SEQ ID NO: 45 and a light chain variable region comprising the amino acid sequence of SEQ ID NO: 49.

In another aspect of the invention, the present disclosure provides an anti-LY6H antibody, or antigen-binding portion thereof, comprising a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In another aspect of the invention, the present disclosure provides an anti-LY6H antibody, or antigen-binding portion thereof, comprising a heavy chain variable region comprising the amino acid sequence of SEQ ID NO: 53 and a light chain variable region comprising the amino acid sequence of SEQ ID NO: 49.

In another aspect of the invention, the present disclosure provides an anti-LY6H antibody, or antigen-binding portion thereof, comprising a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 49, or a sequence having at least 90%, 95%, 96%, 97%, 98%, or 99% identity to SEQ ID NO: 49.

In another aspect of the invention, the present disclosure provides an anti-LY6H antibody, or antigen-binding portion thereof, comprising a heavy chain variable region compris-ing the amino acid sequence of SEQ ID NO: 54 and a light chain variable region comprising the amino acid sequence of SEQ ID NO: 56.

In another aspect of the invention, the present disclosure provides an anti-LY6H antibody, or antigen-binding portion thereof, comprising a heavy chain comprising an amino acid sequence set forth in SEQ ID NO: 54, or a sequence having at least 90%, 95%, 96%, 97%, 98%, or 99% identity to SEQ ID NO: 54, and/or a light chain comprising an amino acid sequence set forth in SEQ ID NO: 56, or a sequence having at least 90%, 95%, 96%, 97%, 98%, or 99% identity to SEQ ID NO: 56.

In another aspect of the invention, the present disclosure provides an anti-LY6H antibody, or antigen-binding portion thereof, comprising a heavy chain variable region comprising the amino acid sequence of SEQ ID NO: 58 and a light chain variable region comprising the amino acid sequence of SEQ ID NO: 56.

In another aspect of the invention, the present disclosure provides an anti-LY6H antibody, or antigen-binding portion thereof, comprising a heavy chain comprising an amino acid sequence set forth in SEQ ID NO: 58, or a sequence having at least 90%, 95%, 96%, 97%, 98%, or 99% identity to SEQ ID NO: 58, and/or a light chain comprising an amino acid sequence set forth in SEQ ID NO: 56, or a sequence having at least 90%, 95%, 96%, 97%, 98%, or 99% identity to SEQ ID NO: 56.

In another aspect of the invention, the present disclosure provides an anti-LY6H antibody, or antigen-binding portion thereof, comprising a heavy chain variable region comprising the amino acid sequence of SEQ ID NO: 60 or SEQ ID NO:70 and a light chain variable region comprising the amino acid sequence of SEQ ID NO: 26.

In another aspect of the invention, the present disclosure provides an anti-LY6H antibody, or antigen-binding portion thereof, comprising a heavy chain comprising an amino acid sequence set forth in SEQ ID NO: 60 or SEQ ID NO:70, or a sequence having at least 90%, 95%, 96%, 97%, 98%, or 99% identity to SEQ ID NO: 60 or SEQ ID NO:70, and/or a light chain comprising an amino acid sequence set forth in SEQ ID NO: 26, or a sequence having at least 90%, 95%, 96%, 97%, 98%, or 99% identity to SEQ ID NO: 26.

In another aspect of the invention, the present disclosure provides an antibody, or antigen-binding portion thereof, that binds to the same epitope as the antibody, or antigen-binding portion thereof, of any one of the preceding claims.

In another aspect of the invention, the present disclosure provides an isolated nucleic acid encoding an antibody, or antigen binding portion thereof, of any one of the preceding claims.

In one aspect of the invention, the present disclosure provides a pharmaceutical composition comprising the antibody, or antigen binding portion thereof, of any one of the preceding claims, and a pharmaceutically acceptable carrier.

In another aspect of the invention, the present disclosure provides an antibody, or antigen binding portion thereof, of any one of the preceding claims, conjugated to at least one drug.

In some aspects, the at least one drug is selected from the group consisting of an anti-apoptotic agent, a mitotic inhibitor, a DNA damaging agent, an anti-tumor antibiotic, an immunomodulating agent, a nucleic acid for gene therapy, an anti-angiogenic agent, an anti-metabolite, a boron-containing agent, a chemoprotective agent, a hormone agent, an anti-hormone agent, a corticosteroid, a photoactive therapeutic agent, an oligonucleotide, a radionuclide agent, a radiosensitizer, a topoisomerase inhibitor, and a tyrosine kinase inhibitor. In other embodiments, the at least one drug is conjugated to the antibody, or antigen-binding portion thereof, via a linker. In another embodiment, the linker is a cleavable linker. In yet other embodiments, the linker is a non-cleavable linker.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 4, a CDR2 domain comprising one of the amino acid sequences selected from SEQ ID NO: 3 and SEQ ID NO: 69, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 63, a CDR2 domain comprising one of the amino acid sequences selected from SEQ ID NO: 62 and SEQ ID NO:71, and a CDR1 domain comprising the amino acid sequence of SEQ ID NO: 61, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 19, a CDR2 domain comprising the amino acid sequence of SEQ ID NO: 11, and a CDR1 domain comprising the amino acid sequence of SEQ ID NO: 18, and a light chain variable region comprising a CDR3 domain comprising the amino acid sequence of SEQ ID NO: 21, a CDR2 domain comprising the amino acid sequence of SEQ ID NO: 15, and a CDR1 domain comprising the amino acid sequence of SEQ ID NO: 14.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 25, a CDR2 domain comprising one of the amino acid sequences selected from SEQ ID NO: 24, SEQ ID NO: 65 and SEQ ID NO: 67, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 30, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 34, a CDR2 domain comprising the amino acid sequence of SEQ ID NO: 33, and a CDR1 domain comprising the amino acid sequence of SEQ ID NO: 32.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 36, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 38, a CDR2 domain comprising the amino acid sequence of SEQ ID NO: 33, and a CDR1 domain comprising the amino acid sequence of SEQ ID NO: 32.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 40, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 44, a CDR2 domain comprising the amino acid sequence of SEQ ID NO:43, and a CDR1 domain comprising the amino acid sequence of SEQ ID NO: 42.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 48, a CDR2 domain comprising the amino acid sequence of SEQ ID NO: 29, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 55, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising a CDR3 domain comprising the amino acid sequence of SEQ ID NO: 59, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable domain comprising an amino acid sequence set forth in SEQ ID NO: 1 or SEQ ID NO: 68, and a light chain variable domain comprising an amino acid sequence set forth in SEQ ID NO: 5.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 1 or SEQ ID NO: 68, or a sequence having at least 90%, 95%, 96%, 97%, 98%, or 99% identity to SEQ ID NO: 1 or SEQ ID NO: 68, and/or a light chain comprising an amino acid sequence set forth in SEQ ID NO: 5, or a sequence having at least 90%, 95%, 96%, 97%, 98%, or 99% identity to SEQ ID NO: 5.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 9 and a light chain variable region comprising the amino acid sequence of SEQ ID NO: 13.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 60 or SEQ ID NO: 70 and a light chain variable region comprising the amino acid sequence of SEQ ID NO: 26.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 60 or SEQ ID NO: 70, or a sequence having at least 90%, 95%, 96%, 97%, 98%, or 99% identity to SEQ ID NO: 60 or SEQ ID NO: 70, and/or a light chain comprising an amino acid sequence set forth in SEQ ID NO: 26, or a sequence having at least 90%, 95%, 96%, 97%, 98%, or 99% identity to SEQ ID NO: 26.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 17 and a light chain variable region comprising the amino acid sequence of SEQ ID NO: 20.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising one of the amino acid sequences selected from SEQ ID NO: 22, SEQ ID NO: 64, and SEQ ID NO: 66 and a light chain variable region comprising the amino acid sequence of SEQ ID NO: 26.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in one of SEQ ID NO: 22, SEQ ID NO: 64 and SEQ ID NO: 66, or a sequence having at least 90%, 95%, 96%, 97%, 98%, or 99% identity to one of SEQ ID NO: 22, SEQ ID NO: 64 and SEQ ID NO: 66, and/or a light chain comprising an amino acid sequence set forth in SEQ ID NO: 26, or a sequence having at least 90%, 95%, 96%, 97%, 98%, or 99% identity to SEQ ID NO: 26.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 27 and a light chain variable region comprising the amino acid sequence of SEQ ID NO: 31.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 27, or a sequence having at least 90%, 95%, 96%, 97%, 98%, or 99% identity to SEQ ID NO: 27, and/or a light chain comprising an amino acid sequence set forth in SEQ ID NO: 31, or a sequence having at least 90%, 95%, 96%, 97%, 98%, or 99% identity to SEQ ID NO: 31.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 35 and a light chain variable region comprising the amino acid sequence of SEQ ID NO: 37.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 37, or a sequence having at least 90%, 95%, 96%, 97%, 98%, or 99% identity to SEQ ID NO: 37.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 39 and a light chain variable region comprising the amino acid sequence of SEQ ID NO: 41.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 39, or a sequence having at least 90%, 95%, 96%, 97%, 98%, or 99% identity to SEQ ID NO: 39, and/or a light chain comprising an amino acid sequence set forth in SEQ ID NO: 41, or a sequence having at least 90%, 95%, 96%, 97%, 98%, or 99% identity to SEQ ID NO: 41.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 45 and a light chain variable region comprising the amino acid sequence of SEQ ID NO: 49.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 53 and a light chain variable region comprising the amino acid sequence of SEQ ID NO: 49.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 49, or a sequence having at least 90%, 95%, 96%, 97%, 98%, or 99% identity to SEQ ID NO: 49.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 54 and a light chain variable region comprising the amino acid sequence of SEQ ID NO: 56.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 54, or a sequence having at least 90%, 95%, 96%, 97%, 98%, or 99% identity to SEQ ID NO: 54, and/or a light chain comprising an amino acid sequence set forth in SEQ ID NO: 56, or a sequence having at least 90%, 95%, 96%, 97%, 98%, or 99% identity to SEQ ID NO: 56.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain variable region comprising the amino acid sequence of SEQ ID NO: 58 and a light chain variable region comprising the amino acid sequence of SEQ ID NO: 56.

In another aspect of the invention, the present disclosure provides an antibody drug conjugate (ADC) comprising an antibody, or antigen binding portion thereof, conjugated to at least one drug, wherein the antibody, or antigen binding portion thereof, comprises a heavy chain comprising an amino acid sequence set forth in SEQ ID NO: 58, or a sequence having at least 90%, 95%, 96%, 97%, 98%, or 99% identity to SEQ ID NO: 58, and/or a light chain comprising an amino acid sequence set forth in SEQ ID NO: 56, or a sequence having at least 90%, 95%, 96%, 97%, 98%, or 99% identity to SEQ ID NO: 56.

In some embodiments, the at least one drug is conjugated via a linker. In other embodiments, the linker is a cleavable linker. In yet other embodiments, the linker is a non-cleavable linker.

In some embodiments, the antibody, or antigen binding portion thereof, is an IgG1 isotype.

In another aspect of the invention, the present disclosure provides a pharmaceutical composition comprising an ADC mixture comprising a plurality of the ADC as described herein, and a pharmaceutically acceptable carrier.

In some embodiments, the ADC mixture has an average drug to antibody ratio (DAR) of 0 to 8.

In another aspect of the invention, the present disclosure provides a method of treating cancer using the antibody, or antigen binding portion thereof, as described herein, or the antibody drug conjugate, as described herein.

In some embodiments, the cancer is small cell lung cancer. In one embodiment, the small cell lung cancer is classic small cell lung cancer. In another embodiment, the small cell lung cancer is a variant small cell lung cancer. In one embodiment, classic SCLC cell lines include but are not limited to, for example, the following cell lines: NCI-H60, NCI-H64, NCI-H69, NCI-H209, DMS79, and NCI-H220. In another embodiment, variant SCLC cell lines include but are not limited to, for example, the following cell lines: NCI-H446, NCI-H526, NCI-H524, and NCI-H82, In some embodiments, the cancer is selected from the groups consisting of gastrointestinal stromal tumor (GIST), T cell acute lymphoblastic leukemia (T-ALL), glioblastoma, and soft tissue sarcoma. In yet other embodiments, the cancer is selected from the group consisting of breast cancer, brain and CNS cancer, head and neck cancer, bladder cancer, renal cancer, ovarian cancer, gastric cancer, esophageal cancer, prostate cancer, uterine cancer, endometrial cancer, pancreatic cancer, liver cancer, colorectal cancer, cervical cancer, or non-small cell lung cancer (NSCLC).

In another aspect of the invention, the present disclosure provides a method of inhibiting or decreasing tumor growth using the antibody, or antigen binding portion thereof, as described herein, or the antibody drug conjugate, as described herein.

In some embodiments, the tumor is small cell lung cancer tumor. In other embodiments, the tumor is gastrointestinal stromal tumor (GIST), glioblastoma, or soft tissue sarcoma.

In some embodiments, the present disclosure provides a method for inhibiting or decreasing the progression of a cancer in a subject that does not generally form a solid tumor, said method comprising administering an effective amount of the antibody or antigen binding portion thereof, as described herein, or the ADC, as described herein, to the subject having the cancer, such that the progression of the cancer is inhibited or decreased. In a particular embodiment, the cancer is T cell acute lymphoblastic leukemia (T-ALL).

In some embodiments, the antibody or antigen binding portion thereof or the ADC is administered in combination with an additional agent or an additional therapy. In other embodiments, the additional agent is an immune checkpoint inhibitor. In yet another embodiment, the immune checkpoint inhibitor is an antibody. In another embodiment, the antibody is selected from the group consisting of an anti-PD1 antibody, an anti-PD-L1 antibody or an anti-CTLA-4 antibody. In other embodiments, the additional therapy is radiation. In yet another embodiment, the additional agent is a chemotherapeutic agent. In some embodiments, the cancer or tumor is characterized as having LY6H expression or overexpression.

In some embodiments, the antibodies, or antigen binding portions thereof, of the invention, bind to LY6H with a $K_d$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, or about 0.01 nM or less, or about 0.001 nM or less.

BRIEF DESCRIPTION OF THE DRAWINGS

FIG. 3A shows binding of anti-LY6H antibodies to human LY6H. FIG. 3B shows binding of anti-LY6H antibodies to *Macaca fascicularis* LY6H. FIG. 3C shows binding of anti-LY6H antibodies to rat LY6H. FIG. 3D shows binding of anti-LY6H antibodies to mouse LY6H. FIG. 3E shows binding of anti-LY6H antibodies to parental 293.

FIG. 8A, FIG. 8B, FIG. 8C, FIG. 8D, FIG. 8E, FIG. 8F, and FIG. 8G show in vitro efficacy of anti-LY6H ADC in SCLC and T-ALL cell lines. 3000-5000 cells were seeded in 96 well plate, and treated with MMAE or PBD conjugated antibodies for 5 days. Then cells were lysed by CellTiter Glo 2.0™ (Promega), results were recorded by luminometer. CBIgG1 (Anti-Hen Egg Lysozyme antibody, CrownBio) and hIgG1 (anti-HBV surface Ag antibody) conjugated antibodies were included as negative controls. IC50 values are listed at the bottom of each graph.

FIG. 9A depicts efficacy of MMAE conjugated antibodies in H446 xenograft model. FIG. 9B depicts Kaplan-Meier survival curve of the study. FIG. 9C shows the body weight of the mice in the study.

FIG. 10A shows efficacy of PBD conjugated antibodies in H446 xenograft model. FIG. 10B shows a Kaplan-Meier survival curve of the study. FIG. 10C shows the mice body weight of the study.

FIG. 11A shows efficacy of MMAE conjugated antibodies in H526 xenograft model. FIG. 11B shows a Kaplan-Meier survival curve of the study. FIG. 11C shows the body weight of the mice in the study.

FIG. 12A shows efficacy of PBD conjugated antibodies in H526 xenograft model. FIG. 12B shows a Kaplan-Meier survival curve of the study. FIG. 12C shows the body weight of the mice in the study.

FIG. 13A shows efficacy of PBD conjugated antibodies in DMS79 xenograft model. FIG. 13B shows a Kaplan-Meier survival curve of the study. FIG. 13C shows the body weight of the mice in the study.

FIG. 14A shows efficacy of PBD conjugated antibodies in H446 xenograft model. FIG. 14B shows a Kaplan-Meier survival curve of the study. FIG. 14C shows the body weight of the mice in the study.

FIG. 15A shows PBD in combination with olaparib. FIG. 15B shows PBD in combination with cisplatin. FIG. 15C shows PBD in combination with etoposide.

FIG. 16A shows PBD in combination with olaparib. FIG. 16B shows PBD in combination with cisplatin. FIG. 16C shows PBD in combination with etoposide.

FIG. 17A shows PBD in combination with olaparib. FIG. 17B shows PBD in combination with cisplatin. FIG. 17C shows PBD in combination with etoposide.

DETAILED DESCRIPTION

Figure 1:
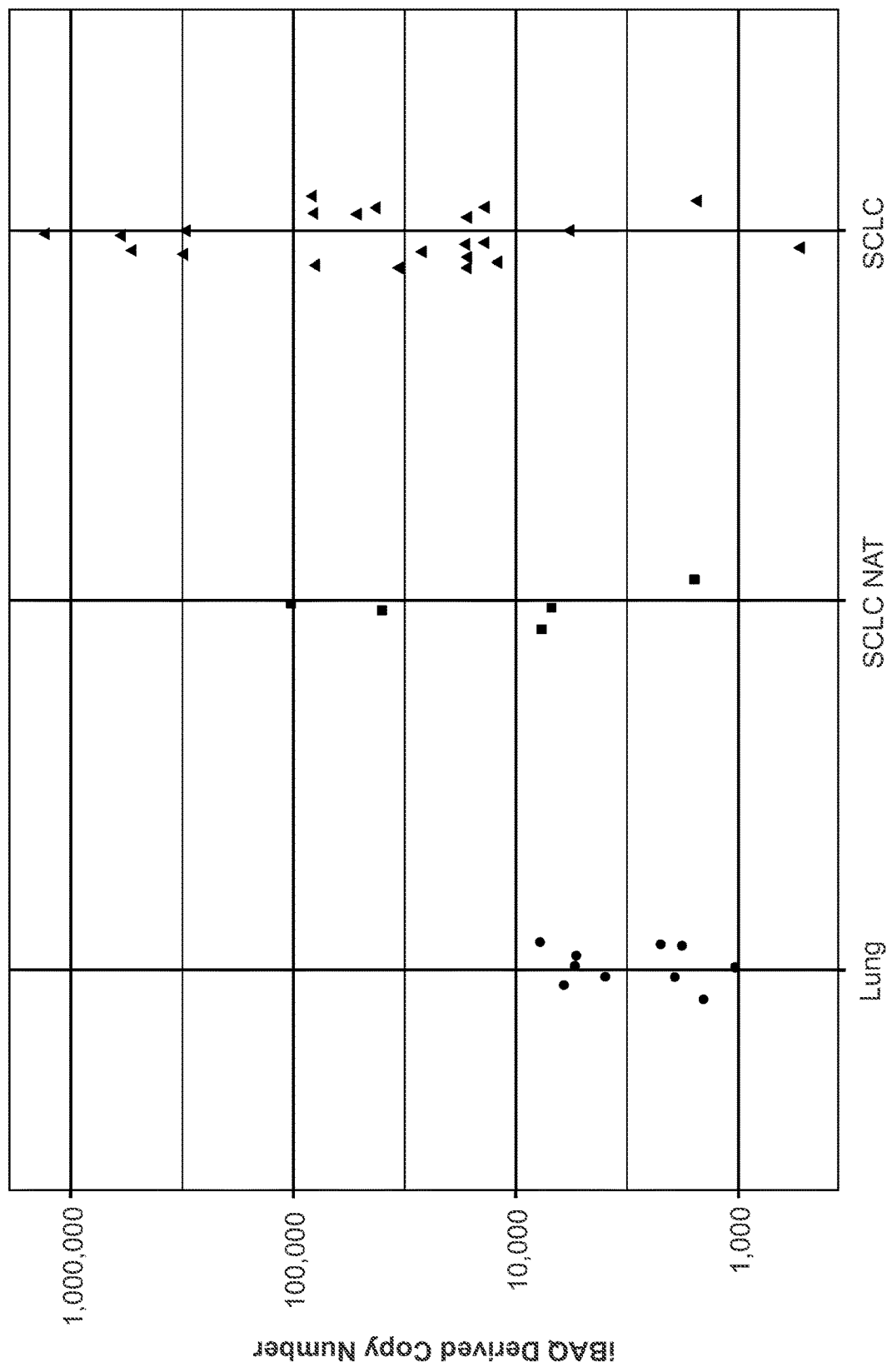
FIG. 1 illustrates that LY6H is differentially expressed in primary SCLC tumors. iBAQ (intensity-based absolute quantification) data is presented. Triangles represent SCLC tumors, squares represent SCLC normal adjacent tissue (NAT), and circles represent normal lung tissue.

Various aspects of the disclosure relate to anti-LY6H antibodies and antibody fragments, anti-LY6H ADCs, and pharmaceutical compositions thereof, as well as nucleic acids, recombinant expression vectors and host cells for making such antibodies and fragments. Methods of using the antibodies and ADCs described herein to detect LY6H, in particular human LY6H, to bind to and inhibit LY6H on LY6H expressing cells, including cancer cells, to undergo internalization in and inhibit LY6H expressing cells, e.g., LY6H expressing tumor and cancer cells, to modulate an immune response in vivo, and/or to treat LY6H-associated disorders, e.g., cancer, including, but not limited to, small cell lung cancer (SCLC). In one embodiment, the anti-LY6H antibodies or ADCs of the invention are administered in combination with one or more immune checkpoint inhibitors (e.g., antibody or small molecule immune checkpoint inhibitors) for the treatment of a cancer. In another embodiment of the invention, anti-LY6H antibody drug conjugates (ADCs) of the invention (e.g., the LY6H antibodies of the invention conjugated to a toxin) are internalized and induce cell death of cells endogenously expressing LY6H.

I. Definitions

In order that the invention may be more readily understood, certain terms are first defined. In addition, it should be noted that whenever a value or range of values of a parameter are recited, it is intended that values and ranges intermediate to the recited values are also intended to be part of this invention.

The terms "lymphocyte antigen 6 complex, locus H antibody," "Lymphocyte Antigen 6H antibody," or "anti-LY6H antibody", used interchangeably herein, refer to an antibody that specifically binds to LY6H, e.g., human LY6H. An antibody "which binds" an antigen of interest, i.e., LY6H, is one capable of binding that antigen with sufficient affinity such that the antibody is useful in targeting a cell expressing the antigen. In a preferred embodiment, the antibody specifically binds to human LY6H (hLY6H). Examples of anti-LY6H antibodies are disclosed in the Examples, below. Unless otherwise indicated, the term "anti-LY6H antibody" is meant to refer to an antibody which binds to wild type LY6H, a variant, or an isoform of LY6H.

Several different isoforms of LY6H have been identified. An exemplary amino acid sequence of wild type human LY6H, which contains 140 amino acids, is provided below as SEQ ID NO: 123 (GenBank LY6H_HUMAN).

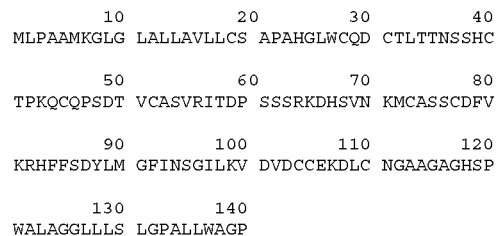

The terms "specific binding" or "specifically binding", as used herein, in reference to the interaction of a LY6H antibody or an ADC with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody or ADC is specific for epitope "A", the presence of a molecule containing epitope A (or free, unlabeled A), in a reaction containing labeled "A" and the antibody, will reduce the amount of labeled A bound to the antibody or ADC.

In one embodiment, the phrase "specifically binds to LY6H" or "specific binding to LY6H", as used herein, refers to the ability of an anti-LY6H antibody or ADC to interact with LY6H (human, monkey, rat or mouse LY6H) with a dissociation constant ($K_D$) of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less. In another embodiment, the phrase "specifically binds to LY6H" or "specific binding to LY6H", as used herein, refers to the ability of an anti-LY6H antibody or ADC to interact with LY6H (human, monkey, rat or mouse LY6H) with a dissociation constant ($K_D$) of between about 1 pM (0.001 nM) to 2,000 nM, between about 500 pM (0.5 nM) to 1,000 nM, between about 500 pM (0.5 nM) to 500 nM, between about 1 nM) to 200 nM, between about 1 nM to 100 nM, between about 1 nM to 50 nM, between about 1 nM to 20 nM, or between about 1 nM to 5 nM. In one embodiment, $K_D$ is determined by surface plasmon resonance. In one embodiment, $K_D$ is determined by surface plasmon resonance or Bio-Layer Interferometry, or by any other method known in the art. Bio-Layer Interferometry refers to an optical phenomenon that allows for the analysis of real-time biospecific interactions by measuring the interference patterns of reflected white light, for example using the Octet™ system (ForteBio, Pall Corp. Fremont, Calif.). For further description of the Octet™ System, see Li, B et al. (2011) *J. Pharm. Biomed. Anal.* 54(2):286-294 and Abdiche, Y. N., et al. (2009) *Anal. Biochem.* 386(2):172-180, the contents of which are incorporated herein by reference.

The term "antibody" broadly refers to an immunoglobulin (Ig) molecule, generally comprised of four polypeptide chains, two heavy (H) chains and two light (L) chains, or any functional fragment, mutant, variant, or derivative thereof, that retains the essential target binding features of an Ig molecule. Such mutant, variant, or derivative antibody formats are known in the art. Non-limiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY) and class (e.g., IgG1, IgG2, IgG3, IgG4, IgA1 and IgA2) or subclass.

The term "antigen binding portion" of an antibody (or simply "antibody portion"), as used herein, refers to one or more fragments of an antibody that retain the ability to specifically bind to an antigen (e.g., hLY6H). It has been shown that the antigen binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen binding portion" of an antibody include (i) a Fab fragment, a monovalent fragment consisting of the VL, VH, CL and CH1 domains; (ii) a F(ab')₂ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883).

Such single chain antibodies are also intended to be encompassed within the term "antigen binding portion" of an antibody. In certain embodiments, scFv molecules may be incorporated into a fusion protein. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad. Sci. USA* 90:6444-6448; Poljak, R. J., et al. (1994) *Structure* 2:1121-1123). Such antibody binding portions are known in the art (Kontermann and Dubel eds., Antibody Engineering (2001) Springer-Verlag. New York. 790 pp. (ISBN 3-540-41354-5).

The term "antibody construct" as used herein refers to a polypeptide comprising one or more the antigen binding portions disclosed herein linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger, P., et al. (1993) *Proc. Natl. Acad. Sci. USA* 90:6444-6448; Poljak, R. J., et al. (1994) *Structure* 2:1121-1123). An immunoglobulin constant domain refers to a heavy or light chain constant domain. Antibody portions, such as Fab and F(ab')₂ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds LY6H is substantially free of antibodies that specifically bind antigens other than LY6H). An isolated antibody that specifically binds LY6H may, however, have cross-reactivity to other antigens, such as LY6H molecules from other species. Moreover, an isolated antibody may be substantially free of other cellular material and/or chemicals.

The term "humanized antibody" refers to antibodies which comprise heavy and light chain variable region sequences from a nonhuman species (e.g., a mouse) but in which at least a portion of the VH and/or VL sequence has been altered to be more "human-like", i.e., more similar to human germline variable sequences. In particular, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab')$_2$, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In other embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG1, IgG2, IgG3 and IgG4. The humanized antibody may comprise sequences from more than one class or isotype, and particular constant domains may be selected to optimize desired effector functions using techniques well-known in the art.

The terms "Kabat numbering," "Kabat definitions," and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) *Sequences of Proteins of Immunological Interest, Fifth Edition*, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the term "CDR" refers to the complementarity determining region within antibody variable sequences. There are three CDRs in each of the variable regions of the heavy chain (HC) and the light chain (LC), which are designated CDR1, CDR2 and CDR3 (or specifically HC CDR1, HC CDR2, HC CDR3, LC CDR1, LC CDR2, and LC CDR3), for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, J. Mol. Biol. 196:901-917 (1987) and Chothia et al., Nature 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (FASEB J. 9:133-139 (1995)) and MacCallum (J Mol Biol 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

"Percent (%) amino acid sequence identity" with respect to a peptide or polypeptide sequence is defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. In one embodiment, the disclosure includes an amino acid sequence having at least 80%, at least 85%, at least 90%, at least 95%, at least 96%, at least 97%, at least 98%, or at least 99% identity to an amino acid sequence described herein.

The term "multivalent antibody" is used herein to denote an antibody comprising two or more antigen binding sites. In certain embodiments, the multivalent antibody may be engineered to have the three or more antigen binding sites, and is generally not a naturally occurring antibody.

The term "multispecific antibody" refers to an antibody capable of binding two or more unrelated antigens.

The term "dual variable domain" or "DVD," as used interchangeably herein, are antigen binding proteins that comprise two or more antigen binding sites and are tetravalent or multivalent binding proteins. Such DVDs may be monospecific, i.e., capable of binding one antigen or multispecific, i.e. capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site. In one embodiment, the CDRs described herein are used in an anti-LY6H DVD.

The term "activity" includes activities such as the binding specificity/affinity of an antibody or ADC for an antigen, for example, an anti-LY6H antibody that binds to a LY6H antigen. In one embodiment, an anti-LY6H antibody or anti-LY6H ADC activity includes, but is not limited to, binding to LY6H in vitro; binding to LY6H on cells expressing LY6H in vivo (such as, for example, LY6H expressing tumor and cancer cells); modulating immune response in vivo; undergoing internalization in and inhibiting LY6H expressing cells, e.g., LY6H expressing tumor and cancer cells; inducing cell death in cells expressing LY6H, including LY6H expressing tumor and cancer cells; inhibiting cancer cell invasion and metastasis; decreasing or inhibiting cancer, e.g., small cell lung cancer (SCLC), gastrointestinal stromal tumor (GIST), T cell acute lymphoblastic leukemia (T-ALL), glioblastoma, and soft tissue sarcoma; and decreasing or inhibiting tumor cellular proliferation or tumor growth in vivo. In some embodiments, the tumor can be a LY6H negative tumor or a LY6H positive tumor. In one embodiment, an anti-LY6H antibody is capable of being internalized into a cell expressing LY6H.

In one embodiment, the antibody, or antigen-binding portion thereof, is capable of inducing antibody dependent cellular cytotoxicity (ADCC). In one embodiment, the antibody, or antigen-binding portion thereof, is not capable of inducing ADCC.

In one embodiment, the antibody, or antigen-binding portion thereof, is capable of inducing complement-dependent cytotoxicity (CDC). In one embodiment, the antibody, or antigen-binding portion thereof, is not capable of inducing CDC.

In one embodiment, the antibody, or antigen-binding portion thereof, is capable of inducing ADCC and CDC. In one embodiment, the antibody, or antigen-binding portion thereof, is not capable of inducing ADCC or CDC.

The term "epitope" refers to a region of an antigen that is bound by an antibody, antibody fragment, or ADC. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson, U., et al. (1993) Ann. Biol. Clin. 51:19-26; Jönsson, U., et al. (1991) Biotechniques 11:620-627; Johnsson, B., et al. (1995) J. Mol. Recognit. 8:125-131; and Johnnson, B., et al. (1991) Anal. Biochem. 198:268-277.

The term "$k_{on}$" or "$k_a$", as used herein, is intended to refer to the on rate constant for association of an antibody to the antigen to form the antibody/antigen complex.

The term "$k_{off}$" or "$k_d$", as used herein, is intended to refer to the off rate constant for dissociation of an antibody from the antibody/antigen complex.

The term "$K_D$", as used herein, is intended to refer to the equilibrium dissociation constant of a particular antibody-antigen interaction. $K_D$ is calculated by $k_a/k_d$. In one embodiment, the antibodies of the invention have a $K_D$ of about 2,000 nM or less, about 1,000 nM or less, about 500 nM or less, about 200 nM or less, about 100 nM or less, about 75 nM or less, about 25 nM or less, about 21 nM or less, about 12 nM or less, about 11 nM or less, about 10 nM or less, about 9 nM or less, about 8 nM or less, about 7 nM or less, about 6 nM or less, about 5 nM or less, about 4 nM or less, about 3 nM or less, about 2 nM or less, about 1 nM or less, about 0.5 nM or less, about 0.3 nM or less, about 0.1 nM or less, about 0.01 nM or less, or about 0.001 nM or less.

The term "competitive binding", as used herein, refers to a situation in which a first antibody competes with a second antibody, for a binding site on a third molecule, e.g., an antigen. In one embodiment, competitive binding between two antibodies is determined using FACS analysis.

The term "competitive binding assay" is an assay used to determine whether two or more antibodies bind to the same epitope. In one embodiment, a competitive binding assay is a competition fluorescent activated cell sorting (FACS) assay which is used to determine whether two or more antibodies bind to the same epitope by determining whether the fluorescent signal of a labeled antibody is reduced due to the introduction of a non-labeled antibody, where competition for the same epitope will lower the level of fluorescence.

The term "labeled antibody" as used herein, refers to an antibody, or an antigen binding portion thereof, with a label incorporated that provides for the identification of the binding protein, e.g., an antibody. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody-drug-conjugate" or "ADC" refers to a binding protein, such as an antibody or antigen binding fragment thereof, chemically linked to one or more chemical drug(s) (also referred to herein as agent(s)) that may optionally be therapeutic or cytotoxic agents. In a preferred embodiment, an ADC includes an antibody, a cytotoxic or therapeutic drug, and a linker that enables attachment or conjugation of the drug to the antibody. An ADC typically has anywhere from 1 to 8 drugs conjugated to the antibody, including drug loaded species of 2, 4, 6, or 8. Non-limiting examples of drugs that may be included in the ADCs are mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, and radiosensitizers.

The terms "lymphocyte antigen 6 complex, locus H antibody drug conjugate," "Lymphocyte Antigen 6H antibody drug conjugate," "anti-LY6H antibody drug conjugate," or "anti-LY6H ADC", used interchangeably herein, refer to an ADC comprising an antibody that specifically binds to LY6H, whereby the antibody is conjugated to one or more chemical agent(s) or payloads. In one embodiment, the chemical agent is linked to the antibody via a linker.

The term "drug-to-antibody ratio" or "DAR" refers to the number of drugs, e.g., IGN, auristatin, or maytansinoid, attached to the antibody of the ADC. The DAR of an ADC can range from 1 to 8, although higher loads, e.g., 10, are also possible depending on the number of linkage site on an antibody. The term DAR may be used in reference to the number of drugs loaded onto an individual antibody, or, alternatively, may be used in reference to the average or mean DAR of a group of ADCs.

The term "LY6H associated disorder," as used herein, includes any disorder or disease (including proliferative disorders, e.g., cancer) that is marked, diagnosed, detected or identified by a phenotypic or genotypic aberration of LY6H genetic components or expression during the course or etiology of the disease or disorder. In this regard a LY6H phenotypic aberration or determinant may, for example, comprise increased or decreased levels of LY6H protein expression on one cell population, e.g., a cancer cell population, or an immune cell population (such as a tumor infiltrating cell population), as compared to another cell population, e.g., a normal cell population, or increased or decreased LY6H protein expression on certain definable cell populations, or increased or decreased LY6H protein expression at an inappropriate phase or stage of a cell lifecycle. It will be appreciated that similar expression patterns of genotypic determinants (e.g., mRNA transcription levels) of LY6H may also be used to classify or detect LY6H associated disorders. An "LY6H associated disorder," as used herein, also includes a disorder characterized by infiltration of cells expressing LY6H, e.g., LY6H expressing tumor and cancer cells. In one embodiment, a LY6H associated disorder is small cell lung cancer (SCLC). In one embodiment, a LY6H associated disorder is gastrointestinal stromal tumor (GIST). In another embodiment, a LY6H associated disorder is T cell acute lymphoblastic leukemia (T-ALL). In another embodiment, a LY6H associated disorder is glioblastoma. In another embodiment, a LY6H associated disorder is soft tissue sarcoma. In one embodiment, a LY6H associated disorder is breast cancer. In one embodiment, a LY6H associated disorder is brain and CNS cancer. In one embodiment, a LY6H associated disorder is head and neck cancer. In one embodiment, a LY6H associated disorder is bladder cancer. In one embodiment, a LY6H associated disorder is renal cancer. In another embodiment, a LY6H associated disorder is ovarian cancer. In one embodiment, a LY6H associated disorder is eosophageal cancer. In another embodiment, a LY6H associated disorder is gastric cancer. In another embodiment, a LY6H associated disorder is prostrate cancer. In another embodiment, a LY6H associated disorder is uterine cancer. In another embodiment, a LY6H associated disorder is colorectal cancer. In one embodiment, a LY6H associated disorder is cervical cancer. In another embodiment, a LY6H associated disorder is non small cell lung cancer (NSCLC). In yet another embodiments, a LY6H associated disorder is endometrial cancer. In one embodiment, a LY6H associated disorder is pancreatic cancer. In another embodiment, a LY6H associated disorder is liver cancer.

In one embodiment, the SCLC is a classic SCLC. In another embodiment, the SCLC is a variant SCLC. "Classic SCLC" and "variant SCLCs" are well known to one of ordinary skill in the art. For example, see Broers et al., *Cytometry*, 9:426-431, 1988; Doyle et al., *Cancer Res*, 49(23):6745-6751, 1989; Carney et al., *Cancer Res.*, 45:2913-2923, 1985; and Koros et al., *Lung Cancer*, 7(4): 225-234, 1991.

The term "cancer," as used herein, is meant to refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include, but are not limited to, breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, gastrointestinal stromal tumor (GIST), testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, T cell acute lymphoblastic leukemia (T-ALL), and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarian serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-LY6H ADC of the present invention can be used to treat a cancer in a subject including, but not limited to Hodgkin's lymphoma, PVNS, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarian serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma. kidney renal clear cell carcinoma, and kidney renal papillary cell carcinoma.

In one embodiment, the antibodies or ADCs of the invention are administered to a patient having a cancer, including but not limited to, small cell lung cancer (SCLC), gastrointestinal stromal tumor (GIST), T cell acute lymphoblastic leukemia (T-ALL), glioblastoma, and soft tissue sarcoma.

In one embodiment, the antibodies or ADCs are administered to a patient having a classic SCLC. In another embodiment, the antibodies or ADCs are administered to a patient having a variant SCLC.

In one embodiment, the antibodies or ADCs of the invention are administered to a patient having a solid tumor, including an advanced solid tumor. In one embodiment, the tumor expresses LY6H or contains tumor infiltrating immune cells expressing LY6H. In another embodiment, the tumor does not express LY6H and/or does not contain tumor infiltrating immune cells expressing LY6H. In another embodiment, administration of the antibodies of the invention to a patient upregulates an immune response in the patient. In another embodiment, administration of ADCs of the invention induce cell death of LY6H expressing cells.

The term "LY6H expressing tumor," as used herein, refers to a tumor which expresses LY6H protein (including a tumor comprising tumor infiltrating cells that express LY6H protein), such as a small cell lung cancer (SCLC) tumor, gastrointestinal stromal tumor (GIST), glioblastoma tumor, and soft tissue sarcoma tumor. In one embodiment, LY6H expression in a tumor is determined using immunohistochemical staining of tumor cell membranes, where any immunohistochemical staining above background level in a tumor sample indicates that the tumor is a LY6H expressing tumor. In another embodiment, a LY6H expressing tumor, e.g., a small cell lung cancer (SCLC) tumor, gastrointestinal stromal tumor (GIST), glioblastoma tumor, and soft tissue sarcoma tumor expressing LY6H, is identified in a patient when greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a tumor sample are positive for LY6H expression. In one embodiment, the LY6H expressing cells in the sample are tumor infiltrating immune cells. In another embodiment, LY6H positive expression is determined based on membrane staining as determined by, e.g., immunohistochemistry (IHC) analysis.

A LY6H expressing tumor is identified as having an "elevated level of LY6H" or "expressing LY6H at an elevated level" when the level of LY6H is higher than in tissue surrounding the cancer.

In some embodiments, an "elevated level of LY6H" is one in which 5% or more of the cells in a tumor sample have membrane staining. In some embodiments a "high level" in regard to LY6H is 5% or more staining, for example, 5, 10, 20, 30, 40, 50, 60, 70, 80, 90, or 100% of the cells in the tumor sample are stained. In some embodiments, the protein expression levels can be measured by IHC analysis. In another embodiment, the LY6H expressing cells in the sample are tumor infiltrating immune cells.

A LY6H expressing tumor is identified as having a "low level of LY6H" or "expressing LY6H at a low level" is one in which 5% or less of the cells in a tumor sample have membrane staining. In some embodiments a "low level" in regard to LY6H is 5% or less staining, for example, 4.9, 4.5, 4, 3, 2, 1, 0.9, 0.8, 0.7, 0.6, 0.5, 0.4, 0.3, 0.2, 0.1% or less of the cells in the tumor sample are stained. In some embodiments, the protein expression levels can be measured by IHC analysis. In another embodiment, the LY6H expressing cells in the sample are tumor infiltrating immune cells.

A cell that expresses no LY6H can also be described as expressing a "low level of LY6H". Thus, the phrase "expresses a low level of LY6H" encompasses no LY6H expression. In some embodiments, a low level of LY6H is within the background staining levels. In some embodiments, a sample that is LY6H "negative" has no LY6H expression or a low level of LY6H. In some embodiments, LY6H staining is negative when no or less than 5%, 4%, 3%, 2%, or 1% of the cells have membrane staining for LY6H.

As used herein, the term "tumor sample" refers to a tumor tissue or cell sample obtained from a tumor, e.g., including, but not limited to, a small cell lung cancer (SCLC) tumor, gastrointestinal stromal tumor (GIST), glioblastoma tumor, and soft tissue sarcoma tumor. The sample can include both tumor cells and tumor infiltrating cells, e.g., tumor infiltrating immune cells.

As used herein, the term "non-cancer sample" or "normal sample" refers to a sample from a normal tissue (e.g., a lung tissue sample). In some embodiments, the non-cancer sample comes from the same subject, but is from a different part of the subject than that being tested. In some embodiments, the non-cancer sample is from a tissue area surrounding or adjacent to the cancer, e.g., small cell lung cancer (SCLC), gastrointestinal stromal tumor (GIST), T cell acute lymphoblastic leukemia (T-ALL), glioblastoma, and soft tissue sarcoma. In some embodiments, the non-cancer sample is not from the subject being tested, but is a sample from a subject known to have, or not to have, a disorder in question (for example, a particular cancer such as small cell lung cancer (SCLC), gastrointestinal stromal tumor (GIST), T cell acute lymphoblastic leukemia (T-ALL), glioblastoma, and soft tissue sarcoma or LY6H related disorder). In some embodiments, the non-cancer sample is from the same subject, but from a point in time before the subject developed cancer. In some embodiments, the reference sample is from a benign tumor or blood sample (for example, benign lung tumor sample), from the same or a different subject.

Methods for detecting expression of LY6H in a tumor are known in the art. For example, immunohistochemistry (IHC) analysis may be used to show that LY6H is, for example, small cell lung cancer (SCLC) tissue, gastrointestinal stromal tumor (GIST) tissue, T cell acute lymphoblastic leukemia (T-ALL) cells, glioblastoma tissue, and soft tissue sarcoma tissue.

The terms "overexpress," "overexpression," or "overexpressed" interchangeably refer to a gene that is transcribed or translated at a detectably greater level, usually in a cancer cell, in comparison to a normal cell. Overexpression therefore refers to both overexpression of protein and RNA (due to increased transcription, post transcriptional processing, translation, post translational processing, altered stability, and altered protein degradation), as well as local overexpression due to altered protein traffic patterns (increased nuclear localization), and augmented functional activity, e.g., as in an increased enzyme hydrolysis of substrate. Thus, overexpression refers to either protein or RNA levels. Overexpression can also be by 5%, 10%, 20%, 30%, 40%, 50%, 60%, 70%, 80%, 90% or more in comparison to a normal cell or comparison cell. In certain embodiments, the anti-LY6H antibodies or ADCs are used to treat tumors likely to overexpress LY6H.

The term "administering" as used herein is meant to refer to the delivery of a substance (e.g., an anti-LY6H antibody or ADC) to achieve a therapeutic objective (e.g., the treatment of an LY6H-associated disorder or the inhibition or reduction of a tumor). Modes of administration may be parenteral, enteral and topical. Parenteral administration is usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The term "combination therapy", as used herein, refers to the administration of two or more therapeutic substances, e.g., an anti-LY6H antibody or ADC and an additional therapeutic agent. The additional therapeutic agent may be administered concomitant with, prior to, or following the administration of the anti-LY6H antibody or ADC. In one embodiment, the anti-LY6H antibodies or ADCs of the invention are administered in combination with one or more immune checkpoint inhibitors (e.g., one or more antibody or small molecule immune checkpoint inhibitors) for the treatment of a cancer.

As used herein, the term "effective amount" or "therapeutically effective amount" refers to the amount of a drug, e.g., an antibody or ADC, which is sufficient to reduce or ameliorate the severity and/or duration of a disorder, e.g., cancer, or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent). The effective amount of an antibody or ADC may, for example, inhibit tumor growth (e.g., inhibit an increase in tumor volume), decrease tumor growth (e.g., decrease tumor volume), reduce the number of cancer cells, and/or relieve to some extent one or more of the symptoms associated with the cancer. The effective amount may, for example, improve disease free survival (DFS), improve overall survival (OS), or decrease likelihood of recurrence.

Various aspects of the invention are described in further detail in the following subsections.

II. Anti-LY6H Antibodies

One aspect disclosed herein provides humanized anti-LY6H antibodies, or antigen binding portions thereof. Another aspect disclosed herein provides human anti-LY6H antibodies, or antigen binding portions thereof. Another aspect disclosed herein provides mouse anti-LY6H antibodies, or antigen binding portions thereof. In one embodiment, the antibodies disclosed herein bind human LY6H. In another embodiment, the antibodies disclosed herein bind cynomolgus monkey LY6H. In another embodiment, the antibodies disclosed herein bind rhesus monkey LY6H. In another embodiment, the antibodies disclosed herein bind human LY6H on cells expressing LY6H, e.g., cancer cells, including, but not limited to, small cell lung cancer (SCLC) cells, e.g., classic SCLC cells or variant SCLC cells, gastrointestinal stromal tumor (GIST) cells, T cell acute lymphoblastic leukemia (T-ALL) cells, glioblastoma cells, and soft tissue sarcoma cells. In another embodiment, the antibodies disclosed herein bind human LY6H expressed on tumor infiltrating cells, e.g., tumor infiltrating immune cells. In another embodiment, the antibodies disclosed herein bind human LY6H expressed on tumor cells.

Another aspect disclosed herein features antibody drug conjugates (ADCs) comprising an anti-LY6H antibody described herein and at least one drug(s). The antibodies or ADCs disclosed herein have characteristics including, but not limited to, binding to human LY6H in vitro; binding human LY6H on cells expressing LY6H in vivo, e.g., LY6H expressing cancer cells; binding human LY6H expressed on tumor infiltrating cells, e.g., tumor infiltrating immune cells; binding human LY6H expressed on tumor cells; regulating an immune response in vivo; undergoing internalization in and inhibiting cells expressing LY6H, e.g., LY6H expressing tumor and cancer cells; inducing cell death in cells expressing LY6H, including, but not limited to, LY6H expressing tumor and cancer cells; inhibiting cancer cell invasion and metastasis; decreasing or inhibiting cancer, including, but not limited to, small cell lung cancer (SCLC), e.g., classic SCLC or variant SCLC, gastrointestinal stromal tumor (GIST), T cell acute lymphoblastic leukemia (T-ALL), glioblastoma, and soft tissue sarcoma; and decreasing or inhibiting tumor cellular proliferation or tumor growth, or tumor invasion and metastasis. ADCs disclosed herein, in particular, have characteristics including, but not limited to, inducing cell death in cells expressing LY6H, e.g., cancer cells expressing LY6H. In one embodiment, an anti-LY6H antibody or ADC disclosed herein is capable of being internalized into a cell expressing LY6H.

In one embodiment, anti-LY6H antibodies are disclosed which have the ability to bind to LY6H, as described in the Examples below. Collectively, the novel antibodies are referred to herein as "LY6H antibodies." In one embodiment, the anti-LY6H antibodies, ADCs, or antigen binding fragments thereof, are able to inhibit or decrease progression of cancer in vivo. In another embodiment, the anti-LY6H antibodies, ADCs, or antigen binding fragments thereof, are able to inhibit or decrease tumor growth in vivo. The tumor can be a LY6H negative tumor or an LY6H expressing tumor. In various embodiments, anti-LY6H antibodies, ADCs, or antigen binding fragments thereof, are capable of modulating a biological function of LY6H. In other embodiments of the foregoing aspects, the anti-LY6H antibodies, ADCs, or antigen binding fragments thereof, bind LY6H on cells expressing LY6H, e.g., tumor and cancer cells expressing LY6H. Thus, the disclosure includes anti-LY6H antibodies, ADCs, or antigen binding fragments thereof, that are effective at inhibiting or decreasing cancer or tumor growth.

In addition, the present inventors have shown that LY6H is expressed by small cell lung cancer (SCLC) cells (see Example 1), e.g., classic SCLC and/or variant SCLC. Increased expression of LY6H has been shown in multiple cancer types (Luo, L. et al. *Oncotarget* 7(10): 11165-11193, 2016). Accordingly, the anti-LY6H antibodies, ADCs, and antigen-binding portions thereof, can be used for the treatment of cancers, including, but not limited to, small cell lung cancer (SCLC), gastrointestinal stromal tumor (GIST), T cell acute lymphoblastic leukemia (T-ALL), glioblastoma, and soft tissue sarcoma in a subject.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a small cell lung cancer (SCLC) tumor sample are positive for LY6H expression. In another embodiment, a SCLC tumor sample has a high level of LY6H expression. For example, in one embodiment, at least 5% or more of the cells in a SCLC tumor sample have membrane staining. In another embodiment, a SCLC tumor sample obtained from the subject displays a low level of expression of LY6H. The expression level of LY6H can be determined by any method known in the art. For example, the expression level of LY6H can be determined via immunohistochemical analysis. In another embodiment, the SCLC has been previously treated with another anti-cancer agent or anti-cancer therapy, e.g., a chemotherapy. In one embodiment, the SCLC is resistant to chemotherapy.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a gastrointestinal stromal tumor (GIST) sample are positive for LY6H expression. In another embodiment, a GIST sample has a high level of LY6H expression. For example, in one embodiment, at least 5% or more of the cells in a GIST sample have membrane staining. In another embodiment, a GIST sample obtained from the subject displays a low level of expression of LY6H. The expression level of LY6H can be determined by any method known in the art. For example, the expression level of LY6H can be determined via immunohistochemical analysis. In another embodiment, the GIST has been previously treated with another anti-cancer agent or anti-cancer therapy, e.g., a chemotherapy. In one embodiment, the GIST is resistant to chemotherapy.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a sample, e.g., blood sample, obtained from a subject having T cell acute lymphoblastic leukemia (T-ALL) are positive for LY6H expression. In another embodiment, a sample obtained from the subject having T-ALL has a high level of LY6H expression. For example, in one embodiment, at least 5% or more of the cells in a sample obtained from the subject having T-ALL have membrane staining. In another embodiment, a sample obtained from the subject having T-ALL displays a low level of expression of LY6H. The expression level of LY6H can be determined by any method known in the art. For example, the expression level of LY6H can be determined via immunohistochemical analysis. In another embodiment, the T-ALL has been previously treated with another anti-cancer agent or anti-cancer therapy, e.g., a chemotherapy. In one embodiment, the T-ALL is resistant to chemotherapy.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a glioblastoma tumor sample are positive for LY6H expression. In another embodiment, a glioblastoma tumor sample has a high level of LY6H expression. For example, in one embodiment, at least 5% or more of the cells in a glioblastoma tumor sample have membrane staining. In another embodiment, a glioblastoma tumor sample obtained from the subject displays a low level of expression of LY6H. The expression level of LY6H can be determined by any method known in the art. For example, the expression level of LY6H can be determined via immunohistochemical analysis. In another embodiment, the glioblastoma has been previously treated with another anti-cancer agent or anti-cancer therapy, e.g., a chemotherapy. In one embodiment, the glioblastoma is resistant to chemotherapy.

In one embodiment, greater than 1%, greater than 2%, greater than 3%, greater than 4%, greater than 5%, greater than 6%, greater than 7%, greater than 8%, greater than 9%, greater than 10%, greater than 15%, greater than 20%, greater than 25%, or greater than 30%, greater than 40%, greater than 50%, greater than 60%, greater than 70%, greater than 80%, greater than 90%, or more of the cells in a soft tissue sarcoma tumor sample are positive for LY6H expression. In another embodiment, a soft tissue sarcoma tumor sample has a high level of LY6H expression. For example, in one embodiment, at least 5% or more of the cells in a soft tissue sarcoma tumor sample have membrane staining. In another embodiment, a soft tissue sarcoma tumor sample obtained from the subject displays a low level of expression of LY6H. The expression level of LY6H can be determined by any method known in the art. For example, the expression level of LY6H can be determined via immunohistochemical analysis. In another embodiment, the soft tissue sarcoma has been previously treated with another anti-cancer agent or anti-cancer therapy, e.g., a chemotherapy. In one embodiment, the soft tissue sarcoma is resistant to chemotherapy.

Antibodies having combinations of any of the aforementioned characteristics are contemplated as aspects of the disclosure. ADCs, described in more detail below, may also have any of the foregoing characteristics.

One aspect of the disclosure features an anti-human LY6H (anti-hLY6H) Antibody Drug Conjugate (ADC) comprising an anti-hLY6H antibody conjugated to a drug via a linker. Exemplary anti-LY6H antibodies (and sequences thereof) that can be used in the ADCs are described herein.

The anti-LY6H antibodies described herein provide the ADCs with the ability to bind to LY6H such that the cytotoxic molecule attached to the antibody may be delivered to the LY6H-expressing cell, particularly a LY6H expressing cancer cell.

While the term "antibody" is used throughout, it should be noted that antibody fragments (i.e., antigen-binding portions of an anti-LY6H antibody) are also included in the disclosure and may be included in the embodiments (methods and compositions) described throughout. For example, an anti-LY6H antibody fragment may be conjugated to the drugs, as described herein. In certain embodiments, an anti-LY6H antibody binding portion is a Fab, a Fab', a F(ab')2, a Fv, a disulfide linked Fv, an scFv, a single domain antibody, or a diabody.

Example 2 describes the generation of human monoclonal LY6H antibodies against the extracellular domain (ECD) of human, monkey, rat, and mouse LY6H, identified herein as 6D11, 11D9, 23F3, 12G7, 22A5, 26F3, 35H10, 1F8, 2B11, 24A10, 34H6, 10B10, 12G7_S54A, 12G7_N52Q, 6D11_41B4, and 10B10_S54A. The heavy and light chain variable region amino acid sequences for the human antibodies are set forth in Table 6.

Thus, in one embodiment, the disclosure includes human anti-LY6H antibodies, or antigen binding portions thereof, comprising a heavy chain variable region comprising an amino acid sequence selected from the group consisting of SEQ ID NOs: 1, 9, 17, 22, 27, 35, 39, 45, 53, 54, 58, 60, 64, 66, 68, and 70; and a light chain variable region comprising an amino acid sequence selected from the group consisting of SEQ ID NOs: 5, 13, 20, 26, 31, 37, 41, 49, and 56.

In one embodiment, the disclosure includes a human anti-LY6H antibody, or antigen binding portion thereof, comprising a Heavy Chain CDR set (CDR1, CDR2, and CDR3) selected from the group consisting of SEQ ID NOs: 2, 3, and 4; SEQ ID NOs: 10, 11, and 12; SEQ ID NOs: 18, 11, and 19; SEQ ID NOs: 23, 24, and 25; SEQ ID NOs: 28, 29, and 30; SEQ ID NOs: 28, 29, and 36; SEQ ID NOs: 28, 29, and 40; SEQ ID NOs: 46, 47, and 48; SEQ ID NOs: 46, 29, and 48; SEQ ID NOs: 28, 29 and 55; SEQ ID NOs: 28, 29, and 59; SEQ ID NOs: 61, 62, and 63; SEQ ID NOs: 23, 65, and 25; SEQ ID NOs: 23, 67, and 25; SEQ ID NOs: 2, 69, and 4; and SEQ ID NOs: 61, 71, and 63; and a Light Chain CDR set (CDR1, CDR2, and CDR3) selected from the group consisting of SEQ ID NOs: 6, 7, and 8; SEQ ID NOs: 14, 15, and 16; SEQ ID NOs: 14, 15, and 21; SEQ ID NOs: 32, 33, and 34; SEQ ID NOs: 32, 33, and 38; SEQ ID NOs: 42, 43, and 44; SEQ ID NOs: 50, 51, and 52; and SEQ ID NOs: 50, 51, and 57.

In one embodiment, an anti-LY6H antibody, or antigen binding portion thereof, is the human antibody 6D11. The 6D11 antibody comprises a heavy chain variable region comprising a CDR3 domain comprising the amino acid sequence of SEQ ID NO: 4, a CDR2 domain comprising the amino acid sequence of SEQ ID NO: 3, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 1 and a light chain variable region comprising the amino acid sequence of SEQ ID NO: 5.

In some embodiments, an anti-LY6H antibody, or antigen-binding portion thereof, comprises a heavy chain comprising an amino acid sequence set forth in SEQ ID NO: 1, or a sequence having at least 90%, 95%, 96%, 97%, 98%, or 99% identity to SEQ ID NO: 1, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, the disclosure features an anti-LY6H antibody, or antigen binding portion thereof, which is the human antibody 11D9. The 11D9 antibody comprises a heavy chain variable region comprising a CDR3 domain comprising the amino acid sequence of SEQ ID NO: 12, a CDR2 domain comprising the amino acid sequence of SEQ ID NO: 11, and a CDR1 domain comprising the amino acid sequence of SEQ ID NO: 10, and a light chain variable region comprising a CDR3 domain comprising the amino acid sequence of SEQ ID NO: 16, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 9 and a light chain variable region comprising the amino acid sequence of SEQ ID NO: 13.

In some embodiments, an anti-LY6H antibody, or antigen-binding portion thereof, comprises a heavy chain comprising an amino acid sequence set forth in SEQ ID NO: 9, or a sequence having at least 90%, 95%, 96%, 97%, 98%, or 99% identity to SEQ ID NO: 9, and/or a light chain comprising an amino acid sequence set forth in SEQ ID NO: 13, or a sequence having at least 90%, 95%, 96%, 97%, 98%, or 99% identity to SEQ ID NO: 13.

In one embodiment, the disclosure features an anti-LY6H antibody, or antigen binding portion thereof, which is the human antibody 23F3. The 23F3 antibody comprises a heavy chain variable region comprising a CDR3 domain comprising the amino acid sequence of SEQ ID NO: 19, a CDR2 domain comprising the amino acid sequence of SEQ ID NO: 11, and a CDR1 domain comprising the amino acid sequence of SEQ ID NO: 18, and a light chain variable region comprising a CDR3 domain comprising the amino acid sequence of SEQ ID NO: 21, a CDR2 domain comprising the amino acid sequence of SEQ ID NO: 15, and a CDR1 domain comprising the amino acid sequence of SEQ ID NO: 14. In further embodiments, the disclosure provides an antibody having a heavy chain variable region comprising the amino acid sequence of SEQ ID NO: 17 and a light chain variable region comprising the amino acid sequence of SEQ ID NO: 20.

In some embodiments, an anti-LY6H antibody, or antigen-binding portion thereof, comprises a heavy chain comprising an amino acid sequence set forth in SEQ ID NO: 17, or a sequence having at least 90%, 95%, 96%, 97%, 98%, or 99% identity to SEQ ID NO: 17, and/or a light chain comprising an amino acid sequence set forth in SEQ ID NO: 20, or a sequence having at least 90%, 95%, 96%, 97%, 98%, or 99% identity to SEQ ID NO: 20.

In one embodiment, the disclosure features an anti-LY6H antibody, or antigen binding portion thereof, which is the human antibody 12G7. The 12G7 antibody comprises a heavy chain variable region comprising a CDR3 domain comprising the amino acid sequence of SEQ ID NO: 25, a CDR2 domain comprising the amino acid sequence of SEQ ID NO: 24, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, the disclosure provides an antibody having a heavy chain variable region comprising the amino acid sequence of SEQ ID NO: 22 and a light chain variable region comprising the amino acid sequence of SEQ ID NO: 26.

In some embodiments, an anti-LY6H antibody, or antigen-binding portion thereof, comprises a heavy chain comprising an amino acid sequence set forth in SEQ ID NO: 22, or a sequence having at least 90%, 95%, 96%, 97%, 98%, or 99% identity to SEQ ID NO: 22, and/or a light chain comprising an amino acid sequence set forth in SEQ ID NO: 26, or a sequence having at least 90%, 95%, 96%, 97%, 98%, or 99% identity to SEQ ID NO: 26.

In one embodiment, an anti-LY6H antibody, or antigen binding portion thereof, is the human antibody 22A5. The 22A5 antibody comprises a heavy chain variable region comprising a CDR3 domain comprising the amino acid sequence of SEQ ID NO: 30, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 34, a CDR2 domain comprising the amino acid sequence of SEQ ID NO: 33, and a CDR1 domain comprising the amino acid sequence of SEQ ID NO: 32. In further embodiments, disclosed herein is an antibody having a heavy chain variable region comprising the amino acid sequence of SEQ ID NO: 27 and a light chain variable region comprising the amino acid sequence of SEQ ID NO: 31.

In some embodiments, an anti-LY6H antibody, or antigen-binding portion thereof, comprises a heavy chain comprising an amino acid sequence set forth in SEQ ID NO: 27, or a sequence having at least 90%, 95%, 96%, 97%, 98%, or 99% identity to SEQ ID NO: 27, and/or a light chain comprising an amino acid sequence set forth in SEQ ID NO: 31, or a sequence having at least 90%, 95%, 96%, 97%, 98%, or 99% identity to SEQ ID NO: 31.

In one embodiment, an anti-LY6H antibody, or antigen binding portion thereof, is the human antibody 26F3. The 26F3 antibody comprises a heavy chain variable region comprising a CDR3 domain comprising the amino acid sequence of SEQ ID NO: 36, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 38, a CDR2 domain comprising the amino acid sequence of SEQ ID NO: 33, and a CDR1 domain comprising the amino acid sequence of SEQ ID NO: 32. In further embodiments, disclosed herein is an antibody having a heavy chain variable region comprising the amino acid sequence of SEQ ID NO: 35 and a light chain variable region comprising the amino acid sequence of SEQ ID NO: 37.

In some embodiments, an anti-LY6H antibody, or antigen-binding portion thereof, comprises a heavy chain comprising an amino acid sequence set forth in SEQ ID NO: 35, or a sequence having at least 90%, 95%, 96%, 97%, 98%, or 99% identity to SEQ ID NO: 35, and/or a light chain comprising an amino acid sequence set forth in SEQ ID NO: 37, or a sequence having at least 90%, 95%, 96%, 97%, 98%, or 99% identity to SEQ ID NO: 37.

In one embodiment, an anti-LY6H antibody, or antigen binding portion thereof, is the human antibody 35H10. The 35H10 antibody comprises a heavy chain variable region comprising a CDR3 domain comprising the amino acid sequence of SEQ ID NO: 40, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 44, a CDR2 domain comprising the amino acid sequence of SEQ ID NO: 43, and a CDR1 domain comprising the amino acid sequence of SEQ ID NO: 42. In further embodiments, disclosed herein is an antibody having a heavy chain variable region comprising the amino acid sequence of SEQ ID NO: 39 and a light chain variable region comprising the amino acid sequence of SEQ ID NO: 41.

In some embodiments, an anti-LY6H antibody, or antigen-binding portion thereof, comprises a heavy chain comprising an amino acid sequence set forth in SEQ ID NO: 39, or a sequence having at least 90%, 95%, 96%, 97%, 98%, or 99% identity to SEQ ID NO: 39, and/or a light chain comprising an amino acid sequence set forth in SEQ ID NO: 41, or a sequence having at least 90%, 95%, 96%, 97%, 98%, or 99% identity to SEQ ID NO: 41.

In one embodiment, an anti-LY6H antibody, or antigen binding portion thereof, is the human antibody 1F8. The 1F81 antibody comprises a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50. In further embodiments, disclosed herein is an antibody having a heavy chain variable region comprising the amino acid sequence of SEQ ID NO: 45 and a light chain variable region comprising the amino acid sequence of SEQ ID NO: 49.

In some embodiments, an anti-LY6H antibody, or antigen-binding portion thereof, comprises a heavy chain comprising an amino acid sequence set forth in SEQ ID NO: 45, or a sequence having at least 90%, 95%, 96%, 97%, 98%, or 99% identity to SEQ ID NO: 45, and/or a light chain comprising an amino acid sequence set forth in SEQ ID NO: 49, or a sequence having at least 90%, 95%, 96%, 97%, 98%, or 99% identity to SEQ ID NO: 49.

In one embodiment, an anti-LY6H antibody, or antigen binding portion thereof, is the human antibody 2B11. The 2B11 antibody comprises a heavy chain variable region comprising a CDR3 domain comprising the amino acid sequence of SEQ ID NO: 48, a CDR2 domain comprising the amino acid sequence of SEQ ID NO: 29, and a CDR1 domain comprising the amino acid sequence of SEQ ID NO: 46, and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50. In further embodiments, disclosed herein is an antibody having a heavy chain variable region comprising the amino acid sequence of SEQ ID NO: 53 and a light chain variable region comprising the amino acid sequence of SEQ ID NO: 49.

In some embodiments, an anti-LY6H antibody, or antigen-binding portion thereof, comprises a heavy chain comprising an amino acid sequence set forth in SEQ ID NO: 53, or a sequence having at least 90%, 95%, 96%, 97%, 98%, or 99% identity to SEQ ID NO: 53, and/or a light chain comprising an amino acid sequence set forth in SEQ ID NO: 49, or a sequence having at least 90%, 95%, 96%, 97%, 98%, or 99% identity to SEQ ID NO: 49.

In one embodiment, an anti-LY6H antibody, or antigen binding portion thereof, is the human antibody 24A10. The 24A10 antibody comprises a heavy chain variable region comprising a CDR3 domain comprising the amino acid sequence of SEQ ID NO: 55, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50. In further embodiments, disclosed herein is an antibody having a heavy chain variable region comprising the amino acid sequence of SEQ ID NO: 54 and a light chain variable region comprising the amino acid sequence of SEQ ID NO: 56.

In some embodiments, an anti-LY6H antibody, or antigen-binding portion thereof, comprises a heavy chain comprising an amino acid sequence set forth in SEQ ID NO: 54, or a sequence having at least 90%, 95%, 96%, 97%, 98%, or 99% identity to SEQ ID NO: 54, and/or a light chain comprising an amino acid sequence set forth in SEQ ID NO: 56, or a sequence having at least 90%, 95%, 96%, 97%, 98%, or 99% identity to SEQ ID NO: 56.

In one embodiment, an anti-LY6H antibody, or antigen binding portion thereof, is the human antibody 34H6. The 34H6 antibody comprises a heavy chain variable region comprising a CDR3 domain comprising the amino acid sequence of SEQ ID NO: 59, a CDR2 domain comprising the amino acid sequence of SEQ ID NO: 29, and a CDR1 domain comprising the amino acid sequence of SEQ ID NO: 28, and a light chain variable region comprising a CDR3 domain comprising the amino acid sequence of SEQ ID NO: 57, a CDR2 domain comprising the amino acid sequence of SEQ ID NO: 51, and a CDR1 domain comprising the amino acid sequence of SEQ ID NO: 50. In further embodiments, disclosed herein is an antibody having a heavy chain variable region comprising the amino acid sequence of SEQ ID NO: 58 and a light chain variable region comprising the amino acid sequence of SEQ ID NO: 56.

In some embodiments, an anti-LY6H antibody, or antigen-binding portion thereof, comprises a heavy chain comprising an amino acid sequence set forth in SEQ ID NO: 58, or a sequence having at least 90%, 95%, 96%, 97%, 98%, or 99% identity to SEQ ID NO: 58, and/or a light chain comprising an amino acid sequence set forth in SEQ ID NO: 56, or a sequence having at least 90%, 95%, 96%, 97%, 98%, or 99% identity to SEQ ID NO: 56.

In one embodiment, an anti-LY6H antibody, or antigen binding portion thereof, is the human antibody 10B10. The 10B10 antibody comprises a heavy chain variable region comprising a CDR3 domain comprising the amino acid sequence of SEQ ID NO: 63, a CDR2 domain comprising the amino acid sequence of SEQ ID NO: 62, and a CDR1 domain comprising the amino acid sequence of SEQ ID NO: 61, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 60 and a light chain variable region comprising the amino acid sequence of SEQ ID NO: 26.

In some embodiments, an anti-LY6H antibody, or antigen-binding portion thereof, comprises a heavy chain comprising an amino acid sequence set forth in SEQ ID NO: 60, or a sequence having at least 90%, 95%, 96%, 97%, 98%, or 99% identity to SEQ ID NO: 60, and/or a light chain comprising an amino acid sequence set forth in SEQ ID NO: 26, or a sequence having at least 90%, 95%, 96%, 97%, 98%, or 99% identity to SEQ ID NO: 26.

In one embodiment, an anti-LY6H antibody, or antigen binding portion thereof, is the human antibody 12G7_S54A. The 12G7_S54A antibody comprises a heavy chain variable region comprising a CDR3 domain comprising the amino acid sequence of SEQ ID NO: 25, a CDR2 domain comprising the amino acid sequence of SEQ ID NO: 65, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 64 and a light chain variable region comprising the amino acid sequence of SEQ ID NO: 26.

In some embodiments, an anti-LY6H antibody, or antigen-binding portion thereof, comprises a heavy chain comprising an amino acid sequence set forth in SEQ ID NO: 64, or a sequence having at least 90%, 95%, 96%, 97%, 98%, or 99% identity to SEQ ID NO: 64, and/or a light chain comprising an amino acid sequence set forth in SEQ ID NO: 26, or a sequence having at least 90%, 95%, 96%, 97%, 98%, or 99% identity to SEQ ID NO: 26.

In one embodiment, an anti-LY6H antibody, or antigen binding portion thereof, is the human antibody 12G7_N52Q. The 12G7_N52Q antibody comprises a heavy chain variable region comprising a CDR3 domain comprising the amino acid sequence of SEQ ID NO: 25, a CDR2 domain comprising the amino acid sequence of SEQ ID NO: 67, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 66 and a light chain variable region comprising the amino acid sequence of SEQ ID NO: 26.

In some embodiments, an anti-LY6H antibody, or antigen-binding portion thereof, comprises a heavy chain comprising an amino acid sequence set forth in SEQ ID NO: 66, or a sequence having at least 90%, 95%, 96%, 97%, 98%, or 99% identity to SEQ ID NO: 66, and/or a light chain comprising an amino acid sequence set forth in SEQ ID NO: 26, or a sequence having at least 90%, 95%, 96%, 97%, 98%, or 99% identity to SEQ ID NO: 26.

In one embodiment, an anti-LY6H antibody, or antigen binding portion thereof, is the human antibody 6D11_41B4. The 6D11_41B4 antibody comprises a heavy chain variable region comprising a CDR3 domain comprising the amino acid sequence of SEQ ID NO: 4, a CDR2 domain comprising the amino acid sequence of SEQ ID NO: 69, and a CDR1 domain comprising the amino acid sequence of SEQ ID NO: 2, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 68 and a light chain variable region comprising the amino acid sequence of SEQ ID NO: 5.

In some embodiments, an anti-LY6H antibody, or antigen-binding portion thereof, comprises a heavy chain comprising an amino acid sequence set forth in SEQ ID NO: 68, or a sequence having at least 90%, 95%, 96%, 97%, 98%, or 99% identity to SEQ ID NO: 68, and/or a light chain comprising an amino acid sequence set forth in SEQ ID NO: 5, or a sequence having at least 90%, 95%, 96%, 97%, 98%, or 99% identity to SEQ ID NO: 5.

In one embodiment, an anti-LY6H antibody, or antigen binding portion thereof, is the human antibody 10B10_S54A. The 10B10_S54A antibody comprises a heavy chain variable region comprising a CDR3 domain comprising the amino acid sequence of SEQ ID NO: 63, a CDR2 domain comprising the amino acid sequence of SEQ ID NO: 71, and a CDR1 domain comprising the amino acid sequence of SEQ ID NO: 61 and a light chain variable region comprising a CDR3 domain comprising the amino acid sequence of SEQ ID NO: 8, a CDR2 domain compris-ing the amino acid sequence of SEQ ID NO: 7, and a CDR1 domain comprising the amino acid sequence of SEQ ID NO: 6. In further embodiments, disclosed herein is an antibody having a heavy chain variable region comprising the amino acid sequence of SEQ ID NO: 70 and a light chain variable region comprising the amino acid sequence of SEQ ID NO: 26.

In some embodiments, an anti-LY6H antibody, or antigen-binding portion thereof, comprises a heavy chain comprising an amino acid sequence set forth in SEQ ID NO: 70, or a sequence having at least 90%, 95%, 96%, 97%, 98%, or 99% identity to SEQ ID NO: 70, and/or a light chain comprising an amino acid sequence set forth in SEQ ID NO: 26, or a sequence having at least 90%, 95%, 96%, 97%, 98%, or 99% identity to SEQ ID NO: 26.

In some embodiments, an anti-LY6H antibody, or antigen-binding portion thereof, comprises a heavy chain comprising an amino acid sequence described herein, or a sequence having at least 90%, 95%, 96%, 97%, 98%, or 99% identity to a sequence described herein, and/or a light chain comprising an amino acid sequence described herein, or a sequence having at least 90%, 95%, 96%, 97%, 98%, or 99% identity to a sequence described herein.

The foregoing anti-LY6H antibody CDR sequences establish a novel family of LY6H binding proteins, isolated in accordance with this disclosure, and comprising antigen binding polypeptides that include the CDR sequences listed in Table 6.

To generate and to select CDRs having preferred LY6H binding and/or neutralizing activity with respect to hLY6H, standard methods known in the art for generating antibodies, or antigen binding portions thereof, and assessing the LY6H binding and/or neutralizing characteristics of those antibodies, or antigen binding portions thereof, may be used, including but not limited to those specifically described herein.

In certain embodiments, the antibody comprises a heavy chain constant region, such as an IgG1, IgG2, IgG3, IgG4, IgA, IgE, IgM, or IgD constant region. In certain embodiments, the anti-LY6H antibody, or antigen binding portion thereof, comprises a heavy chain immunoglobulin constant domain selected from the group consisting of a human IgG constant domain, a human IgM constant domain, a human IgE constant domain, and a human IgA constant domain. In further embodiments, the antibody, or antigen binding portion thereof, has an IgG1 heavy chain constant region, an IgG2 heavy chain constant region, an IgG3 constant region, or an IgG4 heavy chain constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

In certain embodiments, the anti-LY6H antibody binding portion is a Fab, a Fab', a F(ab')2, a Fv, a disulfide linked Fv, an scFv, a single domain antibody, or a diabody.

In certain embodiments, the anti-LY6H antibody, or antigen binding portion thereof, is a multispecific antibody, e.g. a bispecific antibody.

In certain embodiments, the anti-LY6H antibody, or antigen binding portion thereof, comprises a heavy chain constant region comprising the amino acid sequence set forth in SEQ ID NO: 1 and/or a light chain constant region comprising the amino acid sequence set forth in SEQ ID NO: 5.

In certain embodiments, the anti-LY6H antibody, or antigen binding portion thereof, comprises a heavy chain constant region comprising the amino acid sequence set forth in SEQ ID NO: 9 and/or a light chain constant region comprising the amino acid sequence set forth in SEQ ID NO: 13.

In certain embodiments, the anti-LY6H antibody, or antigen binding portion thereof, comprises a heavy chain constant region comprising the amino acid sequence set forth in SEQ ID NO: 17 and/or a light chain constant region comprising the amino acid sequence set forth in SEQ ID NO: 20.

In certain embodiments, the anti-LY6H antibody, or antigen binding portion thereof, comprises a heavy chain constant region comprising the amino acid sequence set forth in SEQ ID NO: 22 and/or a light chain constant region comprising the amino acid sequence set forth in SEQ ID NO: 26.

In certain embodiments, the anti-LY6H antibody, or antigen binding portion thereof, comprises a heavy chain constant region comprising the amino acid sequence set forth in SEQ ID NO: 27 and/or a light chain constant region comprising the amino acid sequence set forth in SEQ ID NO: 31.

In certain embodiments, the anti-LY6H antibody, or antigen binding portion thereof, comprises a heavy chain constant region comprising the amino acid sequence set forth in SEQ ID NO: 35 and/or a light chain constant region comprising the amino acid sequence set forth in SEQ ID NO: 37.

In certain embodiments, the anti-LY6H antibody, or antigen binding portion thereof, comprises a heavy chain constant region comprising the amino acid sequence set forth in SEQ ID NO: 39 and/or a light chain constant region comprising the amino acid sequence set forth in SEQ ID NO: 41.

In certain embodiments, the anti-LY6H antibody, or antigen binding portion thereof, comprises a heavy chain constant region comprising the amino acid sequence set forth in SEQ ID NO: 45 and/or a light chain constant region comprising the amino acid sequence set forth in SEQ ID NO: 49.

In certain embodiments, the anti-LY6H antibody, or antigen binding portion thereof, comprises a heavy chain constant region comprising the amino acid sequence set forth in SEQ ID NO: 53 and/or a light chain constant region comprising the amino acid sequence set forth in SEQ ID NO: 49.

In certain embodiments, the anti-LY6H antibody, or antigen binding portion thereof, comprises a heavy chain constant region comprising the amino acid sequence set forth in SEQ ID NO: 54 and/or a light chain constant region comprising the amino acid sequence set forth in SEQ ID NO: 56.

In certain embodiments, the anti-LY6H antibody, or antigen binding portion thereof, comprises a heavy chain constant region comprising the amino acid sequence set forth in SEQ ID NO: 58 and/or a light chain constant region comprising the amino acid sequence set forth in SEQ ID NO: 56.

In certain embodiments, the anti-LY6H antibody, or antigen binding portion thereof, comprises a heavy chain constant region comprising the amino acid sequence set forth in SEQ ID NO: 60 and/or a light chain constant region comprising the amino acid sequence set forth in SEQ ID NO: 26.

In certain embodiments, the anti-LY6H antibody, or antigen binding portion thereof, comprises a heavy chain constant region comprising the amino acid sequence set forth in SEQ ID NO: 64 and/or a light chain constant region comprising the amino acid sequence set forth in SEQ ID NO: 26.

In certain embodiments, the anti-LY6H antibody, or antigen binding portion thereof, comprises a heavy chain constant region comprising the amino acid sequence set forth in SEQ ID NO: 66 and/or a light chain constant region comprising the amino acid sequence set forth in SEQ ID NO: 26.

In certain embodiments, the anti-LY6H antibody, or antigen binding portion thereof, comprises a heavy chain constant region comprising the amino acid sequence set forth in SEQ ID NO: 68 and/or a light chain constant region comprising the amino acid sequence set forth in SEQ ID NO: 5.

In certain embodiments, the anti-LY6H antibody, or antigen binding portion thereof, comprises a heavy chain constant region comprising the amino acid sequence set forth in SEQ ID NO: 70 and/or a light chain constant region comprising the amino acid sequence set forth in SEQ ID NO: 26.

Replacements of amino acid residues in the Fc portion to alter antibody effector function are have been described (Winter, et al. U.S. Pat. Nos. 5,648,260 and 5,624,821, incorporated by reference herein). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment includes a labeled anti-LY6H antibody, or antibody portion thereof, where the antibody is derivatized or linked to one or more functional molecule(s) (e.g., another peptide or protein). For example, a labeled antibody can be derived by functionally linking an antibody or antibody portion of the disclosure (by chemical coupling, genetic fusion, noncovalent association or otherwise) to one or more other molecular entities, such as another antibody (e.g., a bispecific antibody or a diabody), a detectable agent, a pharmaceutical agent, a protein or peptide that can mediate the association of the antibody or antibody portion with another molecule (such as a streptavidin core region or a polyhistidine tag), and/or a cytotoxic or therapeutic agent selected from the group consisting of a mitotic inhibitor, an antitumor antibiotic, an immunomodulating agent, a vector for gene therapy, an alkylating agent, an antiangiogenic agent, an antimetabolite, a boron-containing agent, a chemoprotective agent, a hormone, an antihormone agent, a corticosteroid, a photoactive therapeutic agent, an oligonucleotide, a radionuclide agent, a topoisomerase inhibitor, a tyrosine kinase inhibitor, a radiosensitizer, and a combination thereof.

Useful detectable agents with which an antibody or antibody portion thereof, may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present the addition of hydrogen peroxide and diaminobenzidine leads to a colored reaction product, which is detectable. An antibody may also be derivatized with biotin, and detected through indirect measurement of avidin or streptavidin binding.

In one embodiment, the antibody is conjugated to an imaging agent. Examples of imaging agents that may be used in the compositions and methods described herein include, but are not limited to, a radiolabel (e.g., indium), an enzyme, a fluorescent label, a luminescent label, a bioluminescent label, a magnetic label, and biotin.

In one embodiment, the antibodies or ADCs are linked to a radiolabel, such as, but not limited to, indium ($^{111}$In). $^{111}$Indium may be used to label the antibodies and ADCs described herein for use in identifying LY6H positive tumors. In a certain embodiment, anti-LY6H antibodies (or ADCs) described herein are labeled with $^{111}$I via a bifunctional chelator which is a bifunctional cyclohexyl diethylenetriaminepentaacetic acid (DTPA) chelate (see U.S. Pat. Nos. 5,124,471; 5,434,287; and 5,286,850, each of which is incorporated herein by reference).

Another embodiment of the disclosure provides a glycosylated binding protein wherein the anti-LY6H antibody or antigen binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick, S. C., et al., *Exp. Med.* (1988) 168:1099-1109; Wright, A., et al., *EMBO J.* (1991) 10:2717-2723).

One aspect of the disclosure is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the disclosure.

In still another embodiment, the glycosylation of the anti-LY6H antibody or antigen binding portion is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication WO2003016466A2, and U.S. Pat. Nos. 5,714,350 and 6,350,861, each of which is incorporated herein by reference in its entirety.

Additionally or alternatively, a modified anti-LY6H antibody can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful may include, but are not limited to, glucose, galactose, mannose, fucose, n-acetylglucosamine and sialic acid. Preferably the glycosylated binding protein comprises glycosyl residues such that the glycosylation pattern is human.

Differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using recombinant techniques, a practitioner may generate antibodies or antigen binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (U.S. patent Publication Nos. 20040018590 and 20020137134 and PCT publication WO2005100584 A2).

Antibodies may be produced by any of a number of techniques. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express antibodies in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies disclosed herein include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the disclosure. For example, it may be desirable to transfect a host cell with DNA encoding functional fragments of either the light chain and/or the heavy chain of an antibody. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the disclosure. In addition, bifunctional antibodies may be produced in which one heavy and one light chain are an antibody of the disclosure and the other heavy and light chain are specific for an antigen other than the antigens of interest by cross-linking an antibody of the disclosure to a second antibody by standard chemical crosslinking methods.

In a preferred system for recombinant expression of an antibody, or antigen binding portion thereof of the invention, a recombinant expression vector encoding both the antibody heavy chain and the antibody light chain is introduced into CHO cell lines with deletions in the dihydrofolate reductase (DHFR) or glutamine synthesis (GS) genes are which are suitable for generating stable cell lines for expression of these antibodies.

In another system for recombinant expression of an antibody, or antigen binding portion thereof, a recombinant expression vector encoding both the antibody heavy chain and the antibody light chain is introduced into dhfr-CHO cells by calcium phosphate-mediated transfection.

Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the disclosure provides a method of synthesizing a recombinant antibody by culturing a host cell in a suitable culture medium until a recombinant antibody is synthesized. Recombinant antibodies may be produced using nucleic acid molecules corresponding to the amino acid sequences disclosed herein. In one embodiment, the nucleic acid molecules set forth in SEQ ID NOs: 97-122 are used in the production of a recombinant antibody. The method can further comprise isolating the recombinant antibody from the culture medium.

III. Anti-LY6H Antibody Drug Conjugates (ADCs)

Anti-LY6H antibodies described herein may be conjugated to a drug moiety to form an anti-LY6H Antibody Drug Conjugate (ADC). Antibody-drug conjugates (ADCs) may increase the therapeutic efficacy of antibodies in treating disease, e.g., cancer, due to the ability of the ADC to selectively deliver one or more drug moiety(s) to target tissues or cells, e.g., LY6H expressing tumors or LY6H expressing cells, such as, LY6H expressing cancer cells. Thus, in certain embodiments, the disclosure provides anti-LY6H ADCs for therapeutic use, e.g., treatment of cancer.

Anti-LY6H ADCs comprise an anti-LY6H antibody, i.e., an antibody that specifically binds to LY6H, linked to one or more drug moieties. The specificity of the ADC is defined by the specificity of the antibody, i.e., anti-LY6H. In one embodiment, an anti-LY6H antibody is linked to one or more cytotoxic drug(s) which is delivered internally to a cancer cell expressing LY6H.

Examples of drugs that may be used in the anti-LY6H ADCs are provided below, as are linkers that may be used to conjugate the antibody and the one or more drug(s). The terms "drug," "agent," and "drug moiety" are used interchangeably herein. The terms "linked" and "conjugated" are also used interchangeably herein and indicate that the antibody and moiety are covalently linked.

In some embodiments, the ADC has the following formula (formula I):

wherein Ab an anti-LY6H antibody described herein, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing LY6H; and n is an integer from 1 to 20. In some embodiments, n ranges from 1 to 8, 1 to 7, 1 to 6, 1 to 5, 1 to 4, 1 to 3, 1 to 2, or is 1. The DAR of an ADC is equivalent to the "n" referred to in Formula I.

Additional details regarding drugs (D of Formula I) and linkers (L of Formula I) that may be used in the ADCs, as well as alternative ADC structures, are described below.

A. Anti-LY6H ADCs: Exemplary Drugs for Conjugation

Anti-LY6H antibodies may be used in ADCs to target one or more drug(s) to a cell of interest, e.g., a cell expressing LY6H. The anti-LY6H ADCs disclosed herein provide a targeted therapy that may, for example, reduce the side effects often seen with anti-cancer therapies, as the one or more drug(s) is delivered to a specific cell. In one embodiment, the drug used in an ADC is saporin. In another embodiment, the drug used in an ADC is dacarbazine. In another embodiment, the drug used in an ADC is carboplatin.

Examples of drugs that may be used in ADCs, i.e., drugs that may be conjugated to the anti-LY6H antibodies, are provided below, and include mitotic inhibitors, antitumor antibiotics, immunomodulating agents, gene therapy vectors, alkylating agents, antiangiogenic agents, antimetabolites, boron-containing agents, chemoprotective agents, hormone agents, glucocorticoids, photoactive therapeutic agents, oligonucleotides, radioactive isotopes, radiosensitizers, topoisomerase inhibitors, tyrosine kinase inhibitors, and combinations thereof.

1. Mitotic Inhibitors

In one aspect, anti-LY6H antibodies may be conjugated to one or more mitotic inhibitor(s) to form an ADC for the treatment of cancer. The term "mitotic inhibitor", as used herein, refers to a cytotoxic and/or therapeutic agent that blocks mitosis or cell division, a biological process particularly important to cancer cells. A mitotic inhibitor disrupts microtubules such that cell division is prevented, often by effecting microtubule polymerization (e.g., inhibiting microtubule polymerization) or microtubule depolymerization (e.g., stabilizing the microtubule cytoskeleton against depolymerization). Thus, in one embodiment, an anti-LY6H antibody of the invention is conjugated to one or more mitotic inhibitor(s) that disrupts microtubule formation by inhibiting tubulin polymerization. In another embodiment, an anti-LY6H antibody of the invention is conjugated to one or more mitotic inhibitor(s) that stabilizes the microtubule cytoskeleton from deploymerization. In one embodiment, the mitotic inhibitor used in the ADCs of the invention is Ixempra (ixabepilone). Examples of mitotic inhibitors that may be used in the anti-LY6H ADCs of the invention are provided below. Included in the genus of mitotic inhibitors are auristatins, described below.

a. Dolastatins

The anti-LY6H antibodies of the invention may be conjugated to at least one dolastatin to form an ADC. Dolastatins are short peptidic compounds isolated from the Indian Ocean sea hare *Dolabella auricularia* (see Pettit et al., *J. Am. Chem. Soc.,* 1976, 98, 4677). Examples of dolastatins include dolastatin 10 and dolatstin 15. Dolastatin 15, a seven-subunit depsipeptide derived from *Dolabella auricularia*, and is a potent antimitotic agent structurally related to the antitubulin agent dolastatin 10, a five-subunit peptide obtained from the same organism. Thus, in one embodiment, the anti-LY6H ADC of the invention comprises an anti-LY6H antibody, as described herein, and at least one dolastatin. Auristatins are synthetic derivatives of dolastatin 10.

b. Auristatins

Anti-LY6H antibodies may be conjugated to at least one auristatin. Auristatins represent a group of dolastatin analogs that have generally been shown to possess anticancer activity by interfering with microtubule dynamics and GTP hydrolysis, thereby inhibiting cellular division. For example, Auristatin E (U.S. Pat. No. 5,635,483) is a synthetic analogue of the marine natural product dolastatin 10, a compound that inhibits tubulin polymerization by binding to the same site on tubulin as the anticancer drug vincristine (G. R. Pettit, Prog. Chem. Org. Nat. Prod, 70: 1-79 (1997)). Dolastatin 10, auristatin PE, and auristatin E are linear peptides having four amino acids, three of which are unique to the dolastatin class of compounds. Exemplary embodiments of the auristatin subclass of mitotic inhibitors include, but are not limited to, monomethyl auristatin D (MMAD or auristatin D derivative), monomethyl auristatin E (MMAE or auristatin E derivative), monomethyl auristatin F (MMAF or auristatin F derivative), auristatin F phenylenediamine (AFP), auristatin EB (AEB), auristatin EFP (AEFP), and 5-benzoylvaleric acid-AE ester (AEVB). The synthesis and structure of auristatin derivatives are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239, 104; 6,034,065; 5,780,588; 5,665,860; 5,663,149; 5,635, 483; 5,599,902; 5,554,725; 5,530,097; 5,521,284; 5,504, 191; 5,410,024; 5,138,036; 5,076,973; 4,986,988; 4,978, 744; 4,879,278; 4,816,444; and 4,486,414, each of which is incorporated by reference herein.

In one embodiment, anti-LY6H antibodies are conjugated to at least one MMAE (mono-methyl auristatin E). Monomethyl auristatin E (MMAE, vedotin) inhibits cell division by blocking the polymerization of tubulin. Because of its super toxicity, it also cannot be used as a drug itself. In recent cancer therapy developments, it is linked to a monoclonal antibody (mAb) that recognizes a specific marker expression in cancer cells and directs MMAE to the cancer cells. In one embodiment, the linker linking MMAE to the anti-LY6H antibody is stable in extracellular fluid (i.e., the medium or environment that is external to cells), but is cleaved by cathepsin once the ADC has bound to the specific cancer cell antigen and entered the cancer cell, thus releasing the toxic MMAE and activating the potent anti-mitotic mechanism.

The structure of MMAE is provided below.

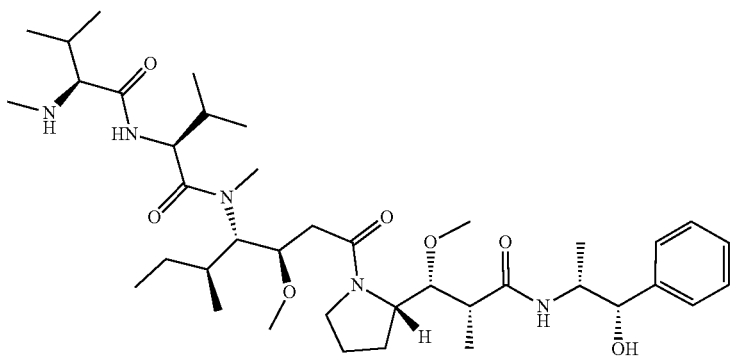

Monomethyl Auristatin E (MMAE)

In one embodiment, the antibody is coupled to a single drug and, therefore, has a DAR of 1. In certain embodiments, the ADC will have a DAR of 2 to 8, 2 to 6, or 2 to 4.

c. Maytansinoids

The anti-LY6H antibodies of the invention may be conjugated to at least one maytansinoid to form an ADC. Maytansinoids are potent antitumor agents that were originally isolated from members of the higher plant families Celastraceae, Rhamnaceae, and Euphorbiaceae, as well as some species of mosses (Kupchan et al, J. Am. Chem. Soc. 94:1354-1356 [1972]; Wani et al, J. Chem. Soc. Chem. Commun. 390: [1973]; Powell et al, J. Nat. Prod. 46:660-666 [1983]; Sakai et al, J. Nat. Prod. 51:845-850 [1988]; and Suwanborirux et al, Experientia 46:117-120 [1990]). Evidence suggests that maytansinoids inhibit mitosis by inhibiting polymerization of the microtubule protein tubulin, thereby preventing formation of microtubules (see, e.g., U.S. Pat. No. 6,441,163 and Remillard et al., Science, 189, 1002-1005 (1975)). Maytansinoids have been shown to inhibit tumor cell growth in vitro using cell culture models, and in vivo using laboratory animal systems. Moreover, the cytotoxicity of maytansinoids is 1,000-fold greater than conventional chemotherapeutic agents, such as, for example, methotrexate, daunorubicin, and vincristine (see, e.g., U.S. Pat. No. 5,208,020).

Maytansinoids to include maytansine, maytansinol, C-3 esters of maytansinol, and other maytansinol analogues and derivatives (see, e.g., U.S. Pat. Nos. 5,208,020 and 6,441,163, each of which is incorporated by reference herein). C-3 esters of maytansinol can be naturally occurring or synthetically derived. Moreover, both naturally occurring and synthetic C-3 maytansinol esters can be classified as a C-3 ester with simple carboxylic acids, or a C-3 ester with derivatives of N-methyl-L-alanine, the latter being more cytotoxic than the former. Synthetic maytansinoid analogues are described in, for example, Kupchan et al., J. Med. Chem., 21, 31-37 (1978).

Suitable maytansinoids for use in ADCs of the invention can be isolated from natural sources, synthetically produced, or semi-synthetically produced. Moreover, the maytansinoid can be modified in any suitable manner, so long as sufficient cytotoxicity is preserved in the ultimate conjugate molecule. In this regard, maytansinoids lack suitable functional groups to which antibodies can be linked. A linking moiety desirably is utilized to link the maytansinoid to the antibody to form the conjugate, and is described in more detail in the linker section below. The structure of an exemplary maytansinoid, mertansine (DM1), is provided below.

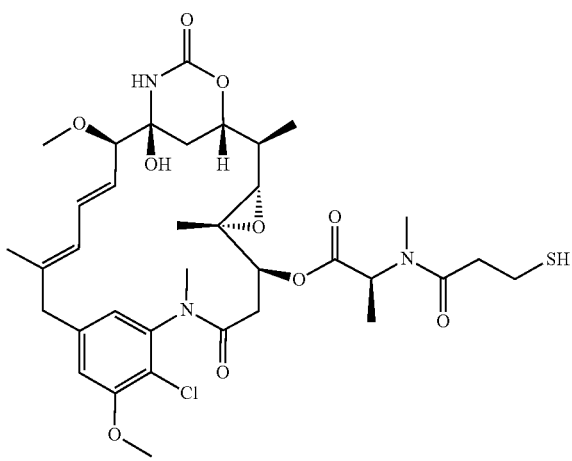

Mertansine (DM1)

Representative examples of maytansinoids include, but are not limited, to DM1 ($N^{2'}$-deacetyl-$N^{2'}$-(3-mercapto-1-oxopropyl)-maytansine; also referred to as mertansine, drug maytansinoid 1; ImmunoGen, Inc.; see also Chari et al. (1992) Cancer Res 52:127), DM2, DM3 ($N^{2'}$-deacetyl-$N^{2'}$-(4-mercapto-1-oxopentyl)-maytansine), DM4 (4-methyl-4-mercapto-1-oxopentyl)-maytansine), and maytansinol (a synthetic maytansinoid analog). Other examples of maytansinoids are described in U.S. Pat. No. 8,142,784, incorporated by reference herein.

Ansamitocins are a group of maytansinoid antibiotics that have been isolated from various bacterial sources. These compounds have potent antitumor activities. Representative examples include, but are not limited to ansamitocin P1, ansamitocin P2, ansamitocin P3, and ansamitocin P4.

In one embodiment of the invention, an anti-LY6H antibody is conjugated to at least one DM1. In one embodiment, an anti-LY6H antibody is conjugated to at least one DM2. In one embodiment, an anti-LY6H antibody is conjugated to at least one DM3. In one embodiment, an anti-LY6H antibody is conjugated to at least one DM4.

2. Antitumor Antibiotics

Anti-LY6H antibodies may be conjugated to one or more antitumor antibiotic(s) for the treatment of cancer. As used herein, the term "antitumor antibiotic" means an antineoplastic drug that blocks cell growth by interfering with DNA and is made from a microorganism. Often, antitumor antibiotics either break up DNA strands or slow down or stop DNA synthesis. Examples of antitumor antibiotics that may be included in the anti-LY6H ADCs include, but are not limited to, actinomycines (e.g., pyrrolo[2,1-c][1,4]benzodiazepines), anthracyclines, calicheamicins, and duocarmycins. In addition to the foregoing, additional antitumor antibiotics that may be used in the anti-LY6H ADCs include bleomycin (Blenoxane, Bristol-Myers Squibb), mitomycin, and plicamycin (also known as mithramycin).

3. Immunomodulating Agents

In one aspect, anti-LY6H antibodies may be conjugated to at least one immunomodulating agent. As used herein, the term "immunomodulating agent" refers to an agent that can stimulate or modify an immune response. In one embodiment, an immunomodulating agent is an immunostimuator which enhances a subject's immune response. In another embodiment, an immunomodulating agent is an immunosuppressant which prevents or decreases a subject's immune response. An immunomodulating agent may modulate myeloid cells (monocytes, macrophages, dendritic cells, megakaryocytes and granulocytes) or lymphoid cells (T cells, B cells and natural killer (NK) cells) and any further differentiated cell thereof. Representative examples include, but are not limited to, Bacillus calmette-guerin (BCG) and levamisole (Ergamisol). Other examples of immunomodulating agents that may be used in the ADCs include, but are not limited to, cancer vaccines, and cytokines.

As used herein, the term "cancer vaccine" refers to a composition (e.g., a tumor antigen and a cytokine) that elicits a tumor-specific immune response. The response is elicited from the subject's own immune system by administering the cancer vaccine, or, in the case of the instant disclosure, administering an ADC comprising an anti-LY6H antibody and a cancer vaccine. In preferred embodiments, the immune response results in the eradication of tumor cells in the body (e.g., primary or metastatic tumor cells). The use of cancer vaccines generally involves the administration of a particular antigen or group of antigens that are, for example, present on the surface a particular cancer cell, or present on the surface of a particular infectious agent shown to facilitate cancer formation. In some embodiments, the use of cancer vaccines is for prophylactic purposes, while in other embodiments, the use is for therapeutic purposes. Non-limiting examples of cancer vaccines that may be used in the anti-LY6H ADCs include, recombinant bivalent human papillomavirus (HPV) vaccine types 16 and 18 vaccine (Cervarix, GlaxoSmithKline), recombinant quadrivalent human papillomavirus (HPV) types 6, 11, 16, and 18 vaccine (Gardasil, Merck & Company), and sipuleucel-T (Provenge, Dendreon). Thus, in one embodiment, the anti-LY6H antibody is conjugated to at least one cancer vaccine that is either an immunostimulator or is an immunosuppressant.

The anti-LY6H antibodies may be conjugated to at least one cytokine. The term "cytokine" generally refers to proteins released by one cell population which act on another cell as intercellular mediators. Cytokines directly stimulate immune effector cells and stromal cells at the tumor site and enhance tumor cell recognition by cytotoxic effector cells (Lee and Margolin (2011) *Cancers* 3:3856). Numerous animal tumor model studies have demonstrated that cytokines have broad anti-tumor activity and this has been translated into a number of cytokine-based approaches for cancer therapy (Lee and Margoli, supra). Recent years have seen a number of cytokines, including GM-CSF, IL-7, IL-12, IL-15, IL-18 and IL-21, enter clinical trials for patients with advanced cancer (Lee and Margoli, supra).

Examples of cytokines that may be used in the ADCs include, but are not limited to, parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor; mullerian-inhibiting substance; mouse gonadotropin-associated peptide; inhibin; activin; vascular endothelial growth factor; integrin; thrombopoietin (TPO); nerve growth factors such as NGF; platelet-growth factor; transforming growth factors (TGFs); insulin-like growth factor-I and -II; erythropoietin (EPO); osteoinductive factors; interferons such as interferon α, β, and γ, colony stimulating factors (CSFs); granulocyte-macrophage-C-SF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-11, IL-12; tumor necrosis factor; and other polypeptide factors including LIF and kit ligand (KL). As used herein, the term cytokine includes proteins from natural sources or from recombinant cell culture and biologically active equivalents of the native sequence cytokines. Thus, in one embodiment, the disclosure provides an ADC comprising an anti-LY6H antibody described herein and a cytokine.

The anti-LY6H antibodies may be conjugated to at least one colony stimulating factor (CSF). Colony stimulating factors (CSFs) are growth factors that assist the bone marrow in making red blood cells. Because some cancer treatments (e.g., chemotherapy) can affect white blood cells (which help fight infection), colony-stimulating factors may be introduced to help support white blood cell levels and strengthen the immune system. Colony-stimulating factors may also be used following a bone marrow transplant to help the new marrow start producing white blood cells. Representative examples of CSFs that may be used in the anti-LY6H ADCs include, but are not limited to erythropoietin (Epoetin), filgrastim (Neopogen (also known as granulocyte colony-stimulating factor (G-CSF); Amgen, Inc.), sargramostim (leukine (granulocyte-macrophage colony-stimulating factor and GM-CSF); Genzyme Corporation), promegapoietin, and Oprelvekin (recombinant IL-11; Pfizer, Inc.). Thus, in one embodiment, an ADC may comprise an anti-LY6H antibody described herein and a CSF.

4. Alkylating Agents

The anti-LY6H antibodies may be conjugated to one or more alkylating agent(s). Alkylating agents are a class of antineoplastic compounds that attaches an alkyl group to DNA. Examples of alkylating agents that may be used in the ADCs include, but are not limited to, alkyl sulfonates, ethylenimimes, methylamine derivatives, epoxides, nitrogen mustards, nitrosoureas, triazines and hydrazines.

5. DNA Damaging Agents

In one embodiment, the antibodies and antigen-binding portions thereof described herein may be conjugated to one or more DNA damaging agents. The term "DNA damaging agents", as used herein, refers to any chemical compound or treatment method that induces DNA damage. Examples of DNA damaging agents that may be used in the ADCs include, but are not limited to, actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorethamine, mitomycin, mitoxantrone, nemorubicin (MMDX), nitrosourea, plicamycin, procarbazine, PNU-159682 (3'-deamino-3",4'-anhydro-[2"(S)-methoxy-3"(R)-hydroxy-4"-morpholinyl] doxorubicin), taxol, taxotere, teniposide, triethylenethiophosphoramide and etoposide (VP16).

In one embodiment, anti-LY6H antibodies are conjugated to PNU-159682. PNU-159682 is a bioactivation product of nemorubicin (MMDX), and has a potency in vitro that is more than 1000 times that of the nemorubicin drug and shows high antitumor activity in vivo (Sabatino, M. A., et al. *Mol Cancer.* 9: 259. 2010). In one embodiment, the anti-LY6H antibodies are conjugated to PNU-159682 via a linker. In one embodiment, the linker conjugating the anti-LY6H antibody to PNU-159682 is a cleavable linker. In yet another embodiment, the linker conjugating the anti-LY6H antibody to PNU-159682 is a non-cleavable linker. In one embodiment, the antibody is coupled to a single drug and, therefore, has a DAR of 1. In certain embodiments, the ADC will have a DAR of 2 to 8, 2 to 6, or 2 to 4.

DNA damaging agents include DNA alkylating agents. DNA alkylating agents are a class of antineoplastic compounds that attaches an alkyl group ($C_nH_{2n+1}$) to DNA at a guanine base of DNA. Examples of DNA alkylating agents that may be used in the ADCs include, but are not limited to, alkyl sulfonates (e.g., busulfan), ethylenimimes (e.g., altretamine and thiotepa), methylamine derivatives, epoxides, nitrogen mustards (e.g., bendamustine, chlorambucil, cyclophosphamide, ifosfamide, mechlorethamine, melphalan), nitrosoureas (e.g., carmustine, lomustine, and streptozocin), triazines (e.g., dacarbazine and temozolomide), and hydrazines.

DNA damaging agents also include indolino-benzodiazepines (IGNs). IGNs represent a chemical class of cytotoxic molecules with high in vitro potency ($IC_{50}$ values in the low pmol/L range) toward cancer cells. Examples of IGN DNA alkylating agents that can be used as a cytotoxic payload in an ADC are described in Miller et al. (2016) *Molecular Cancer Therapeutics,* 15(8)). The IGN compounds described in Miller et al. bind to the minor groove of DNA followed by covalent reaction of guanine residues with the two imine functionalities in the molecule resulting in cross-linking of DNA. The structure of an exemplary IGN is provided below.

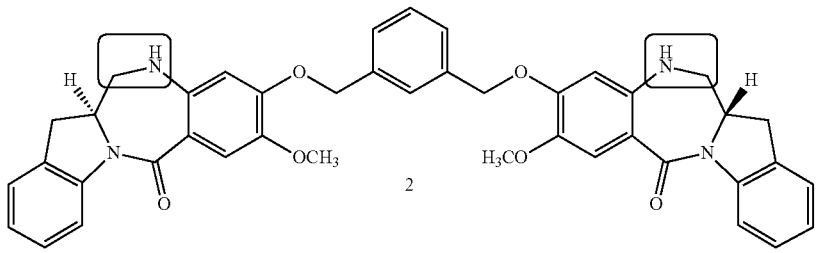 [SMILES: COc1cc2c(cc1OCc1cccc(COc3cc4c(cc3OC)C(=O)N3c5ccccc5C[C@H]3CN4)c1)NC[C@@H]1Cc3ccccc3N1C2=O]

In one embodiment, a DNA damaging agent may also include a pyrrolobenzodiazepine (PBD) or pyridinobenzodiazepine (PDD) (see, e.g., N. Veillard et al. "Pyridinobenzodiazepines (PDDs): A new class of sequence-selective DNA mono-alkylating ADC payloads with low hydrophobicity" [abstract]. In: Proceedings of the 109th Annual Meeting of the American Association for Cancer Research; 2018 Apr. 14-18; Chicago, Ill. Philadelphia (Pa.): AACR; 2018. Abstract no 736/3 and Stefano J. E., et al. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.)).

In another embodiment, the DNA damaging agent is a PARP inhibitor, e.g., olaparib, rucaparib, niraparib, or iniparib. In one embodiment, the PARP inhibitor is olaparib. In one embodiment, the PARP inhibitor is rucaparib. In one embodiment, the PARP inhibitor is niraparib. In one embodiment, the PARP inhibitor is iniparib. In one embodiment, the agent is a saporin toxin.

6. Antiangiogenic Agents

In one aspect, the anti-LY6H antibodies described herein are conjugated to at least one antiangiogenic agent. Antiangiogenic agents inhibit the growth of new blood vessels. Antiangiogenic agents exert their effects in a variety of ways. In some embodiments, these agents interfere with the ability of a growth factor to reach its target. For example, vascular endothelial growth factor (VEGF) is one of the primary proteins involved in initiating angiogenesis by binding to particular receptors on a cell surface. Thus, certain antiangiogenic agents, that prevent the interaction of VEGF with its cognate receptor, prevent VEGF from initiating angiogenesis. In other embodiments, these agents interfere with intracellular signaling cascades. For example, once a particular receptor on a cell surface has been triggered, a cascade of other chemical signals is initiated to promote the growth of blood vessels. Thus, certain enzymes, for example, some tyrosine kinases, that are known to facilitate intracellular signaling cascades that contribute to, for example, cell proliferation, are targets for cancer treatment. In other embodiments, these agents interfere with intercellular signaling cascades. Yet, in other embodiments, these agents disable specific targets that activate and promote cell growth or by directly interfering with the growth of blood vessel cells. Angiogenesis inhibitory properties have been discovered in more than 300 substances with numerous direct and indirect inhibitory effects.

Representative examples of antiangiogenic agents that may be used in the ADCs include, but are not limited to, angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

7. Antimetabolites

The anti-LY6H antibodies may be conjugated to at least one antimetabolite. Antimetabolites are types of chemotherapy treatments that are very similar to normal substances within the cell. When the cells incorporate an antimetabolite into the cellular metabolism, the result is negative for the cell, e.g., the cell is unable to divide. Antimetabolites are classified according to the substances with which they interfere. Examples of antimetabolites that may be used in the ADCs include, but are not limited to, a folic acid antagonist (e.g., methotrexate), a pyrimidine antagonist (e.g., 5-Fluorouracil, Foxuridine, Cytarabine, Capecitabine, and Gemcitabine), a purine antagonist (e.g., 6-Mercaptopurine and 6-Thioguanine) and an adenosine deaminase inhibitor (e.g., Cladribine, Fludarabine, Nelarabine and Pentostatin), as described in more detail below.

8. Boron-Containing Agents

The anti-LY6H antibody may be conjugated to at least one boron containing agent. Boron-containing agents comprise a class of cancer therapeutic compounds which interfere with cell proliferation. Representative examples of boron containing agents include, but are not limited to, borophycin and bortezomib (Velcade, Millenium Pharmaceuticals).

9. Chemoprotective Agents

The anti-LY6H antibodies may be conjugated to at least one chemoprotective agent. Chemoprotective drugs are a class of compounds, which help protect the body against specific toxic effects of chemotherapy. Chemoprotective agents may be administered with various chemotherapies in order to protect healthy cells from the toxic effects of chemotherapy drugs, while simultaneously allowing the cancer cells to be treated with the administered chemotherapeutic. Representative chemoprotective agents include, but are not limited to amifostine (Ethyol, Medimmune, Inc.), which is used to reduce renal toxicity associated with cumulative doses of cisplatin, dexrazoxane (Totect, Apricus Pharma; Zinecard), for the treatment of extravasation caused by the administration of anthracycline (Totect), and for the treatment of cardiac-related complications caused by the administration of the antitumor antibiotic doxorubicin (Zinecard), and mesna (Mesnex, Bristol-Myers Squibb), which is used to prevent hemorrhagic cystitis during chemotherapy treatment with ifocfamide.

10. Photoactive Therapeutic Agents

The anti-LY6H antibodies may be conjugated to at least one photoactive therapeutic agent. Photoactive therapeutic agents include compounds that can be deployed to kill treated cells upon exposure to electromagnetic radiation of a particular wavelength. Therapeutically relevant compounds absorb electromagnetic radiation at wavelengths which penetrate tissue. In preferred embodiments, the compound is administered in a non-toxic form that is capable of producing a photochemical effect that is toxic to cells or tissue upon sufficient activation. In other preferred embodiments, these compounds are retained by cancerous tissue and are readily cleared from normal tissues. Non-limiting examples include various chromagens and dyes.

11. Radionuclide Agents (Radioactive Isotopes)

The anti-LY6H antibodies may be conjugated to at least one radionuclide agent. Radionuclide agents comprise agents that are characterized by an unstable nucleus that is capable of undergoing radioactive decay. The basis for successful radionuclide treatment depends on sufficient concentration and prolonged retention of the radionuclide by the cancer cell. Other factors to consider include the radionuclide half-life, the energy of the emitted particles, and the maximum range that the emitted particle can travel. In preferred embodiments, the therapeutic agent is a radionuclide selected from the group consisting of $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb. Also preferred are radionuclides that substantially decay with Auger-emitting particles. For example, Co-58, Ga-67, Br-80m, Tc-99m, Rh-103m, Pt-109, In-11 1, Sb-119, I-125, Ho-161, Os-189m and Ir-192. Decay energies of useful beta-particle-emitting nuclides are preferably Dy-152, At-211, Bi-212, Ra-223, Rn-219, Po-215, Bi-211, Ac-225, Fr-221, At-217, Bi-213 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$T, $^{66}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

12. Radiosensitizers

The anti-LY6H antibodies may be conjugated to at least one radiosensitizer. The term "radiosensitizer," as used herein, is defined as a molecule, preferably a low molecular weight molecule, administered to animals in therapeutically effective amounts to increase the sensitivity of the cells to be radiosensitized to electromagnetic radiation and/or to promote the treatment of diseases that are treatable with electromagnetic radiation. Radiosensitizers are agents that make cancer cells more sensitive to radiation therapy, while typically having much less of an effect on normal cells. Thus, the radiosensitizer can be used in combination with a radiolabeled antibody or ADC. The addition of the radiosensitizer can result in enhanced efficacy when compared to treatment with the radiolabeled antibody or antibody fragment alone. Radiosensitizers are described in D. M. Goldberg (ed.), Cancer Therapy with Radiolabeled Antibodies, CRC Press (1995). Examples of radiosensitizers include gemcitabine, 5-fluorouracil, taxane, and cisplatin.

Radiosensitizers may be activated by the electromagnetic radiation of X-rays. Representative examples of X-ray activated radiosensitizers include, but are not limited to, the following: metronidazole, misonidazole, desmethylmisonidazole, pimonidazole, etanidazole, nimorazole, mitomycin C, RSU 1069, SR 4233, E09, RB 6145, nicotinamide, 5-bromodeoxyuridine (BUdR), 5-iododeoxyuridine (IUdR), bromodeoxycytidine, fluorodeoxyuridine (FUdR), hydroxyurea, cisplatin, and therapeutically effective analogs and derivatives of the same. Alternatively, radiosensitizers may be activated using photodynamic therapy (PDT). Representative examples of photodynamic radiosensitizers include, but are not limited to, hematoporphyrin derivatives, Photofrin(r), benzoporphyrin derivatives, NPe6, tin etioporphyrin (SnET2), pheoborbide a, bacteriochlorophyll a, naphthalocyanines, phthalocyanines, zinc phthalocyanine, and therapeutically effective analogs and derivatives of the same.

13. Topoisomerase Inhibitors

The anti-LY6H antibodies may be conjugated to at least one topoisomerase inhibitor. Topoisomerase inhibitors are chemotherapy agents designed to interfere with the action of topoisomerase enzymes (topoisomerase I and II), which are enzymes that control the changes in DNA structure by catalyzing then breaking and rejoining of the phosphodiester backbone of DNA strands during the normal cell cycle. Representative examples of DNA topoisomerase I inhibitors include, but are not limited to, camptothecins and its derivatives irinotecan (CPT-11, Camptosar, Pfizer, Inc.) and topotecan (Hycamtin, GlaxoSmithKline Pharmaceuticals). Representative examples of DNA topoisomerase II inhibitors include, but are not limited to, amsacrine, daunorubicin, doxotrubicin, epipodophyllotoxins, ellipticines, epirubicin, etoposide, razoxane, and teniposide.

14. Tyrosine Kinase Inhibitors

The anti-LY6H antibodies may be conjugated to at least one tyrosine kinase inhibitor. Tyrosine kinases are enzymes within the cell that function to attach phosphate groups to the amino acid tyrosine. By blocking the ability of protein tyrosine kinases to function, tumor growth may be inhibited. Examples of tyrosine kinases that may be used on the ADCs include, but are not limited to, Axitinib, Bosutinib, Cediranib, Dasatinib, Erlotinib, Gefitinib, Imatinib, Lapatinib, Lestaurtinib, Nilotinib, Semaxanib, Sunitinib, and Vandetanib.

15. Other Agents

Examples of other agents that may be used in the ADCs include, but are not limited to, abrin (e.g. abrin A chain), alpha toxin, *Aleurites fordii* proteins, amatoxin, crotin, curcin, dianthin proteins, diptheria toxin (e.g. diphtheria A chain and nonbinding active fragments of diphtheria toxin), deoxyribonuclease (Dnase), gelonin, mitogellin, modeccin A chain, *Momordica charantia* inhibitor, neomycin, onconase, phenomycin, *Phytolaca americana* proteins (PAPI, PAPII, and PAP-S), pokeweed antiviral protein, *Pseudomonas* endotoxin, *Pseudomonas* exotoxin (e.g. exotoxin A chain (from *Pseudomonas aeruginosa*)), restrictocin, ricin A chain, ribonuclease (Rnase), *Sapaonaria officinalis* inhibitor, saporin, alpha-sarcin, Staphylcoccal enterotoxin-A, tetanus toxin, cisplatin, carboplatin, and oxaliplatin (Eloxatin, Sanofi Aventis), proteasome inhibitors (e.g. PS-341 [bortezomib or Velcade]), HDAC inhibitors (vorinostat (Zolinza, Merck & Company, Inc.)), belinostat, entinostat, mocetinostat, and panobinostat), COX-2 inhibitors, substituted ureas, heat shock protein inhibitors (e.g. Geldanamycin and its numerous analogs), adrenocortical suppressants, and the tricothecenes. (See, for example, WO 93/21232). Other agents also include asparaginase (Espar, Lundbeck Inc.), hydroxyurea, levamisole, mitotane (Lysodren, Bristol-Myers Squibb), and tretinoin (Renova, Valeant Pharmaceuticals Inc.).

It should be noted that the aforementioned groups of drug moieties that may be used in the anti-LY6H ADCs are not exclusive, in that certain examples of drugs may be found in more than one category, e.g., ansamitocins are both mitotic inhibitors and antitumor antibiotics.

All stereoisomers of the above drug moieties are contemplated for use herein, i.e. any combination of R and S configurations at the chiral carbons of D.

The above agents (i.e., naked agents not conjugated to an antibody) may also be used in combination therapies with the anti-LY6H antibodies described herein. In one embodiment, anti-LY6H antibodies or ADCs are used with any of the foregoing agents in a combination therapy to treat cancer, where the agent is administered prior to, at the same time as, or following administration of the anti-LY6H antibody or ADC to the subject.

B. Anti-LY6H ADCs: Exemplary Linkers

An anti-LY6H ADC comprises an anti-LY6H antibody and at least one drug(s), whereby the antibody and the at least one drug are conjugated by a linker. The term "linker," as used herein, refers to a chemical moiety that may be bifunctional or multifunctional, and is used to attach an antibody to a drug moiety. A linker may include one conjugating component or may include multiple components. For example, the linker may include a spacer, which is a moiety that extends the drug linkage to avoid, for example, shielding the active site of the antibody or improving the solubility of the ADC. Other examples of components of linkers include a stretcher unit and an amino acid unit.

Two methods are commonly used for conjugating drugs to antibodies: alkylation of reduced interchain cysteine disulfides through an enzymatically non-cleavable maleimido or simple and cleavable disulfide linker, and acylation of lysines by cleavable linear amino acids.

In one aspect, a linker covalently attaches an antibody to a drug moiety. An ADC is prepared using a linker having reactive functionality for binding to the antibody and the drug. For example, a cysteine thiol, or an amine, e.g., N-terminus or amino acid side chain such as lysine, of the antibody may form a bond with a functional group of the linker.

In one aspect, a linker has a functionality that is capable of reacting with a free cysteine present on an antibody to form a covalent bond. Nonlimiting exemplary such reactive functionalities include maleimide, haloacetamides, α-haloacetyl, activated esters such as succinimide esters, 4-nitrophenyl esters, pentafluorophenyl esters, tetrafluorophenyl esters, anhydrides, acid chlorides, sulfonyl chlorides, isocyanates, and isothiocyanates. See, e.g., the conjugation method at page 766 of Klussman, et al (2004), Bioconjugate Chemistry 15(4):765-773.

In some embodiments, a linker has a functionality that is capable of reacting with an electrophilic group present on an antibody. Exemplary such electrophilic groups include, but are not limited to, aldehyde and ketone carbonyl groups. In some embodiments, a heteroatom of the reactive functionality of the linker can react with an electrophilic group on an antibody and form a covalent bond to an antibody unit. Nonlimiting exemplary such reactive functionalities include, but are not limited to, hydrazide, oxime, amino, hydrazine, thiosemicarbazone, hydrazine carboxylate, and arylhydrazide.

Suitable linkers include, for example, cleavable and non-cleavable linkers. A linker may be a "cleavable linker," facilitating release of a drug. Nonlimiting exemplary cleavable linkers include acid-labile linkers (e.g., comprising hydrazone), protease-sensitive (e.g., peptidase-sensitive) linkers, photolabile linkers, or disulfide-containing linkers (Chari et al., Cancer Research 52:127-131 (1992); U.S. Pat. No. 5,208,020). A cleavable linker is typically susceptible to cleavage under intracellular conditions. Suitable cleavable linkers include, for example, a peptide linker cleavable by an intracellular protease, such as lysosomal protease or an endosomal protease. In exemplary embodiments, the linker can be a dipeptide linker, such as a valine-citrulline (val-cit) or a phenylalanine-lysine (phe-lys) linker.

Linkers are preferably stable extracellularly in a sufficient manner to be therapeutically effective. Before transport or delivery into a cell, the ADC is preferably stable and remains intact, i.e. the antibody remains conjugated to the drug moiety. Linkers that are stable outside the target cell may be cleaved at some efficacious rate once inside the cell. Thus, an effective linker will: (i) maintain the specific binding properties of the antibody; (ii) allow delivery, e.g., intracellular delivery, of the drug moiety; and (iii) maintain the therapeutic effect, e.g., cytotoxic effect, of a drug moiety.

In one embodiment, the linker is cleavable under intracellular conditions, such that cleavage of the linker sufficiently releases the drug from the antibody in the intracellular environment to be therapeutically effective. In some embodiments, the cleavable linker is pH-sensitive, i.e., sensitive to hydrolysis at certain pH values. Typically, the pH-sensitive linker is hydrolyzable under acidic conditions. For example, an acid-labile linker that is hydrolyzable in the lysosome (e.g., a hydrazone, semicarbazone, thiosemicarbazone, cis-aconitic amide, orthoester, acetal, ketal, or the like) can be used. (See, e.g., U.S. Pat. Nos. 5,122,368; 5,824,805; 5,622,929; Dubowchik and Walker, 1999, *Pharm. Therapeutics* 83:67-123; Neville et al., 1989, *Biol. Chem.* 264: 14653-14661.) Such linkers are relatively stable under neutral pH conditions, such as those in the blood, but are unstable at below pH 5.5 or 5.0, the approximate pH of the lysosome. In certain embodiments, the hydrolyzable linker is a thioether linker (such as, e.g., a thioether attached to the therapeutic agent via an acylhydrazone bond (see, e.g., U.S. Pat. No. 5,622,929).

In other embodiments, the linker is cleavable under reducing conditions (e.g., a disulfide linker). A variety of disulfide linkers are known in the art, including, for example, those that can be formed using SATA (N-succinimidyl-5-acetylthioacetate), SPDP (N-succinimidyl-3-(2-pyridyldithio)propionate), SPDB (N-succinimidyl-3-(2-pyridyldithio)butyrate) and SMPT (N-succinimidyloxycarbonyl-alpha-methyl-alpha-(2-pyridyl-dithio)toluene), SPDB and SMPT. (See, e.g., Thorpe et al., 1987, Cancer Res. 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.).

In some embodiments, the linker is cleavable by a cleaving agent, e.g., an enzyme, that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to hydrolyze dipeptide drug derivatives resulting in the release of active drug inside target cells (see, e.g., Dubowchik and Walker, 1999, Pharm. Therapeutics 83:67-123). Most typical are peptidyl linkers that are cleavable by enzymes that are present in LY6H-expressing cells. Examples of such linkers are described, e.g., in U.S. Pat. No. 6,214,345, incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In other embodiments, the linker is a malonate linker (Johnson et al., 1995, Anticancer Res. 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10): 1305-12).

In yet other embodiments, the linker unit is not cleavable and the drug is released, for example, by antibody degradation. See U.S. Publication No. 20050238649 incorporated by reference herein in its entirety. An ADC comprising a non-cleavable linker may be designed such that the ADC remains substantially outside the cell and interacts with certain receptors on a target cell surface such that the binding of the ADC initiates (or prevents) a particular cellular signaling pathway.

In some embodiments, the linker is substantially hydrophilic linker (e.g., PEG4Mal and sulfo-SPDB). A hydrophilic linker may be used to reduce the extent to which the drug may be pumped out of resistant cancer cells through MDR (multiple drug resistance) or functionally similar transporters.

In other embodiments, upon cleavage, the linker functions to directly or indirectly inhibit cell growth and/or cell proliferation. For example, in some embodiments, the linker, upon cleavage, can function as an intercalating agent, thereby inhibiting macromolecular biosynthesis (e.g. DNA replication, RNA transcription, and/or protein synthesis).

In other embodiments, the linker is designed to facilitate bystander killing (the killing of neighboring cells) through diffusion of the linker-drug and/or the drug alone to neighboring cells. In other, embodiments, the linker promotes cellular internalization.

The presence of a sterically hindered disulfide can increase the stability of a particular disulfide bond, enhancing the potency of the ADC. Thus, in one embodiment, the linker includes a sterically hindered disulfide linkage. A sterically hindered disulfide refers to a disulfide bond present within a particular molecular environment, wherein the environment is characterized by a particular spatial arrangement or orientation of atoms, typically within the same molecule or compound, which prevents or at least partially inhibits the reduction of the disulfide bond. Thus, the presence of bulky (or sterically hindering) chemical moieties and/or bulky amino acid side chains proximal to the disulfide bond prevents or at least partially inhibits the disulfide bond from potential interactions that would result in the reduction of the disulfide bond.

Notably, the aforementioned linker types are not mutually exclusive. For example, in one embodiment, the linker used in the anti-LY6H ADCs described herein is a non-cleavable linker that promotes cellular internalization.

In some embodiments, the ADC has the following formula (formula I):

$$\text{Ab-(L-D)}_n \qquad (I)$$

or a pharmaceutically acceptable salt or solvate thereof; wherein Ab is the antibody, e.g., anti-LY6H antibody, and (L-D) is a Linker-Drug moiety. The Linker-Drug moiety is made of L- which is a Linker, and -D, which is a drug moiety having, for example, cytostatic, cytotoxic, or otherwise therapeutic activity against a target cell, e.g., a cell expressing LY6H; and n is an integer from 1 to 20.

In some embodiments, n ranges from 1 to 8, 1 to 7, 1 to 6, 1 to 5, 1 to 4, 1 to 3, 1 to 2, or is 1.

In some embodiments, the -D moieties are the same. In yet another embodiment, the -D moieties are different.

In some embodiments, a linker component comprises an "amino acid unit." In some such embodiments, the amino acid unit allows for cleavage of the linker by a protease, thereby facilitating release of the drug from the immunoconjugate upon exposure to intracellular proteases, such as lysosomal enzymes (Doronina et al. (2003) Nat. Biotechnol. 21:778-784). Exemplary amino acid units include, but are not limited to, dipeptides, tripeptides, tetrapeptides, and pentapeptides. Exemplary dipeptides include, but are not limited to, valine-citrulline (vc or val-cit), alanine-phenylalanine (af or ala-phe); phenylalanine-lysine (fk or phe-lys); phenylalanine-homolysine (phe-homolys); and N-methylvaline-citrulline (Me-val-cit). Exemplary tripeptides include, but are not limited to, glycine-valine-citrulline (gly-val-cit) and glycine-glycine-glycine (gly-gly-gly). An amino acid unit may comprise amino acid residues that occur naturally and/or minor amino acids and/or non-naturally occurring amino acid analogs, such as citrulline Amino acid units can be designed and optimized for enzymatic cleavage by a particular enzyme, for example, a tumor-associated protease, cathepsin B, C and D, or a plasmin protease.

In one embodiment, the amino acid unit is valine-citrulline (vc or val-cit). In another aspect, the amino acid unit is phenylalanine-lysine (i.e., fk). In yet another aspect of the amino acid unit, the amino acid unit is N-methylvaline-citrulline. In yet another aspect, the amino acid unit is 5-aminovaleric acid, homo phenylalanine lysine, tetraisoquinolinecarboxylate lysine, cyclohexylalanine lysine, isopecotic acid lysine, beta-alanine lysine, glycine serine valine glutamine and isopecotic acid.

Another approach for the generation of ADCs involves the use of heterobifunctional cross-linkers which link the anti-LY6H antibody to the drug moiety. Examples of cross-linkers that may be used include N-succinimidyl 4-(5-nitro-2-pyridyldithio)-pentanoate or the highly water-soluble analog N-sulfosuccinimidyl 4-(5-nitro-2-pyridyldithio)-pentanoate, N-succinimidyl-4-(2-pyridyldithio) butyrate (SPDB), N-succinimidyl-4-(5-nitro-2-pyridyldithio) butyrate (SNPB), and N-sulfosuccinimidyl-4-(5-nitro-2-pyridyldithio) butyrate (SSNPB), N-succinimidyl-4-methyl-4-(5-nitro-2-pyridyldithio)pentanoate (SMNP), N-succinimidyl-4-(5-N,N-dimethylcarboxamido-2-pyridyldithio) butyrate (SCPB) or N-sulfosuccinimidyl4-(5-N,N-dimethyl-carboxamido-2-pyridyldithio) butyrate (SSCPB)). The antibodies may be modified with the cross-linkers N-succinimidyl 4-(5-nitro-2-pyridyldithio)-pentanoate, N-sulfosuccinimidyl 4-(5-nitro-2-pyridyldithio)-pentanoate, SPDB, SNPB, SSNPB, SMNP, SCPB, or SSCPB can then react with a small excess of a particular drug that contains a thiol moiety to give excellent yields of an ADC (see also U.S. Pat. No. 6,913,748, incorporated by reference herein).

In one embodiment, charged linkers (also referred to as pro-charged linkers) are used to conjugate anti-LY6H antibodies to drugs to form ADCs. Charged linkers include linkers that become charged after cell processing. The presence of a charged group(s) in the linker of a particular ADC or on the drug after cellular processing provides several advantages, such as (i) greater water solubility of the ADC, (ii) ability to operate at a higher concentration in aqueous solutions, (iii) ability to link a greater number of drug molecules per antibody, potentially resulting in higher potency, (iv) potential for the charged conjugate species to be retained inside the target cell, resulting in higher potency, and (v) improved sensitivity of multidrug resistant cells, which would be unable to export the charged drug species from the cell. Examples of some suitable charged or pro-charged cross-linkers and their synthesis are shown in FIGS. 1 to 10 of U.S. Pat. No. 8,236,319, and are incorporated by reference herein. Preferably, the charged or pro-charged cross-linkers are those containing sulfonate, phosphate, carboxyl or quaternary amine substituents that significantly increase the solubility of the ADCs, especially for ADCs with 2 to 20 conjugated drugs. Conjugates prepared from linkers containing a pro-charged moiety would produce one or more charged moieties after the conjugate is metabolized in a cell.

Additional examples of linkers that can be used with the compositions and methods include valine-citrulline; maleimidocaproyl; amino benzoic acids; p-aminobenzylcarbamoyl (PAB); lysosomal enzyme-cleavable linkers; maleimidocaproyl-polyethylene glycol (MC(PEG)6-OH); N-methyl-valine citrulline; N-succinimidyl 4-(N-maleimidomethyl)cyclohexane-1-carboxylate (SMCC); N-Succinimidyl 4-(2-pyridyldithio)butanoate (SPDB); and N-Succinimidyl 4-(2-pyridylthio)pentanoate (SPP) (See also US 2011/0076232). Another linker for use includes an avidin-biotin linkage to provide an avidin-biotin-containing ADC (See also U.S. Pat. No. 4,676,980, PCT publication Nos. WO1992/022332A2, WO1994/016729A1, WO1995/015770A1, WO1997/031655A2, WO1998/035704A1, WO1999/019500A1, WO2001/09785A2, WO2001/090198A1, WO2003/093793A2, WO2004/050016A2, WO2005/081898A2, WO2006/083562A2, WO2006/089668A1, WO2007/150020A1, WO2008/135237A1, WO2010/111198A1, WO2011/057216A1, WO2011/058321A1, WO2012/027494A1, and EP77671B1), wherein some such linkers are resistant to biotinidase cleavage. Additional linkers that may be used include a cohesin/dockerin pair to provide a cohesion-dockerin-containing ADC (See PCT publication Nos. WO2008/097866A2, WO2008/097870A2, WO2008/103947A2, and WO2008/103953A2).

Additional linkers may contain non-peptide polymers (examples include, but are not limited to, polyethylene glycol, polypropylene glycol, polyoxyethylated polyols, polyvinyl alcohol, polysaccharides, dextran, polyvinyl ethyl ether, PLA (poly(lactic acid)), PLGA (poly(lactic acid-glycolic acid)), and combinations thereof, wherein a preferred polymer is polyethylene glycol) (See also PCT publication No. WO2011/000370). Additional linkers are also described in WO 2004-010957, U.S. Publication No. 20060074008, U.S. Publication No. 20050238649, and U.S. Publication No. 20060024317, each of which is incorporated by reference herein in its entirety).

For an ADC comprising a maytansinoid, many positions on maytansinoids can serve as the position to chemically link the linking moiety. In one embodiment, maytansinoids comprise a linking moiety that contains a reactive chemical group are C-3 esters of maytansinol and its analogs where the linking moiety contains a disulfide bond and the chemical reactive group comprises a N-succinimidyl or N-sulfosuccinimidyl ester. For example, the C-3 position having a hydroxyl group, the C-14 position modified with hydroxymethyl, the C-15 position modified with hydroxy and the C-20 position having a hydroxy group are all useful. The linking moiety most preferably is linked to the C-3 position of maytansinol.

The conjugation of the drug to the antibody via a linker can be accomplished by any technique known in the art. A number of different reactions are available for covalent attachment of drugs and linkers to antibodies. This may be accomplished by reaction of the amino acid residues of the antibody, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody. Also available for attachment of drugs to antibodies is the Schiff base reaction. This method involves the periodate oxidation of a drug that contains glycol or hydroxy groups, thus forming an aldehyde which is then reacted with the binding agent. Attachment occurs via formation of a Schiff base with amino groups of the antibody. Isothiocyanates can also be used as coupling agents for covalently attaching drugs to antibodies. Other techniques are known to the skilled artisan and within the scope of the disclosure.

In certain embodiments, an intermediate, which is the precursor of the linker, is reacted with the drug under appropriate conditions. In certain embodiments, reactive groups are used on the drug or the intermediate. The product of the reaction between the drug and the intermediate, or the derivatized drug, is subsequently reacted with the anti-LY6H antibody under appropriate conditions. The synthesis and structure of exemplary linkers, stretcher units, amino acid units, self-immolative spacer units are described in U.S. Patent Application Publication Nos. 20030083263, 20050238649 and 20050009751, each if which is incorporated herein by reference.

Stability of the ADC may be measured by standard analytical techniques such as mass spectroscopy, HPLC, and the separation/analysis technique LC/MS.

IV. Uses of Anti-LY6H Antibodies and Anti-LY6H ADCs

The antibodies and antibody portions (and ADCs) preferably are capable of neutralizing LY6H activity, in particular human LY6H activity, both in vivo and in vitro. Accordingly, such antibodies and antibody portions can be used to inhibit hLY6H activity, e.g., in a cell culture containing hLY6H, in human subjects or in other mammalian subjects having LY6H with which an antibody disclosed herein cross-reacts. In one embodiment, the disclosure provides a method for inhibiting hLY6H activity comprising contacting hLY6H with an antibody or antibody portion such that hLY6H activity is inhibited. For example, in a cell culture containing, or suspected of containing hLY6H, an antibody or antibody portion can be added to the culture medium to inhibit hLY6H activity in the culture.

In another embodiment, disclosed herein is a method for reducing hLY6H activity in a subject, advantageously from a subject suffering from a LY6H associated disorder, e.g., cancer, including, but not limited to, small cell lung cancer (SCLC), e.g., classic SCLC or variant SCLC, gastrointestinal stromal tumor (GIST), T cell acute lymphoblastic leukemia (T-ALL), glioblastoma and soft tissue sarcoma, or a disorder in which LY6H activity is detrimental. The disclosure provides methods for reducing LY6H activity in a subject suffering from such a disease or disorder, which method comprises administering to the subject an antibody or antibody portion of the disclosure such that LY6H activity in the subject is reduced. Preferably, the LY6H is human LY6H, and the subject is a human subject. Alternatively, the subject can be a mammal expressing a LY6H to which antibodies of the disclosure are capable of binding. Still further the subject can be a mammal into which LY6H has been introduced (e.g., by administration of LY6H or by expression of a LY6H transgene). Antibodies of the disclosure can be administered to a human subject for therapeutic purposes. Moreover, antibodies of the disclosure can be administered to a non-human mammal expressing a LY6H with which the antibody is capable of binding for veterinary purposes or as an animal model of human disease. Regarding the latter, such animal models may be useful for evaluating the therapeutic efficacy of antibodies of the disclosure (e.g., testing of dosages and time courses of administration).

As used herein, the term "a disorder in which LY6H activity is detrimental" is intended to include diseases and other disorders in which the presence of LY6H in a subject suffering from the disorder has been shown to be or is suspected of being either responsible for the pathophysiology of the disorder or a factor that contributes to a worsening of the disorder. Accordingly, a disorder in which LY6H activity is detrimental is a disorder in which reduction of LY6H activity is expected to alleviate the symptoms and/or progression of the disorder. Such disorders may be evidenced, for example, by an increase in the concentration of LY6H in a biological cell, fluid or tissue of a subject suffering from the disorder (e.g., an increase in the concentration of LY6H in a tumor, serum, plasma, synovial fluid, etc. of the subject), which can be detected, for example, using an anti-LY6H antibody as described above.

Non-limiting examples of disorders that can be treated with the antibodies, or antigen binding fragments thereof, include those disorders discussed below. For example, suitable disorders include, but are not limited to, a variety of cancers including, but not limited to, small cell lung cancer (SCLC), e.g., classic SCLC or variant SCLC, gastrointestinal stromal tumor (GIST), T cell acute lymphoblastic leukemia (T-ALL), glioblastoma, soft tissue sarcoma, breast cancer, brain and CNS cancer, head and neck cancer, bladder cancer, renal cancer, ovarian cancer, esophageal cancer, gastric cancer, prostate cancer, uterine cancer, endometrial cancer, pancreatic cancer, liver cancer, colorectal cancer, cervical cancer and non small cell lung cancer (NSCLC).

Other examples of cancers that may be treated using the compositions and methods disclosed herein include, but are not limited to carcinoma, lymphoma, blastoma, sarcoma, and leukemia or lymphoid malignancies. More particular examples of such cancers include but are not limited to breast cancer (Luminal A, TNBC, Ductal), prostate cancer, squamous cell tumors, squamous cell carcinoma (e.g., squamous cell lung cancer or squamous cell head and neck cancer), neuroendocrine tumors, urothelial cancer, vulvar cancer, mesothelioma, liver cancer, bone cancer, pancreatic cancer, skin cancer, cancer of the head or neck, lung cancer, small cell lung cancer, non-small cell lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, environmentally induced cancers including those induced by asbestos, hematologic malignancies including, for example, multiple myeloma, B-cell lymphoma, Hodgkin lymphoma/primary mediastinal B-cell lymphoma, non-Hodgkin's lymphomas, acute myeloid lymphoma, chronic myelogenous leukemia, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, T-cell lymphoma, and precursor T-lymphoblastic lymphoma, and any combinations of said cancers. PVNS, acute myeloid leukemia, adrenocortico carcinoma, ladder urothelial carcinoma, cervical squamous cell carcinoma, endocervical adenocarcinoma, diffuse large B cell lymphoma, glioblastoma multiforme, chronic lymphocytic leukemia, brain lower grade glioma, head and neck squamous cell carcinoma, hepatocellular carcinoma, lung adenocarcinoma, large squamous cell carcinoma, cutaneous melanoma, ovarial serous cystadenocarcinoma, gastric cancer, soft tissue sarcoma, testicular germ cell cancer, thymoma, thyroid carcinoma, uterine corpus endometrial carcinoma, uterine carcinosarcoma, kidney renal clear cell carcinoma, and kidney renal papillary cell carcinoma. The present invention is also applicable to treatment of metastatic cancers.

In one embodiment, an anti-LY6H ADC of the present invention can be used to treat a cancer in a subject including, but not limited to Hodgkin's lymphoma, PVNS, acute myeloid leukemia, adrenocortico carcinoma, ladder urothelial carcinoma, breast cancer (Luminal A, TNBC, Ductal), cervical squamous cell carcinoma, endocervical adenocarcinoma, colorectal adenocarcinoma, diffuse large B cell lymphoma, non-hodgkin's lymphoma, glioblastoma multiforme, chronic lymphocytic leukemia, brain lower grade glioma, head and neck squamous cell carcinoma, hepatocellular carcinoma, lung adenocarcinoma, small cell lung cancer, large squamous cell carcinoma, cutaneous melanoma, ovarial serous cystadenocarcinoma, gastric cancer, soft tissue sarcoma, mesothelioma, pancreatic adenocarcinoma, testicular germ cell cancer, thymoma, thyroid carcinoma, uterine corpus endometrial carcinoma, uterine carcinosarcoma. kidney renal clear cell carcinoma, and kidney renal papillary cell carcinoma.

In one embodiment, the antibodies and ADCs disclosed herein are used to treat a solid tumor, e.g., inhibit growth of or decrease size of a solid tumor, overexpressing LY6H or which is LY6H positive. In one embodiment, the antibodies and ADCs disclosed herein are used to treat cancer, including, but not limited to, small cell lung cancer (SCLC), gastrointestinal stromal tumor (GIST), T cell acute lymphoblastic leukemia (T-ALL), glioblastoma, and soft tissue sarcoma. Diseases and disorders described herein may be treated by anti-LY6H antibodies or ADCs, as well as pharmaceutical compositions comprising such anti-LY6H antibodies or ADCs.

In certain embodiments, the antibodies and ADCs disclosed herein are administered to a subject in need thereof in order to treat advanced solid tumor types likely to exhibit elevated levels of LY6H. In certain embodiments, the disclosure includes a method for inhibiting or decreasing solid tumor growth in a subject having a solid tumor, said method comprising administering an anti-LY6H antibody or ADC described herein, to the subject having the solid tumor, such that the solid tumor growth is inhibited or decreased. In one embodiment, the solid tumor is a small cell lung cancer (SCLC) tumor. In another embodiment, the solid tumor is a gastrointestinal stromal tumor (GIST). In some embodiments, the solid tumor is a glioblastoma tumor. In another embodiment, the solid tumor is a soft tissue sarcoma tumor. In further embodiments, the solid tumor is an LY6H expressing solid tumor. In certain embodiments, the disclosure includes a method for treating a cancer that generally does not form a solid tumor in a subject, e.g., T cell acute lymphoblastic leukemia (T-ALL), said method comprising administering an anti-LY6H antibody or ADC described herein, to the subject having T cell acute lymphoblastic leukemia (T-ALL), such that T cell acute lymphoblastic leukemia (T-ALL) is inhibited or decreased. In certain embodiments the anti-LY6H antibodies or ADCs described herein are administered to a subject having a cancer, including, but not limited to, small cell lung cancer (SCLC), gastrointestinal stromal tumor (GIST), T cell acute lymphoblastic leukemia (T-ALL), glioblastoma, and soft tissue sarcoma, alone or in combination with an additional agent, e.g., radiation and/or chemotherapy, or an immune checkpoint inhibitor.

In certain embodiments, the disclosure includes a method for inhibiting or decreasing solid tumor growth in a subject having a solid tumor which was identified as an LY6H expressing or LY6H positive tumor, said method comprising administering an anti-LY6H antibody or ADC described herein, to the subject having the solid tumor, such that the solid tumor growth is inhibited or decreased. In further embodiments, the solid tumor is a primary tumor.

In certain embodiments, the disclosure includes a method for inhibiting or decreasing solid tumor growth in a subject having a solid tumor which was identified as an LY6H expressing tumor, said method comprising administering an anti-LY6H antibody or ADC described herein, to the subject having the solid tumor, such that the solid tumor growth is inhibited or decreased. Methods for identifying LY6H expressing tumors are known in the art, and include FDA-approved tests and validation assays. For example, these assays may use primers that are specific for the LY6H gene and/or cDNA and result in the amplification of the LY6H gene/cDNA, or a portion thereof. The amplified PCR products may be subsequently analyzed, for example, by gel electrophoresis using standard methods known in the art to determine the size of the PCR products. Such tests may be used to identify tumors that may be treated with the methods and compositions described herein.

In another aspect, this application features a method of treating (e.g., curing, suppressing, ameliorating, delaying or preventing the onset of, or preventing recurrence or relapse of) or preventing a LY6H-associated disorder, in a subject. The method includes: administering to the subject a LY6H binding agent (particularly an antagonist), e.g., an anti-LY6H antibody or fragment thereof as described herein, in an amount sufficient to treat or prevent the LY6H-associated disorder.

The LY6H antagonist, e.g., the anti-LY6H antibody or fragment thereof, can be administered to the subject, alone or in combination with other therapeutic modalities as described herein.

In some embodiments, the anti-LY6H antibody or fragment thereof used in the methods of the invention is a human or humanized anti-LY6H antibody or fragment thereof.

In another embodiment, antibody-dependent cell-mediated cytotoxicity (ADCC) activity is not necessary for anti-LY6H antibodies to inhibit tumor growth or reduce tumor size. Accordingly, in one embodiment, an antibody, or antigen binding portion thereof, of the invention comprises an isotype lacking effector function (e.g., human $IgG_4$).

Antibodies or ADCs, or antigen binding portions thereof, can be used alone or in combination to treat such diseases. It should be understood that the antibodies or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody. The additional agent also can be an agent that imparts a beneficial attribute to the therapeutic composition, e.g., an agent which affects the viscosity of the composition.

It should further be understood that the combinations which are to be included within this disclosure are those combinations useful for their intended purpose. The agents set forth below are illustrative for purposes and not intended to be limited. The combinations, which are part of this disclosure, can be the antibodies of the disclosure and at least one additional agent selected from the lists below. The combination can also include more than one additional agent, e.g., two or three additional agents if the combination is such that the formed composition can perform its intended function.

The combination therapy can include one or more LY6H antagonists, e.g., anti-LY6H antibodies or fragments thereof, formulated with, and/or co-administered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, mitotic inhibitors, antitumor antibiotics, immunomodulating agents, vectors for gene therapy, alkylating agents, antiangiogenic agents, antimetabolites, boron-containing agents, chemoprotective agents, hormones, antihormone agents, corticosteroids, photoactive therapeutic agents, oligonucleotides, radionuclide agents, topoisomerase inhibitors, tyrosine kinase inhibitors, or radiosensitizers, as described in more herein.

In a particular embodiment, the anti-LY6H antibodies disclosed herein are used in combination with an anti-cancer agent or an antineoplastic agent. The terms "anti-cancer agent" and "antineoplastic agent" refer to drugs used to treat malignancies, such as cancerous growths. In one embodiment, the anti-LY6H antibodies or ADCs of the invention are administered in combination with one or more immune checkpoint inhibitors (e.g., antibody or small molecule immune checkpoint inhibitors) for the treatment of a cancer. In some embodiments, the immune checkpoint inhibitor (ICI) is an inhibitor (e.g., an antibody) of Programmed Death-Ligand 1 (PD-L1, also known as B7-H1, CD274), Programmed Death 1 (PD-1), CTLA-4, PD-L2 (B7-DC, CD273), LAG3, TIM3, 2B4, 4-1BB, A2aR, B7H1, B7H3, BTLA, CD2, CD6, CD27, CD28, CD30, CD38, CD39, CD40, CD47, CD70, CD73, CD80, CD86, CD137, CD160, CD166, CD200, CD200R1, CD226, CD276, DR3, GAL9, GITR, HAVCR2, HVEM, IDO1, ID02, ICOS (inducible T cell costimulator), KIR, LAG3, LAIR1, TREM2, LILRB1, LILRB2, LILRB3, LILRB4, LIGHT, MARCO (macrophage receptor with collageneous structure), PS (phosphatidylserine), OX-40, SLAM, SIRPA, CSF1R, CD47, SIRPA, TIGHT, TGFβ, VISTA, or any combinations thereof.

In some embodiments, the immune checkpoint inhibitor is an anti-CTLA-4, PD-L1, or PD-1 antibody therapy such as, but not limited to Yervoy® (ipilimumab; Bristol-Myers Squibb), Opdivo® (nivolumab; Bristol-Myers Squibb), Keytruda® (pembrolizumab; Merck), and Tecentriq® (atezolizumab; Roche).

In other embodiments, the immune checkpoint inhibitor is an anti-CD38 antibody therapy such as isatuximab (Sanofi), Darzalex® (daratumumab; Genmab A/S and Janssen Biotech), MOR202 (MorphoSys AG), and Tusk Therapeutics Ltd.'s anti-CD38 monoclonal antibody.

In some embodiments, the checkpoint inhibitor is an antibody or small molecule currently undergoing clinical testing, including, for example, an antibody against IDO (Epacadostat and Indoximod and BMS-986205), 4-1BB/CD137 (Utomilumab and Urelumab), KIR (Lirilulmab), CD40 (CP-870,893), CD27 (Varlilumab), LAG-3 (Relatilimab), MHCII (Eftilagimod Alpha).

In one embodiment, the anti-LY6H antibodies or ADCs of the invention are administered in combination with one checkpoint inhibitor, e.g., an anti-CTLA-4, CD38, PD-L1, or PD-1 antibody. In other embodiments, the anti-LY6H antibodies or ADCs of the invention are administered in combination with more than one checkpoint inhibitor, e.g., an anti-LY6H antibody or ADC of the invention in combination with an anti-CD38 antibody and an anti-PD-L1 antibody, or an anti-LY6H antibody or ADC of the invention in combination with an anti-CD38 antibody and an anti-PD-1 antibody.

Drug therapy may be used alone, or in combination with other treatments such as surgery or radiation therapy. Several classes of drugs may be used in cancer treatment, depending on the nature of the organ involved. For example, breast cancers are commonly stimulated by estrogens, and may be treated with drugs which inactive the sex hormones. Similarly, prostate cancer may be treated with drugs that inactivate androgens, the male sex hormone.

Provided herein are methods for treating cancer, e.g., a small cell lung cancer (SCLC), e.g., classic SCLC or variant SCLC, gastrointestinal stromal tumor (GIST), T cell acute lymphoblastic leukemia (T-ALL), glioblastoma, soft tissue sarcoma, breast cancer, brain and CNS cancer, head and neck cancer, bladder cancer, renal cancer, ovarian cancer, esophageal cancer, gastric cancer, prostate cancer, uterine cancer, endometrial cancer, pancreatic cancer, liver cancer, colorectal cancer, cervical cancer and non small cell lung cancer (NSCLC), or a disorder in which LY6H activity is detrimental, in a patient comprising administering to the patient an anti-LY6H antibody, or fragment thereof, or an ADC of the invention wherein the combination therapy exhibits synergy, e.g., therapeutic synergy, in the subject. As used herein, "synergy" or "therapeutic synergy" refers to a phenomenon where treatment of patients with a combination of therapeutic agents manifests a therapeutically superior outcome to the outcome achieved by each individual constituent of the combination used at its optimum dose (Corbett, T. H. et al., Cancer Treatment Reports, 66:1187 (1982)). For example, a therapeutically superior outcome is one in which the patients either a) exhibit fewer incidences of adverse events while receiving a therapeutic benefit that is equal to or greater than that where individual constituents of the combination are each administered as monotherapy at the same dose as in the combination, or b) do not exhibit dose-limiting toxicities while receiving a therapeutic benefit that is greater than that of treatment with each individual constituent of the combination when each constituent is administered in at the same doses in the combination(s) as is administered as individual components.

In particular embodiments, the anti-LY6H antibodies or ADCs can be administered alone or with another anti-cancer agent which acts in conjunction with or synergistically with the antibody to treat the disease associated with LY6H activity. Such anti-cancer agents include, for example, one or more agents well known in the art (e.g., cytotoxins, chemotherapeutic agents, such as gemcitabine, carboplatin, and 5-Fu, small molecules and radiation) or one or more immune checkpoint inhibitor as set forth above. In one embodiment, the one or more chemotherapeutic agent is pemetrexed (Alimta®) and/or platinum chemotherapy, e.g., cisplatin or carboplatin (see e.g., Gandhi et al. *New England Journal of Medicine* DOI: 10.1056/NEJMoa1801005, Apr. 16, 2018).

Other examples of anti-cancer agents include, but are not limited to, Panorex (Glaxo-Welcome), Rituxan (IDEC/Genentech/Hoffman la Roche), Mylotarg (Wyeth), Campath (Millennium), Zevalin (IDEC and Schering AG), Bexxar (Corixa/GSK), Erbitux (Imclone/BMS), Avastin (Genentech) and Herceptin (Genentech/Hoffman la Roche). Examples of anti-cancer agents that can be administered in combination with an anti-LY6H antibody or ADC of the invention include any one or more of those agents described above in Section III (A) of this disclosure.

In one embodiment, the anti-LY6H antibodies or ADCs of the invention are administered in combination with one or more compound which is capable of decreasing T regulatory cells and/or increasing effector T cell:T regulatory cell ratio in a subject (see, e.g., Eriksson et al. (2016) *Journal of Translational Medicine* 14:282). In one embodiment, the compound is, for example, gemcitabine.

In another embodiment, the anti-LY6H antibodies or ADCs can be administered in combination with an anti-cancer agent that regulates the tumor micro-environment, including inhibiting the activity or population of MDSCs and macrophages, such as, for example, CSF-1R antibodies, all-trans retinoic acid, gemcitabine, COX2 inhibitor (SC58236), amino-biphosphonate, phosphodiesterase-5 inhibitor (sildenafil and tadalafil), KIT-specific antibody, nitroaspirin, titerpenoid, 25-hydroxyvitamin D3, VEGF-trap, VEGF-specific antibody (e.g., Avastin), doxorubicin-cyclophosphamide, antagonists for CXCR2 (e.g., S-265610) and CXCR4 (e.g., AMD3100), tyrosine kinase inhibitor (e.g., Sunitinib), and PROK2-specific antibody (see V. Bronte and D. Gabrilovich, Myeloid derived suppressor cells, *Nature Rev. Immunology poster*, available through Biolegend.com).

In another embodiment, the anti-LY6H antibodies or ADCs can be administered in combination with anti-cancer agents that modulate tumor agiogenesis such as, but not limited to angiostatin, ABX EGF, C1-1033, PKI-166, EGF vaccine, EKB-569, GW2016, ICR-62, EMD 55900, CP358, PD153035, AG1478, IMC-C225 (Erbitux, ZD1839 (Iressa), OSI-774, Erlotinib (tarceva), angiostatin, arrestin, endostatin, BAY 12-9566 and w/fluorouracil or doxorubicin, canstatin, carboxyamidotriozole and with paclitaxel, EMD121974, S-24, vitaxin, dimethylxanthenone acetic acid, IM862, Interleukin-12, Interleukin-2, NM-3, HuMV833, PTK787, RhuMab, angiozyme (ribozyme), IMC-1C11, Neovastat, marimstat, prinomastat, BMS-275291, COL-3, MM1270, SU101, SU6668, SU11248, SU5416, with paclitaxel, with gemcitabine and cisplatin, and with irinotecan and cisplatin and with radiation, tecogalan, temozolomide and PEG interferon α2b, tetrathiomolybdate, TNP-470, thalidomide, CC-5013 and with taxotere, tumstatin, 2-methoxyestradiol, VEGF trap, mTOR inhibitors (deforolimus, everolimus (Afinitor, Novartis Pharmaceutical Corporation), and temsirolimus (Torisel, Pfizer, Inc.)), tyrosine kinase inhibitors (e.g., erlotinib (Tarceva, Genentech, Inc.), imatinib (Gleevec, Novartis Pharmaceutical Corporation), gefitinib (Iressa, AstraZeneca Pharmaceuticals), dasatinib (Sprycel, Brystol-Myers Squibb), sunitinib (Sutent, Pfizer, Inc.), nilotinib (Tasigna, Novartis Pharmaceutical Corporation), lapatinib (Tykerb, GlaxoSmithKline Pharmaceuticals), sorafenib (Nexavar, Bayer and Onyx), phosphoinositide 3-kinases (PI3K).

In some embodiments, the antibody or antigen binding portion thereof or the ADC is administered in combination with IL-6 and/or interferon-gamma (IFN-γ). For example, IL-6 and/or IFN-γ may be administered prior to the antibody or antigen binding portion thereof or the ADC.

In another embodiment, the antibody or antigen binding portion thereof or the ADC is administered in combination with a DNA alkylator (e.g., cisplatin) and/or a PARP inhibitor.

Other anti-cancer agents include, but are not limited to, those disclosed in U.S. Pat. No. 7,598,028 and International Publication No. WO2008/100624, the contents of which are hereby incorporated by reference. One or more anti-cancer agents may be administered either simultaneously or before or after administration of an antibody or antigen binding portion thereof.

In particular embodiments of the invention, the anti-LY6H antibodies or ADCs described herein can be used in a combination therapy with an inhibitor of NAMPT (see examples of inhibitors in US 2013/0303509; AbbVie, Inc., incorporated by reference herein) to treat a subject in need thereof. NAMPT (also known as pre-B-cell-colony-enhancing factor (PBEF) and visfatin) is an enzyme that catalyzes the phosphoribosylation of nicotinamide and is the rate-limiting enzyme in one of two pathways that salvage NAD. In one embodiment, anti-LY6H antibodies and ADCs described herein are administered in combination with a NAMPT inhibitor for the treatment of cancer in a subject.

In particular embodiments, the anti-LY6H antibodies or ADCs described herein can be used in a combination therapy with SN-38, which is the active metabolite of the topoisomerase inhibitor irinotecan.

The pharmaceutical compositions may include a "therapeutically effective amount" or a "prophylactically effective amount" of an antibody or antibody portion. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an ADC, an antibody or antibody portion is 0.1-20 mg/kg, more preferably 1-10 mg/kg. It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

In another aspect, this application provides a method for detecting the presence of LY6H in a sample in vitro (e.g., a biological sample, such as serum, plasma, tissue, biopsy). The subject method can be used to diagnose a disorder, e.g., a cancer. The method includes: (i) contacting the sample or a control sample with the anti-LY6H antibody or fragment thereof as described herein; and (ii) detecting formation of a complex between the anti-LY6H antibody or fragment thereof, and the sample or the control sample, wherein a statistically significant change in the formation of the complex in the sample relative to the control sample is indicative of the presence of LY6H in the sample.

Given their ability to bind to human LY6H, the anti-human LY6H antibodies, or portions thereof, (as well as ADCs thereof) can be used to detect human LY6H (e.g., in a biological sample, such as serum or plasma), using a conventional immunoassay, such as an enzyme linked immunosorbent assays (ELISA), an radioimmunoassay (RIA) or tissue immunohistochemistry. In one aspect, the disclosure provides a method for detecting human LY6H in a biological sample comprising contacting a biological sample with an antibody, or antibody portion, and detecting either the antibody (or antibody portion) bound to human LY6H or unbound antibody (or antibody portion), to thereby detect human LY6H in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{3}H$ $^{14}C$, $^{35}S$, $^{90}Y$, $^{99}Tc$, $^{111}In$, $^{125}I$, $^{131}I$, $^{177}Lu$, $^{166}Ho$, or $^{153}Sm$.

Alternative to labeling the antibody, human LY6H can be assayed in biological fluids by a competition immunoassay utilizing rhLY6H standards labeled with a detectable substance and an unlabeled anti-human LY6H antibody. In this assay, the biological sample, the labeled rhLY6H standards and the anti-human LY6H antibody are combined and the amount of labeled rhLY6H standard bound to the unlabeled antibody is determined. The amount of human LY6H in the biological sample is inversely proportional to the amount of labeled rhLY6H standard bound to the anti-LY6H antibody. Similarly, human LY6H can also be assayed in biological fluids by a competition immunoassay utilizing rhLY6H standards labeled with a detectable substance and an unlabeled anti-human LY6H antibody.

In yet another aspect, this application provides a method for detecting the presence of LY6H in vivo (e.g., in vivo imaging in a subject). The subject method can be used to diagnose a disorder, e.g., a LY6H-associated disorder. The method includes: (i) administering the anti-LY6H antibody or fragment thereof as described herein to a subject or a control subject under conditions that allow binding of the antibody or fragment to LY6H; and (ii) detecting formation of a complex between the antibody or fragment and LY6H, wherein a statistically significant change in the formation of the complex in the subject relative to the control subject is indicative of the presence of LY6H.

V. Pharmaceutical Compositions

The disclosure also provides pharmaceutical compositions comprising an antibody, or antigen binding portion thereof, or ADC and a pharmaceutically acceptable carrier. The pharmaceutical compositions comprising antibodies or ADCs are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies. In another embodiment, the pharmaceutical composition comprises one or more antibodies or ADCs and one or more prophylactic or therapeutic agents other than antibodies or ADCs for treating a disorder in which LY6H activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions or ADCs can be incorporated into pharmaceutical compositions suitable for administration to a subject. Typically, the pharmaceutical composition comprises an antibody or antibody portion and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion or ADC.

Various delivery systems are known and can be used to administer one or more antibodies or ADCs or the combination of one or more antibodies and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, J. Biol. Chem. 262:4429-4432 (1987)), construction of a nucleic acid as part of a retroviral or other vector, etc. Methods of administering a prophylactic or therapeutic agent include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934, 272, 5,874,064, 5,855,913, 5,290, 540, and 4,880,078; and PCT Publication Nos. WO 92/19244, WO 97/32572, WO 97/44013, WO 98/31346, and WO 99/66903, each of which is incorporated herein by reference their entireties. In one embodiment, an antibody, combination therapy, or a composition is administered using Alkermes AIR® pulmonary drug delivery technology (Alkermes, Inc., Cambridge, Mass.). In a specific embodiment, prophylactic or therapeutic agents are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies antagonists is administered locally to the affected area to a subject to prevent, treat, manage, and/or ameliorate a disorder or a symptom thereof. In another embodiment, an effective amount of one or more antibodies is administered locally to the affected area in combination with an effective amount of one or more therapies (e.g., one or more prophylactic or therapeutic agents) other than an antibody of a subject to prevent, treat, manage, and/or ameliorate a disorder or one or more symptoms thereof.

A pharmaceutical composition is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

If the method of the disclosure comprises oral administration, compositions can be formulated orally in the form of tablets, capsules, cachets, gel caps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the disclosure also provides that one or more of the prophylactic or therapeutic agents, or pharmaceutical compositions is packaged in a hermetically sealed container such as an ampoule or sachette indicating the quantity of the agent. In one embodiment, one or more of the prophylactic or therapeutic agents, or pharmaceutical compositions is supplied as a dry sterilized lyophilized powder or water free concentrate in a hermetically sealed container and can be reconstituted (e.g., with water or saline) to the appropriate concentration for administration to a subject. The antibodies and antibody-portions or ADCs can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

It will be readily apparent to those skilled in the art that other suitable modifications and adaptations of the methods of the invention described herein are obvious and may be made using suitable equivalents without departing from the scope of the invention or the embodiments disclosed herein. Having now described the invention in detail, the same will be more clearly understood by reference to the following examples, which are included for purposes of illustration only and are not intended to be limiting.

EXAMPLES

Example 1. LY6H is Differentially and Abundantly Expressed in Primary Small Cell Lung Cancer (SCLC) Tumors by Proteomics Experiments were performed to determine LY6H protein expression in SCLC tumors using the following methods.

Methods

TMT10-Plex Analysis of Membrane Proteins from Human Tumors Primary SCLC tumors, normal adjacent tissue from primary tumors, and normal lung tissues were acquired as either fresh frozen or in formalin fixed paraffin embedded blocks (FFPE). Samples were enriched using standard in-house methods, digested and labeled with TMT. Up to ten samples were combined to create a TMT10-plex, which was fractionated by bRP liquid chromatography. Fractions were subjected to multi-notch LC-MS$^3$ on an Orbitrap Fusion Lumos mass spectrometer.

From 22 SCLC specimens, 867,028 peptides were identified with a false discovery rate (FDR) of 0.25%, mapping to 11,465 collapsed proteins with an FDR<2%. This filtered dataset was further processed for high quality quantification events in an automated fashion using standard in-house software described, e.g., in McAlister, G. C. et al. Multi-Notch MS3 enables accurate, sensitive, and multiplexed detection of differential expression across cancer cell line proteomes (McAlister, G. C., et al. *Anal Chem* 86, 7150-7158, 2014). iBAQ (intensity-based absolute quantification) data were presented.

Results

To identify cell surface targets that are differentially expressed in small cell lung cancer (SCLC), 22 primary small cell lung cancer (SCLC) specimens, 16 chemotherapy refractory specimens, 5 normal adjacent specimens, and 10 normal lung specimens were obtained and profiled by proteomics. LY6H was observed to be highly expressed in 68% of SCLC patients (FIG. 1). The average copy number expression of LY6H in human SCLC tumors is approximately 230,000 copies per cell, suggesting that LY6H is abundantly expressed in SCLC tumors. DLL3, which is currently being pursued in clinical trials as an antibody-drug-conjugate (ADC) in SCLC, was used as a reference (Table 1)

TABLE 1

LY6H is abundantly expressed in SCLC tumors

| Target | % pat > 5(FC) | Avg Copy# | % PDXs (RNA) | Cell Line Models | Chemo-refractory expression | PTMs in Cancer |
|---|---|---|---|---|---|---|
| LY6H | 68% | 230,000 | 17% | Limited | ✓ | n/a |
| DLL3 | 91% | 4,500 | 76% | Yes | ✓ | n/a |

% pat > 5: Percentage of patients with a >5 fold-change compared to vital organs.
Avg Copy#: Average number of Molecules/tumor lysate determined using targeted proteomics (estimating 15,000 cells = 1 ug of input protein).
% PDXs: Percentage of CrownBio SCLC PDX models > 4 on a log2 FPKM scale for given target.
Chemo-refractory expression: ✓ = expression of protein shows similar profile to primary tumors.
PTMs In Cancer: Post-translational modifications reported in PhosPhoSitePlus (phosphosite.org) in cancer cell lines or tumors.

Example 2. Generation of Human Monoclonal Antibodies Against the LY6H Extracellular Domain Experiments were performed to generate fully human antibodies against LY6H-ECD using the following methods.

Methods

Immunizations in Humanized Mice

Monoclonal antibodies were obtained by immunizing Harbour H2L2 mice with either recombinant human LY6H-ECD or BaF3 cell lines expressing full-length LY6H tagged with MYC-DDK at the C-terminus. H2L2 mice were engineered with the capacity to produce human immunoglobulins at the variable region. The mice received 5 rounds of either recombinant protein or cells by intraperitoneal injection (IP) and allowed to rest for one month. Then, the mice were boosted 4 and 2 days prior to fusion of the spleen with rabbit splenocytes expressing full length LY6H or recombinant protein of the extracelluar domain (ECD) of LY6H. Human LY6H-ECD recombinant protein was expressed in EBNA293 cells.

Recombinant LY6H Cloning

Human LY6H cDNA was purchased from Origene (RC205136, Rockville, Md.) and named BBP. The encoded protein aligns 100% with GenBank LY6H_HUMAN. *Macaca fascicularis*, rat, and mouse LY6H cDNA, were synthesized from Gen9 (Cambridge, Mass.).

Ectodomains of human, *Macaca fascicularis*, rat and mouse were cloned by either PCR (human) or synthetic genes (*Macaca fascicularis*, rat, mouse). The synthetic genes were based on GenBank sequences (Table 2). All DNA sequences were cloned into appropriate CMV-based expression vectors with non-native signal peptides and C-terminal histidine tags for purification.

TABLE 2

Source of LY6H protein sequences

| Species | GenBank Protein Reference | Sequence | SEQ ID NO |
|---|---|---|---|
| Homo sapiens (human) | LY6H_HUMAN NP_002338.3 | MLPAAMKGLGLALLAVLLCSAPAHGL WCQDCTLTTNSSHCTPKQCQPSDTVCA SVRITDPSSSRKDHSVNKMCASSDFVKR HFFSDYLMGFINSGILKVDVDCCEKDLC NGAAGAGHSPWALAGGLLLSLGPALL WAGP | 123 |
| Macaca fascicularis | LY6H_MACFA Sp_Q4R5M8 | MLPAAMKGLGLALLAVLLCSAPAHGL WCQDCTLTTNSSHCTPKQCQPSDTVCA SVRITDPSSSRKDHSVNKMCASSCDFVK RHFFSDYLMGFINSGILKVDVDCYEKDL CNGVAGAGHSPWALAGGLLLSLGPALL WAGP | 124 |
| Rattus novegicus (rat) | NP_001128311.1 | MLPAAMKSLGLALLALLLCPSPAHGLW CQDCTLANSSHCAPKQCQPTDTVCASV RITDPSSSRKDHSVNKMCASSCDFVKR HFFSDYLMGFINSGILKDVDCCEKDLCN GASAAGRSPWALAGGLLLSLGPALLW AGP | 125 |
| Mus musculus (mouse) | LY6H_MOUSE NP_035967.1 | MLPAAMKSLGLALLALLLCPSPAHGLW CQDCTLANSSHCAPKQCQPTDTVCASV RITDPSSSRKDHSVNKMCASSCDFVKR HFFSDYLMGFINSGILKVDVDCCEKDLC | 126 |

TABLE 2-continued

Source of LY6H protein sequences

| Species | GenBank Protein Reference | Sequence | SEQ ID NO |
|---|---|---|---|
| | | NGASVAGRSPWALAGGLLLSLGPALL WAGP | |

The retroviral MSCV construct was used to express full-length human LY6H protein on the surface of HEK-293T, BaF3 cells, and rabbit splenocytes (see Table 3). Mouse, rat and *Macaca fascicularis* LY6H were also expressed on the surface of HEK-293T.

TABLE 3

LY6H cell-surface expression vectors

| Plasmid name | Species | Sequence feature | Comment |
|---|---|---|---|
| BBP491 | Human | M1-P140 (Plus Myc-DDK) | Full construct |
| BBP 492/598 | *macaca Fascicularis* | M1-P140 (Plus Myc-DDK) | Full construct |
| BBP493 | Rat | M1-P139 (Plus Myc-DDK) | Full construct |
| BBP494 | Mouse | M1-P160 (Plus Myc-DDK) | Full construct |

Cloning VH and VL Sequences from Hybridomas For determination of CDR sequences, total RNA was isolated from hybridoma cells using an RNeasy® kit (Qiagen, Hilden, Germany). First and second-strand cDNA synthesis was performed using a OneTaq® One-Step RT-PCR kit (New England BioLabs, Ipswich, Mass.). Several primer sets were used (Table 4). PCR products were separated by agarose electrophoresis and fragments were excised and purified by a QIAquick® gel extraction kit (Qiagen, Hilden, Germany). Fragments were cloned directly into expression vectors with BspQI (New England BioLabs, Ipswich, Mass.) by Golden Gate cloning techniques. Four colonies from each reaction were scaled up for miniprep-scale plasmid purification by SequeMid® DNA Purification Kit (Aline Biosciences, Woburn, Mass.).

TABLE 4

Oligonucleotide Sequences

| SEQ ID NO: | Oligonucleotide Sequence | Oligonucleotide Purpose |
|---|---|---|
| 97 | ATAGCTCTTCAGGGaccATGAARCAYCTGTGGTTCTTCCT | IGHV4 leader |
| 98 | ATAGCTCTTCAGGGaccATGGACATACTTTGTTCCACGC | IGHV2 leader |
| 99 | ATAGCTCTTCAGGGaccATGGACACACTTTGCTACACAC | IGHV2-26 leader |
| 100 | ATAGCTCTTCAGGGaccATGTCTGTCTCCTTCCTCATCT | IGHV6 leader |
| 101 | ATAGCTCTTCAGGGaccATGGACTGGACCTGGAGVATC | IGHV1 leader |
| 102 | ATAGCTCTTCAGGGaccATGGACTGGATTTGGAGGRTC | IGHV1-58 leader |
| 103 | ATAGCTCTTCAGGGaccATGGACTGCACCTGGAGGATC | IGHV1-24 leader |
| 104 | ATAGCTCTTCAGGGaccATGGACTGGACCTGGAGGKTC | IGHV1-69/1-46/7-4-1 leader |
| 105 | ATAGCTCTTCAGGGaccATGGAGTTKGGRCTGAGCTGG | IGHV3 leader |
| 106 | ATAGCTCTTCAGGGaccATGGAGTTTKGGCTKAGCTGG | IGHV3-53/3-49 leader |
| 107 | ATAGCTCTTCAGGGaccATGGAACTGGGGCTCCGCTGG | IGHV3-21 leader |
| 108 | ATAGCTCTTCAGGGaccATGGARTTGGGGCTGWGCTGG | IGHV3-48/3-7 leader |
| 109 | ATAGCTCTTCAGGGaccATGGGGTCAACCGCCATCCTC | IGHV5 leader |
| 110 | ATAGCTCTTCAGGGaccATGGACATGAGGGTSCCYGCTCAGCTC | IgkV1a leader |
| 111 | ATAGCTCTTCAGGGaccATGGACATGAGRGTCCTCGCTCAGCTC | IgkV1b leader |
| 112 | ATAGCTCTTCAGGGaccATGGAAGCCCCAGCDCAGCTTCTC | IgkV3 leader |
| 113 | ATAGCTCTTCAGGGaccATGGAAACCCCAGCGCAGCTTCTC | IgkV3-20 leader |
| 114 | ATAGCTCTTCAGGGaccATGGTGTTGCAGACCCAGGTCTTC | IgkV4 leader |
| 115 | ATAGCTCTTCAGGGaccATGGGGTCCCAGGTTCACCTCCTC | IgkV5 leader |

TABLE 4-continued

Oligonucleotide Sequences

| SEQ ID NO: | Oligonucleotide Sequence | Oligonucleotide Purpose |
|---|---|---|
| 116 | ATAGCTCTTCAGGGaccATGAGGCTCCYTGCTCAGCTCCTG | IgkV2 leader |
| 117 | ATAGCTCTTCTTCGTTTGATCTCCASCTTGGTC | Kappa FW4 |
| 118 | ATAGCTCTTCTTCGTTTAATCTCCAGTCGTGTC | Kappa FW4 |
| 119 | ATAGCTCTTCTGGCTGAGGAGACGGTGACC | Heavy FW4 |
| 120 | ATAGCTCTTCATGTGACGCTGTTGTGACTCAGGA | VL-FOR L1 |
| 121 | ATAGCTCTTCATGTGACCYTGTGCTCACTCAGTC | VL-FOR L2 |
| 122 | GATGCTCTTCTGGGCTGGCCTAGGACAGTCAMCYTGG | VL-REV L |

Identification of Functional, Recombinant VH and VL Sequences

For each hybridoma, each plasmid was sent for Sanger Sequencing. These plasmids were subjected to DNA sequence determination and analysis. Unique recombinant heavy chains were paired with unique recombinant light chains. These plasmid pairs were transfected into CHO cells in 24-well plates. Ten days later conditioned medium from each pairing was screened by FLOW™ or Octet™ for binding to LY6H.

Transient Expression System of Medium Scale Antibody Production or Recombinant Proteins The LY6H recombinant proteins and anti-LY6H antibodies were expressed in Chinese hamster ovary (CHO) cells in a 100 ml volume flask using recommended transfection and media components of the ExpiCHO™ system (Invitrogen, Carlsbad, Calif.). Cell culture supernatants were harvested 14 days post-transfection, centrifuged, and filtered (0.22 um).

Purification of Recombinant His-Tagged Proteins

Conditioned medium from CHO cell cultures was clarified, filtered, and loaded onto an ÄKTAprime Plus™ system with a 5 mL HisTrap™ FF column (GE Healthcare). Fractions were collected, analyzed by SDS-PAGE, pooled, and dialyzed against PBS.

Antibody Purification

Conditioned medium from CHO cell cultures was clarified, filtered, and purified by loading onto an ÄKTA Pure™ system with a 5 mL MabSelect SuRe® column (GE Healthcare). Antibodies were eluted with 100 mM glycine, pH 3.5 and neutralized with 1M Tris-Cl, pH 8.5.

Recombinant Antibody Analyses

Concentration: Concentration of recombinant antibodies was determined on a Fortebio Octet Red™ (Pall ForteBio, Fremont, Calif.) instrument using Protein A tips and a human IgG1 antibody for the standard curve.

Purity testing by SDS-PAGE: Purity testing was performed by sodium dodecyl sulfate polyacrylamide gel electrophoresis (SDS-PAGE) of reduced and non-reduced samples. Samples (10 ug) were mixed with loading buffer (+/−β-mercaptoethanol), heated, and electrophoresed on a 4-20% gel (Invitrogen, Carlsbad, Calif.). Bands were visualized by Coomassie InstantBlue™ (Expedeon, San Diego, Calif.) staining.

Purity testing by Endotoxin: Endotoxin concentrations were measured by the Limulus amoebocyte lysate (LAL) kinetic turbidometric method using the Endosafe-PTS system (Charles River Laboratories, Wilmington, Mass.).

Purity testing by HPLC-SEC: Samples were screened for aggregation or other forms of antibody on a 1260 Infinity System™ (Agilent, Santa Clara, Calif.) with a TSKgel UltraSW Aggregate Guard™ column and HPLC column (Tosoh Bioscience). Samples and standards were detected by absorbance at 280 nm. Comparison against the standard curve provided the molar mass of sample components.

Affinity: The affinity of antibodies to various recombinant LY6H protein was determined on an Octet Red™ instrument. After loading reagents into a 96-well plate, the Octet Red with Protein A-conjugated biosensors was programmed as follows: 30 seconds for baseline #1; 120 seconds to immobilize the antibody; 30 seconds for baseline #2; 300 seconds for association of antibody to recombinant LY6H; and 300-600 seconds for dissociation of recombinant LY6H from the antibody.

Binding Competition Binning: Binding competition among different antibodies was determined using a real-time, interferometry assay on an Octet Red™ instrument with Protein A-conjugated biosensors. To assess whether two antibodies competed for binding to a recombinant LY6H protein, the assay was performed as follows. Protein A biosensors were first submerged into wells containing 10 ug/mL of individual monoclonal antibodies for 5 minutes. Following the capture step, the biosensors were dipped briefly (15 seconds) into buffer and then any unoccupied sites on the biosensor were saturated by submerging them for 5 minutes into wells containing 100 ug/mL of an irrelevant monoclonal antibody. The Octet biosensors were then dipped briefly (15 seconds) in buffer before immersion for 1 minute into wells containing recombinant LY6H. The biosensors were dipped briefly (15 seconds) in buffer before immersion for 1 minute into wells containing a second recombinant antibody.

For the control case where the second antibody was the same as the first, there was no increase in signal, because there was no additional binding to the recombinant target.

For the control case where buffer was used instead of the first antibody, no recombinant target bound the non-quenching antibody on the biosensor and no second antibody bound the biosensor.

For cases where a boost in signal was seen with the second antibody, the two antibodies were determined not to compete.

For cases where no boost in signal was seen with the second antibody, the two antibodies were determined to compete for binding.

Immunofluorescence (IF) Based High Content Screening (HCS)

High content immunofluorescence was used to identify wells that contain immunoglobulin that preferentially bound cells expressing LY6H. Briefly, 293 cells, 293-hLY6H, and H446 cells seeded 24 hours before the assay were incubated for 60 minutes at 37° C. with hybridoma supernatant diluted 2-fold in DMEM+10% fetal bovine serum (FBS). After incubation, cells were fixed in 4% formaldehyde, washed with PBS, permeabilized with 0.3% Triton-X-100, and labeled with anti-rat Alexa 488 (at hybridoma stage) or anti-human Alexa 488 secondary antibodies (with recombinant LY6H antibodies) for 1 hour at room temperature. Unbound secondary antibody was removed with PBS washes, and cells were stained with DNA dye (propidium iodide and Hoechst 33342).

Potential hits were initially identified via low-resolution, high throughput screening using a TTP Labtech Acumen eX3 (TTP Labtech, Cambridge, Mass.), quantifying the fluorescence differential for each sample on both positive and negative cell lines. Those hits were subsequently verified and the subcellular localization of each sample was characterized using a Thermo ArrayScan VTi (Thermo Fisher Scientific, Waltham, Mass.) to obtain high-resolution images of both cell lines.

Flow Cytometry

Staining for flow cytometry was performed in 1× cold PBS with 0.5% BSA. Primary antibodies (1 ug/ml) were incubated with live cells on ice for 30 minutes, after a brief wash, cells were incubated with Alexa Fluro® 488-conjugated anti-human IgG secondary antibody @1:1000 (709-546-149, Jackson ImmunoResearch). Acquisition of the data was performed on a MACSQuant® Flow Cytometers (Miltenyi Biotec) and analyzed with FlowJo software.

Results

Figure 2:
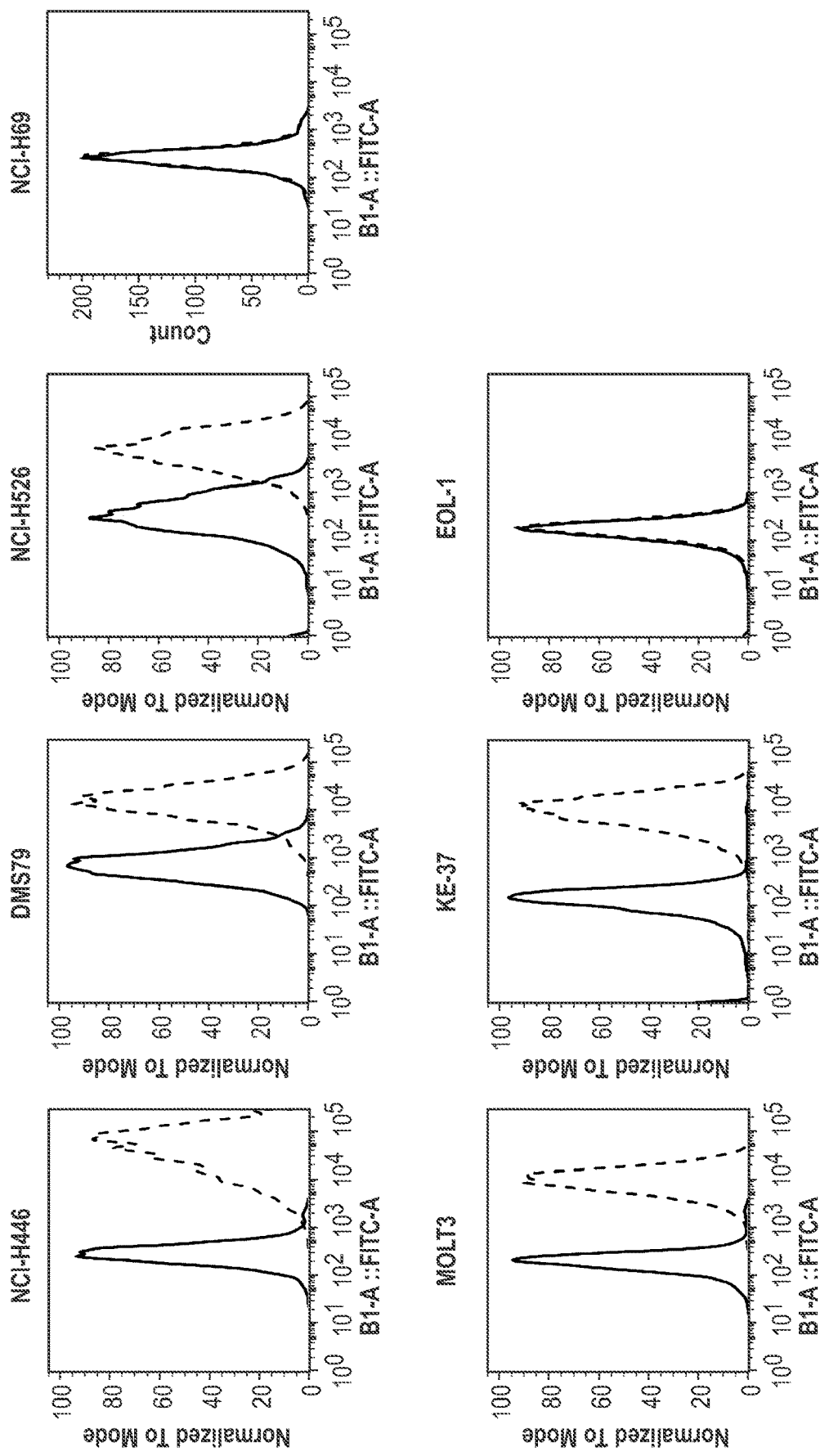
FIG. 2 shows that anti-LY6H antibody (12G7) binds both LY6H positive SCLC and T cell acute lymphoblastic leukemia (T-ALL) cell lines. Dotted lines represent LY6H antibody.

Fully human antibodies against LY6H were generated by hybridoma procedures. Briefly, H2L2 mice were immunized with either recombinant human Ly6H-ECD or BaF3 cells over-expressing LY6H and boosted with rabbit splenocytes expressing full length human LY6H or with ECD of LY6H recombinant protein. Splenocytes were fused with the mouse myeloma cell line X63-Ag8.653. Clones from H2L2 mice were identified by immunofluorescence (IF) based high content screening (HCS) on 293 cells overexpressing hLY6H, ratLy6H, and parental 293 cells not expressing LY6H, as well as endogenous small cell lung cancer (SCLC) cell line, H446. From H2L2 mice receiving either whole cell or recombinant hLY6H-ECD immunizations, over 1000 hits were identified that showed MFI ratio>10 in 293-human LY6H vs. parental 293 cells, and bind endogenous H446 SCLC cell line. 270 hits were cryopreserved and stored in liquid nitrogen. Approximately 100 clones were selected for molecular cloning. Based on unique CDR3 sequences from the heavy chain variable domain, 10 antibodies from 8 families were chosen and confirmed by flow cytometry (MACSQuant® miltenybiotec.com) on the following cell lines. The small-cell-lung cancer cells (SCLC) included H446, DMS79, and H526 cells. The T-cell acute lymphoblastic leukemia (T-ALL) cancer cells included MOLT3 and KE-37 cells. Binding properties of a representative antibody clone 12G7 is shown in FIG. 2, and summarized in Table 5.

TABLE 5

Summary of Anti-Ly6H antibodies binding to endogenous cell lines by flow cytometry

| Ab families | Clone ID | H446 | H69 | DMS79 | MOLT3 | KE-37 | EOL1 |
|---|---|---|---|---|---|---|---|
| 1 | 23F3_19B2 | (++++) | (+/−) | (+/++) | (+/++) | | (−) |
| 2 | 24A10_19B3 | (++++) | (−) | (++) | (+/++) | | (−) |
|  | 34H6_20A1 | (++++) | (+/−) | (+++) | (+++) | (+++) | (−) |
| 3 | 26F3_19B5 | (+++) | (+/−) | (++) | (+/++) | | (−) |
| 4 | 11D9_19D5 | (++++) | (+) | (+++) | (+++) | (+++) | (+) |
| 5 | 12G7_19A2 | (++++) | (−) | (+++) | (+++) | (++++) | (−) |
| 6 | 1F8_25B6 | (++++) | (−) | (+++) | (+++) | (+++) | (−) |
|  | 2B11_25D1 | (++++) | (−) | (+++) | (++/+++) | (+++) | (−) |
| 7 | 10B10_25A1 | (++++) | (+/−) | (+++) | (+++) | (++++) | (+/−) |
| 8 | 6D11_25D6 | (++++) | (+/−) | (+++) | (+++) | (++++) | (+/−) |

(−) No binding
(+) Weak binding
(++) Moderate binding
(+++) Strong binding
(++++) Very strong binding Complete amino acid sequences of the heavy and light chains from these antibodies are set forth in Table 6.

TABLE 6

CDR and variable region sequencs of human antibodies

| SEQ ID NO: | Clone Name | Protein Domain | Sequences |
|---|---|---|---|
| 1 | 6D11 | VH | QVQLQQWGAGLFKPSETLSLTCAVYGGSFSGSLWSWIRQPPGKGLEWIGEINHSGSTNYTPSLKSRVTISVDTSKNQFSLKLTSVTAADTAVYYCARGRHIVVVTAIHSPFDYWGQGTLVTVSS |

TABLE 6-continued

CDR and variable region sequences of human antibodies

| SEQ ID NO: | Clone Name | Protein Domain | Sequences |
|---|---|---|---|
| 2 | 6D11 | CDR-H1 | GGSFSGSLWS |
| 3 | 6D11 | CDR-H2 | EINHSGSTNYTPSLKS |
| 4 | 6D11 | CDR-H3 | GRHIVVVTAIHSPFDY |
| 5 | 6D11 | VL | DIQMTQSPSSLSASVGDRVTITCRASQGISNYLAWYQQKPGKVPKLL IFAASTLQSGVPSRFSGSGSGTDFTLTISSLQPEDVATYYCQKYNSA PRTFGQGTKLEIK |
| 6 | 6D11 | CDR-L1 | RASQGISNYLA |
| 7 | 6D11 | CDR-L2 | AASTLQS |
| 8 | 6D11 | CDR-L3 | QKYNSAPRT |
| 9 | 11D9 | VH | QVQLQESGPGLVKPSGTLSLTCTVSGGSISSSSWWSWVRLPPGKGLE WIGEIYHSGSTNYNPSLKSRVTISVDKSKNQFSLKLSSVTAADTAVY YCGGVRGVVMAFDIWGQGTMVTVSS |
| 10 | 11D9 | CDR-H1 | GGSISSSSWWS |
| 11 | 11D9 | CDR-H2 | EIYHSGSTNYNPSLKS |
| 12 | 11D9 | CDR-H3 | VRGVVMAFDI |
| 13 | 11D9 | VL | DIQMTQSPSSLSASVGDRVTITCRASQSISSYLNWYQQKPGKAPKLL IYAASSLQSGVPSRFSGSGSGTDFTLTISSLQPEDFATYYCQQSYST PLTFGGGTKVEIK |
| 14 | 11D9 | CDR-L1 | RASQSISSYLN |
| 15 | 11D9 | CDR-L2 | AASSLQS |
| 16 | 11D9 | CDR-L3 | QQSYSTPLT |
| 17 | 23F3 | VH | QVQLQESGPGLVKPSGTLSLTCAVSGGSISSSNWWSWVRQPPGKGLE WIGEIYHSGSTNYNPSLKSRVTISVDKSKNQFSLKLSSVTAADTAVY YCARVDILTGGNFDYWGQGTLVTVSS |
| 18 | 23F3 | CDR-H1 | GGSISSSNWWS |
| 11 | 23F3 | CDR-H2 | EIYHSGSTNYNPSLKS |
| 19 | 23F3 | CDR-H3 | VDILTGGNFDY |
| 20 | 23F3 | VL | DIQMTQSPSSLSASVGDRVTITCRASQSISSYLNWYQQKPGKAPKLL IYAASSLQSGVPSRFSGSGSGTDFTLTISSLQPEDFATYYCQQSYST PITFGQGTRLEIK |
| 14 | 23F3 | CDR-L1 | RASQSISSYLN |
| 15 | 23F3 | CDR-L2 | AASSLQS |
| 21 | 23F3 | CDR-L3 | QQSYSTPIT |
| 22 | 12G7 | VH | QVQLQQWGAGLLKPSETLSLTCAVYGGSFSGYYWSWIRQPPGKGLEW IGEINHSGSTYYNPSLKSRVTMSVDTSKNQFSLKLSSVTAADTAVYY CAKRWELGAFDIWGQGTMVTVSS |
| 23 | 12G7 | CDR-H1 | GGSFSGYYWS |
| 24 | 12G7 | CDR-H2 | EINHSGSTYYNPSLKS |
| 25 | 12G7 | CDR-H3 | RWELGAFDI |
| 26 | 12G7 | VL | DIQMTQSPSSLSASVGDRVTITCRASQGISNYLAWYQQKPGKVPKLL IYAASTLQSGVPSRFSGSGSGTDFTLTISSLQPEDVATYYCQKYNSA PRTFGQGTKLEIK |
| 6 | 12G7 | CDR-L1 | RASQGISNYLA |
| 7 | 12G7 | CDR-L2 | AASTLQS |

TABLE 6-continued

CDR and variable region sequences of human antibodies

| SEQ ID NO: | Clone Name | Protein Domain | Sequences |
|---|---|---|---|
| 8 | 12G7 | CDR-L3 | QKYNSAPRT |
| 27 | 22A5 | VH | QVQLVESGGGVVQPGRSLRLSCAASGFTFSSYGMHWVRQAPGRGLEWVAVIWYDGSNKYYADSVKGRFTISRDNSKNTLYLQMNSLRAEDTAVYYCARDLWFGESRGGMDVWGQGTTVTVSS |
| 28 | 22A5 | CDR-H1 | GFTFSSYGMH |
| 29 | 22A5 | CDR-H2 | VIWYDGSNKYYADSVKG |
| 30 | 22A5 | CDR-H3 | DLWFGESRGGMDV |
| 31 | 22A5 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPHTFGQGTKVEIK |
| 32 | 22A5 | CDR-L1 | RSSQSLLHSNGYNYLD |
| 33 | 22A5 | CDR-L2 | LGSNRAS |
| 34 | 22A5 | CDR-L3 | MQALQTPHT |
| 35 | 26F3 | VH | QVQLVESGGGVVQPGRSLRLSCAASGFTFSSYGMHWVRQAPGRGLEWVAVIWYDGSNKYYADSVKGRFTISRDNSKNTLYLQMNSLRAEDTAVYYCARRFGELLPFDYWGQGTLVTVSS |
| 28 | 26F3 | CDR-H1 | GFTFSSYGMH |
| 29 | 26F3 | CDR-H2 | VIWYDGSNKYYADSVKG |
| 36 | 26F3 | CDR-H3 | RFGELLPFDY |
| 37 | 26F3 | VL | DIVMTQSPLSLPVTPGEPASISCRSSQSLLHSNGYNYLDWYLQKPGQSPQLLIYLGSNRASGVPDRFSGSGSGTDFTLKISRVEAEDVGVYYCMQALQTPWTFGQGTKVEIK |
| 32 | 26F3 | CDR-L1 | RSSQSLLHSNGYNYLD |
| 33 | 26F3 | CDR-L2 | LGSNRAS |
| 38 | 26F3 | CDR-L3 | MQALQTPWT |
| 39 | 35H10 | VH | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARDGGQWLVQGYFDYWGQGTLVTVSS |
| 28 | 35H10 | CDR-H1 | GFTFSSYGMH |
| 29 | 35H10 | CDR-H2 | VIWYDGSNKYYADSVKG |
| 40 | 35H10 | CDR-H3 | DGGQWLVQGYFDY |
| 41 | 35H10 | VL | DIQMTQSPSTLSASVGDRVTITCRASQSISSWLAWYQQKPGKAPKLLIYKASSLESGVPSRFSGSGSGTEFTLTISSLQPDDFATYYCQQYNSYSRTFGQGTKVEIK |
| 42 | 35H10 | CDR-L1 | RASQSISSWLA |
| 43 | 35H10 | CDR-L2 | KASSLES |
| 44 | 35H10 | CDR-L3 | QQYNSYSRT |
| 45 | 1F8 | VH | QVQLVESGGGVVQPGRSLRLSCAASGFTFSNYGMHWVRQAPGKGLEWVAVIWYDGSYKYYADSVKGRFTISRDNSKNTLYLQMNSLRTEDTAVYYCARSIVVVTATLDYWGQGTLVTVSS |
| 46 | 1F8 | CDR-H1 | GFTFSNYGMH |
| 47 | 1F8 | CDR-H2 | VIWYDGSYKYYADSVKG |
| 48 | 1F8 | CDR-H3 | SIVVVTATLDY |
| 49 | 1F8 | VL | EIVMTQSPATLSVSPGERATLSCRASQSVSSNLAWYQQKPGQAPRLLIYGASTRATGIPARFSGSGSGTEFTLTISSLQSEDFAVYYCQHYNNWPPLTFGGGTKLEIK |

TABLE 6-continued

CDR and variable region sequences of human antibodies

| SEQ ID NO: | Clone Name | Protein Domain | Sequences |
|---|---|---|---|
| 50 | 1F8 | CDR-L1 | RASQSVSSNLA |
| 51 | 1F8 | CDR-L2 | GASTRAT |
| 52 | 1F8 | CDR-L3 | QHYNNWPPLT |
| 53 | 2B11 | VH | QVQLVESGGGVVQPGRSLRLSCAASGFTFSNYGMHWVRQAPGKGLEWVAVIWYDGSNKYYADSVKGRFTISRDNSKNTLYLQMNSLRTEDTAVYYCARSIVVVTATLDYWGQGTLVTVSS |
| 46 | 2B11 | CDR-H1 | GFTFSNYGMH |
| 29 | 2B11 | CDR-H2 | VIWYDGSNKYYADSVKG |
| 48 | 2B11 | CDR-H3 | SIVVVTATLDY |
| 49 | 2B11 | VL | EIVMTQSPATLSVSPGERATLSCRASQSVSSNLAWYQQKPGQAPRLLIYGASTRATGIPARFSGSGSGTEFTLTISSLQSEDFAVYYCQHYNNWPPLTFGGGTKLEIK |
| 50 | 2B11 | CDR-L1 | RASQSVSSNLA |
| 51 | 2B11 | CDR-L2 | GASTRAT |
| 52 | 2B11 | CDR-L3 | QHYNNWPPLT |
| 54 | 24A10 | VH | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARSIVVVVAVLDYWGQGTLVTVSS |
| 28 | 24A10 | CDR-H1 | GFTFSSYGMH |
| 29 | 24A10 | CDR-H2 | VIWYDGSNKYYADSVKG |
| 55 | 24A10 | CDR-H3 | SIVVVVAVLDY |
| 56 | 24A10 | VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPPITFGQGTRLEIK |
| 50 | 24A10 | CDR-L1 | RASQSVSSNLA |
| 51 | 24A10 | CDR-L2 | GASTRAT |
| 57 | 24A10 | CDR-L3 | QQYNNWPPIT |
| 58 | 34H6 | VH | QVQLVESGGGVVQPGRSLRLSCAASGFTFSSYGMHWVRQAPGKGLEWVAVIWYDGSNKYYADSVKGRFTISRDNSKNTLYLQMNSLRAEDTAVYYCARSIVVVTGFGDYWGQGTLVTVSS |
| 28 | 34H6 | CDR-H1 | GFTFSSYGMH |
| 29 | 34H6 | CDR-H2 | VIWYDGSNKYYADSVKG |
| 59 | 34H6 | CDR-H3 | SIVVVTGFGDY |
| 56 | 34H6 | VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPPITFGQGTRLEIK |
| 50 | 34H6 | CDR-L1 | RASQSVSSNLA |
| 51 | 34H6 | CDR-L2 | GASTRAT |
| 57 | 34H6 | CDR-L3 | QQYNNWPPIT |
| 60 | 10B10 | VH | QVQLQQWGAGLLKPSETLSLTCAVYGGSFSGYYWHWIRQPPGKGLEWIGEINHSESTKYNPSLKSRVTISVDTSKNQFSLKLSSVTGADTAVYYCARGQHIVVVTDSLGDYWGQGTLVTVSS |
| 61 | 10B10 | CDR-H1 | GGSFSGYYWH |
| 62 | 10B10 | CDR-H2 | EINHSESTKYNPSLKS |

TABLE 6-continued

CDR and variable region sequencs of human antibodies

| SEQ ID NO: | Clone Name | Protein Domain | Sequences |
|---|---|---|---|
| 63 | 10B10 | CDR-H3 | GQHIVVVTDSLGDY |
| 26 | 10B10 | VL | DIQMTQSPSSLSASVGDRVTITCRASQGISNYLAWYQQKPGKVPKLL IYAASTLQSGVPSRFSGSGSGTDFTLTISSLQPEDVATYYCQKYNSA PRTFGQGTKLEIK |
| 6 | 10B10 | CDR-L1 | RASQGISNYLA |
| 7 | 10B10 | CDR-L2 | AASTLQS |
| 8 | 10B10 | CDR-L3 | QKYNSAPRT |
| 64 | 12G7-S54A | VH | QVQLQQWGAGLLKPSETLSLTCAVYGGSFSGYYWSWIRQPPGKGLEW IGEINHAGSTYYNPSLKSRVTMSVDTSKNQFSLKLSSVTAADTAVYY CAKRWELGAFDIWGQGTMVTVSS |
| 23 | 12G7-S54A | CDR-H1 | GGSFSGYYWS |
| 65 | 12G7-S54A | CDR-H2 | EINHAGSTYYNPSLKS |
| 25 | 12G7-S54A | CDR-H3 | RWELGAFDI |
| 26 | 12G7-S54A | VL | DIQMTQSPSSLSASVGDRVTITCRASQGISNYLAWYQQKPGKVPKLL IYAASTLQSGVPSRFSGSGSGTDFTLTISSLQPEDVATYYCQKYNSA PRTFGQGTKLEIK |
| 6 | 12G7-S54A | CDR-L1 | RASQGISNYLA |
| 7 | 12G7-S54A | CDR-L2 | AASTLQS |
| 8 | 12G7-S54A | CDR-L3 | QKYNSAPRT |
| 66 | 12G7-N52Q | VH | QVQLQQWGAGLLKPSETLSLTCAVYGGSFSGYYWSWIRQPPGKGLEW IGEIQHSGSTYYNPSLKSRVTMSVDTSKNQFSLKLSSVTAADTAVYY CAKRWELGAFDIWGQGTMVTVSS |
| 23 | 12G7-N52Q | CDR-H1 | GGSFSGYYWS |
| 67 | 12G7-N52Q | CDR-H2 | EIQHSGSTYYNPSLKS |
| 25 | 12G7-N52Q | CDR-H3 | RWELGAFDI |
| 26 | 12G7-N52Q | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPRTFGQGTKLEIK |
| 6 | 12G7-N52Q | CDR-L1 | RASQGISNYLA |
| 7 | 12G7-N52Q | CDR-L2 | AASTLQS |
| 8 | 12G7-N52Q | CDR-L3 | QKYNSAPRT |
| 68 | 6D11-41B4 | VH | QVQLQQWGAGLFRPSETLSLTCAVYGGSFSGSLWSWIRQPPGRGLE WIGEINHAGSTQYTPSLKSRVTISVDTSKNQFSLKLTSVTAADTAV YYCARGRHIVVVTAIHSPFDYWGQGTLVTVSS |
| 2 | 6D11-41B4 | CDR-H1 | GGSFSGSLWS |
| 69 | 6D11-41B4 | CDR-H2 | EINHAGSTQYTPSLKS |

TABLE 6-continued

CDR and variable region sequencs of human antibodies

| SEQ ID NO: | Clone Name | Protein Domain | Sequences |
|---|---|---|---|
| 4 | 6D11-41B4 | CDR-H3 | GRHIVVVTAIHSPFDY |
| 5 | 6D11-41B4 | VL | DIQMTQSPSSLSASVGDRVTITCRASQGISNYLAWYQQKPGKVPKL LIFAASTLQSGVPSRFSGSGSGTDFTLTISSLQPEDVATYYCQKYN SAPRTFGQGTKLEIK |
| 6 | 6D11-41B4 | CDR-L1 | RASQGISNYLA |
| 7 | 6D11-41B4 | CDR-L2 | AASTLQS |
| 8 | 6D11-41B4 | CDR-L3 | QKYNSAPRT |
| 70 | 10B10-S54A | VH | QVQLQQWGAGLLKPSETLSLTCAVYGGSFSGYYWHWIRQPPGKGLE WIGEINHAESTKYNPSLKSRVTISVDTSKNQFSLKLSSVTGADTAV YYCARGQHIVVVTDSLGDYWGQGTLVTVSS |
| 61 | 10B10-S54A | CDR-H1 | GGSFSGYYWH |
| 71 | 10B10-S54A | CDR-H2 | EINHAESTKYNPSLKS |
| 63 | 10B10-S54A | CDR-H3 | GQHIVVVTDSLGDY |
| 26 | 10B10-S54A | VL | DIQMTQSPSSLSASVGDRVTITCRASQGISNYLAWYQQKPGKVPKL LIYAASTLQSGVPSRFSGSGSGTDFTLTISSLQPEDVATYYCQKYN SAPRTFGQGTKLEIK |
| 6 | 10B10-S54A | CDR-L1 | RASQGISNYLA |
| 7 | 10B10-S54A | CDR-L2 | AASTLQS |
| 8 | 10B10-S54A | CDR-L3 | QKYNSAPRT |

The nucleotide (DNA) sequences of the heavy and light chains from the antibodies described in Table 6 are set forth in Table 7.

TABLE 7

Variable region DNA sequencs of human antibodies

| SEQ ID NO: | Clone Name | Protein Domain | DNA Sequences |
|---|---|---|---|
| 72 | 6D11 | VH | CAGGTGCAGCTACAGCAATGGGGCGCAGGACTGTTTAAGCCTTCGGA GACCCTGTCCCTCACCTGCGCTGTCTATGGTGGGTCCTTCAGTGGTT CCCTCTGGAGCTGGATCCGCCAGCCCCCAGGGAAGGGGCTGGAGTGG ATTGGGGAAATCAATCATAGTGGAAGCACCAACTACACCCCGTCCCT CAAGAGTCGAGTCACCATATCAGTAGACACGTCCAAGAACCAGTTCT CTCTGAAGCTGACCTCTGTGACCGCCGCGGACACGGCTGTGTATTAC TGTGCGAGAGGCCGGCATATTGTGGTGGTGACTGCTATCCATTCGCC TTTTGACTACTGGGGCCAGGGAACCCTGGTCACCGTCTCCTCA |
| 73 | 6D11 | VL | GACATCCAGATGACCCAGTCTCCATCCTCCCTGTCTGCATCTGTAGG AGACAGAGTCACCATCACTTGCCGGGCGAGTCAGGGCATTAGCAATT ATTTAGCCTGGTATCAGCAGAAACCAGGGAAAGTTCCTAAGCTCCTG ATCTTTGCTGCATCCACTTTGCAATCAGGGGTCCCATCTCGGTTCAG TGGCAGTGGATCTGGGACAGATTTCACTCTCACCATCAGCAGCCTGC AGCCTGAAGATGTTGCAACTTATTACTGTCAAAAGTATAACAGTGCC CCTCGGACGTTCGGCCAAGGGACCAAGCTGGAGATCAAA |

TABLE 7-continued

Variable region DNA sequencs of human antibodies

| SEQ ID NO: | Clone Name | Protein Domain | DNA Sequences |
|---|---|---|---|
| 74 | 11D9 | VH | CAGGTGCAGCTGCAGGAGTCGGGCCCAGGACTGGTGAAGCCTTCGGG GACCCTGTCCCTCACCTGCACTGTCTCTGGTGGCTCCATCAGCAGTA GTAGCTGGTGGAGTTGGGTCCGCCTGCCCCCAGGGAAGGGGCTGGAG TGGATTGGGGAAATCTATCATAGTGGGAGCACCAACTACAACCCGTC CCTCAAGAGTCGAGTCACCATATCAGTGGACAAGTCCAAGAACCAGT TCTCCCTGAAGCTGAGCTCTGTGACCGCCGCGGACACGGCCGTCTAT TACTGTGGAGGGGTTCGGGGAGTTGTGATGGCTTTTGATATCTGGGG CCAAGGGACAATGGTCACCGTCTCCTCA |
| 75 | 11D9 | VL | GACATCCAGATGACCCAGTCTCCATCCTCCCTGTCTGCATCTGTAGG AGACAGAGTCACCATCACTTGCCGGGCAAGTCAGAGCATTAGCAGTT ATTTAAATTGGTATCAGCAGAAACCAGGGAAAGCCCCTAAGCTCCTG ATCTATGCTGCATCCAGTTTGCAAAGTGGGGTCCCATCAAGGTTCAG TGGCAGTGGATCTGGGACAGACTTCACTCTCACCATCAGCAGTCTGC AACCTGAAGATTTTGCAACTTACTACTGTCAACAGAGTTACAGTACC CCGCTCACTTTCGGCGGAGGGACCAAGGTGGAGATCAAA |
| 76 | 23F3 | VH | CAGGTGCAGCTGCAGGAGTCGGGCCCAGGACTGGTGAAGCCTTCGGG GACCCTGTCCCTCACCTGCGCTGTCTCTGGTGGCTCCATCAGCAGTA GTAACTGGTGGAGTTGGGTCCGCCAGCCCCCAGGGAAGGGGCTGGAG TGGATTGGGGAAATCTATCATAGTGGGAGCACCAACTACAACCCGTC CCTCAAGAGTCGAGTCACCATATCAGTAGACAAGTCCAAGAACCAGT TCTCCCTGAAGCTGAGCTCTGTGACCGCCGCGGACACGGCCGTGTAT TACTGTGCGAGAGTCGATATTTTGACTGGTGGTAACTTTGACTACTG GGGCCAGGGAACCCTGGTCACCGTCTCCTCA |
| 77 | 23F3 | VL | GACATCCAGATGACCCAGTCTCCATCCTCCCTGTCTGCATCTGTAGG AGACAGAGTCACCATCACTTGCCGGGCAAGTCAGAGCATTAGCAGCT ATTTAAATTGGTATCAGCAGAAACCAGGGAAAGCCCCTAAGCTCCTG ATCTATGCTGCATCCAGTTTGCAAAGTGGGGTCCCATCAAGGTTCAG TGGCAGTGGATCTGGGACAGATTTCACTCTCACCATCAGCAGTCTGC AACCTGAAGATTTTGCAACTTACTACTGTCAACAGAGTTACAGTACC CCGATCACCTTCGGCCAAGGGACACGACTGGAGATTAAA |
| 78 | 12G7 | VH | CAGGTGCAGCTACAGCAGTGGGGCGCAGGACTGTTGAAGCCTTCGGA GACCCTGTCCCTCACCTGCGCTGTCTATGGTGGGTCCTTCAGTGGTT ACTACTGGAGCTGGATCCGCCAGCCCCCAGGGAAGGGGCTGGAGTGG ATTGGGGAAATCAATCATAGTGGAAGCACCTACTACAACCCGTCCCT CAAGAGTCGAGTCACCATGTCAGTAGACACGTCCAAGAACCAGTTCT CCCTGAAGCTGAGCTCTGTGACCGCCGCGGACACGGCTGTTTATTAC TGTGCGAAAAGATGGGAGCTTGGTGCTTTTGATATCTGGGGCCAAGG GACAATGGTCACCGTCTCCTCA |
| 79 | 12G7 | VL | GACATCCAGATGACCCAGTCTCCATCCTCCCTGTCTGCATCTGTAGG AGACAGAGTCACCATCACTTGCCGGGCGAGTCAGGGCATTAGCAATT ATTTAGCCTGGTATCAGCAGAAACCAGGGAAAGTTCCTAAGCTCCTG ATCTATGCTGCATCCACTTTGCAATCAGGGGTCCCATCTCGGTTCAG TGGCAGTGGATCTGGGACAGATTTCACTCTCACCATCAGCAGCCTGC AGCCTGAAGATGTTGCAACTTATTACTGTCAAAAGTATAACAGTGCC CCTCGGACGTTCGGCCAAGGGACCAAGCTGGAGATCAAA |
| 80 | 22A5 | VH | CAGGTGCAGCTGGTGGAGTCTGGGGGAGGCGTGGTCCAGCCTGGGAG GTCCCTGAGACTCTCCTGTGCAGCGTCTGGATTCACCTTCAGTAGCT ATGGCATGCACTGGGTCCGCCAGGCTCCAGGCAAGGGGCTGGAGTGG GTGGCAGTTATATGGTATGATGGAAGTAATAAATACTATGCAGACTC CGTGAAGGGCCGATTCACCATCTCCAGAGACAATTCCAAGAACACGC TGTATCTGCAAATGAACAGCCTGAGAGCCGAGGACACGGCTGTGTAT TACTGTGCGAGAGATCTATGGTTCGGGGAGTCCCGGGGCGGTATGGA CGTCTGGGGCCAAGGGACCACGGTCACCGTCTCCTCA |
| 81 | 22A5 | VL | GATATTGTGATGACTCAGTCTCCACTCTCCCTGCCCGTCACCCCTGG AGAGCCGGCCTCCATCTCCTGCAGGTCTAGTCAGAGCCTCCTGCATA GTAATGGATACAACTATTTGGATTGGTACCTGCAGAAGCCAGGGCAG TCTCCACAGCTCCTGATCTATTTGGGTTCTAATCGGGCCTCCGGGGT CCCTGACAGGTTCAGTGGCAGTGGATCAGGCACAGATTTTACACTGA AAATCAGCAGAGTGGAGGCTGAGGATGTTGGGGTTTATTACTGCATG CAAGCTCTACAAACTCCTCACACTTTTGGCCAGGGGACCAAGGTGGA GATCAAA |
| 82 | 26F3 | VH | CAGGTGCAGCTGGTGGAGTCTGGGGGAGGCGTGGTCCAGCCTGGGAG GTCCCTGAGACTCTCCTGTGCAGCGTCTGGATTCACCTTCAGTAGCT ATGGCATGCACTGGGTCCGCCAGGCTCCAGGCAAGGGGCTGGAGTGG GTGGCAGTTATATGGTATGATGGAAGTAATAAATACTATGCAGACTC CGTGAAGGGCCGATTCACCATCTCCAGAGACAATTCCAAGAACACGC |

TABLE 7-continued

Variable region DNA sequencs of human antibodies

| SEQ ID NO: | Clone Name | Protein Domain | DNA Sequences |
|---|---|---|---|
| | | | TGTATCTGCAAATGAACAGCCTGAGAGCCGAGGACACGGCTGTGTAT<br>TACTGTGCGAGGAGGTTCGGGGAGTTATTGCCTTTTGACTACTGGGG<br>CCAGGGAACCCTGGTCACCGTCTCCTCA |
| 83 | 26F3 | VL | GACATCCAGTTGACCCAGTCTCCATCCTTCCTGTCTGCATCTGTAGG<br>AGACAGAGTCACCATCACTTGCCGGGCCAGTCAGGGCATTAGCAGTT<br>ATTTAGCCTGGTATCAGCAAAAACCAGGGAAAGCCCCTAAGCTCCTG<br>ATCTATGCTGCATCCACTTTGCAAAGTGGGGTCCCATCAAGGTTCAG<br>CGGCAGTGGATCTGGGACAGAATTCACTCTCACAATCAGCAGCCTGC<br>AGCCTGAAGATTTTGCAACTTATTACTGTCAACAGCTTAATAGTTAC<br>CCGCTCACTTTCGGCGGAGGGACCAAGCTGGAGATCAAA |
| 84 | 35H10 | VH | CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAGCT<br>ATGGCATGCACTGGGTCCGCCAGGCTCCAGGCAAGGGGCTGGAGTGG<br>GTGGCAGTTATATGGTATGATGGAAGTAATAAATACTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGAGATGGAGGGCAGTGGCTGGTACAAGGCTACTTTGA<br>CTACTGGGGCCAGGGAACCCTGGTCACCGTCTCCTCA |
| 85 | 35H10 | VL | GACATCCAGATGACCCAGTCTCCTTCCACCCTGTCTGCATCTGTAGG<br>AGACAGAGTCACCATCACTTGCCGGGCCAGTCAGAGTATTAGTAGCT<br>GGTTGGCCTGGTATCAGCAGAAACCAGGGAAAGCCCCTAAGCTCCTG<br>ATCTATAAGGCGTCTAGTTTAGAAAGTGGGGTCCCATCAAGGTTCAG<br>CGGCAGTGGATCTGGGACAGAATTCACTCTCACCATCAGCAGCCTGC<br>AGCCTGATGATTTTGCAACTTATTACTGCCAACAGTATAATAGTTAT<br>TCTCGGACGTTCGGCCAAGGGACCAAGGTGGAGATCAAA |
| 86 | 1F8 | VH | CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAACT<br>ATGGCATGCACTGGGTCCGCCAGGCTCCAGGCAAGGGGCTGGAGTGG<br>GTGGCAGTTATATGGTATGATGGAAGTTATAAATACTATGCAGACTC<br>CGTGAAGGGCCGATTCACCATCTCCAGAGACAATTCCAAGAACACGC<br>TGTATCTGCAAATGAACAGCCTGAGAACCGAGGACACGGCTGTATAT<br>TATTGTGCGAGGTCTATTGTGGTGGTGACTGCTACTCTTGACTACTG<br>GGGCCAGGGAACCCTGGTCACCGTCTCCTCA |
| 87 | 1F8 | VL | GAAATAGTGATGACGCAGTCTCCAGCCACCCTGTCTGTGTCTCCAGG<br>GGAAAGAGCCACCCTCTCCTGCAGGGCCAGTCAGAGTGTTAGCAGCA<br>ACTTAGCCTGGTACCAGCAGAAACCTGGCCAGGCTCCCAGGCTCCTC<br>ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCACTATAATAACTGG<br>CCTCCCCTCACTTTCGGCGGAGGGACCAAGCTGGAGATCAAA |
| 88 | 2B11 | VH | CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAACT<br>ATGGCATGCACTGGGTCCGCCAGGCTCCAGGCAAGGGGCTGGAGTGG<br>GTGGCAGTTATATGGTATGATGGAAGTAATAAATACTATGCAGACTC<br>CGTGAAGGGCCGATTCACCATCTCCAGAGACAATTCCAAGAACACGC<br>TGTATCTGCAAATGAACAGCCTGAGAACCGAGGACACGGCTGTGTAT<br>TACTGTGCGAGGTCTATTGTGGTGGTGACTGCTACTCTTGACTACTG<br>GGGCCAGGGAACCCTGGTCACCGTCTCCTCA |
| 87 | 2B11 | VL | GAAATAGTGATGACGCAGTCTCCAGCCACCCTGTCTGTGTCTCCAGG<br>GGAAAGAGCCACCCTCTCCTGCAGGGCCAGTCAGAGTGTTAGCAGCA<br>ACTTAGCCTGGTACCAGCAGAAACCTGGCCAGGCTCCCAGGCTCCTC<br>ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCACTATAATAACTGG<br>CCTCCCCTCACTTTCGGCGGAGGGACCAAGCTGGAGATCAAA |
| 89 | 24A10 | VH | CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAGCT<br>ATGGCATGCACTGGGTCCGCCAGGCTCCAGGCAAGGGGCTGGAGTGG<br>GTGGCAGTTATATGGTATGATGGAAGTAATAAATACTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGAAGTATTGTAGTGGTGGTAGCTGTCCTTGACTACTG<br>GGGCCAGGGAACCCTGGTCACCGTCTCCTCA |
| 90 | 24A10 | VL | GAAATAGTGATGACGCAGTCTCCAGCCACCCTGTCTGTGTCTCCAGG<br>GGAAAGAGCCACCCTCTCCTGCAGGGCCAGTCAGAGTGTTAGCAGCA<br>ACTTAGCCTGGTACCAGCAGAAACCTGGCCAGGCTCCCAGGCTCCTC |

TABLE 7-continued

Variable region DNA sequencs of human antibodies

| SEQ ID NO: | Clone Name | Protein Domain | DNA Sequences |
|---|---|---|---|
| | | | ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCAGTATAATAACTGG<br>CCTCCGATCACCTTCGGCCAAGGGACACGACTGGAGATTAAA |
| 91 | 34H6 | VH | CAGGTGCAGCTGGTGGAGTCTGGGGGAGGCGTGGTCCAGCCTGGGAG<br>GTCCCTGAGACTCTCCTGTGCAGCGTCTGGATTCACCTTCAGTAGCT<br>ATGGCATGCACTGGGTCCGCCAGGCTCCAGGCAAGGGGCTGGAGTGG<br>GTGGCAGTTATATGGTATGATGGAAGTAATAAATACTATGCAGACTC<br>CGTGAAGGGCCGATTCACCATCTCCAGAGACAATTCCAAGAACACGC<br>TGTATCTGCAAATGAACAGCCTGAGAGCCGAGGACACGGCTGTGTAT<br>TACTGTGCGAGGTCTATTGTGGTGGTGACTGGATTCGGGGACTACTG<br>GGGCCAGGGAACCCTGGTCACCGTCTCCTCA |
| 90 | 34H6 | VL | GAAATAGTGATGACGCAGTCTCCAGCCACCCTGTCTGTGTCTCCAGG<br>GGAAAGAGCCACCCTCTCCTGCAGGGCCAGTCAGAGTGTTAGCAGCA<br>ACTTAGCCTGGTACCAGCAGAAACCTGGCCAGGCTCCCAGGCTCCTC<br>ATCTATGGTGCATCCACCAGGGCCACTGGTATCCCAGCCAGGTTCAG<br>TGGCAGTGGGTCTGGGACAGAGTTCACTCTCACCATCAGCAGCCTGC<br>AGTCTGAAGATTTTGCAGTTTATTACTGTCAGCAGTATAATAACTGG<br>CCTCCGATCACCTTCGGCCAAGGGACACGACTGGAGATTAAA |
| 92 | 10B10 | VH | CAGGTGCAGTTACAGCAGTGGGGCGCAGGACTGTTGAAGCCTTCGGA<br>GACCCTGTCCCTCACCTGCGCTGTCTATGGTGGGTCCTTCAGTGGTT<br>ACTACTGGCACTGGATCCGCCAGCCCCCAGGGAAGGGGCTGGAGTGG<br>ATTGGGGAAATCAATCATAGTGAAAGCACCAAGTACAACCCGTCCCT<br>CAAGAGTCGAGTCACCATATCAGTAGACACGTCCAAGAACCAGTTCT<br>CCCTGAAGCTGAGCTCTGTGACCGGCGCGGACACGGCTGTGTATTAC<br>TGTGCGAGAGGCCAACATATTGTGGTGGTGACTGATTCTCTGGGGGA<br>CTACTGGGGCCAGGGAACCCTGGTCACCGTCTCCTCA |
| 79 | 10B10 | VL | GACATCCAGATGACCCAGTCTCCATCCTCCCTGTCTGCATCTGTAGG<br>AGACAGAGTCACCATCACTTGCCGGGCGAGTCAGGGCATTAGCAATT<br>ATTTAGCCTGGTATCAGCAGAAACCAGGGAAAGTTCCTAAGCTCCTG<br>ATCTATGCTGCATCCACTTTGCAATCAGGGGTCCCATCTCGGTTCAG<br>TGGCAGTGGATCTGGGACAGATTTCACTCTCACCATCAGCAGCCTGC<br>AGCCTGAAGATGTTGCAACTTATTACTGTCAAAAGTATAACAGTGCC<br>CCTCGGACGTTCGGCCAAGGGACCAAGCTGGAGATCAAA |
| 93 | 12G7-S54A | VH | CAGGTGCAGCTACAGCAGTGGGGCGCAGGACTGTTGAAGCCTTCGGA<br>GACCCTGTCCCTCACCTGCGCTGTCTATGGTGGGTCCTTCAGTGGTT<br>ACTACTGGAGCTGGATCCGCCAGCCCCCAGGGAAGGGGCTGGAGTGG<br>ATTGGGGAAATCAATCATgcTGGAAGCACCTACTACAACCCGTCCCT<br>CAAGAGTCGAGTCACCATGTCAGTAGACACGTCCAAGAACCAGTTCT<br>CCCTGAAGCTGAGCTCTGTGACCGCCGCGGACACGGCTGTTTATTAC<br>TGTGCGAAAAGATGGGAGCTTGGTGCTTTTGATATCTGGGGCCAAGG<br>GACAATGGTCACCGTCTCCTCA |
| 79 | 12G7-S54A | VL | GACATCCAGATGACCCAGTCTCCATCCTCCCTGTCTGCATCTGTAGG<br>AGACAGAGTCACCATCACTTGCCGGGCGAGTCAGGGCATTAGCAATT<br>ATTTAGCCTGGTATCAGCAGAAACCAGGGAAAGTTCCTAAGCTCCTG<br>ATCTATGCTGCATCCACTTTGCAATCAGGGGTCCCATCTCGGTTCAG<br>TGGCAGTGGATCTGGGACAGATTTCACTCTCACCATCAGCAGCCTGC<br>AGCCTGAAGATGTTGCAACTTATTACTGTCAAAAGTATAACAGTGCC<br>CCTCGGACGTTCGGCCAAGGGACCAAGCTGGAGATCAAA |
| 94 | 12G7-N52Q | VH | CAGGTGCAGCTACAGCAGTGGGGCGCAGGACTGTTGAAGCCTTCGGA<br>GACCCTGTCCCTCACCTGCGCTGTCTATGGTGGGTCCTTCAGTGGTT<br>ACTACTGGAGCTGGATCCGCCAGCCCCCAGGGAAGGGGCTGGAGTGG<br>ATTGGGGAAATCcAgCATAGTGGAAGCACCTACTACAACCCGTCCCT<br>CAAGAGTCGAGTCACCATGTCAGTAGACACGTCCAAGAACCAGTTCT<br>CCCTGAAGCTGAGCTCTGTGACCGCCGCGGACACGGCTGTTTATTAC<br>TGTGCGAAAAGATGGGAGCTTGGTGCTTTTGATATCTGGGGCCAAGG<br>GACAATGGTCACCGTCTCCTCA |
| 79 | 12G7-N52Q | VL | GACATCCAGATGACCCAGTCTCCATCCTCCCTGTCTGCATCTGTAG<br>GAGACAGAGTCACCATCACTTGCCGGGCGAGTCAGGGCATTAGCAA<br>TTATTTAGCCTGGTATCAGCAGAAACCAGGGAAAGTTCCTAAGCTC<br>CTGATCTATGCTGCATCCACTTTGCAATCAGGGGTCCCATCTCGGT<br>TCAGTGGCAGTGGATCTGGGACAGATTTCACTCTCACCATCAGCAG<br>CCTGCAGCCTGAAGATGTTGCAACTTATTACTGTCAAAAGTATAAC<br>AGTGCCCCTCGGACGTTCGGCCAAGGGACCAAGCTGGAGATCAAA |
| 95 | 6D11-41B4 | VH | CAGGTGCAGCTACAGCAATGGGGCGCAGGACTGTTTAAGCCTTCGG<br>AGACCCTGTCCCTCACCTGCGCTGTCTATGGTGGGTCCTTCAGTGG |

TABLE 7-continued

Variable region DNA sequencs of human antibodies

| SEQ ID NO: | Clone Name | Protein Domain | DNA Sequences |
|---|---|---|---|
| | | | TTCCCTCTGGAGCTGGATCCGCCAGCCCCAGGGAAGGGGCTGGAG<br>TGGATTGGGGAAATCAATCATGCTGGAAGCACCCAGTACACCCCGT<br>CCCTCAAGAGTCGAGTCACCATATCAGTAGACACGTCCAAGAACCA<br>GTTCTCTCTGAAGCTGACCTCTGTGACCGCCGCGGACACGGCTGTG<br>TATTACTGTGCGAGAGGCCGGCATATTGTGGTGGTGACTGCTATCC<br>ATTCGCCTTTTGACTACTGGGGCCAGGGAACCCTGGTCACCGTCTC<br>CTCA |
| 73 | 6D11-41B4 | VL | GACATCCAGATGACCCAGTCTCCATCCTCCCTGTCTGCATCTGTAG<br>GAGACAGAGTCACCATCACTTGCCGGGCGAGTCAGGGCATTAGCAA<br>TTATTTAGCCTGGTATCAGCAGAAACCAGGGAAAGTTCCTAAGCTC<br>CTGATCTTTGCTGCATCCACTTTGCAATCAGGGGTCCCATCTCGGT<br>TCAGTGGCAGTGGATCTGGGACAGATTTCACTCTCACCATCAGCAG<br>CCTGCAGCCTGAAGATGTTGCAACTTATTACTGTCAAAAGTATAAC<br>AGTGCCCCTCGGACGTTCGGCCAAGGGACCAAGCTGGAGATCAAA |
| 96 | 10B10-S54A | VH | CAGGTGCAGTTACAGCAGTGGGGCGCAGGACTGTTGAAGCCTTCGG<br>AGACCCTGTCCCTCACCTGCGCTGTCTATGGTGGGTCCTTCAGTGG<br>TTACTACTGGCACTGGATCCGCCAGCCCCAGGGAAGGGGCTGGAG<br>TGGATTGGGGAAATCAATCATGCTGAAAGCACCAAGTACAACCCGT<br>CCCTCAAGAGTCGAGTCACCATATCAGTAGACACGTCCAAGAACCA<br>GTTCTCCCTGAAGCTGAGCTCTGTGACCGGCGCGGACACGGCTGTG<br>TATTACTGTGCGAGAGGCCAACATATTGTGGTGGTGACTGATTCTC<br>TGGGGGACTACTGGGGCCAGGGAACCCTGGTCACCGTCTCCTCA |
| 79 | 10B10-S54A | VL | GACATCCAGATGACCCAGTCTCCATCCTCCCTGTCTGCATCTGTAG<br>GAGACAGAGTCACCATCACTTGCCGGGCGAGTCAGGGCATTAGCAA<br>TTATTTAGCCTGGTATCAGCAGAAACCAGGGAAAGTTCCTAAGCTC<br>CTGATCTATGCTGCATCCACTTTGCAATCAGGGGTCCCATCTCGGT<br>TCAGTGGCAGTGGATCTGGGACAGATTTCACTCTCACCATCAGCAG<br>CCTGCAGCCTGAAGATGTTGCAACTTATTACTGTCAAAAGTATAAC<br>AGTGCCCCTCGGACGTTCGGCCAAGGGACCAAGCTGGAGATCAAA |

Some antibody sequences with a nonconsensus N-linked glycosylation site have been modified at either the Asn site or the Ser/Thr site. Where possible, the Asn or Ser/Thr codons can be mutated back to the germline sequence. In addition, replacing the Asn with Gln or similar amino acid and the Ser or Thr with a similar or smaller amino acid offer a reasonable chance of success.

In one case, antibody 12G7 with a dissociation constant (KD) value of 4 nM, contained a non-consensus N-linked glycosylation site in CDR2 of the VH sequence. This heavy chain was engineered to contain a Ser54Ala mutation. The new heavy chain plasmid was paired with the original light chain sequence and transfected into CHO cells. The antibody was screened for expression and affinity for human LY6H. The 12G7-S54A antibody had a KD value of 4 nM.

In a second case, antibody 10B10 with a dissociation constant (KD) value of 47 nM, contained a non-consensus N-linked glycosylation site in CDR2 of the VH sequence. This heavy chain was engineered to contain a Ser54Ala mutation. The new heavy chain plasmid was paired with the original light chain sequence and transfected into CHO cells. The antibody was screened for expression and affinity for human LY6H. The 10B10-S54A antibody had a KD value of 42 nM.

In a third case, antibody 6D11 with a dissociation constant (KD) value of 22 nM, contained two non-consensus N-linked glycosylation sites in CDR2 of the VH sequence. This heavy chain was engineered to contain Ser54Ala or Ser54Ala/Asn58Gln or Ser54Ala/Thr60Ala mutations. The new heavy chain plasmids were paired with the original light chain sequence and transfected into CHO cells. The antibody was screened for expression and affinity for human LY6H. The 6D11-41B4 antibody containing the Ser54Ala/Asn58Gn mutations had a KD value of 25 nM.

Affinity constant values (KD) of several anti-LY6H antibodies are set forth in Table 8.

TABLE 8

Affinity constant values of antibodies to human LY6H

| Antibody | KD (nM) |
|---|---|
| 12G7 | 4 |
| 12G7-S54A | 4 |
| 6D11 | 22 |
| 6D11-41B4 | 25 |
| 11D9 | 31 |
| 1F8 | 33 |
| 10B10 | 47 |
| 10B10-S54A | 42 |

Example 3. Antigen Density of LY6H in SCLC Cell Lines

Experiments were performed to determine LY6H antigen density in SCLC cell lines. The following methods were used.

Methods

Tissue Culture and Cell Lines

Human SCLC cancer cell lines H446, DMS79, NCI-H526, H69, NCI-H220, NCI-H1092, NCI-H2141, CORL47, and CORL95 were obtained from American Type Culture Collection (ATCC). Human leukemia cell lines MOLT3 and KE-37 were purchased from DSMZ. NCI-H1092 and NCI-H2141 cells were maintained in HITS medium. Other cell lines were maintained in RPMI-1640 medium (Invitrogen) with 10% fetal bovine serum (FBS) (Sigma).

Antigen Density Measurement

The antigen density of LY6H on the cell surface of cancer cell lines was quantified using BD Quantibrite™ Beads PE fluorescence Quantitation kit (BD Bioscience, Cat. #340495) and a human LY6H antibody (12G7) conjugated to the fluorochrome PE.

Results

PE conjugated anti-LY6H antibody (12G7) was chosen to evaluate antigen density in SCLC, and T-ALL (MOLT3, KE-37) cell lines, with H69 cell line as a negative control. Cell surface LY6H density is estimated at 0-250,000 sites per cell for the panel of cancer cell lines tested, with the highest surface expression level in H446 cells (Table 9).

TABLE 9

Antigen density of LY6H in a panel of cancer cell lines.

| Cell lines | Cell Surface Ag density |
| --- | --- |
| H446 | 251543 |
| DMS79 | 39203 |
| H526 | 10083 |
| CORL47 | 10986 |
| CORL95 | 19101 |
| CORL279 | 768 |
| NCI-H220 | 36983 |
| NCI-H1092 | 44286 |
| NCI-H2141 | 16193 |
| H69 | 0 |
| MOLT3 | 12539 |
| KE-37 | 24811 |

Example 4. Binding of Anti-LY6H Monoclonal Antibodies to LY6H Orthologs

Experiments were performed to determine the binding of anti-LY6H human monoclonal antibodies to LY6H in different species using the following methods.

Methods

Tissue Culture and Cell Lines 293T cell line was purchased from American Type Culture Collection (ATCC). 293T cells expressing human, Macaca fascicularis, rat, and mouse LY6H were maintained in DMEM medium (Invitrogen) with 10% fetal bovine serum (FBS) (Sigma) in the presence of 2 ug/ml puromycin (Invitrogen).

Flow Cytometry

Staining for flow cytometry was performed in 1× cold PBS with 0.5% BSA. Primary antibodies (1 ug/ml) were incubated with live cells on ice for 30 minutes. After a brief wash, cells were incubated with Alexa Fluro® 488-conjugated anti-human IgG secondary antibody @1:1000 (709-546-149, Jackson ImmunoResearch). Acquisition of the data was performed on a MACSQuant© Flow Cytometers (Miltenyi Biotec) and analyzed with FlowJo™ software.

Results

Figure 3A:
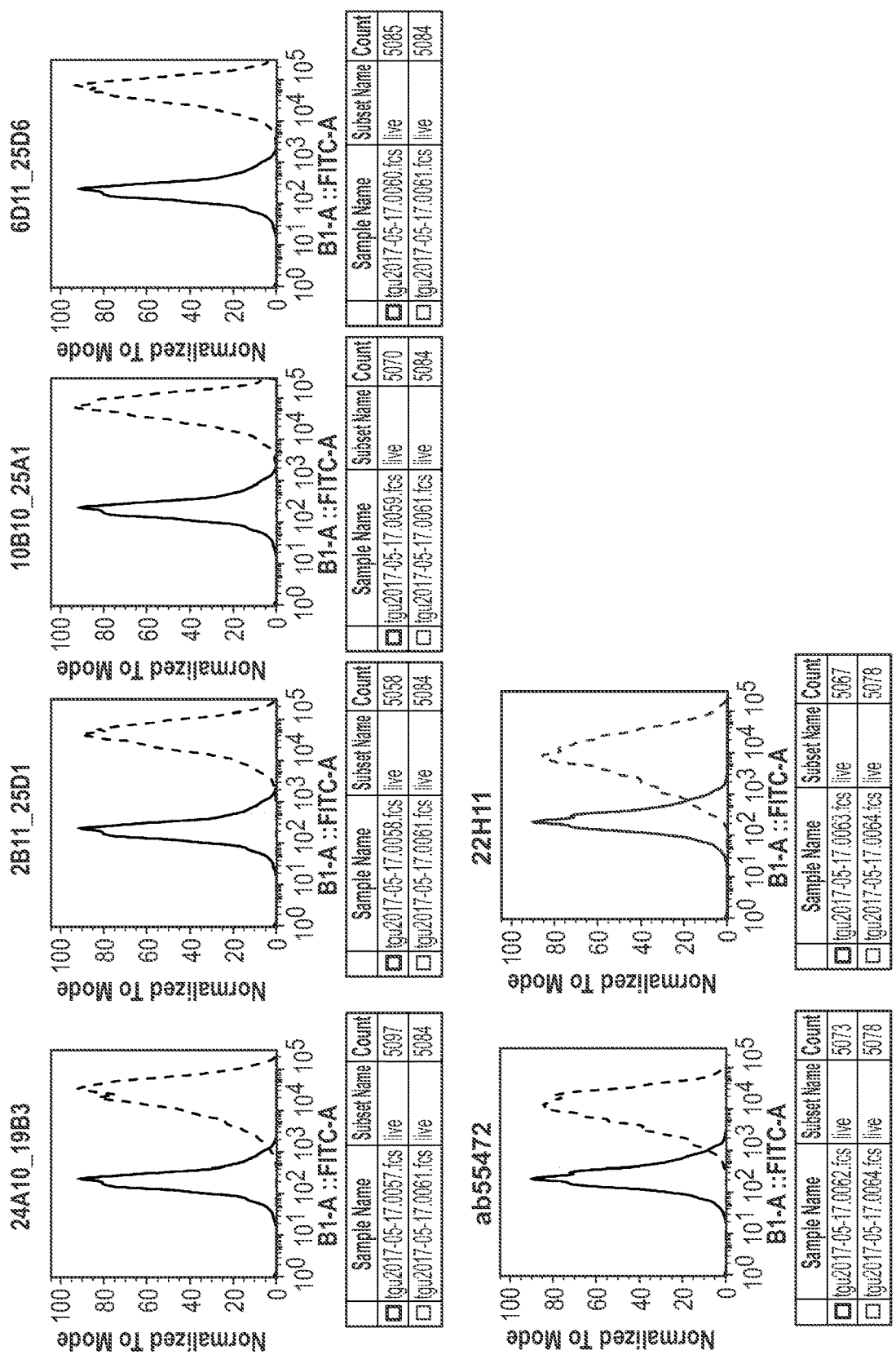
FIG. 3A, FIG. 3B, FIG. 3C, FIG. 3D, and FIG. 3E show internalization and in vitro efficacy of anti-LY6H antibodies. Anti-LY6H antibodies were evaluated for cell surface binding to 293 cells expressing human (A), *Macaca fascicularis* (B), rat (C), mouse LY6H (D), and mock transfection (E) by flow. ab55472 (abeam) and 22H11 are mouse antibodies against human LY6H. Dotted lines represent LY6H antibody. hIgG1 (antibody against HBV surface antigen) was included as a negative control (solid lines).
Figure 3B:
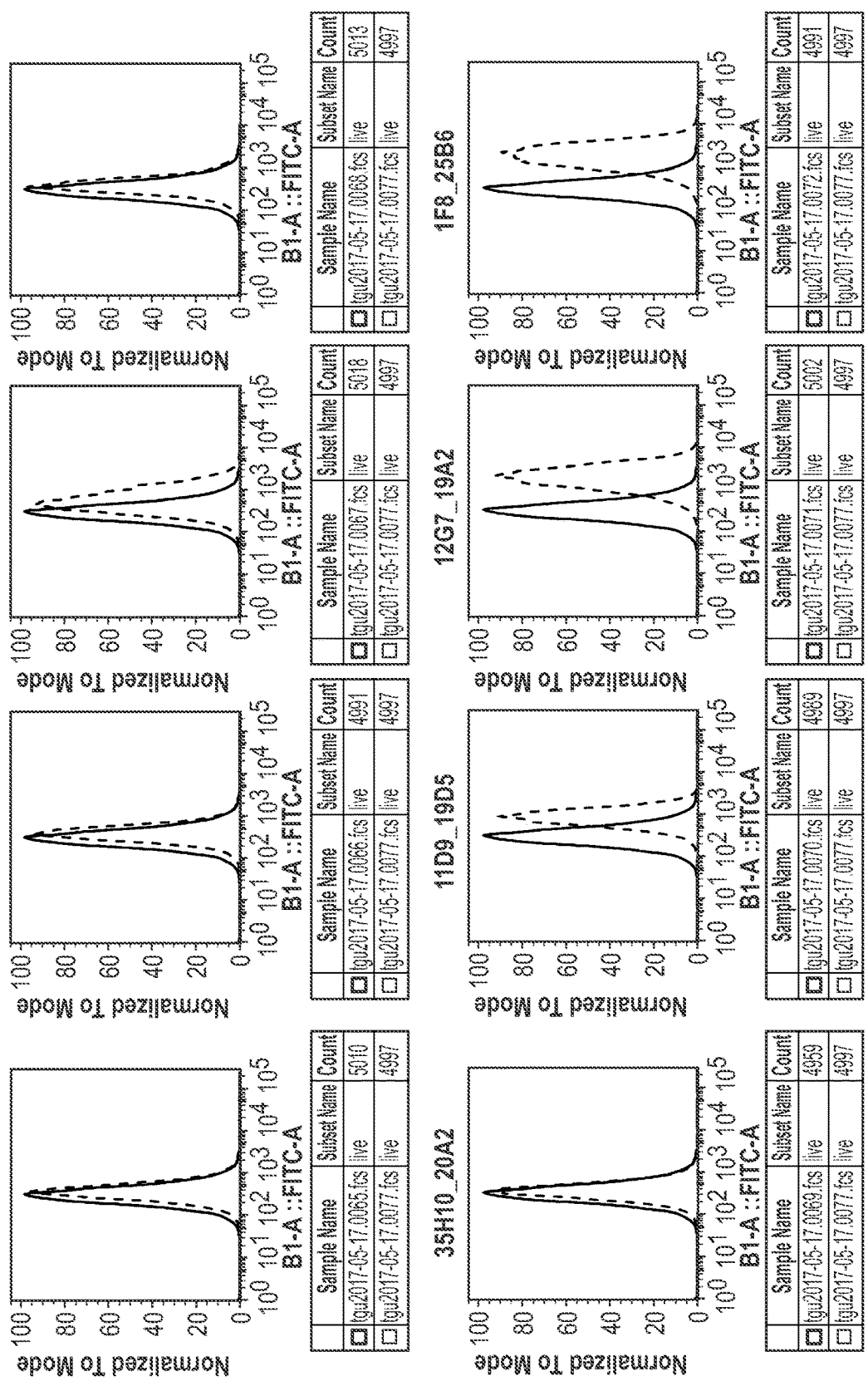
Figure 3B:
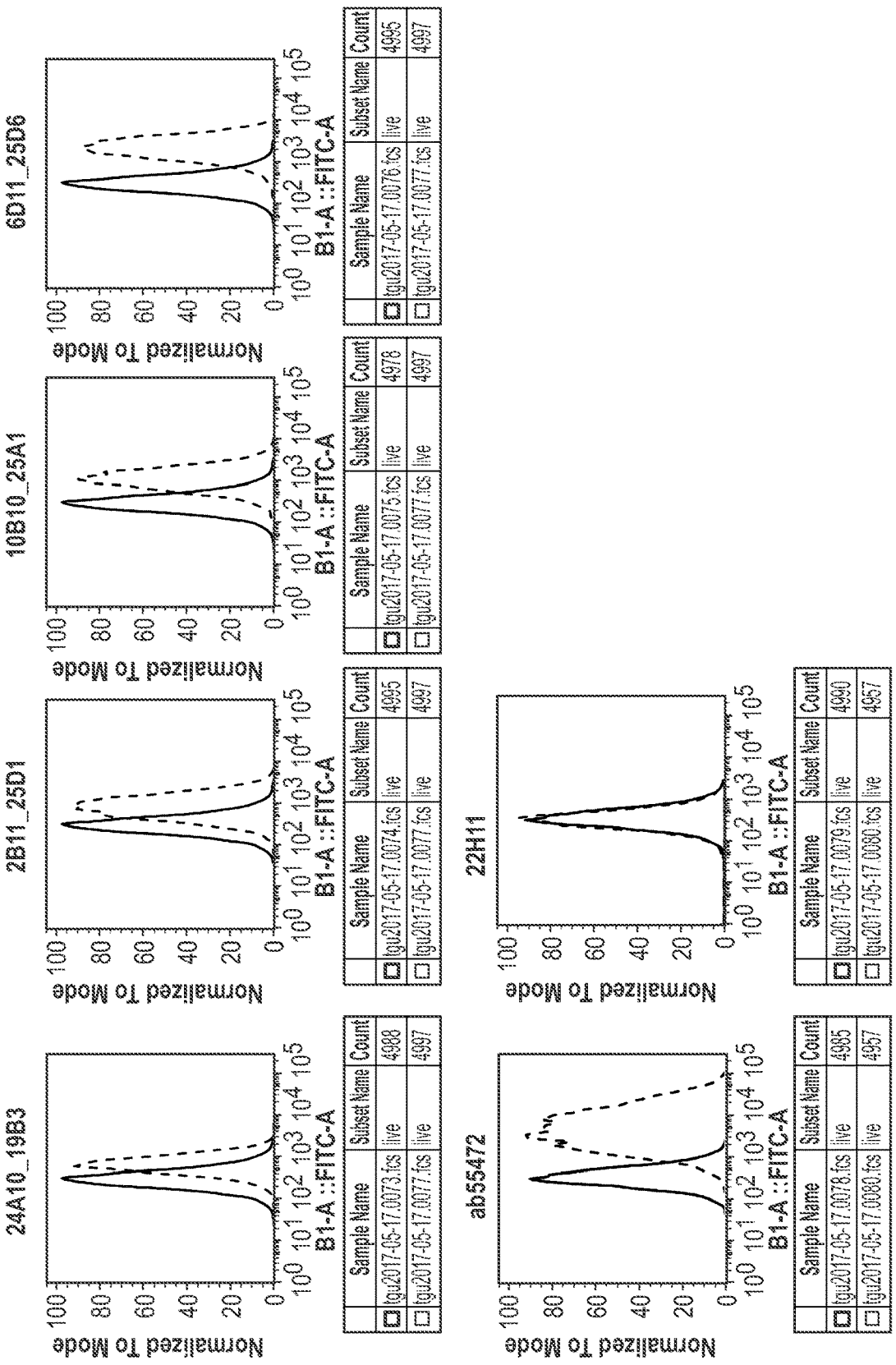
Figure 3C:
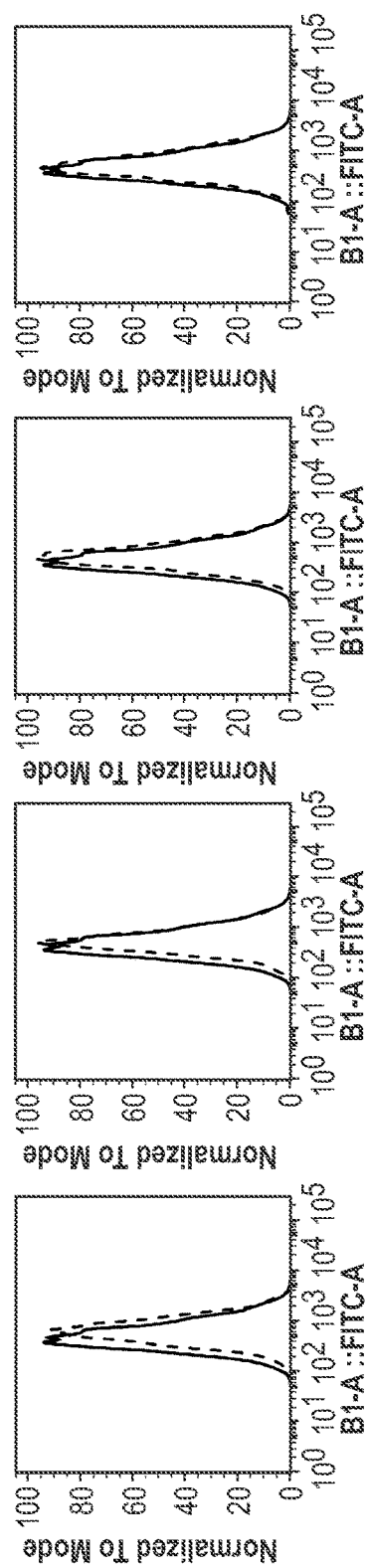
Figure 3C:
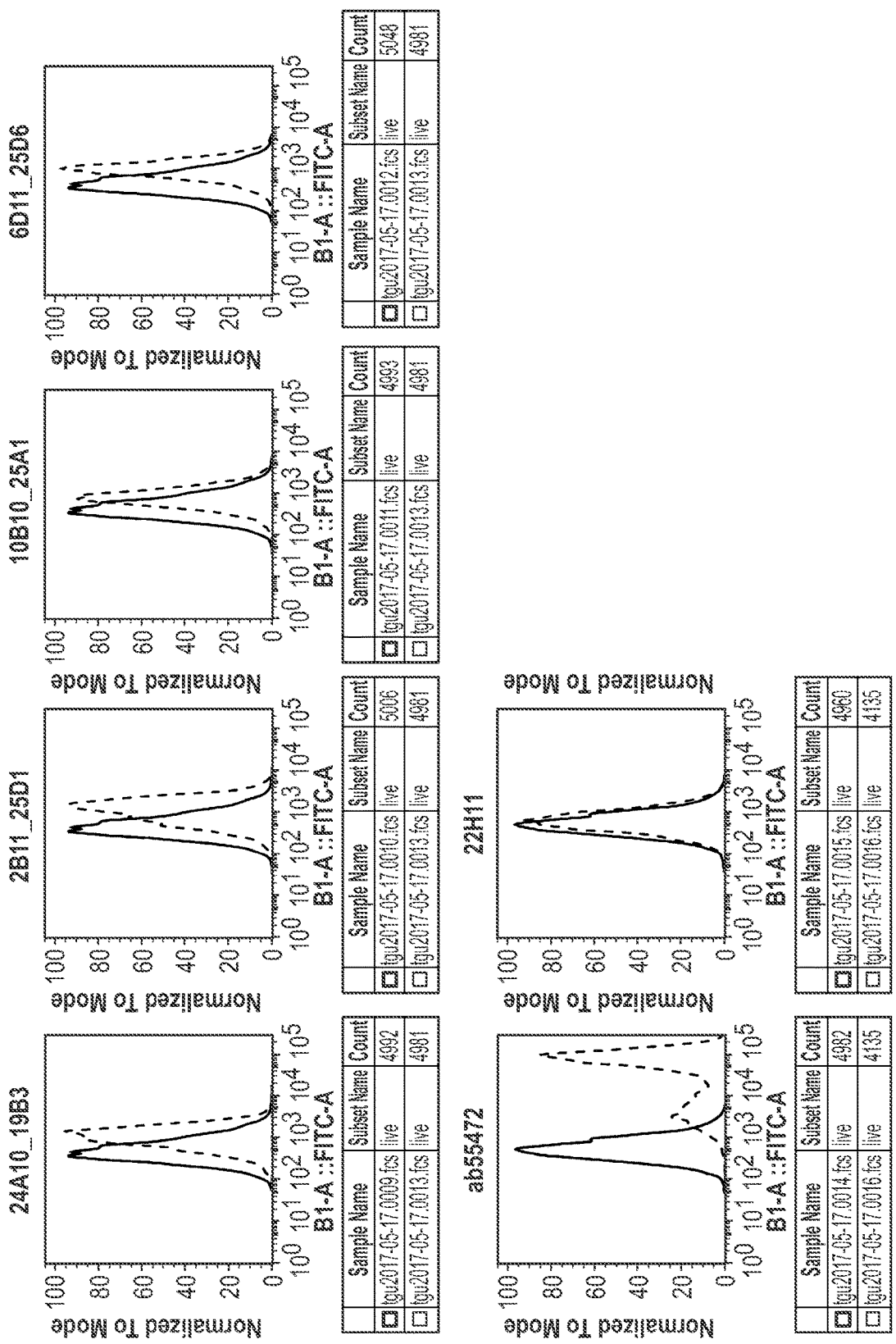
Figure 3D:
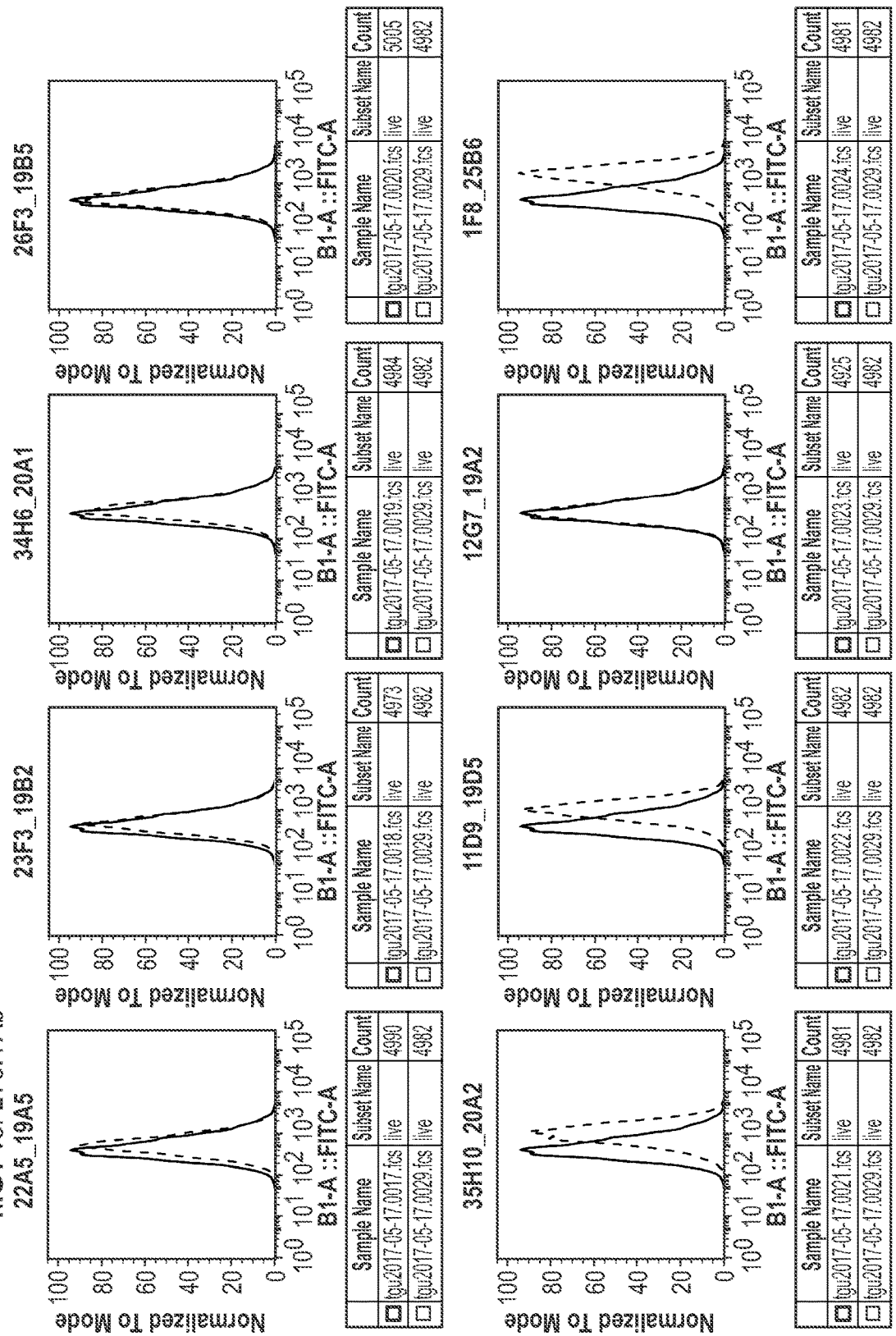
Figure 3D:
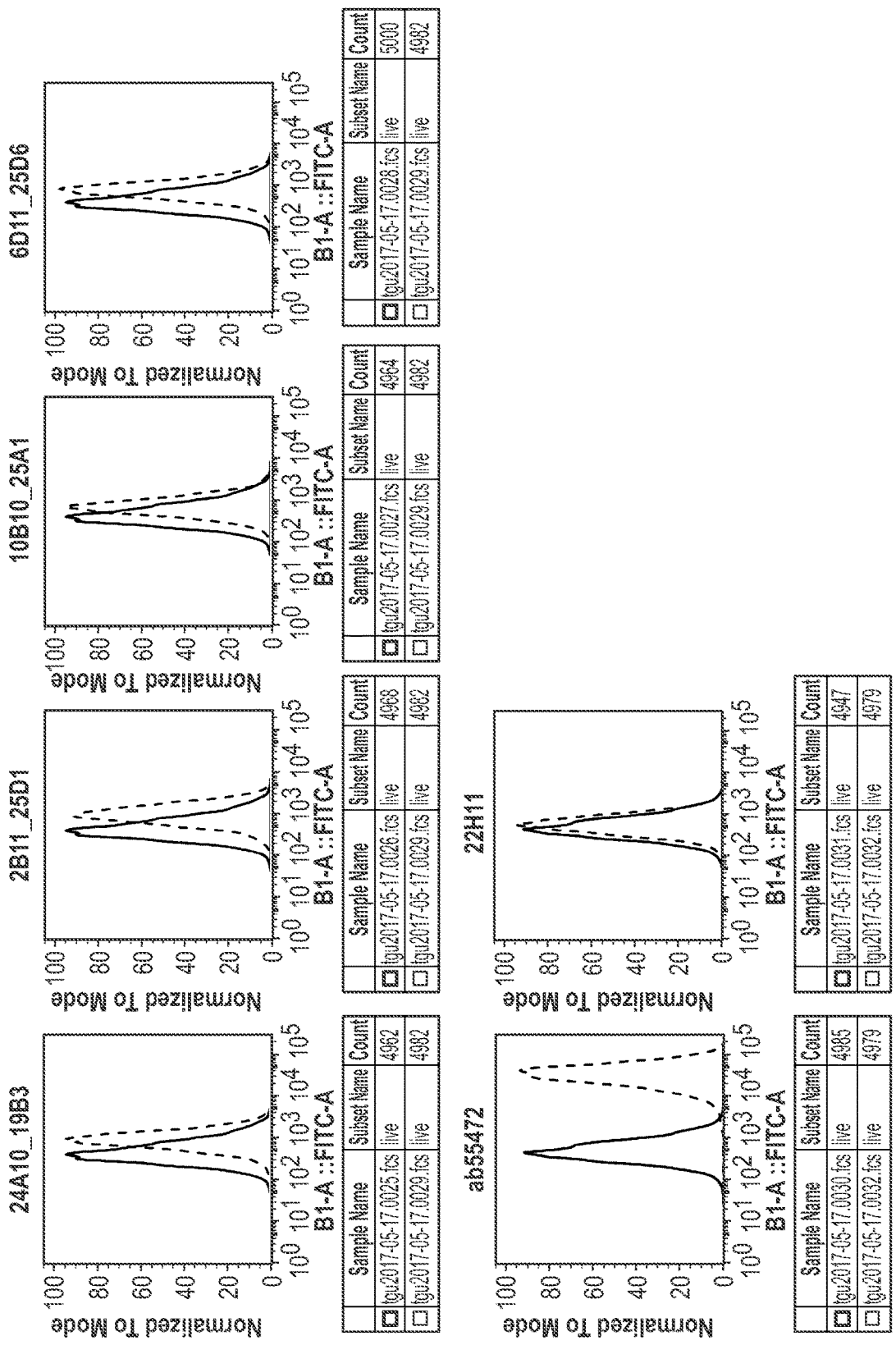
Figure 3E:
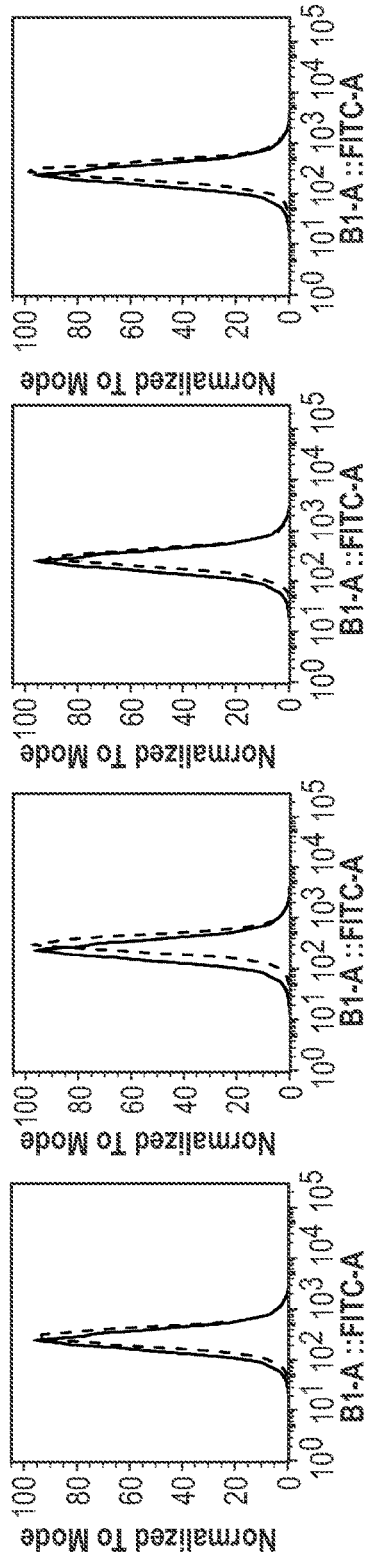
Figure 3E:
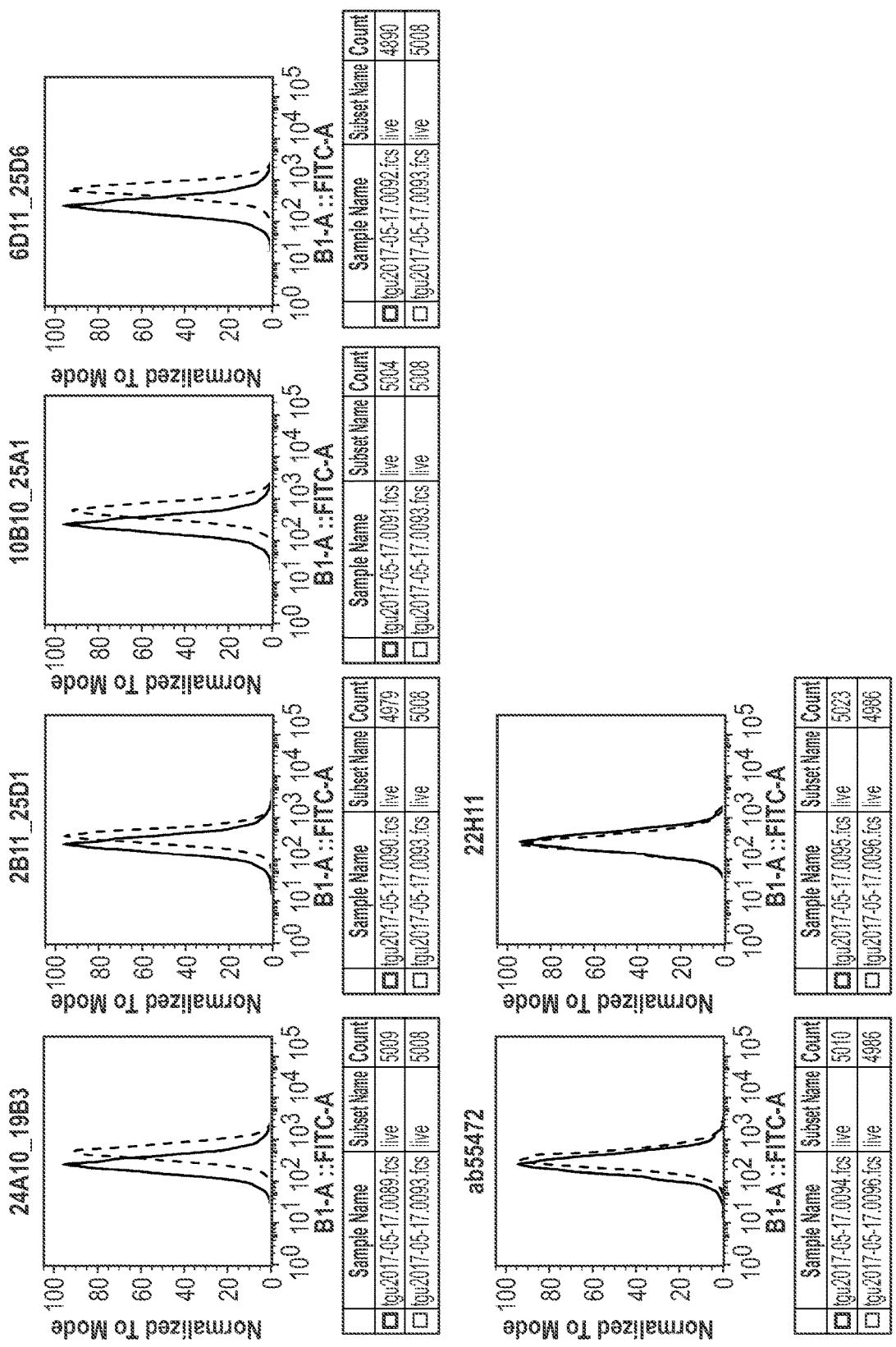

To evaluate the binding of anti-LY6H human monoclonal antibodies to LY6H in different species. 293 cells overexpressing human, Macaca fascicularis, rat, and mouse LY6H were generated. While all antibodies bind human and Macaca fascicularis LY6H (FIG. 3A and FIG. 3B), none of them bind efficiently to 293 cells expressing either rat or mouse LY6H (FIG. 3C and FIG. 3D).

Example 5. Estimation of Apparent Antibody Affinity by Flow-Based Assay

Experiments were performed to characterize $EC_{50}$ of anti-LY6H antibodies using the following methods.

Methods

Measurement of Antibody $EC_{50}$ by Flow Cytometry The assay uses 3-5 fold dilutions (from 100 nM to 0.1 nM) of antibody of a stock antibody concentration (100 nM) in binding buffer. Serial diluted antibodies were incubated with live cells on ice for 30 minutes, after a brief wash, cells were incubated with Alexa Fluro® 488-conjugated anti-human IgG secondary antibody @1:100, or 15 ug/ml (709-546-149, Jackson ImmunoResearch). Acquisition of the MFI (Median Fluorescent Intensity) was performed on a MACSQuant® Flow Cytometers (Miltenyi Biotec). $EC_{50}$ was calculated using Dose-response $EC_{50}$ shift by global fitting from GraphPad Prism.

Figures 4A, 4B:
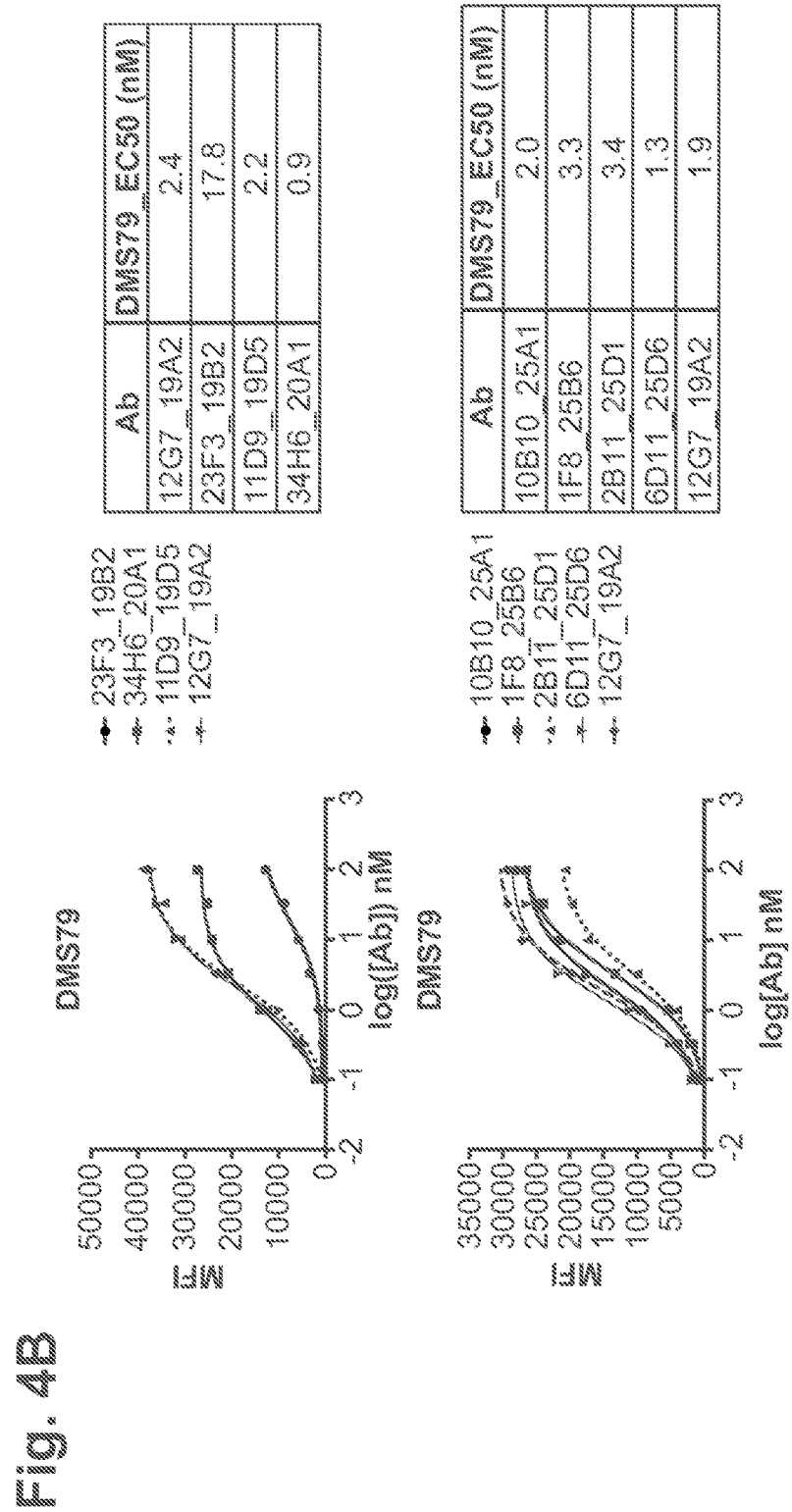
FIG. 4A, FIG. 4B, FIG. 4C and FIG. 4D show half maximal effective concentration ($EC_{50}$) of anti-LY6H antibodies in SCLC and T-ALL cell lines.
Figure 4C:
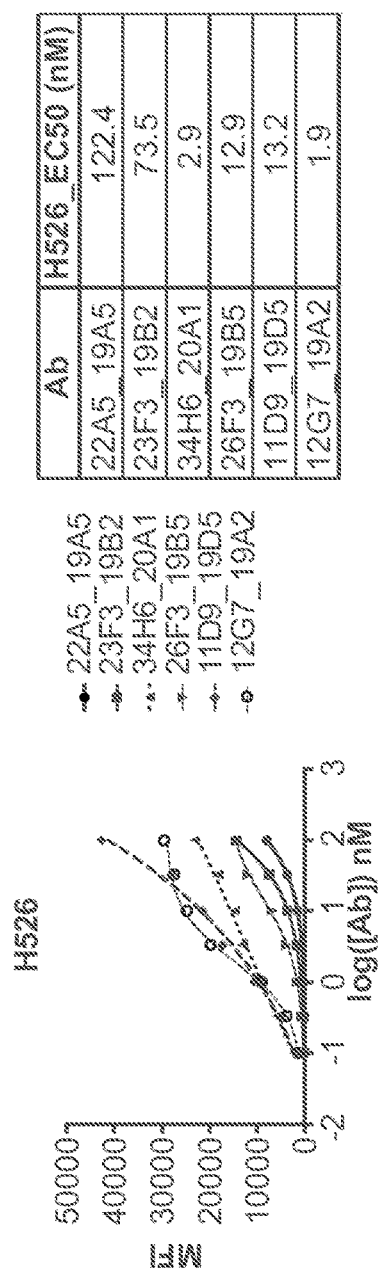
Figure 4D:
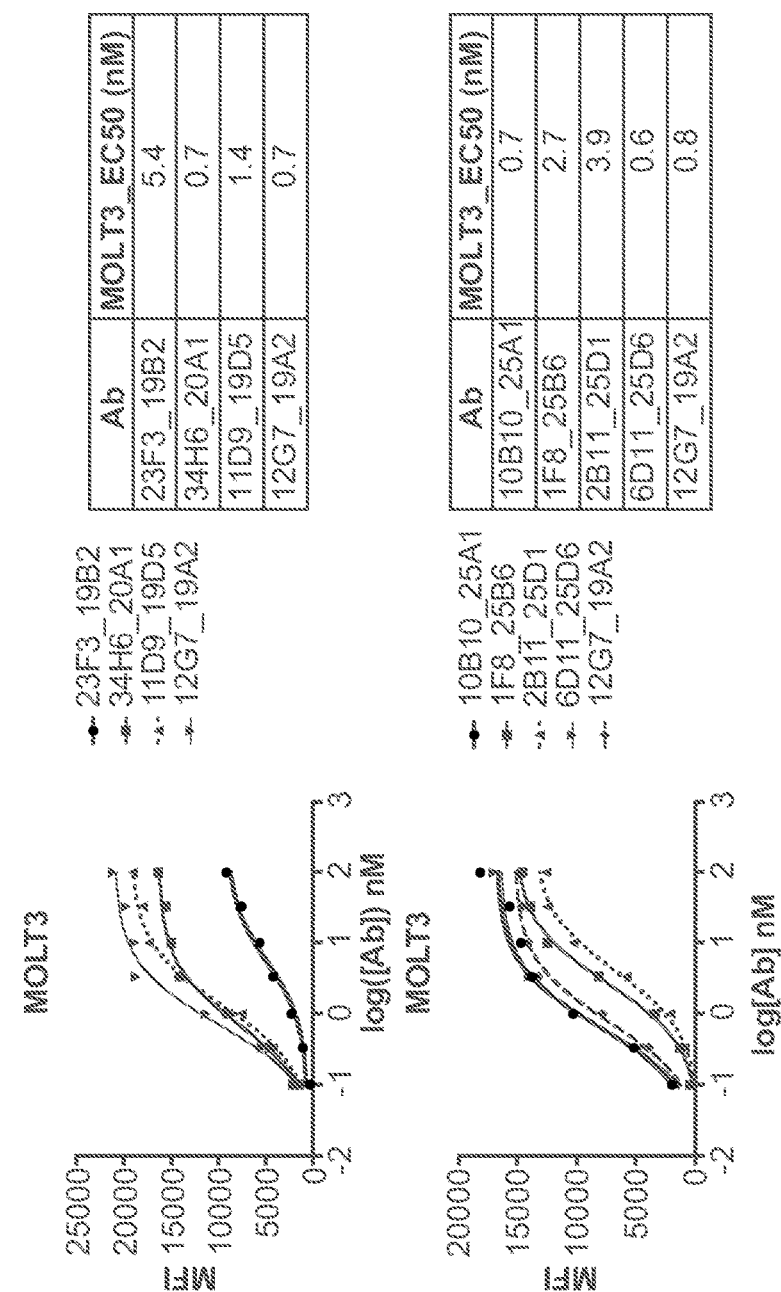

Results $EC_{50}$ or the concentration of antibody that gives half-maximal binding is determined by direct and saturable binding of an antibody dilution series to both target positive and negative cell lines. An estimate of affinity is interpreted from one-half the concentration at which antibody binding first achieves saturation. $EC_{50}$ was measured in the following cell lines H446, DMS79, H526, and MOLT3 (FIG. 4). Though $EC_{50}$ may not provide an accurate measure of affinity, it allows for ranking ordering of antibodies. 12G7, 11D9, 10B10, and 6D11 were ranked top, followed by 34H6, 1F8, and 2B11.

Example 6. Measurement of Antibody Affinity by Flow Cytometry

Experiments were performed to measure Kd of anti-LY6H antibodies on 293T cells expressing LY6H. The following methods were used.

Methods

Measurement of Ab Affinity by Flow Cytometry 1 nM PE conjugated antibody was incubated with 2 fold serial dilutions (from 100 nM to 0.05 nM) of unconjugated antibody in binding buffer. Serial diluted antibodies were incubated with live cells on ice for 4 hours, after a brief wash. Acquisition of the MFI (Median Fluorescent Intensity) was performed on a MACSQuant® Flow Cytometers (Miltenyi Biotec). On cell affinity (Kd) was calculated using Dose-response EC50 shift by global fitting from GraphPad Prism™

Results

Figure 5:
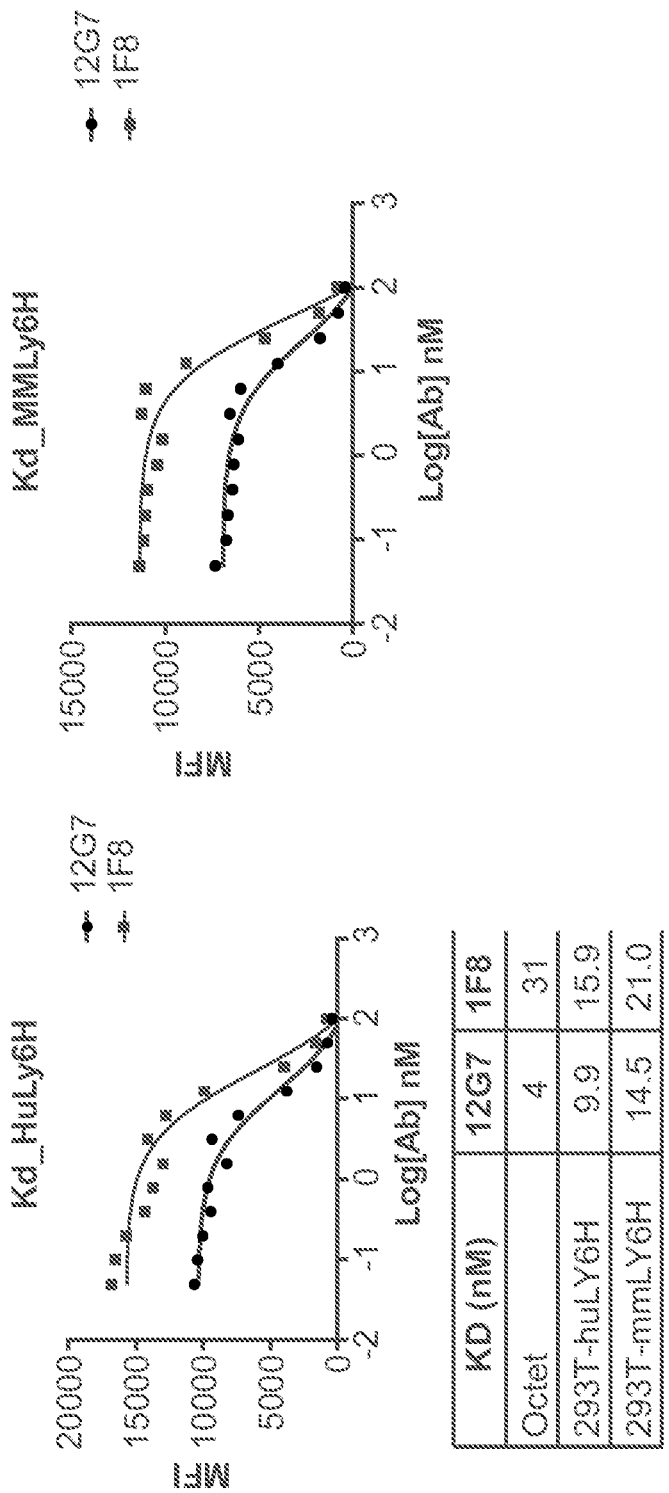
FIG. 5 shows on cell antibody affinity of anti-LY6H antibodies. 1 nM PE conjugated 12G7 and 1F8 antibodies were incubated with 2 fold serial dilutions (from 100 nM to 0.05 nM) of unconjugated Ab in binding buffer. Serial diluted antibodies were incubated with 293 cells expressing either human or *Macaca fascicularis* on ice for 4 hours, after a brief wash. Acquisition of the MFI (Median Fluorescent Intensity) was performed on a MACSQuant® Flow Cytometers (Miltenyi Biotec). On cell affinity (Kd) was calculated using dose-response EC50 shift by global fitting from GraphPad Prism™

To measure on cell antibody affinity by flow, 12G7 and IF8 were conjugated with PE. 293T cells expressing either human Ly6H or Macaca fascicularis Ly6H were incubated with PE conjugated antibodies in the presence of serial dilution of unconjugated antibody. As shown in FIG. 5, antibodies bind human and monkey LY6H with similar affinity. In addition, cell based affinities are very similar to those measured by Octet™.

Example 7. Internalization of Anti-LY6H Antibody in H446 Cell Line

Experiments were performed to characterize anti-LY6H antibody internalization in H446 cells. The following methods were used.

Methods
Tissue Culture and Cell Lines

Human leukemia cell line H446 was obtained from American Type Culture Collection (ATCC). The cells were maintained in RPMI-1640 medium (Invitrogen) with 10% fetal bovine serum (FBS) (Sigma).

Internalization Assay

Live H446 cells were incubated with 12G7 antibody for 30 minutes at 37° C. After cytospin, cells were fixed with 4% PFA and permeablized with 100% methanol, and stained with LAMP1 antibody (#9091, Cell Signaling Technology, Inc.).

Results

Figure 6:
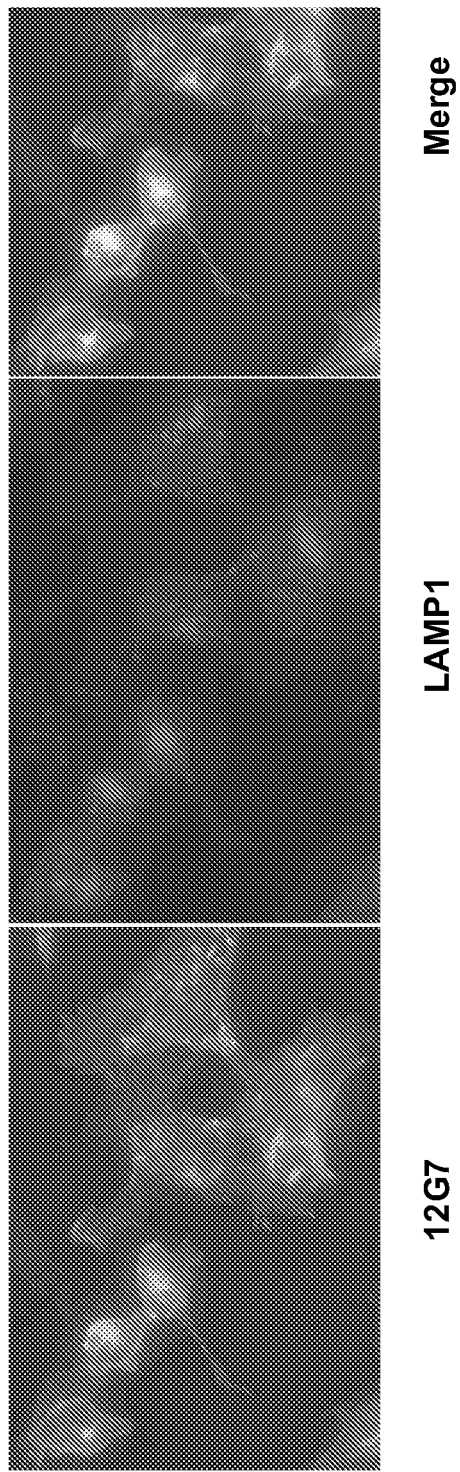
FIG. 6 shows internalization of 12G7 into H446 cells. Live H446 cells were incubated with 12G7 for 2 hours, cells were then fixed, permeablized, and co-stained with LAMP1 antibody.

Antibody 12G7 was co-localized to lysozyme, marked by LAMP1 antibody (see FIG. 6).

Example 8. Antibody Internalization and In Vitro Cytotoxicity by $2^{nd}$ ADC

Experiments were performed to characterize anti-LY6H antibody internalization and in vitro cytotoxicity. The following methods were used.

Methods
Tissue Culture and Cell Lines

Human SCLC cancer cell lines H446, DMS79, NCI-H526, H69 were obtained from American Type Culture Collection (ATCC). Human leukemia cell lines MOLT3, KE-37, EOL1 were purchased from DSMZ. Cells were maintained in RPMI-1640 medium (Invitrogen) with 10% fetal bovine serum (FBS) (Sigma).

Internalization and In Vitro Cytotoxicity 5000 cells/50 ul/well of different cell lines were plated in 96-well microplates. Primary antibodies (0.01 ug/ml, or 0.1 ug/ml final concentration) and Fab-Zap or FabFc-Zap @ 0.2 ug/ml final concentration (Advanced Targeting Systems) were added in a volume of 50 ul. The plates were incubated for 72 hours at 37° C. in the presence of 5% CO2. For each plate, 100 ul/well of Cell Titer-Glo™ reagent (#G7573 and #G9243, Promega) was added and allowed to shake for 2 minutes and incubate at room temperature for 30 minutes prior to reading on a luminescent plate reader, and data analyzed using GraphPad Prism™. Transferrin receptor (TR) and hIgG1 antibodies were included as positive and negative controls.

Results

Figure 7A:
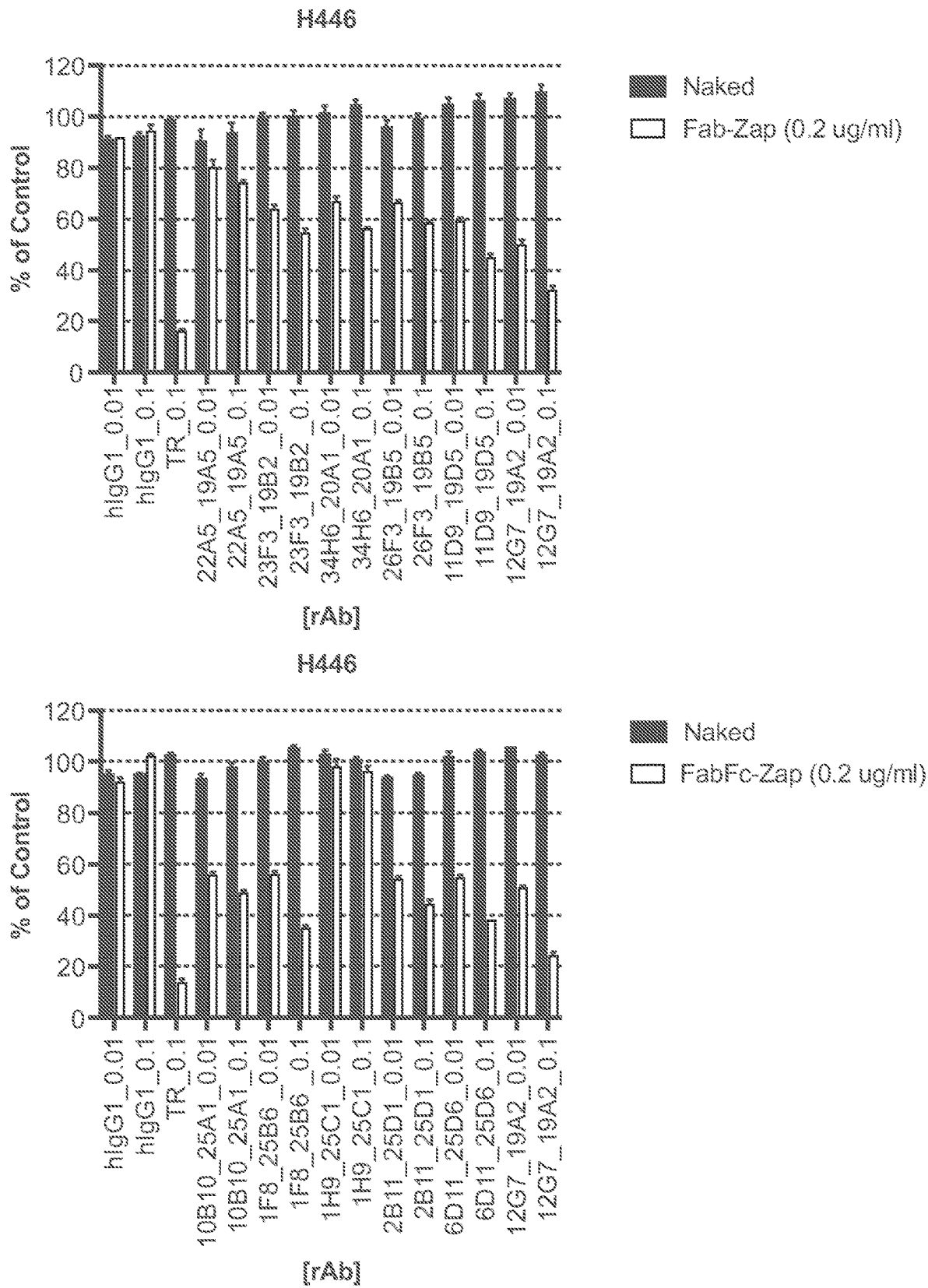
FIG. 7A, FIG. 7B, and FIG. 7C show internalization of anti-LY6H antibodies and in vitro efficacy.
Figure 7B:
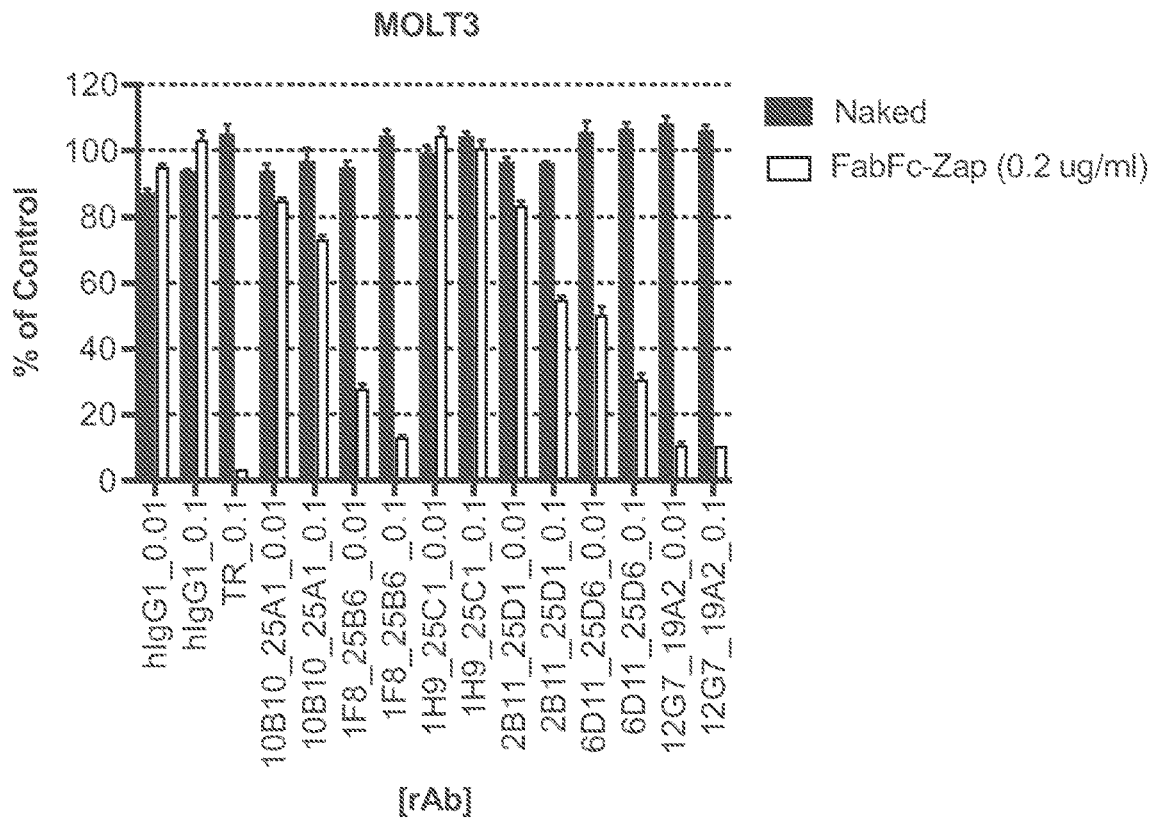
Figure 7C:
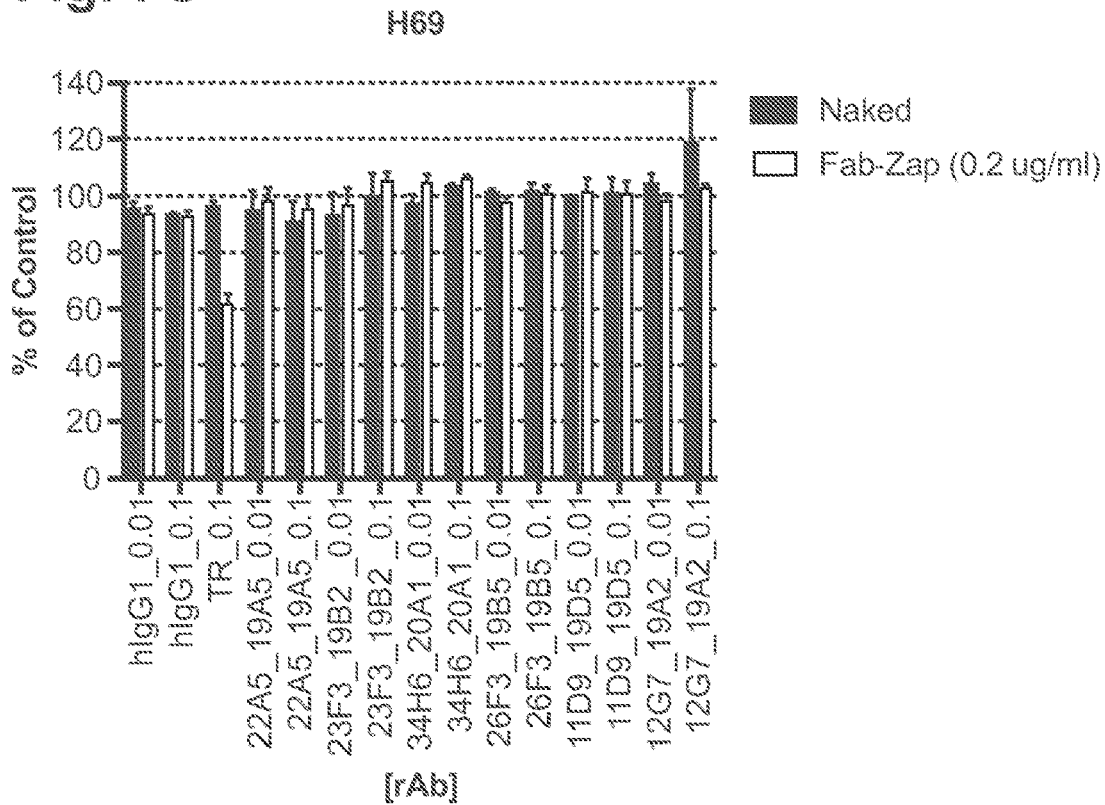

Antibody internalization and secondary ADC efficacy was evaluated with Fab-Za™p (or FabFc-Zap™) as a conjugated secondary reagent. Fab-ZAP™ uses a human primary antibody to target and eliminate cells. This secondary conjugate is used to evaluate the potential of a primary antibody to internalize. Most antibodies showed good efficacy in both H446 (FIG. 7A) and MOLT3 (FIG. 7B) cell lines, indicating that these antibodies underwent internalization, released saporin toxin inside cells, and these two cell lines were sensitive to saporin. On the other hand, there was no cytotoxicity in LY6H negative H69 cell line (FIG. 7C).

Example 9. In Vitro Cytotoxicity by Primary Antibody Drug Conjugates

Experiments were performed to characterize anti-LY6H MMAE or PBD conjugated antibody in vitro efficacy. The following methods were used.

Methods
Tissue Culture and Cell Lines

Human SCLC cancer cell lines H446, DMS79, NCI-H526, H69, NCI-H1092, and CORL95 were obtained from American Type Culture Collection (ATCC). Human leukemia cell lines MOLT3, KE-37, EOL1 were purchased from DSMZ. Cells were maintained in RPMI-1640 medium (Invitrogen) with 10% fetal bovine serum (FBS) (Sigma).

Antibody Drug Conjugation

Human monoclonal antibodies were conjugated to the valine-alanine-pyrrolobenzodiazepine, MA-PEG8-VA-PAB-SG3199 (PBD) or maleimidocaproyl-valine-citrulline-p-aminobenzoyloxycarbonyl-monomethyl auristatin E (MMAE) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.).

Briefly, each antibody was partially reduced with an appropriate molar amount of TCEP for 2 hours at 37° C. After incubation, the antibodies were cooled to room temperature and a 6-fold molar excess of PBD or MMAE was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 12G7-MMAE, 1F8-MMAE was 3.14 and 2.0, respectively. The drug to antibody ratio for control human IgG1-vc-MMAE (Ctrl) was 3.2. The drug to antibody ratio for 12G7-PBD and 1F8-PBD was 2.1 and 2.5, respectively. The drug to antibody ratio for control human IgG1-PBD (Ctrl) was 3.0.

In Vitro Efficacy

Cells were seeded onto 96 well plate at 3000-5000 cells/well. ADCs were added to the wells in complete culture medium in a serial dilution. Each treatment was replicated in 2 wells. 5 days later, cell viability was measured by CellTiter Glo Luminescent Cell™ viability assay (Promega) according to manufacturer's instructions. Cell viability was graphed by Prism™ using ratio of cell viability of test conditions to that of control wells that are treated with growth medium only.

Results

Figure 8C:
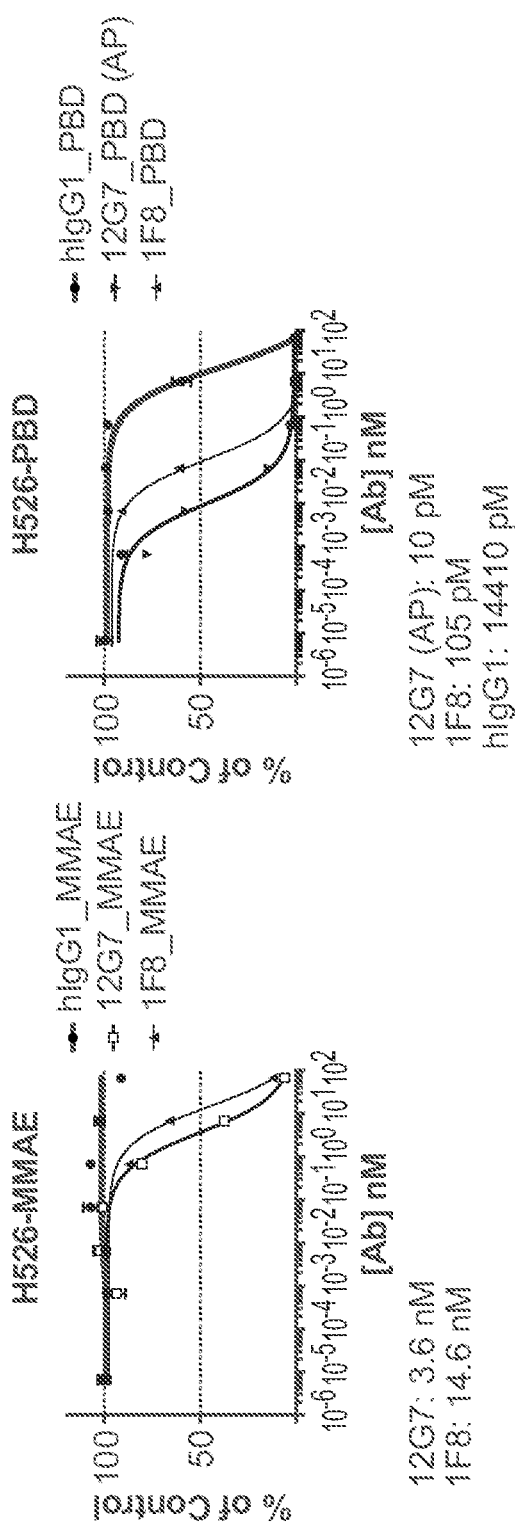
Figure 8D:
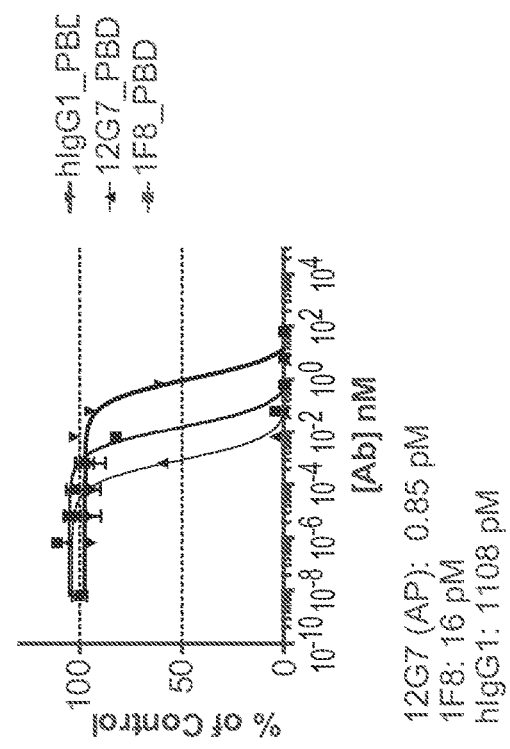
Figure 8D:
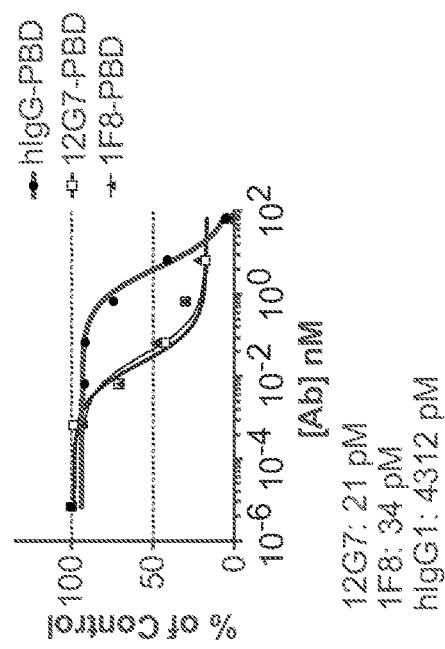
Figure 8E:
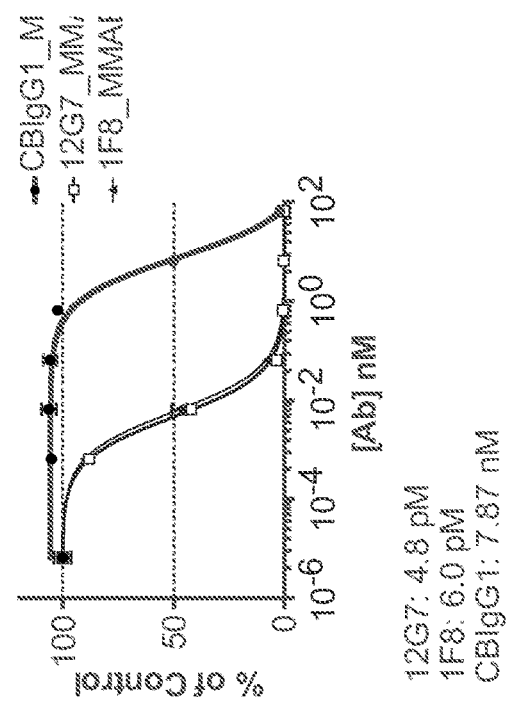

12G7 and 1F8 were selected to be conjugated to either vcMMAE, a microtubule inhibitor, or Tesirine PBD, a DNA damage agent. Primary conjugated antibodies were evaluated for in vitro efficacy against a panel of SCLC and T cell acute lymphoblastic leukemia (T-ALL) cell lines. DMS79, NCI-H1092, and CORL95 are classic SCLC cell lines, which represents 70-80% primary SCLC tumors. H446 and NCI-H526 are considered to be variant SCLC cell lines, and represent 20-30% primary SCLC tumors. PBD conjugated antibodies showed great efficacy in all SCLC and T-ALL cell lines expressing LY6H, MMAE conjugated antibodies were efficacious only in H446 (SCLC) and MOLT3 (T-ALL cell line) (FIG. 8A-8F), suggesting DNA damaging agents, such as PBD are more efficacious than MMAE in a variety of SCLC cell lines. H69 served as a negative control cell line (FIG. 8G).

Example 10. In Vivo Efficacy by Primary Antibody Drug Conjugates

Experiments were performed to characterize in vivo efficacy of drug conjugated antibodies against H446, a variant SCLC cell line. The following methods were used.

Methods

Tissue Culture and Cell Lines

Human SCLC cancer cell line H446 was obtained from American Type Culture Collection (ATCC). Cells were maintained in RPMI-1640 medium (Invitrogen) with 10% fetal bovine serum (FBS) (Sigma).

Antibody Drug Conjugation

Human monoclonal antibodies were conjugated to the valine-alanine-pyrrolobenzodiazepine, MA-PEG8-VA-PAB-SG3199 (PBD) or maleimidocaproyl-valine-citrulline-p-aminobenzoyloxycarbonyl-monomethyl auristatin E (MMAE) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.) Briefly, each antibody was partially reduced with an appropriate molar amount of TCEP for 2 hours at 37° C. After incubation, the antibodies were cooled to room temperature and a 6-fold molar excess of PBD or MMAE was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 12G7-MMAE was 3.14. The drug to antibody ratio for control human IgG1-vc-MMAE (Ctrl) was 3.2. The drug to antibody ratio for 12G7-PBD and 1F8-PBD was 2.1 and 2.5, respectively. The drug to antibody ratio for control human IgG1-PBD (Ctrl) was 3.0.

Tumor Implantation

For efficacy studies with antibody drug conjugates, 6-8 weeks old female Nu/Nu mice obtained from Taconic were inoculated subcutaneously in the dorsal right flank with 2.5 million H446 cells in 1×PBS with equal volume of Matrigel™ (#356234, Corning). When tumor volumes reached 150-200 mm3 (day 0), animals were randomized into 3 groups of 6-7 each and administered BIW×2 IV injection of antibody drug conjugates. Tumor volumes were determined using digital calipers (Fred V. Fowler Company, Inc.) using the formula (length×width$^2$)/2. Measurement was performed twice weekly for the first 30 days after initial dosing, then once a week until the end of the study.

Toxicity

Animals were weighed weekly for the study. The mice were observed frequently for overt signs of any adverse, treatment-related side effects, and clinical signs of toxicity were recorded when observed. Acceptable toxicity is defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy or if due to unknown causes during the dosing period or within 10 days of the last dose. A death is classified as an NTR if there is no evidence that death was related to treatment side effects.

Results

Figure 9A:
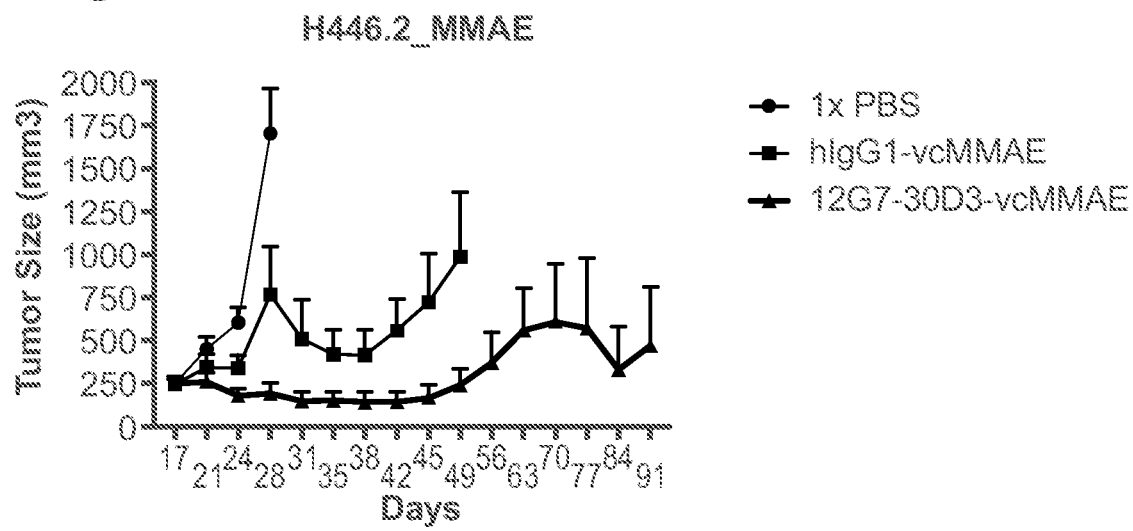
FIG. 9A, FIG. 9B, and FIG. 9C show MMAE conjugated antibody inhibits tumor growth in vivo.
Figure 9B:
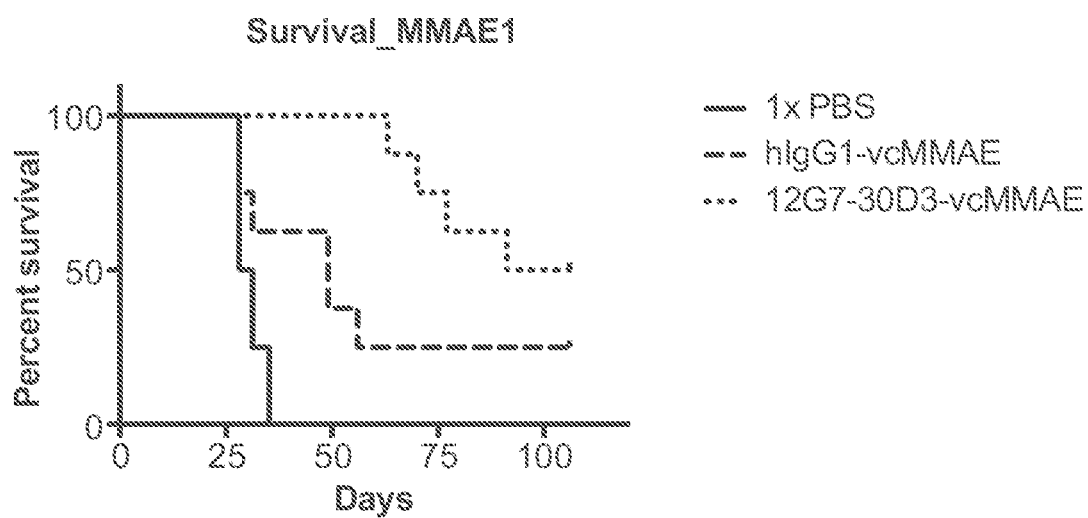
Figure 9C:
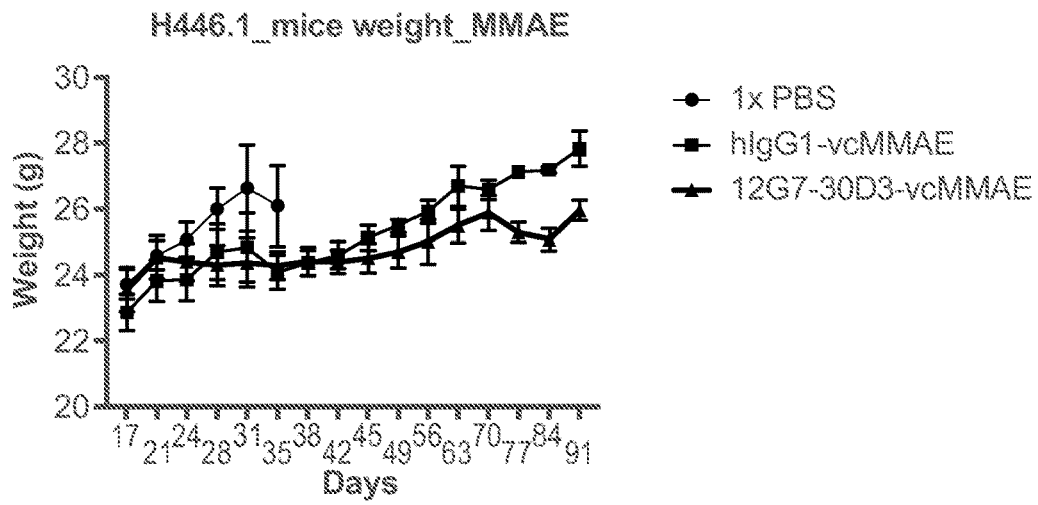
Figure 10A:
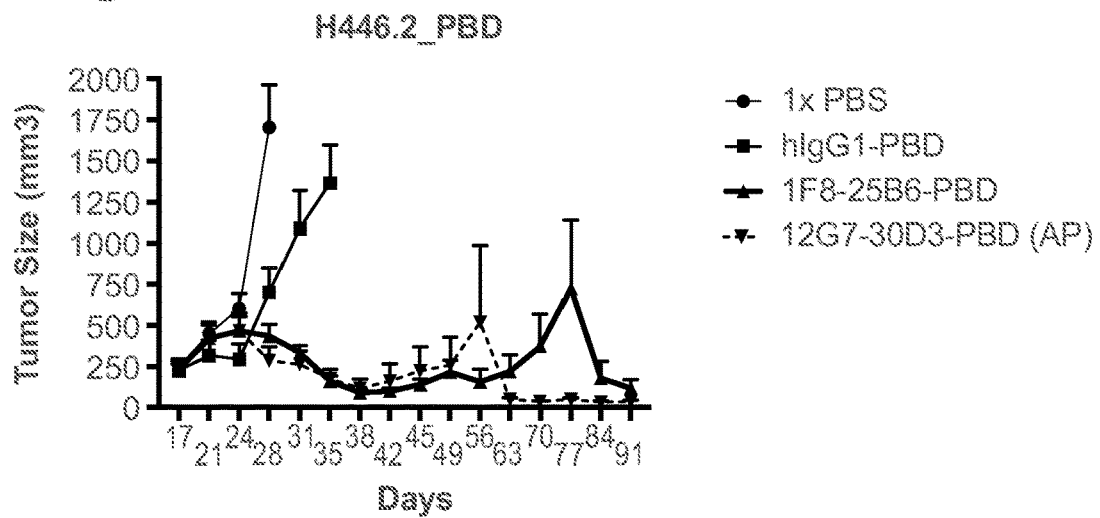
FIG. 10A, FIG. 10B, and FIG. 10C show Tesirine PBD conjugated antibody inhibits tumor growth in vivo.
Figure 10B:
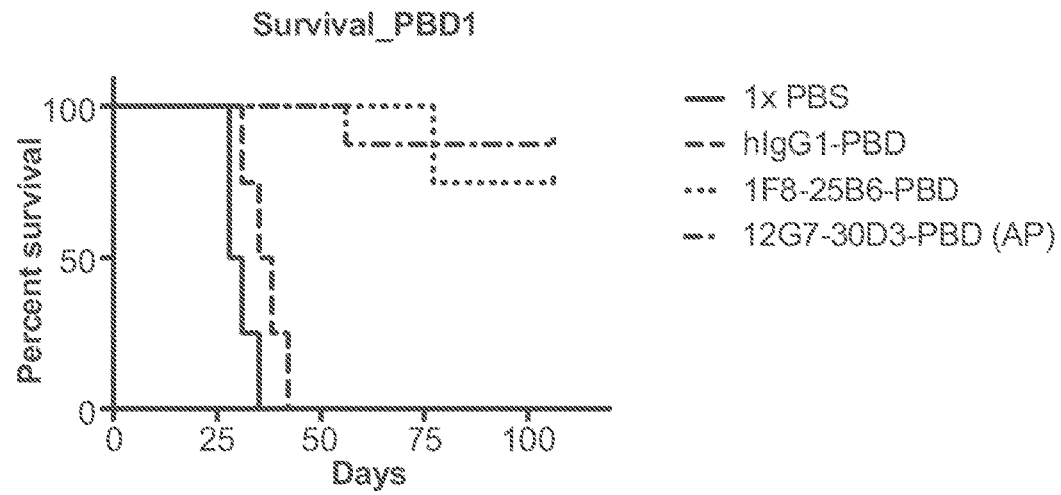
Figure 10C:
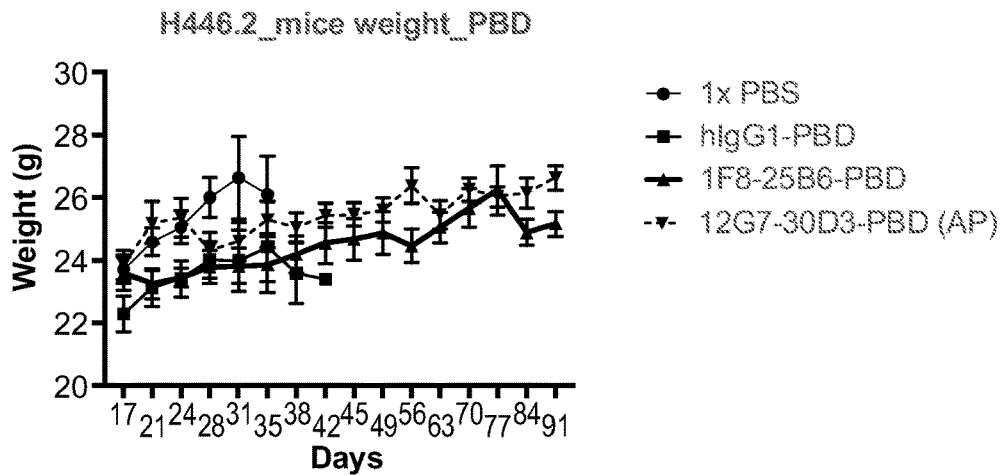

MMAE conjugated antibodies were dosed at 5 mg/kg 4 times in 2 weeks. The 12G7-MMAE treated group showed tumor growth inhibition and survival advantage over the control groups (FIG. 9). Meanwhile, Tesirine PBD conjugated antibodies dosed at 1 mg/kg 3 times every 4 days showed tumor regression, excellent efficacy and survival advantage over the control groups (FIG. 10).

Example 11. In Vivo Efficacy by Primary Antibody Drug Conjugates

Experiments were performed to characterize in vivo efficacy of drug conjugated antibodies against H526, a variant SCLC cell line. The following methods were used.

Methods

Tissue Culture and Cell Lines Human SCLC cancer cell line H526 was obtained from American Type Culture Collection (ATCC). Cells were maintained in RPMI-1640 medium (Invitrogen) with 10% fetal bovine serum (FBS) (Sigma).

Antibody Drug Conjugation

Human monoclonal antibodies were conjugated to the valine-alanine-pyrrolobenzodiazepine, MA-PEG8-VA-PAB-SG3199 (PBD) or maleimidocaproyl-valine-citrulline-p-aminobenzoyloxycarbonyl-monomethyl auristatin E (MMAE) as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.) Briefly, each antibody was partially reduced with an appropriate molar amount of TCEP for 2 hours at 37° C. After incubation, the antibodies were cooled to room temperature and a 6-fold molar excess of PBD or MMAE was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 12G7-MMAE was 3.14. The drug to antibody ratio for control human IgG1-vc-MMAE (Ctrl) was 3.2. The drug to antibody ratio for 12G7-PBD and 1F8-PBD was 2.1 and 2.5, respectively. The drug to antibody ratio for control human IgG1-PBD (Ctrl) was 3.0.

Tumor Implantation

For efficacy studies with antibody drug conjugates, 6-8 weeks old female Nu/Nu mice from Taconic were inoculated subcutaneously in the dorsal right flank with 2.5 million H526 cells in 1×PBS with equal volume of Matrigel (#356234, Corning). When tumor volumes reached 150-200 mm3 (day 0), animals were randomized into 3 groups of 6-7 each and administered BIW×2 IV injection of antibody drug conjugates. Tumor volumes were determined using digital calipers (Fred V. Fowler Company, Inc.) using the formula (length×width$^2$)/2. Measurement was performed twice weekly for the first 30 days after initial dosing, then once a week till the end of the study.

Toxicity

Animals were weighed weekly for the study. The mice were observed frequently for overt signs of any adverse, treatment-related side effects, and clinical signs of toxicity were recorded when observed. Acceptable toxicity is defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy or if due to unknown causes during the dosing period or within 10 days of the last dose. A death is classified as an NTR if there is no evidence that death was related to treatment side effects.

Results

Figure 11A:
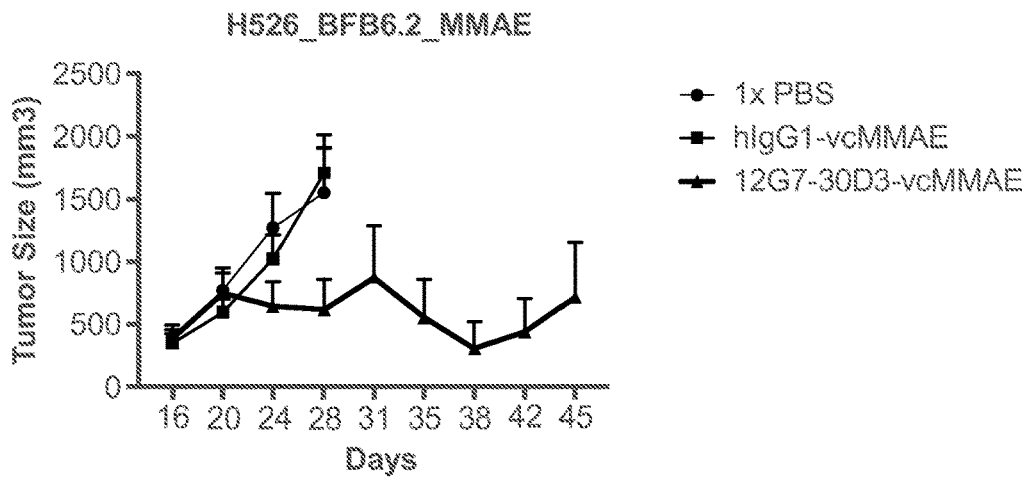
FIG. 11A, FIG. 11B, and FIG. 11C show that MMAE conjugated antibody showed limited tumor growth inhibition in vivo.
Figure 11B:
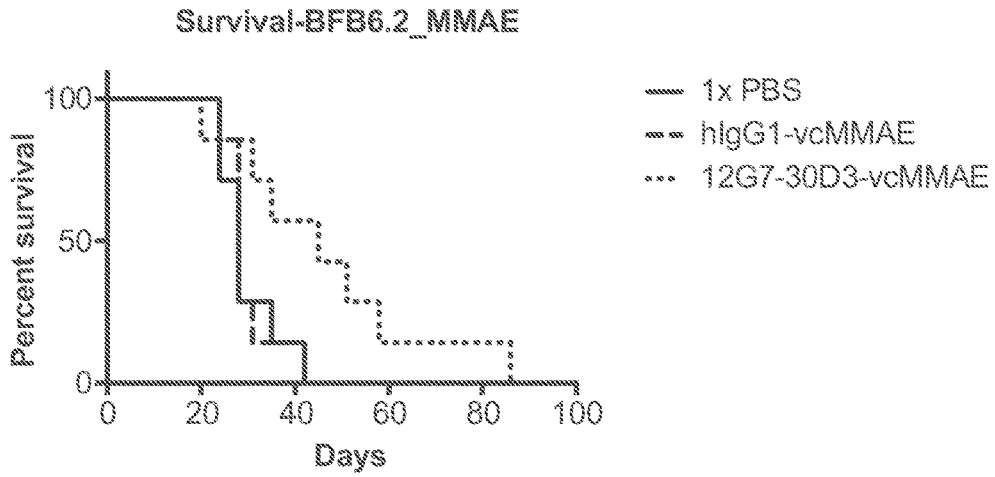
Figure 11C:
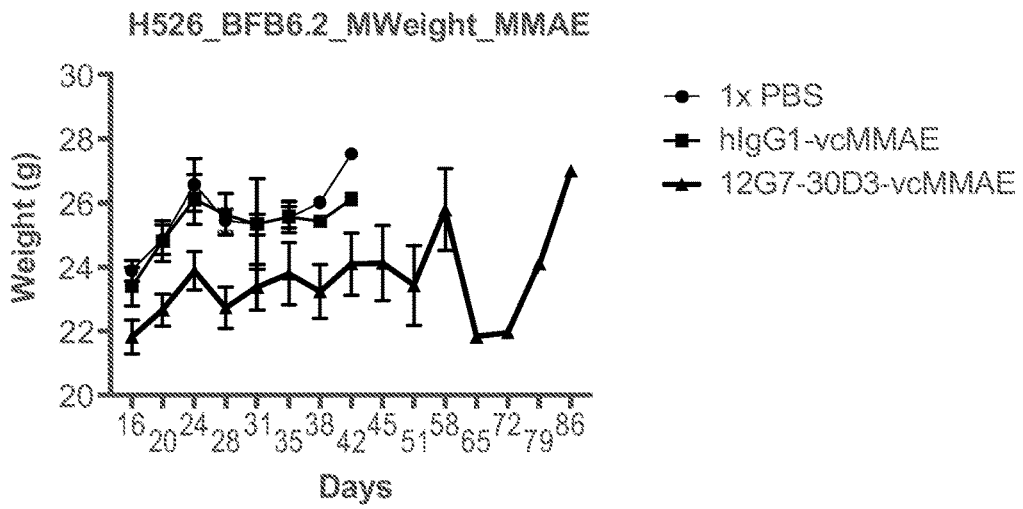
Figure 12A:
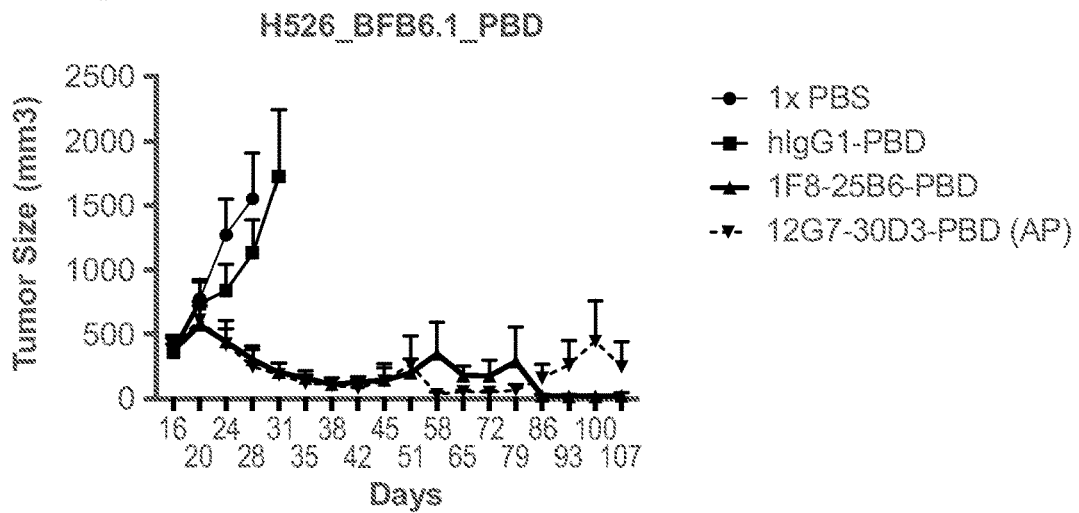
FIG. 12A, FIG. 12B, and FIG. 12C show Tesirine PBD conjugated antibody inhibits tumor growth in vivo.
Figure 12B:
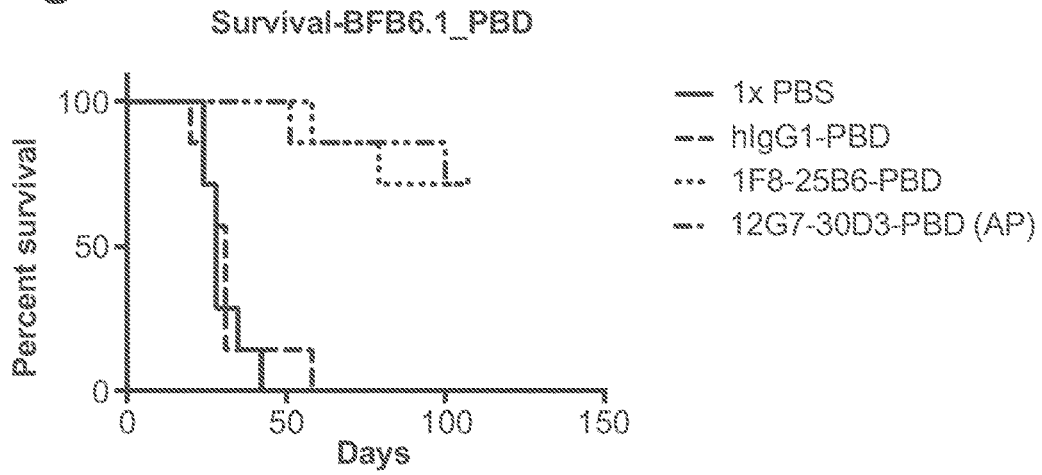
Figure 12C:
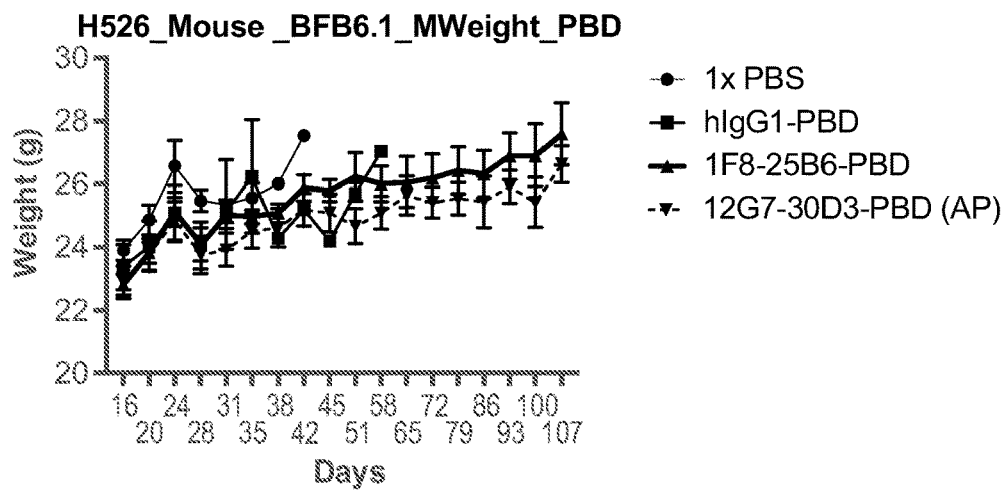

MMAE conjugated antibodies were dosed at 5 mg/kg 4 times in 2 weeks. The 12G7-MMAE treated group showed some tumor growth inhibition and survival advantage over the control groups (FIG. 11). On the other hand, Tesirine PBD conjugated antibodies dosed at 1 mg/kg 3 times every 4 days showed tumor regression, excellent efficacy and survival advantage over the control groups (FIG. 12). Little or no mice body weight loss was observed for the study (FIGS. 11C and 12C).

Example 12. In Vivo Efficacy by Single Dose Primary Antibody Drug Conjugates Experiments were performed to characterize in vivo efficacy of drug conjugated antibodies against DMS79, a classic SCLC cell line. The following methods were used.

Methods

Tissue Culture and Cell Lines

Human SCLC cancer cell line DMS79 was obtained from American Type Culture Collection (ATCC). Cells were maintained in RPMI-1640 medium (Invitrogen) with 10% fetal bovine serum (FBS) (Sigma).

Antibody Drug Conjugation

Human monoclonal antibodies were conjugated to the valine-alanine-pyrrolobenzodiazepine, MA-PEG8-VA-PAB-SG3199 (PBD as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.). Briefly, each antibody was partially reduced with an appropriate molar amount of TCEP for 2 hours at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 12G7-PBD was 2.0. The drug to antibody ratio for control human IgG1-PBD (Ctrl) was 2.9.

Tumor Implantation

For efficacy studies with antibody drug conjugates, 6-8 weeks old female Nu/Nu mice from Taconic were inoculated subcutaneously in the dorsal right flank with 2.5 million DMS79 cells in 1×PBS with equal volume of Matrigel (#356234, Corning). When tumor volumes reached 150-200 mm3 (day 0), animals were randomized into 3 groups of 7-8 each and administered once IV injection of antibody drug conjugates. Tumor volumes were determined using digital calipers (Fred V. Fowler Company, Inc.) using the formula (length×width$^2$)/2. Measurement was performed twice weekly for the first 30 days after initial dosing, then once a week till the end of the study.

Toxicity

Animals were weighed weekly for the study. The mice were observed frequently for overt signs of any adverse, treatment-related side effects, and clinical signs of toxicity were recorded when observed. Acceptable toxicity is defined as a group mean body-weight loss of less than 20% during the study and not more than one treatment-related (TR) death among ten treated animals. Any dosing regimen that results in greater toxicity is considered above the maximum tolerated dose (MTD). A death is classified as TR if attributable to treatment side effects as evidenced by clinical signs and/or necropsy or if due to unknown causes during the dosing period or within 10 days of the last dose. A death is classified as an NTR if there is no evidence that death was related to treatment side effects.

Results

Figure 13A:
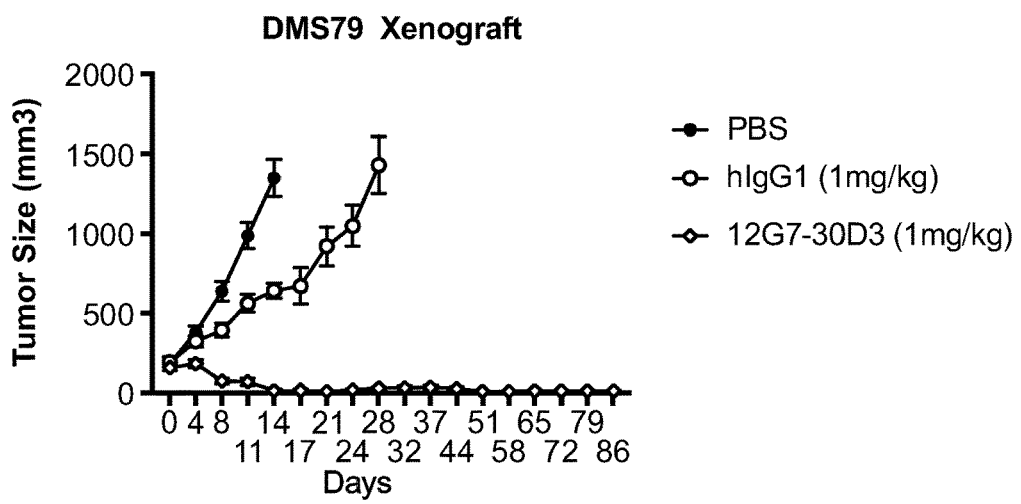
FIG. 13A, FIG. 13B, and FIG. 13C show a single dose of Tesirine PBD conjugated antibody inhibits tumor growth in vivo.
Figure 13B:
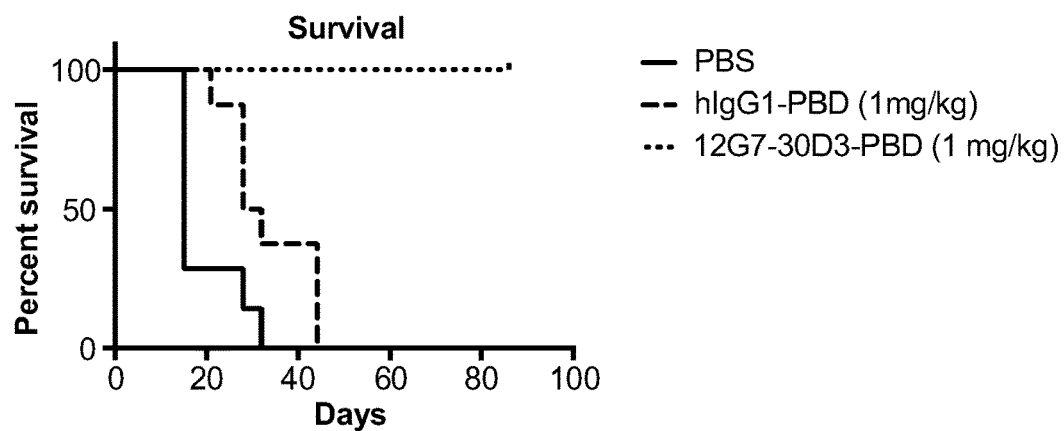
Figure 13C:
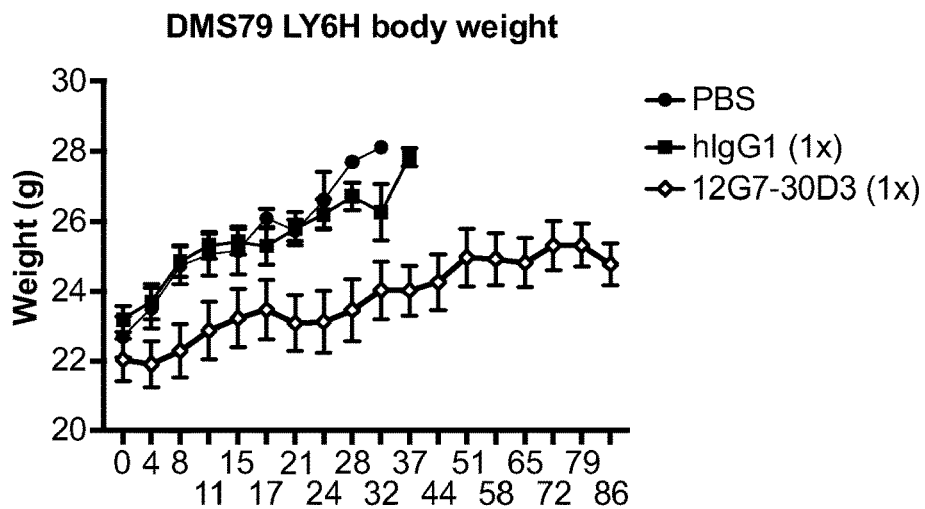

DMS79 is a classic SCLC cell line, which refers to the usual recognized form of SCLC, with typical morphology, expression of neuroendocrine (NE) properties and a non-adherent growth pattern in vitro. Tesirine PBD conjugated antibody (12G7-PBD) was dosed at 1 mg/kg once, and showed tumor regression, excellent efficacy and survival advantage over the control groups (FIG. 13), with no loss of body weight.

Example 13. In Vivo Efficacy by Single Dose Primary Antibody Drug Conjugates Experiments were performed to characterize in vivo efficacy of drug conjugated antibodies against H446, a variant SCLC cell line. The following methods were used.

Methods

Tissue Culture and Cell Lines

Human SCLC cancer cell line H446 was obtained from American Type Culture Collection (ATCC). Cells were maintained in RPMI-1640 medium (Invitrogen) with 10% fetal bovine serum (FBS) (Sigma).

Antibody Drug Conjugation

Human monoclonal antibodies were conjugated to the valine-alanine-pyrrolobenzodiazepine, MA-PEG8-VA-PAB-SG3199 (PBD as previously described (Stefano J. E., Busch M., Hou L., Park A., Gianolio D. A. (2013) Micro- and Mid-Scale Maleimide-Based Conjugation of Cytotoxic Drugs to Antibody Hinge Region Thiols for Tumor Targeting. In: Ducry L. (eds) Antibody-Drug Conjugates. Methods in Molecular Biology (Methods and Protocols), vol 1045. Humana Press, Totowa, N.J.) Briefly, each antibody was partially reduced with an appropriate molar amount of TCEP for 2 hours at 37° C. After incubation, the antibodies were cooled to room temperature and a 6-fold molar excess of PBD was added to the partially reduced antibody for 1 hour. After this incubation, the entire mixture was run over a gel filtration column to remove free drug. A fraction of the eluate was then used for concentration and DAR determination using A280 and HIC respectively. The drug to antibody ratio for 12G7-PBD and 1F8-PBD was 2.3 and 2.2, respectively. The drug to antibody ratio for control human IgG1-PBD (Ctrl) was 2.1.

Tumor Implantation

For efficacy studies with antibody drug conjugates, 6-8 weeks old female Nu/Nu mice from Taconic were inoculated subcutaneously in the dorsal right flank with 2.5 million H446 cells in 1×PBS with equal volume of Matrigel (#356234, Corning). When tumor volumes reached 150-200 mm3 (day 0), animals were randomized into 3 groups of 7-8 each and administered once IV injection of antibody drug conjugates. Tumor volumes were determined using digital calipers (Fred V. Fowler Company, Inc.) using the formula (length×width$^2$)/2. Measurement was performed twice weekly for the first 30 days after initial dosing, then once a week till the end of the study.

Toxicity

Animals were weighed weekly for the study. The mice were observed frequently for overt signs of any adverse, treatment-related side effects, and clinical signs of toxicity were recorded when observed. Acceptable toxicity is defined as a group mean body-weight loss of less than 20% during the study and not more than one treatment-related (TR)

death among ten treated animals. Any dosing regimen that results in greater toxicity is considered above the maximum tolerated dose (MTD). A death is classified as TR if attributable to treatment side effects as evidenced by clinical signs and/or necropsy or if due to unknown causes during the dosing period or within 10 days of the last dose. A death is classified as an NTR if there is no evidence that death was related to treatment side effects.

Results

H446 is a variant subtype of SCLC cell line, characterized by larger cells with prominent nucleoli, partial or complete loss of neuroendocrine (NE) cell properties, partial adherent growth in vitro, frequent MYC amplification and epithelial-mesenchymal transition.

Figure 14A:
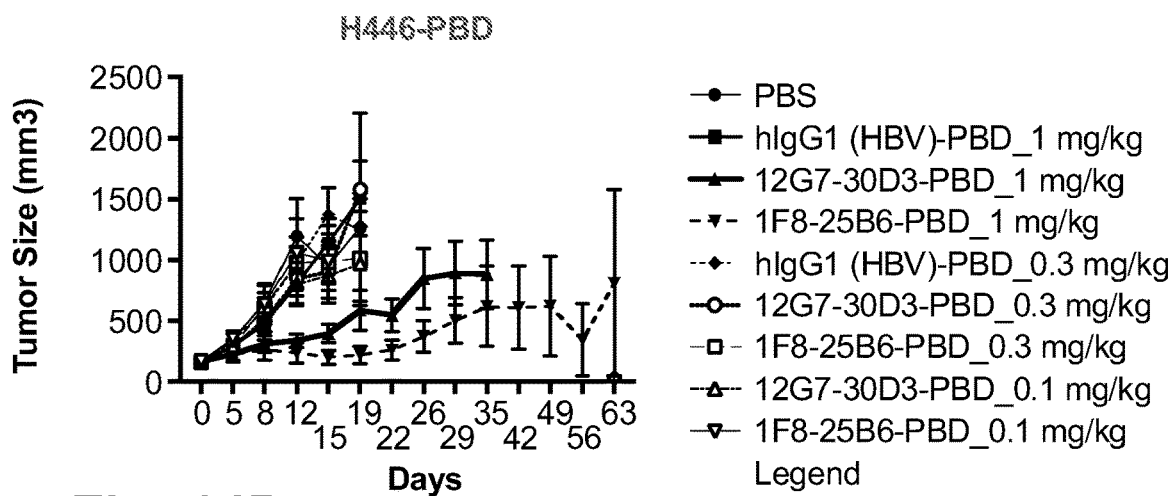
FIG. 14A, FIG. 14B, and FIG. 14C show in vivo efficacy of a single dose of Tesirine PBD conjugated antibody in H446 cells.
Figure 14B:
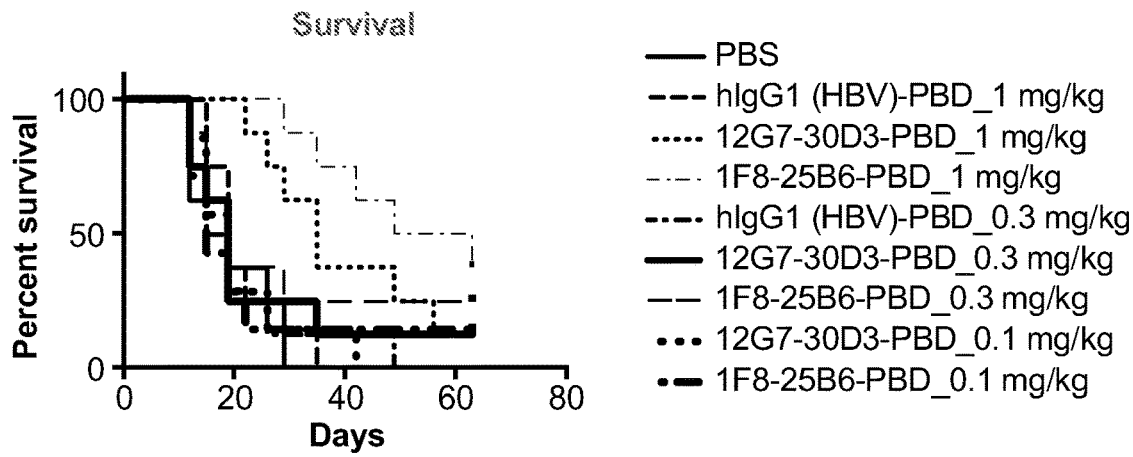
Figure 14C:
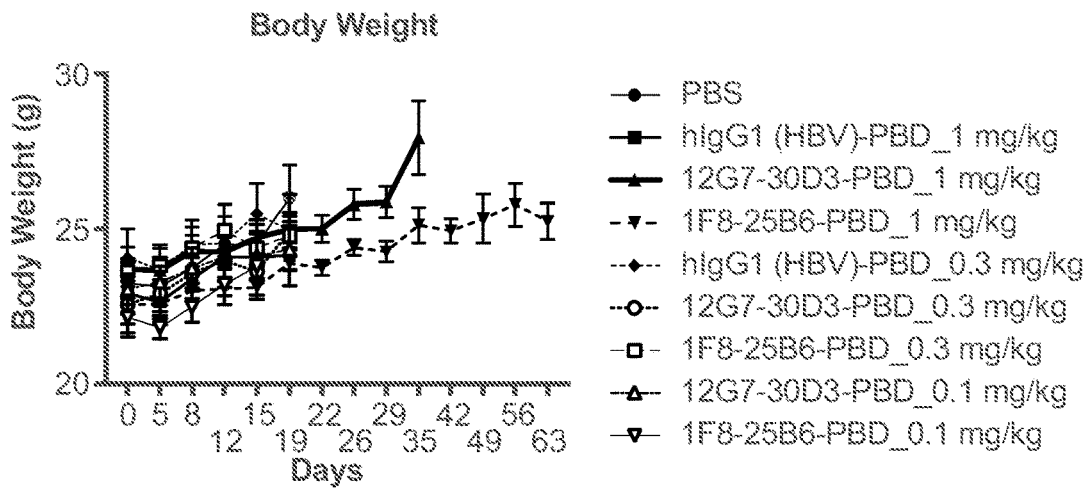

Tesirine PBD conjugated antibodies were dosed at 0.1, 0.3, and 1 mg/kg once. While there was little efficacy when mice were dosed at 0.1 and 0.3 mg/kg, when mice were dosed at 1 mg/kg, tumor growth inhibition and survival advantage over the control groups was shown, especially with 1F8 PBD conjugated antibody (FIG. 14). There was no loss of mice body weight during the study.

Example 14: In Vitro Efficacy of an Anti-LY6H-PBD Antibody Combined with Olaparib, Cisplatin, or Etoposide Cisplatin and etoposide have been used as first line treatment for SCLC patients. Thus, a combination of an anti-LY6H antibody conjugated to PBD (12G7-PBD) with cisplatin or etoposide was tested. Furthermore, Poly [ADP-ribose] polymerase 1 (PARP1) was identified to be highly expressed at the mRNA and protein level in SCLC (Byers, L. A., et al, Proteomic Profiling Identifies Dysregulated Pathways in Small Cell Lung Cancer and Novel Therapeutic Targets Including PARP1, Cancer Discov., 2012). Thus, PARP inhibitor and olaparib were combined, with 12G7-PBD to determine the effect on growth in three classic SCLC cell lines (DMS79, CORL95, and NCI-H1092) in vitro.

Methods

SCLC cells were seeded onto 96 well plates at 3000-5,000 cells/well on the day of treatment. To distinguish synergy from additivity of the combination of LY6H-PBD with Olaparib (selleckchem, Cat #S1060), etoposide (Cell Signaling Technology, Cat #2200S) or cisplatin (Sigma, Cat #P4394), for each combination, a specific isobologram was constructed. IC50 value was defined as the drug concentration reducing by 50% the growth of treated cells compared with control. IC50 values of each drug was determined by plating cells and adding 12G7-PBD, olaparib, cisplatin, or etoposide at 10-fold dilutions spanning their probable range of activity. Concentrations ranging from 0.0001-10 ug/ml were used for 12G7-PBD, from 0.0001 to 100 uM for olaparib, cisplatin, and etoposide. Cell viability was measured 5 days later by CellTiter Glo® Luminescent Cell viability Assay™ (Promega, Madison, Wis.) according to manufacturer's instructions. Each IC50 was graphically derived from the growth curve graphed by Prism™ showing percent survival vs log drug concentrations.

The 50% growth-inhibitory activity of the drug combinations was measured after 5 days of treatment. The line of additivity for the isobologram was constructed by interpolating the two points corresponding to the IC50 of the two drugs alone. Graphically, synergy, additivity, and antagonism are indicated by a point plotted below, on, or above the line of additivity, respectively.

Results

Figure 15A:
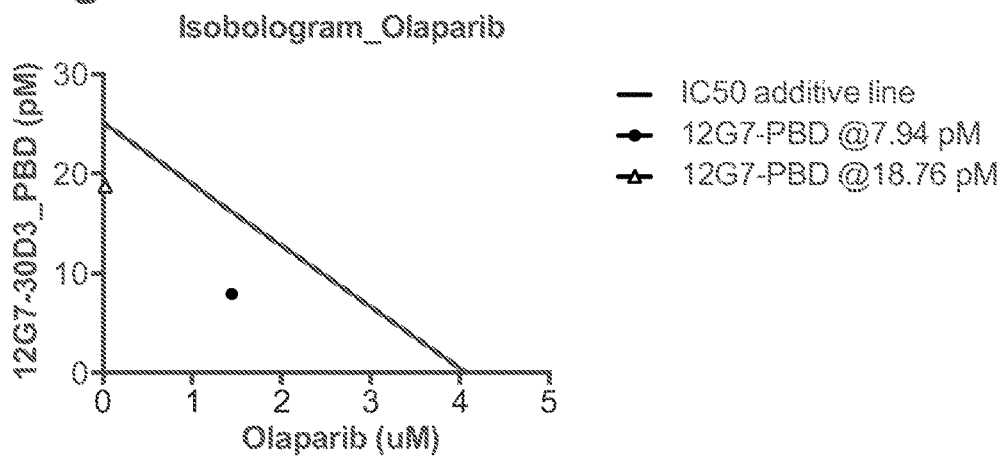
FIG. 15A, FIG. 15B, and FIG. 15C show isobologram analysis of combination treatments of anti-LY6H-PBD with olaparib, cisplatin, or etoposide in DMS79 cells. Combination treatments were performed with a constant concentration of 12G7-PBD and titrating doses of olaparib (A), cisplatin (B) or etoposide (C). IC50 values were recorded for single treatments or combinations to calculate isobologram points.
Figure 15B:
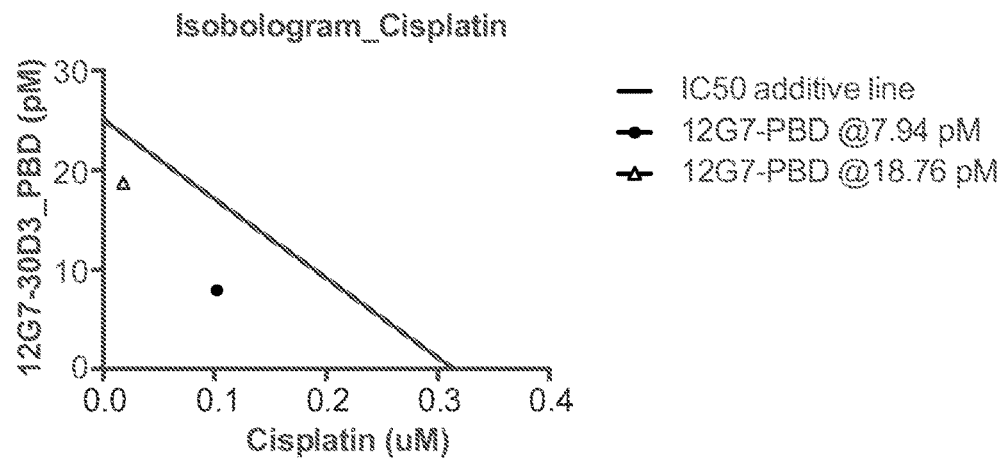
Figure 15C:
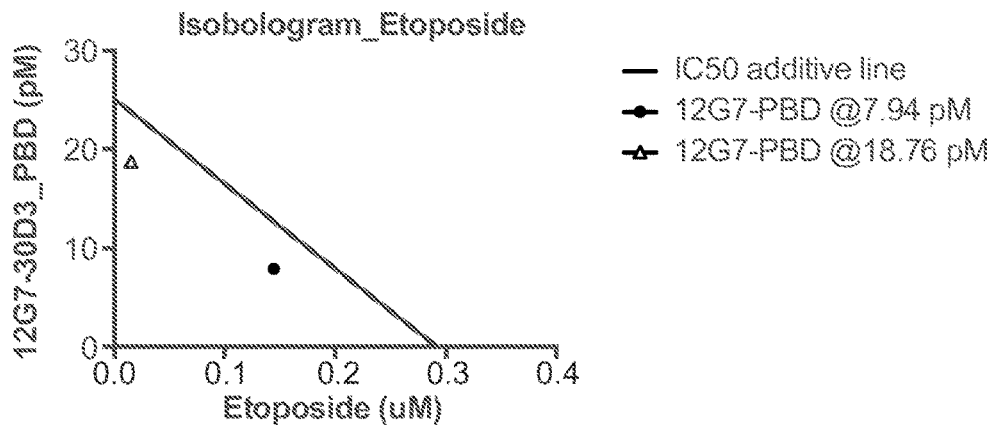

The IC50 value of 12G7-PBD, olaparib, cisplatin, and etoposide alone was determined in DMS79 cell line. The IC50 of 12G7-PBD was 25.12 pM in DMS79 cell line. The IC50 of olaparib was 4.07 uM. The IC50 of cisplatin was 0.31 uM. The IC50 of etoposide was 0.29 uM. An isobologram analysis was performed of the combination of 12G7-PBD at 7.9 pM, or 18.8 pM with titrating concentrations of olaparib, cisplatin, or etoposide (see FIG. 15A-15C). It was then assessed if the combination results in additive or synergistic effect based on the isobologram.

Figure 16A:
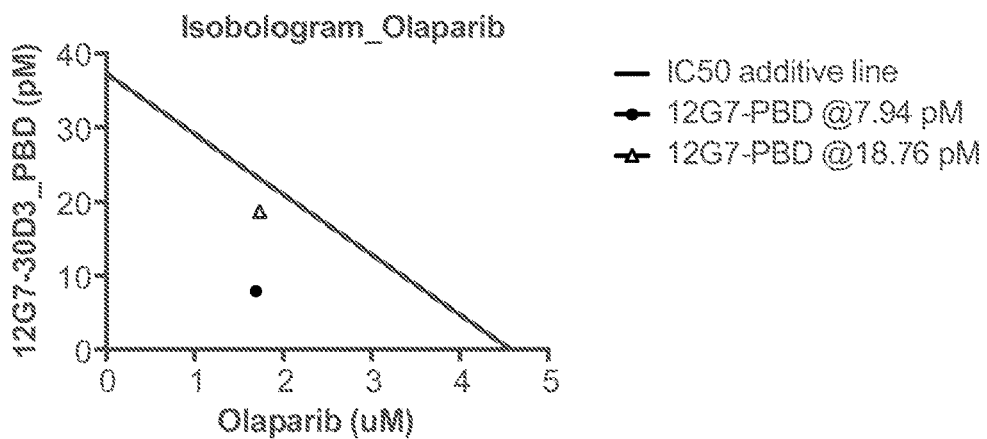
FIG. 16A, FIG. 16B, and FIG. 16C show isobologram analysis of combination treatments of anti-LY6H-PBD with olaparib, cisplatin, or etoposide in CORL95 cells. Combination treatments were performed with a constant concentration of 12G7-PBD and titrating doses of olaparib (A), cisplatin (B) or etoposide (C). IC50 values were recorded for single treatments or combinations to calculate isobologram points.
Figure 16B:
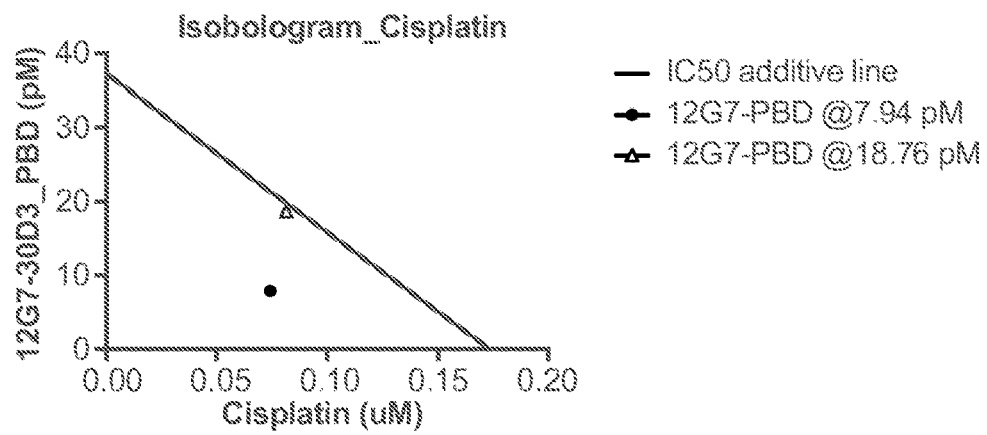
Figure 16C:
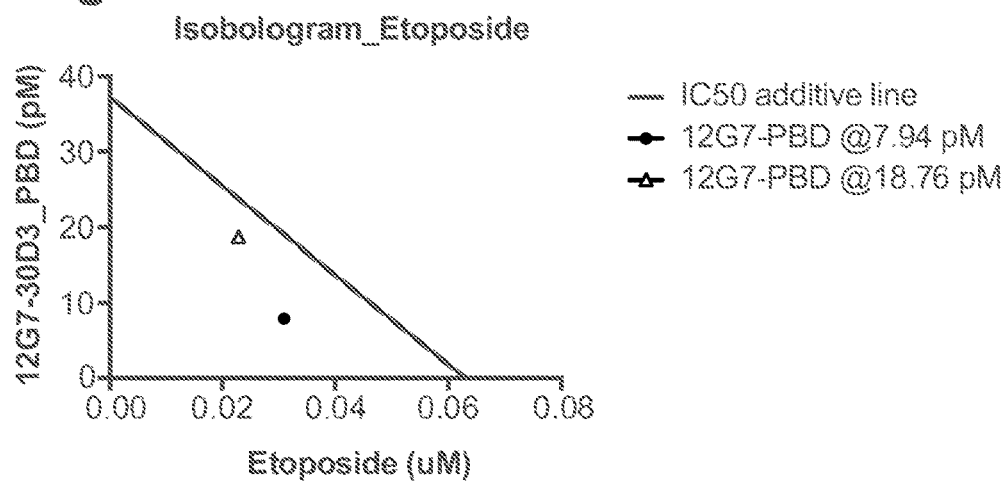
Figure 17A:
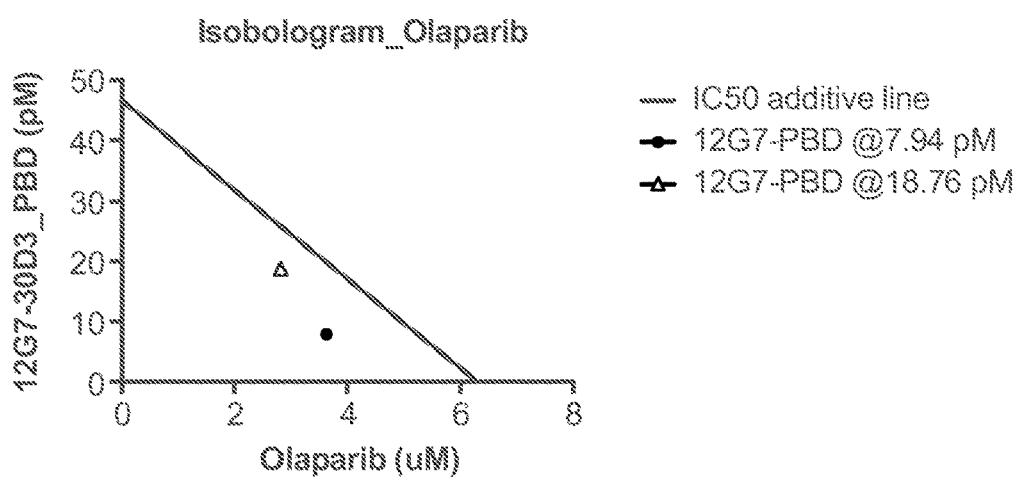
FIG. 17A, FIG. 17B, and FIG. 17C show isobologram analysis of combination treatments of anti-LY6H-PBD with olaparib, cisplatin, or etoposide in NCI-H1092 cells. Combination treatments were performed with a constant concentration of 12G7-PBD and titrating doses of olaparib (A), cisplatin (B) or etoposide (C). IC50 values were recorded for single treatments or combinations to calculate isobologram points.
Figure 17B:
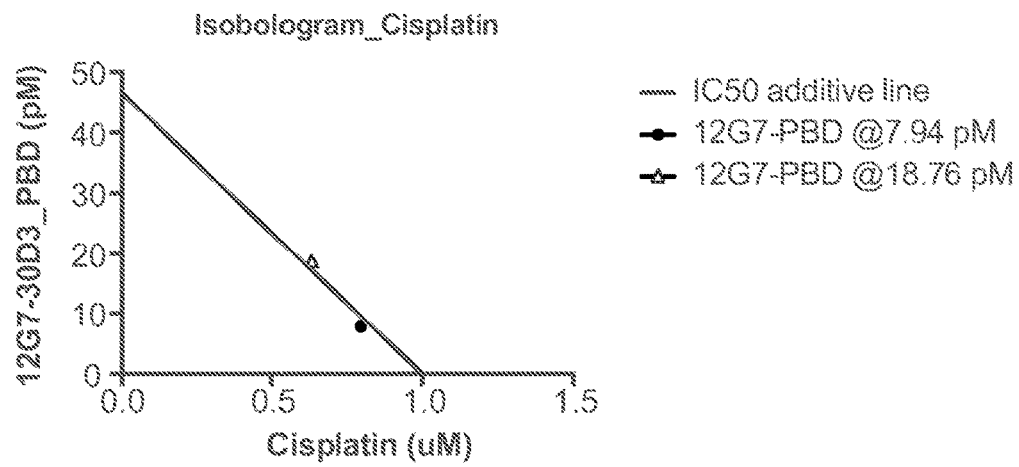
Figure 17C:
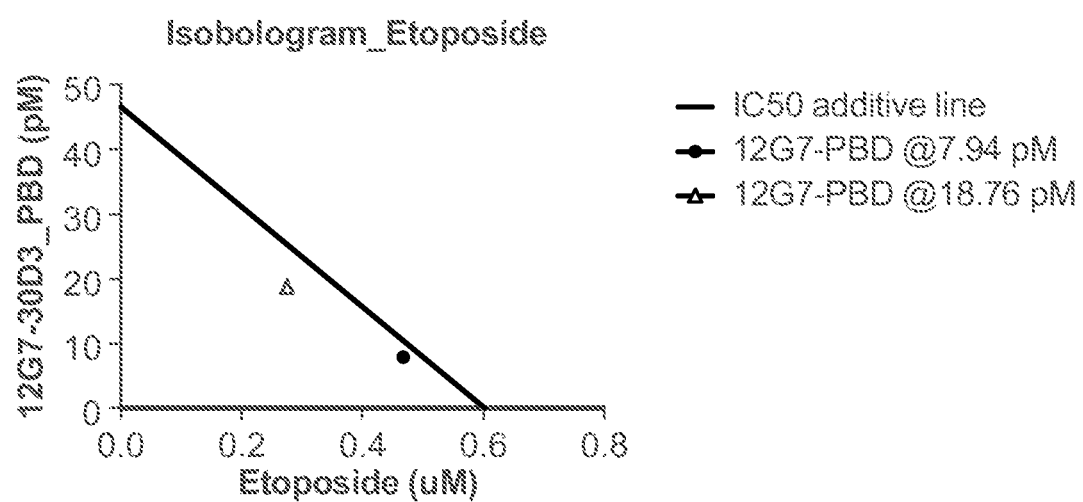

When 12G7-PBD was combined with olaparib, cisplatin, or etoposide, synergistic effect in DMS79 cells was observed (FIG. 15). Similar synergistic effects were observed in CORL95 cells (FIG. 16). In addition, synergistic effect was observed in NCI-H1092 cells when 12G7-PBD was combined with either olaparib or etoposide (FIGS. 17A, 17C). Additive effect was observed when 12G7-PBD was combined with cisplatin (FIG. 17B).

Sequence Summary

| SEQ ID NO: | Description |
| --- | --- |
| 1 | 6D11 VH amino acid sequence |
| 2 | 6D11, 6D11_41B4 VH CDR1 amino acid sequence |
| 3 | 6D11 VH CDR2 amino acid sequence |
| 4 | 6D11, 6D11_41B4 VH CDR3 amino acid sequence |
| 5 | 6D11, 6D11_41B4 VL amino acid sequence |
| 6 | 6D11, 12G7, 10B10, 12G7_S54A, 12G7_N52Q, 6D11_41B4, 10B10_S54A VL CDR1 amino acid sequence |
| 7 | 6D11, 12G7, 10B10, 12G7_S54A, 12G7_N52Q, 6D11_41B4, 10B10_S54A VL CDR2 amino acid sequence |
| 8 | 6D11, 12G7, 10B10, 12G7_S54A, 12G7_N52Q, 6D11_41B4, 10B10_S54A VL CDR3 amino acid sequence |
| 9 | 11D9 VH amino acid sequence |
| 10 | 11D9 VH CDR1 amino acid sequence |
| 11 | 11D9, 23F3 VH CDR2 amino acid sequence |
| 12 | 11D9 VH CDR3 amino acid sequence |
| 13 | 11D9 VL amino acid sequence |
| 14 | 11D9, 23F3 VL CDR1 amino acid sequence |
| 15 | 11D9, 23F3 VL CDR2 amino acid sequence |
| 16 | 11D9 VL CDR3 amino acid sequence |
| 17 | 23F3 VH amino acid sequence |
| 18 | 23F3 VH CDR1 amino acid sequence |
| 19 | 23F3 VH CDR3 amino acid sequence |
| 20 | 23F3 VL amino acid sequence |
| 21 | 23F3 VL CDR3 amino acid sequence |
| 22 | 12G7 VH amino acid sequence |
| 23 | 12G7, 12G7_S54A,, 12G7_N52Q VH CDR1 amino acid sequence |
| 24 | 12G7 VH CDR2 amino acid sequence |
| 25 | 12G7, 12G7_S54A, 12G7_N52Q VH CDR3 amino acid sequence |
| 26 | 12G7, 10B10, 12G7_S54A, 12G7_N52Q, 10B10_S54A VL amino acid sequence |
| 27 | 22A5 VH amino acid sequence |
| 28 | 22A5, 26F3, 35H10, 24A10, 34H6 VH CDR1 amino acid sequence |
| 29 | 22A5, 26F3, 35H10, 2B11, 24A10, 34H6 VH CDR2 amino acid sequence |
| 30 | 22A5 VH CDR3 amino acid sequence |
| 31 | 22A5 VL amino acid sequence |
| 32 | 22A5, 26F3 VL CDR1 amino acid sequence |
| 33 | 22A5, 26F3 VL CDR2 amino acid sequence |
| 34 | 22A5 VL CDR3 amino acid sequence |
| 35 | 26F3 VH amino acid sequence |
| 36 | 26F3 VH CDR3 amino acid sequence |
| 37 | 26F3 VL amino acid sequence |
| 38 | 26F3 VL CDR3 amino acid sequence |
| 39 | 35H10 VH amino acid sequence |
| 40 | 35H10 VH CDR3 amino acid sequence |
| 41 | 35H10 VL amino acid sequence |
| 42 | 35H10 VL CDR1 amino acid sequence |

| SEQ ID NO: | Description |
|---|---|
| 43 | 35H10 VL CDR2 amino acid sequence |
| 44 | 35H10 VL CDR3 amino acid sequence |
| 45 | 1F8 VH amino acid sequence |
| 46 | 1F8, 2B11 VH CDR1 amino acid sequence |
| 47 | 1F8 VH CDR2 amino acid sequence |
| 48 | 1F8, 2B11 VH CDR3 amino acid sequence |
| 49 | 1F8, 2B11 VL amino acid sequence |
| 50 | 1F8, 2B11, 24A10, 34H6 VL CDR1 amino acid sequence |
| 51 | 1F8, 2B11, 24A10, 34H6 VL CDR2 amino acid sequence |
| 52 | 1F8, 2B11 VL CDR3 amino acid sequence |
| 53 | 2B11 VH amino acid sequence |
| 54 | 24A10 VH amino acid sequence |
| 55 | 24A10 VH CDR3 amino acid sequence |
| 56 | 24A10, 34H6, 34H6 VL amino acid sequence |
| 57 | 24A10, 34H6, 34H6 VL CDR3 amino acid sequence |
| 58 | 34H6 VH amino acid sequence |
| 59 | 34H6 VH CDR3 amino acid sequence |
| 60 | 10B10 VH amino acid sequence |
| 61 | 10B10, 10B10_S54A VH CDR1 amino acid sequence |
| 62 | 10B10 VH CDR2 amino acid sequence |
| 63 | 10B10, 10B10_S54A VH CDR3 amino acid sequence |
| 64 | 12G7_S54A VH amino acid sequence |
| 65 | 12G7_S54A VH CDR2 amino acid sequence |
| 66 | 12G7_N52Q VH amino acid sequence |
| 67 | 12G7_N52Q VH CDR2 amino acid sequence |
| 68 | 6D11_41B4 VH amino acid sequence |
| 69 | 6D11_41B4 VH CDR2 amino acid sequence |
| 70 | 10B10_S54A VH amino acid sequence |
| 71 | 10B10_S54A CDR2 amino acid sequence |
| 72 | 6D11 VH DNA sequence |
| 73 | 6D11, 6D11_41B4 VL DNA sequence |
| 74 | 11D9 VH DNA sequence |
| 75 | 11D9 VL DNA sequence |
| 76 | 23F3 VH DNA sequence |
| 77 | 23F3 VL DNA sequence |
| 78 | 12G7 VH DNA sequence |
| 79 | 12G7, 10B10, 12G7_S54A, 12G7_N52Q, 10B10_S54A VL DNA sequence |
| 80 | 22A5 VH DNA sequence |
| 81 | 22A5 VL DNA sequence |
| 82 | 26F3 VH DNA sequence |
| 83 | 26F3 VL DNA sequence |
| 84 | 35H10 VH DNA sequence |
| 85 | 35H10 VL DNA sequence |
| 86 | 1F8 VH DNA sequence |
| 87 | 1F8, 2B11 VL DNA sequence |
| 88 | 2B11 VH DNA sequence |
| 89 | 24A10 VH DNA sequence |
| 90 | 24A10, 34H6 VL DNA sequence |
| 91 | 34H6 VH DNA sequence |
| 92 | 10B10 VH DNA sequence |
| 93 | 12G7_S54A VH DNA sequence |
| 94 | 12G7_N52O VH DNA sequence |
| 95 | 6D11_41B4 VH DNA sequence |
| 96 | 10B10_S54A VH DNA sequence |
| 97 | IGHV4 leader |
| 98 | IGHV2 leader |
| 99 | IGHV2-26 leader |
| 100 | IGHV6 leader |
| 101 | IGHV1 leader |
| 102 | IGHV1-58 leader |
| 103 | IGHV1-24 leader |
| 104 | IGHV1-69/1-46/7-4-1 leader |
| 105 | IGHV3 leader |
| 106 | IGHV3-53/3-49 leader |
| 107 | IGHV3-21 leader |
| 108 | IGHV3-48/3-7 leader |
| 109 | IGHV5 leader |
| 110 | IgkV1a leader |
| 111 | IgkV1b leader |
| 112 | IgkV3 leader |
| 113 | IgkV3-20 leader |
| 114 | IgkV4 leader |
| 115 | IgkV5 leader |
| 116 | IgkV2 leader |
| 117 | Kappa FW4 |
| 118 | Kappa FW4 |
| 119 | Heavy FW4 |
| 120 | VL-FOR L1 |
| 121 | VL-FOR L2 |
| 122 | VL-REV L |
| 123 | LY6H_HUMAN |
| 124 | LY6H_MACFA |
| 125 | NP_001128311.1 |
| 126 | LY6H_MOUSE |

INCORPORATION BY REFERENCE

The contents of all references, patents, pending patent applications and published patents, Sequence Listing, Sequence Summary, and Accession Numbers, cited throughout this application are hereby expressly incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

The invention claimed is:

1. An anti-LY6H antibody, or antigen-binding portion thereof, comprising a heavy chain variable region comprising a CDR3 domain comprising the amino acid sequence of SEQ ID NO: 25, a CDR2 domain comprising one of the amino acid sequences selected from SEQ ID NO: 24, SEQ ID NO: 65 and SEQ ID NO: 67, and a CDR1 domain comprising the amino acid sequence of SEQ ID NO: 23, and a light chain variable region comprising a CDR3 domain comprising the amino acid sequence of SEQ ID NO: 8, a CDR2 domain comprising the amino acid sequence of SEQ ID NO: 7, and a CDR1 domain comprising the amino acid sequence of SEQ ID NO: 6; or a heavy chain variable region comprising a CDR3 domain comprising the amino acid sequence of SEQ ID NO: 48, a CDR2 domain comprising the amino acid sequence of SEQ ID NO: 47, and a CDR1 domain comprising the amino acid sequence of SEQ ID NO: 46; and a light chain variable region comprising a CDR3 domain comprising the amino acid sequence of SEQ ID NO: 52, a CDR2 domain comprising the amino acid sequence of SEQ ID NO: 51, and a CDR1 domain comprising the amino acid sequence of SEQ ID NO: 50.

2. The anti-LY6H antibody, or antigen-binding portion thereof, of claim 1,
wherein the heavy chain variable region comprises an amino acid sequence selected from the group consisting of SEQ ID NO: 22, SEQ ID NO: 64, and SEQ ID NO: 66 and the light chain variable region comprises the amino acid sequence of SEQ ID NO: 26; or
wherein the heavy chain variable region comprises the amino acid sequence of SEQ ID NO: 45 and the light chain variable region comprises the amino acid sequence of SEQ ID NO: 49.

3. The anti-LY6H antibody, or antigen-binding portion thereof, of claim 1, wherein
the antibody comprises a heavy chain comprising an amino acid sequence set forth in one of SEQ ID NO: 22, SEQ ID NO: 64 and SEQ ID NO: 66, or a sequence having at least 90%, 95%, 96%, 97%, 98%, or 99% identity to one of SEQ ID NO: 22, SEQ ID NO: 64 and SEQ ID NO: 66, and a light chain comprising the amino acid sequence set forth in SEQ ID NO: 26, or a sequence having at least 90%, 95%, 96%, 97%, 98%, or 99% identity to SEQ ID NO: 26; or
the heavy chain variable region comprises an amino acid sequence having at least 90%, 95%, 96%, 97%, 98%, or 99% identity to SEQ ID NO: 45 and the light chain variable region comprises an amino acid sequence having at least 90%, 95%, 96%, 97%, 98%, or 99% identity to SEQ ID NO: 49.

4. A pharmaceutical composition comprising the antibody, or antigen binding portion thereof, of claim 1, and a pharmaceutically acceptable carrier.

5. An antibody, or antigen binding portion thereof, of claim 1, conjugated to at least one drug.

6. The antibody, or antigen binding portion thereof, of claim 1, wherein the antibody, or antigen binding portion thereof, is an IgG1 isotype.

7. A method of treating cancer characterized as having LY6H expression or overexpression in a subject, the method comprising administering a therapeutically effective amount of the antibody, or antigen binding portion thereof, of claim 5, to the subject, thereby treating the cancer.

8. The method of claim 7, wherein the cancer is small cell lung cancer.

9. The method of claim 7, wherein the antibody, or antigen binding portion thereof is administered in combination with an additional agent or an additional therapy.

10. The method of claim 9, wherein the additional agent is an immune checkpoint inhibitor, wherein the immune checkpoint inhibitor is an antibody.

11. The method of claim 10, wherein the antibody is selected from the group consisting of an anti-PD1 antibody, an anti-PD-L1 antibody or an anti-CTLA-4 antibody.

12. A method of inhibiting or decreasing tumor growth in a subject, the method comprising administering a therapeutically effective amount of the antibody, or antigen binding portion thereof, of claim 5 to the subject, thereby inhibiting or decreasing tumor growth in the subject, wherein the tumor is characterized as having LY6H expression or overexpression.

* * * * *

SEQUENCE LISTING

<160> NUMBER OF SEQ ID NOS: 126

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Gln Val Gln Leu Gln Gln Trp Gly Ala Gly Leu Phe Lys Pro Ser Glu
1               5                   10                  15

Thr Leu Ser Leu Thr Cys Ala Val Tyr Gly Gly Ser Phe Ser Gly Ser
            20                  25                  30

```
Leu Trp Ser Trp Ile Arg Gln Pro Pro Gly Lys Gly Leu Glu Trp Ile
        35                  40                  45

Gly Glu Ile Asn His Ser Gly Ser Thr Asn Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Gly Arg His Ile Val Val Val Thr Ala Ile His Ser Pro Phe Asp
            100                 105                 110

Tyr Trp Gly Gln Gly Thr Leu Val Thr Val Ser Ser
        115                 120

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Gly Ser Phe Ser Gly Ser Leu Trp Ser
1               5                   10

<210> SEQ ID NO 3
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Ile Asn His Ser Gly Ser Thr Asn Tyr Thr Pro Ser Leu Lys Ser
1               5                   10                  15

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Arg His Ile Val Val Val Thr Ala Ile His Ser Pro Phe Asp Tyr
1               5                   10                  15

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30
```

```
Leu Ala Trp Tyr Gln Gln Lys Pro Gly Lys Val Pro Lys Leu Leu Ile
            35                  40                  45

Phe Ala Ala Ser Thr Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Leu Glu Ile Lys
            100                 105
```

```
<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Gly Ile Ser Asn Tyr Leu Ala
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ala Ala Ser Thr Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gln Lys Tyr Asn Ser Ala Pro Arg Thr
1               5

<210> SEQ ID NO 9
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Gly
1               5                   10                  15

Thr Leu Ser Leu Thr Cys Thr Val Ser Gly Gly Ser Ile Ser Ser Ser
            20                  25                  30

Ser Trp Trp Ser Trp Val Arg Leu Pro Pro Gly Lys Gly Leu Glu Trp
        35                  40                  45
```

```
Ile Gly Glu Ile Tyr His Ser Gly Ser Thr Asn Tyr Asn Pro Ser Leu
    50                  55                  60
Lys Ser Arg Val Thr Ile Ser Val Asp Lys Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Gly Gly Val Arg Gly Val Val Met Ala Phe Asp Ile Trp Gly Gln Gly
            100                 105                 110
Thr Met Val Thr Val Ser Ser
        115

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Gly Ser Ile Ser Ser Ser Ser Trp Trp Ser
1               5                   10

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Glu Ile Tyr His Ser Gly Ser Thr Asn Tyr Asn Pro Ser Leu Lys Ser
1               5                   10                  15

<210> SEQ ID NO 12
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Arg Gly Val Val Met Ala Phe Asp Ile
1               5                   10

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
             20                  25                  30
Leu Asn Trp Tyr Gln Gln Lys Pro Gly Lys Ala Pro Lys Leu Leu Ile
         35                  40                  45
```

```
Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Pro Leu
                 85                  90                  95

Thr Phe Gly Gly Gly Thr Lys Val Glu Ile Lys
            100                 105

<210> SEQ ID NO 14
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Ala Ser Gln Ser Ile Ser Ser Tyr Leu Asn
 1               5                   10

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Ala Ala Ser Ser Leu Gln Ser
 1               5

<210> SEQ ID NO 16
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Gln Gln Ser Tyr Ser Thr Pro Leu Thr
 1               5

<210> SEQ ID NO 17
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Pro Gly Leu Val Lys Pro Ser Gly
 1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60
```

```
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Val Asp Ile Leu Thr Gly Gly Asn Phe Asp Tyr Trp Gly Gln
            100                 105                 110

Gly Thr Leu Val Thr Val Ser Ser
        115                 120

<210> SEQ ID NO 18
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gly Gly Ser Ile Ser Ser Ser Asn Trp Trp Ser
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Val Asp Ile Leu Thr Gly Gly Asn Phe Asp Tyr
1               5                   10

<210> SEQ ID NO 20
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Ile
                85                  90                  95

Thr Phe Gly Gln Gly Thr Arg Leu Glu Ile Lys
            100                 105

<210> SEQ ID NO 21
<211> LENGTH: 9
<212> TYPE: PRT
<213> ORGANISM: Artificial Sequence
<220> FEATURE:
```

<223> OTHER INFORMATION: Description of Artificial Sequence: Synthetic
peptide

<400> SEQUENCE: 21

Gln Gln Ser Tyr Ser Thr Pro Ile Thr
1               5

<210> SEQ ID NO 22
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 22

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Tyr Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Arg Trp Glu Leu Gly Ala Phe Asp Ile Trp Gly Gln Gly Thr Met
            100                 105                 110

Val Thr Val Ser Ser
        115

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 23

Gly Gly Ser Phe Ser Gly Tyr Tyr Trp Ser
1               5                   10

<210> SEQ ID NO 24
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 24

Glu Ile Asn His Ser Gly Ser Thr Tyr Tyr Asn Pro Ser Leu Lys Ser
1               5                   10                  15

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 25

Arg Trp Glu Leu Gly Ala Phe Asp Ile
1               5

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Tyr Gln Gln Lys Pro Gly Lys Val Pro Lys Leu Leu Ile
        35                  40                  45

Tyr Ala Ala Ser Thr Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Lys Tyr Asn Ser Ala Pro Arg
                85                  90                  95

Thr Phe Gly Gln Gly Thr Lys Leu Glu Ile Lys
            100                 105

<210> SEQ ID NO 27
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Leu Trp Phe Gly Glu Ser Arg Gly Gly Met Asp Val Trp
            100                 105                 110

Gly Gln Gly Thr Thr Val Thr Val Ser Ser
        115                 120

<210> SEQ ID NO 28
<211> LENGTH: 10
<212> TYPE: PRT
<213> ORGANISM: Artificial Sequence
<220> FEATURE:

-continued

```
<223> OTHER INFORMATION: Description of Artificial Sequence: Synthetic
      peptide

<400> SEQUENCE: 28

Gly Phe Thr Phe Ser Ser Tyr Gly Met His
1               5                   10

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Val Ile Trp Tyr Asp Gly Ser Asn Lys Tyr Tyr Ala Asp Ser Val Lys
1               5                   10                  15

Gly

<210> SEQ ID NO 30
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Asp Leu Trp Phe Gly Glu Ser Arg Gly Gly Met Asp Val
1               5                   10

<210> SEQ ID NO 31
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro His Thr Phe Gly Gln Gly Thr Lys Val Glu Ile Lys
            100                 105                 110

<210> SEQ ID NO 32
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 32

Arg Ser Ser Gln Ser Leu Leu His Ser Asn Gly Tyr Asn Tyr Leu Asp
1               5                   10                  15

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Leu Gly Ser Asn Arg Ala Ser
1               5

<210> SEQ ID NO 34
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Met Gln Ala Leu Gln Thr Pro His Thr
1               5

<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Phe Gly Glu Leu Leu Pro Phe Asp Tyr Trp Gly Gln Gly
            100                 105                 110

Thr Leu Val Thr Val Ser Ser
        115

<210> SEQ ID NO 36
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 36

Arg Phe Gly Glu Leu Leu Pro Phe Asp Tyr
1               5                   10

<210> SEQ ID NO 37
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Tyr Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Ala
                85                  90                  95

Leu Gln Thr Pro Trp Thr Phe Gly Gln Gly Thr Lys Val Glu Ile Lys
            100                 105                 110

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Met Gln Ala Leu Gln Thr Pro Trp Thr
1               5

<210> SEQ ID NO 39
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Gln Trp Leu Val Gln Gly Tyr Phe Asp Tyr Trp
            100                 105                 110

Gly Gln Gly Thr Leu Val Thr Val Ser Ser
        115                 120

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Asp Gly Gly Gln Trp Leu Val Gln Gly Tyr Phe Asp Tyr
1               5                   10

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Arg
                85                  90                  95

Thr Phe Gly Gln Gly Thr Lys Val Glu Ile Lys
            100                 105

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Arg Ala Ser Gln Ser Ile Ser Ser Trp Leu Ala
1               5                   10

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 43

Lys Ala Ser Ser Leu Glu Ser
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Gln Tyr Asn Ser Tyr Ser Arg Thr
1               5

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Tyr Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Ser Ile Val Val Val Thr Ala Thr Leu Asp Tyr Trp Gly Gln
            100                 105                 110

Gly Thr Leu Val Thr Val Ser Ser
        115                 120

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Phe Thr Phe Ser Asn Tyr Gly Met His
1               5                   10

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 47

Val Ile Trp Tyr Asp Gly Ser Tyr Lys Tyr Tyr Ala Asp Ser Val Lys
1               5                   10                  15

Gly

<210> SEQ ID NO 48
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Ile Val Val Val Thr Ala Thr Leu Asp Tyr
1               5                   10

<210> SEQ ID NO 49
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln His Tyr Asn Asn Trp Pro Pro
                85                  90                  95

Leu Thr Phe Gly Gly Gly Thr Lys Leu Glu Ile Lys
            100                 105

<210> SEQ ID NO 50
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Arg Ala Ser Gln Ser Val Ser Ser Asn Leu Ala
1               5                   10

<210> SEQ ID NO 51
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 51

Gly Ala Ser Thr Arg Ala Thr
1               5

<210> SEQ ID NO 52
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln His Tyr Asn Asn Trp Pro Pro Leu Thr
1               5                   10

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Thr Glu Asp Thr Ala Val Tyr Tyr Cys
                85                  90                  95

Ala Arg Ser Ile Val Val Val Thr Ala Thr Leu Asp Tyr Trp Gly Gln
            100                 105                 110

Gly Thr Leu Val Thr Val Ser Ser
        115                 120

<210> SEQ ID NO 54
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

```
Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ser Ile Val Val Val Ala Val Leu Asp Tyr Trp Gly Gln
                100                 105                 110

Gly Thr Leu Val Thr Val Ser Ser
        115                 120

<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Ser Ile Val Val Val Ala Val Leu Asp Tyr
 1               5                  10

<210> SEQ ID NO 56
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Ile Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
 50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Asn Asn Trp Pro Pro
                 85                  90                  95

Ile Thr Phe Gly Gln Gly Thr Arg Leu Glu Ile Lys
                100                 105

<210> SEQ ID NO 57
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Gln Tyr Asn Asn Trp Pro Pro Ile Thr
 1               5                  10
```

```
<210> SEQ ID NO 58
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ile Val Val Val Thr Gly Phe Gly Asp Tyr Trp Gly Gln
            100                 105                 110

Gly Thr Leu Val Thr Val Ser Ser
            115                 120

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Ile Val Val Val Thr Gly Phe Gly Asp Tyr
1               5                   10

<210> SEQ ID NO 60
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 60

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp His Trp Ile Arg Gln Pro Pro Gly Lys Gly Leu Glu Trp Ile
            35                  40                  45

Gly Glu Ile Asn His Ser Glu Ser Thr Lys Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Gly Ala Asp Thr Ala Val Tyr Tyr Cys Ala
                85                  90                  95
```

```
Arg Gly Gln His Ile Val Val Val Thr Asp Ser Leu Gly Asp Tyr Trp
            100                 105                 110

Gly Gln Gly Thr Leu Val Thr Val Ser Ser
        115                 120
```

<210> SEQ ID NO 61
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

```
Gly Gly Ser Phe Ser Gly Tyr Tyr Trp His
1               5                   10
```

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

```
Glu Ile Asn His Ser Glu Ser Thr Lys Tyr Asn Pro Ser Leu Lys Ser
1               5                   10                  15
```

<210> SEQ ID NO 63
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

```
Gly Gln His Ile Val Val Val Thr Asp Ser Leu Gly Asp Tyr
1               5                   10
```

<210> SEQ ID NO 64
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

```
Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ala Gly Ser Thr Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95
```

Lys Arg Trp Glu Leu Gly Ala Phe Asp Ile Trp Gly Gln Gly Thr Met
            100                 105                 110

Val Thr Val Ser Ser
        115

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Glu Ile Asn His Ala Gly Ser Thr Tyr Tyr Asn Pro Ser Leu Lys Ser
1               5                   10                  15

<210> SEQ ID NO 66
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Gln His Ser Gly Ser Thr Tyr Tyr Asn Pro Ser Leu Lys
    50                  55                  60

Ser Arg Val Thr Met Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Lys Arg Trp Glu Leu Gly Ala Phe Asp Ile Trp Gly Gln Gly Thr Met
            100                 105                 110

Val Thr Val Ser Ser
        115

<210> SEQ ID NO 67
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Glu Ile Gln His Ser Gly Ser Thr Tyr Tyr Asn Pro Ser Leu Lys Ser
1               5                   10                  15

<210> SEQ ID NO 68
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Gln Val Gln Leu Gln Gln Trp Gly Ala Gly Leu Phe Lys Pro Ser Glu
1               5                   10                  15

Thr Leu Ser Leu Thr Cys Ala Val Tyr Gly Gly Ser Phe Ser Gly Ser
            20                  25                  30

Leu Trp Ser Trp Ile Arg Gln Pro Pro Gly Lys Gly Leu Glu Trp Ile
        35                  40                  45

Gly Glu Ile Asn His Ala Gly Ser Thr Gln Tyr Thr Pro Ser Leu Lys
    50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Tyr Cys Ala
                85                  90                  95

Arg Gly Arg His Ile Val Val Thr Ala Ile His Ser Pro Phe Asp
            100                 105                 110

Tyr Trp Gly Gln Gly Thr Leu Val Thr Val Ser Ser
        115                 120

<210> SEQ ID NO 69
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Glu Ile Asn His Ala Gly Ser Thr Gln Tyr Thr Pro Ser Leu Lys Ser
1               5                   10                  15

<210> SEQ ID NO 70
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp His Trp Ile Arg Gln Pro Pro Gly Lys Gly Leu Glu Trp Ile
        35                  40                  45

Gly Glu Ile Asn His Ala Glu Ser Thr Lys Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Gly Ala Asp Thr Ala Val Tyr Tyr Cys Ala
                85                  90                  95

Arg Gly Gln His Ile Val Val Thr Asp Ser Leu Gly Asp Tyr Trp
            100                 105                 110

Gly Gln Gly Thr Leu Val Thr Val Ser Ser
        115                 120

<210> SEQ ID NO 71
<211> LENGTH: 16
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 71

Glu Ile Asn His Ala Glu Ser Thr Lys Tyr Asn Pro Ser Leu Lys Ser
1               5                   10                  15

<210> SEQ ID NO 72
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72
caggtgcagc tacagcaatg gggcgcagga ctgtttaagc cttcggagac cctgtccctc    60
acctgcgctg tctatggtgg gtccttcagt ggttccctct ggagctggat ccgccagccc   120
ccagggaagg ggctggagtg gattggggaa atcaatcata gtggaagcac caactacacc   180
ccgtccctca agagtcgagt caccatatca gtagacacgt ccaagaacca gttctctctg   240
aagctgacct ctgtgaccgc cgcggacacg gctgtgtatt actgtgcgag aggccggcat   300
attgtggtgg tgactgctat ccattcgcct tttgactact ggggccaggg aaccctggtc   360
accgtctcct ca                                                        372

<210> SEQ ID NO 73
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 73
gacatccaga tgacccagtc tccatcctcc ctgtctgcat ctgtaggaga cagagtcacc    60
atcacttgcc gggcgagtca gggcattagc aattatttag cctggtatca gcagaaacca   120
gggaaagttc ctaagctcct gatctttgct gcatccactt tgcaatcagg ggtcccatct   180
cggttcagtg gcagtggatc tgggacagat ttcactctca ccatcagcag cctgcagcct   240
gaagatgttg caacttatta ctgtcaaaag tataacagtg cccctcggac gttcggccaa   300
gggaccaagc tggagatcaa a                                              321

<210> SEQ ID NO 74
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 74
caggtgcagc tgcaggagtc gggcccagga ctggtgaagc cttcggggac cctgtccctc    60
acctgcactg tctctggtgg ctccatcagc agtagtagct ggtggagttg gtccgcctg   120 cccccaggga aggggctgga gtggattggg gaaatctatc atagtgggag caccaactac   180
aacccgtccc tcaagagtcg agtcaccata tcagtggaca gtccaagaa ccagttctcc   240

```
ctgaagctga gctctgtgac cgccgcggac acggccgtct attactgtgg aggggttcgg    300
ggagttgtga tggcttttga tatctggggc caagggacaa tggtcaccgt ctcctca      357

<210> SEQ ID NO 75
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 75
gacatccaga tgacccagtc tccatcctcc ctgtctgcat ctgtaggaga cagagtcacc    60
atcacttgcc gggcaagtca gagcattagc agttatttaa attggtatca gcagaaacca  120
gggaaagccc ctaagctcct gatctatgct gcatccagtt tgcaaagtgg ggtcccatca  180
aggttcagtg gcagtggatc tgggacagac ttcactctca ccatcagcag tctgcaacct  240
gaagattttg caacttacta ctgtcaacag agttacagta ccccgctcac tttcggcgga  300
gggaccaagg tggagatcaa a                                             321

<210> SEQ ID NO 76
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 76
caggtgcagc tgcaggagtc gggcccagga ctggtgaagc cttcggggac cctgtccctc    60
acctgcgctg tctctggtgg ctccatcagc agtagtaact ggtggagttg ggtccgccag  120
cccccaggga aggggctgga gtggattggg gaaatctatc atagtgggag caccaactac  180
aacccgtccc tcaagagtcg agtcaccata tcagtagaca agtccaagaa ccagttctcc  240
ctgaagctga gctctgtgac cgccgcggac acggccgtgt attactgtgc gagagtcgat  300
attttgactg gtggtaactt tgactactgg ggccagggaa ccctggtcac cgtctcctca  360

<210> SEQ ID NO 77
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 77
gacatccaga tgacccagtc tccatcctcc ctgtctgcat ctgtaggaga cagagtcacc    60
atcacttgcc gggcaagtca gagcattagc agctatttaa attggtatca gcagaaacca  120
gggaaagccc ctaagctcct gatctatgct gcatccagtt tgcaaagtgg ggtcccatca  180
aggttcagtg gcagtggatc tgggacagat ttcactctca ccatcagcag tctgcaacct  240
gaagattttg caacttacta ctgtcaacag agttacagta ccccgatcac cttcggccaa  300
gggacacgac tggagattaa a                                             321

<210> SEQ ID NO 78
<211> LENGTH: 351
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 78

| | |
|---|---|
| caggtgcagc tacagcagtg gggcgcagga ctgttgaagc cttcggagac cctgtccctc | 60 |
| acctgcgctg tctatggtgg gtccttcagt ggttactact ggagctggat ccgccagccc | 120 |
| ccagggaagg ggctggagtg gattggggaa atcaatcata gtggaagcac ctactacaac | 180 |
| ccgtccctca agagtcgagt caccatgtca gtagacacgt ccaagaacca gttctccctg | 240 |
| aagctgagct ctgtgaccgc cgcggacacg gctgtttatt actgtgcgaa aagatgggag | 300 |
| cttggtgctt ttgatatctg gggccaaggg acaatggtca ccgtctcctc a | 351 |

<210> SEQ ID NO 79
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 79

| | |
|---|---|
| gacatccaga tgacccagtc tccatcctcc ctgtctgcat ctgtaggaga cagagtcacc | 60 |
| atcacttgcc gggcgagtca gggcattagc aattatttag cctggtatca gcagaaacca | 120 |
| gggaaagttc ctaagctcct gatctatgct gcatccactt tgcaatcagg ggtcccatct | 180 |
| cggttcagtg gcagtggatc tgggacagat ttcactctca ccatcagcag cctgcagcct | 240 |
| gaagatgttg caacttatta ctgtcaaaag tataacagtg cccctcggac gttcggccaa | 300 |
| gggaccaagc tggagatcaa a | 321 |

<210> SEQ ID NO 80
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 80

| | |
|---|---|
| caggtgcagc tggtggagtc tgggggaggc gtggtccagc ctgggaggtc cctgagactc | 60 |
| tcctgtgcag cgtctggatt caccttcagt agctatggca tgcactgggt ccgccaggct | 120 |
| ccaggcaagg ggctggagtg ggtggcagtt atatggtatg atggaagtaa taaatactat | 180 |
| gcagactccg tgaagggccg attcaccatc tccagagaca attccaagaa cacgctgtat | 240 |
| ctgcaaatga acagcctgag agccgaggac acggctgtgt attactgtgc gagagatcta | 300 |
| tggttcgggg agtcccgggg cggtatggac gtctggggcc aagggaccac ggtcaccgtc | 360 |
| tcctca | 366 |

<210> SEQ ID NO 81
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 81

| | | | | | |
|---|---|---|---|---|---|
| gatattgtga | tgactcagtc | tccactctcc | ctgcccgtca | cccctggaga | gccggcctcc | 60 |
| atctcctgca | ggtctagtca | gagcctcctg | catagtaatg | gatacaacta | tttggattgg | 120 |
| tacctgcaga | agccagggca | gtctccacag | ctcctgatct | atttgggttc | taatcgggcc | 180 |
| tccggggtcc | ctgacaggtt | cagtggcagt | ggatcaggca | cagattttac | actgaaaatc | 240 |
| agcagagtgg | aggctgagga | tgttggggtt | tattactgca | tgcaagctct | acaaactcct | 300 |
| cacacttttg | gccaggggac | caaggtggag | atcaaa | | | 336 |

<210> SEQ ID NO 82
<211> LENGTH: 357
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 82

| | | | | | |
|---|---|---|---|---|---|
| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agccgaggac | acggctgtgt | attactgtgc | gaggaggttc | 300 |
| ggggagttat | tgccttttga | ctactggggc | cagggaaccc | tggtcaccgt | ctcctca | 357 |

<210> SEQ ID NO 83
<211> LENGTH: 321
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 83

| | | | | | |
|---|---|---|---|---|---|
| gacatccagt | tgacccagtc | tccatccttc | ctgtctgcat | ctgtaggaga | cagagtcacc | 60 |
| atcacttgcc | gggccagtca | gggcattagc | agttatttag | cctggtatca | gcaaaaacca | 120 |
| gggaaagccc | ctaagctcct | gatctatgct | gcatccactt | tgcaaagtgg | ggtcccatca | 180 |
| aggttcagcg | gcagtggatc | tgggacagaa | ttcactctca | caatcagcag | cctgcagcct | 240 |
| gaagattttg | caacttatta | ctgtcaacag | cttaatagtt | acccgctcac | tttcggcgga | 300 |
| gggaccaagc | tggagatcaa | a | | | | 321 |

<210> SEQ ID NO 84
<211> LENGTH: 366
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 84

| | | | | | |
|---|---|---|---|---|---|
| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |

```
ctgcaaatga acagcctgag agccgaggac acggctgtgt attactgtgc gagagatgga      300
gggcagtggc tggtacaagg ctactttgac tactggggcc agggaaccct ggtcaccgtc      360
tcctca                                                                 366

<210> SEQ ID NO 85
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 85
gacatccaga tgacccagtc tccttccacc ctgtctgcat ctgtaggaga cagagtcacc       60
atcacttgcc gggccagtca gagtattagt agctggttgg cctggtatca gcagaaacca      120
gggaaagccc ctaagctcct gatctataag gcgtctagtt tagaaagtgg ggtcccatca      180
aggttcagcg gcagtggatc tgggacagaa ttcactctca ccatcagcag cctgcagcct      240
gatgattttg caacttatta ctgccaacag tataatagtt attctcggac gttcggccaa      300
gggaccaagg tggagatcaa a                                                321

<210> SEQ ID NO 86
<211> LENGTH: 360
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 86
caggtgcagc tggtggagtc tgggggaggc gtggtccagc ctgggaggtc cctgagactc       60
tcctgtgcag cgtctggatt caccttcagt aactatggca tgcactgggt ccgccaggct      120
ccaggcaagg gctggagtg gtggcagtt atatggtatg atggaagtta taaatactat       180
gcagactccg tgaagggccg attcaccatc tccagagaca attccaagaa cacgctgtat      240
ctgcaaatga acagcctgag aaccgaggac acggctgtat attattgtgc gaggtctatt      300
gtggtggtga ctgctactct tgactactgg ggccagggaa ccctggtcac cgtctcctca      360

<210> SEQ ID NO 87
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 87
gaaatagtga tgacgcagtc tccagccacc ctgtctgtgt ctccagggga aagagccacc       60
ctctcctgca gggccagtca gagtgttagc agcaacttag cctggtacca gcagaaacct      120
ggccaggctc ccaggctcct catctatggt gcatccacca gggccactgg tatcccagcc      180
aggttcagtg gcagtgggtc tgggacagag ttcactctca ccatcagcag cctgcagtct      240
gaagattttg cagtttatta ctgtcagcac tataataact ggcctcccct cactttcggc      300
ggagggacca agctggagat caaa                                             324

<210> SEQ ID NO 88
<211> LENGTH: 360
```

<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 88

| caggtgcagc | tggtggagtc | tgggggaggc | gtggtccagc | ctgggaggtc | cctgagactc | 60 |
| tcctgtgcag | cgtctggatt | caccttcagt | aactatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |
| ctgcaaatga | acagcctgag | aaccgaggac | acggctgtgt | attactgtgc | gaggtctatt | 300 |
| gtggtggtga | ctgctactct | tgactactgg | ggccagggaa | ccctggtcac | cgtctcctca | 360 |

<210> SEQ ID NO 89
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 89

| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agccgaggac | acggctgtgt | attactgtgc | gagaagtatt | 300 |
| gtagtggtgg | tagctgtcct | tgactactgg | ggccagggaa | ccctggtcac | cgtctcctca | 360 |

<210> SEQ ID NO 90
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 90

| gaaatagtga | tgacgcagtc | tccagccacc | ctgtctgtgt | ctccagggga | aagagccacc | 60 |
| ctctcctgca | gggccagtca | gagtgttagc | agcaacttag | cctggtacca | gcagaaacct | 120 |
| ggccaggctc | ccaggctcct | catctatggt | gcatccacca | gggccactgg | tatcccagcc | 180 |
| aggttcagtg | gcagtgggtc | tgggacagag | ttcactctca | ccatcagcag | cctgcagtct | 240 |
| gaagattttg | cagtttatta | ctgtcagcag | tataataact | ggcctccgat | caccttcggc | 300 |
| caagggacac | gactggagat | taaa | | | | 324 |

<210> SEQ ID NO 91
<211> LENGTH: 360
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 91

| caggtgcagc | tggtggagtc | tgggggaggc | gtggtccagc | ctgggaggtc | cctgagactc | 60 |
| tcctgtgcag | cgtctggatt | caccttcagt | agctatggca | tgcactgggt | ccgccaggct | 120 |
| ccaggcaagg | ggctggagtg | ggtggcagtt | atatggtatg | atggaagtaa | taaatactat | 180 |
| gcagactccg | tgaagggccg | attcaccatc | tccagagaca | attccaagaa | cacgctgtat | 240 |
| ctgcaaatga | acagcctgag | agccgaggac | acggctgtgt | attactgtgc | gaggtctatt | 300 |
| gtggtggtga | ctggattcgg | ggactactgg | ggccagggaa | ccctggtcac | cgtctcctca | 360 |

<210> SEQ ID NO 92
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 92

| caggtgcagt | tacagcagtg | gggcgcagga | ctgttgaagc | cttcggagac | cctgtccctc | 60 |
| acctgcgctg | tctatggtgg | gtccttcagt | ggttactact | ggcactggat | ccgccagccc | 120 |
| ccagggaagg | ggctggagtg | gattggggaa | atcaatcata | gtgaaagcac | caagtacaac | 180 |
| ccgtccctca | agagtcgagt | caccatatca | gtagacacgt | ccaagaacca | gttctccctg | 240 |
| aagctgagct | ctgtgaccgg | cgcggacacg | gctgtgtatt | actgtgcgag | aggccaacat | 300 |
| attgtggtgg | tgactgattc | tctgggggac | tactggggcc | agggaaccct | ggtcaccgtc | 360 |
| tcctca | | | | | | 366 |

<210> SEQ ID NO 93
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 93

| caggtgcagc | tacagcagtg | gggcgcagga | ctgttgaagc | cttcggagac | cctgtccctc | 60 |
| acctgcgctg | tctatggtgg | gtccttcagt | ggttactact | ggagctggat | ccgccagccc | 120 |
| ccagggaagg | ggctggagtg | gattggggaa | atcaatcatg | ctggaagcac | ctactacaac | 180 |
| ccgtccctca | agagtcgagt | caccatgtca | gtagacacgt | ccaagaacca | gttctccctg | 240 |
| aagctgagct | ctgtgaccgc | cgcggacacg | gctgtttatt | actgtgcgaa | aagatgggag | 300 |
| cttggtgctt | ttgatatctg | gggccaaggg | acaatggtca | ccgtctcctc | a | 351 |

<210> SEQ ID NO 94
<211> LENGTH: 351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 94

| caggtgcagc | tacagcagtg | gggcgcagga | ctgttgaagc | cttcggagac | cctgtccctc | 60 |
| acctgcgctg | tctatggtgg | gtccttcagt | ggttactact | ggagctggat | ccgccagccc | 120 |
| ccagggaagg | ggctggagtg | gattgggaa | atccagcata | gtggaagcac | ctactacaac | 180 |

```
ccgtccctca agagtcgagt caccatgtca gtagacacgt ccaagaacca gttctccctg    240
aagctgagct ctgtgaccgc cgcggacacg gctgtttatt actgtgcgaa agatggggag    300
cttggtgctt ttgatatctg gggccaaggg acaatggtca ccgtctcctc a             351
```

<210> SEQ ID NO 95
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95

```
caggtgcagc tacagcaatg gggcgcagga ctgtttaagc cttcggagac cctgtccctc    60
acctgcgctg tctatggtgg gtccttcagt ggttccctct ggagctggat ccgccagccc    120
ccagggaagg ggctggagtg gattggggaa atcaatcatg ctggaagcac ccagtacacc    180
ccgtccctca agagtcgagt caccatatca gtagacacgt ccaagaacca gttctctctg    240
aagctgacct ctgtgaccgc cgcggacacg gctgtgtatt actgtgcgag aggccggcat    300
attgtggtgg tgactgctat ccattcgcct tttgactact ggggccaggg aaccctggtc    360
accgtctcct ca                                                        372
```

<210> SEQ ID NO 96
<211> LENGTH: 366
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96

```
caggtgcagt tacagcagtg gggcgcagga ctgttgaagc cttcggagac cctgtccctc    60
acctgcgctg tctatggtgg gtccttcagt ggttactact ggcactggat ccgccagccc    120
ccagggaagg ggctggagtg gattggggaa atcaatcatg ctgaaagcac caagtacaac    180
ccgtccctca agagtcgagt caccatatca gtagacacgt ccaagaacca gttctccctg    240
aagctgagct ctgtgaccgg cgcggacacg gctgtgtatt actgtgcgag aggccaacat    300
attgtggtgg tgactgattc tctgggggac tactggggcc aggaaccct ggtcaccgtc    360 tcctca                                                               366
```

<210> SEQ ID NO 97
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 97

```
atagctcttc agggaccatg aarcayctgt ggttcttcct                           40
```

<210> SEQ ID NO 98
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 98
atagctcttc agggaccatg gacatacttt gttccacgc                  39

<210> SEQ ID NO 99
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
atagctcttc agggaccatg gacacacttt gctacacac                  39

<210> SEQ ID NO 100
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
atagctcttc agggaccatg tctgtctcct tcctcatct                  39

<210> SEQ ID NO 101
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
atagctcttc agggaccatg gactggacct ggagvatc                   38

<210> SEQ ID NO 102
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
atagctcttc agggaccatg gactggattt ggaggrtc                   38

<210> SEQ ID NO 103
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 103
atagctcttc agggaccatg gactgcacct ggaggatc                   38

<210> SEQ ID NO 104
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 104
atagctcttc agggaccatg gactggacct ggaggktc        38

<210> SEQ ID NO 105
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 105
atagctcttc agggaccatg gagttkggrc tgagctgg        38

<210> SEQ ID NO 106
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 106
atagctcttc agggaccatg gagtttkggc tkagctgg        38

<210> SEQ ID NO 107
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 107
atagctcttc agggaccatg gaactggggc tccgctgg        38

<210> SEQ ID NO 108
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 108
atagctcttc agggaccatg garttggggc tgwgctgg        38

<210> SEQ ID NO 109
<211> LENGTH: 38
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
atagctcttc agggaccatg gggtcaaccg ccatcctc        38

<210> SEQ ID NO 110
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
atagctcttc agggaccatg gacatgaggg tsccygctca gctc          44

<210> SEQ ID NO 111
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
atagctcttc agggaccatg gacatgagrg tcctcgctca gctc          44

<210> SEQ ID NO 112
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
atagctcttc agggaccatg gaagccccag cdcagcttct c          41

<210> SEQ ID NO 113
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
atagctcttc agggaccatg gaaaccccag cgcagcttct c          41

<210> SEQ ID NO 114
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
atagctcttc agggaccatg gtgttgcaga cccaggtctt c          41

<210> SEQ ID NO 115
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
atagctcttc agggaccatg gggtcccagg ttcacctcct c          41

<210> SEQ ID NO 116
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 116
atagctcttc agggaccatg aggctccytg ctcagctcct g        41

<210> SEQ ID NO 117
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
atagctcttc ttcgtttgat ctccascttg gtc                 33

<210> SEQ ID NO 118
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
atagctcttc ttcgtttaat ctccagtcgt gtc                 33

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
atagctcttc tggctgagga gacggtgacc                     30

<210> SEQ ID NO 120
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 120
atagctcttc atgtgacgct gttgtgactc agga                34

<210> SEQ ID NO 121
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121
atagctcttc atgtgaccyt gtgctcactc agtc                34

<210> SEQ ID NO 122
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 122
gatgctcttc tgggctggcc taggacagtc amcytgg     37

<210> SEQ ID NO 123
<211> LENGTH: 139
<212> TYPE: PRT
<213> ORGANISM: Homo sapiens

<400> SEQUENCE: 123

Met Leu Pro Ala Ala Met Lys Gly Leu Gly Leu Ala Leu Leu Ala Val
1               5                   10                  15

Leu Leu Cys Ser Ala Pro Ala His Gly Leu Trp Cys Gln Asp Cys Thr
                20                  25                  30

Leu Thr Thr Asn Ser Ser His Cys Thr Pro Lys Gln Cys Gln Pro Ser
            35                  40                  45

Asp Thr Val Cys Ala Ser Val Arg Ile Thr Asp Pro Ser Ser Ser Arg
        50                  55                  60

Lys Asp His Ser Val Asn Lys Met Cys Ala Ser Ser Asp Phe Val Lys
65                  70                  75                  80

Arg His Phe Phe Ser Asp Tyr Leu Met Gly Phe Ile Asn Ser Gly Ile
                85                  90                  95

Leu Lys Val Asp Val Asp Cys Cys Glu Lys Asp Leu Cys Asn Gly Ala
                100                 105                 110

Ala Gly Ala Gly His Ser Pro Trp Ala Leu Ala Gly Gly Leu Leu Leu
            115                 120                 125

Ser Leu Gly Pro Ala Leu Leu Trp Ala Gly Pro
        130                 135

<210> SEQ ID NO 124
<211> LENGTH: 140
<212> TYPE: PRT
<213> ORGANISM: Macaca fascicularis

<400> SEQUENCE: 124

Met Leu Pro Ala Ala Met Lys Gly Leu Gly Leu Ala Leu Leu Ala Val
1               5                   10                  15

Leu Leu Cys Ser Ala Pro Ala His Gly Leu Trp Cys Gln Asp Cys Thr
                20                  25                  30

Leu Thr Thr Asn Ser Ser His Cys Thr Pro Lys Gln Cys Gln Pro Ser
            35                  40                  45

Asp Thr Val Cys Ala Ser Val Arg Ile Thr Asp Pro Ser Ser Ser Arg
        50                  55                  60

Lys Asp His Ser Val Asn Lys Met Cys Ala Ser Ser Cys Asp Phe Val
65                  70                  75                  80

Lys Arg His Phe Phe Ser Asp Tyr Leu Met Gly Phe Ile Asn Ser Gly
                85                  90                  95

Ile Leu Lys Val Asp Val Asp Cys Tyr Glu Lys Asp Leu Cys Asn Gly
                100                 105                 110

Val Ala Gly Ala Gly His Ser Pro Trp Ala Leu Ala Gly Gly Leu Leu
            115                 120                 125

Leu Ser Leu Gly Pro Ala Leu Leu Trp Ala Gly Pro
        130                 135                 140

<210> SEQ ID NO 125
<211> LENGTH: 138
<212> TYPE: PRT
<213> ORGANISM: Rattus norvegicus

<400> SEQUENCE: 125

```
Met Leu Pro Ala Ala Met Lys Ser Leu Gly Leu Ala Leu Leu Ala Leu
1               5                   10                  15

Leu Leu Cys Pro Ser Pro Ala His Gly Leu Trp Cys Gln Asp Cys Thr
            20                  25                  30

Leu Ala Asn Ser Ser His Cys Ala Pro Lys Gln Cys Gln Pro Thr Asp
                35                  40                  45

Thr Val Cys Ala Ser Val Arg Ile Thr Asp Pro Ser Ser Ser Arg Lys
        50                  55                  60

Asp His Ser Val Asn Lys Met Cys Ala Ser Ser Cys Asp Phe Val Lys
65                  70                  75                  80

Arg His Phe Phe Ser Asp Tyr Leu Met Gly Phe Ile Asn Ser Gly Ile
                85                  90                  95

Leu Lys Asp Val Asp Cys Cys Glu Lys Asp Leu Cys Asn Gly Ala Ser
                100                 105                 110

Ala Ala Gly Arg Ser Pro Trp Ala Leu Ala Gly Gly Leu Leu Leu Ser
            115                 120                 125

Leu Gly Pro Ala Leu Leu Trp Ala Gly Pro
        130                 135
```

<210> SEQ ID NO 126
<211> LENGTH: 139
<212> TYPE: PRT
<213> ORGANISM: Mus musculus

<400> SEQUENCE: 126

```
Met Leu Pro Ala Ala Met Lys Ser Leu Gly Leu Ala Leu Leu Ala Leu
1               5                   10                  15

Leu Leu Cys Pro Ser Pro Ala His Gly Leu Trp Cys Gln Asp Cys Thr
            20                  25                  30

Leu Ala Asn Ser Ser His Cys Ala Pro Lys Gln Cys Gln Pro Thr Asp
                35                  40                  45

Thr Val Cys Ala Ser Val Arg Ile Thr Asp Pro Ser Ser Ser Arg Lys
        50                  55                  60

Asp His Ser Val Asn Lys Met Cys Ala Ser Ser Cys Asp Phe Val Lys
65                  70                  75                  80

Arg His Phe Phe Ser Asp Tyr Leu Met Gly Phe Ile Asn Ser Gly Ile
                85                  90                  95

Leu Lys Val Asp Val Asp Cys Cys Glu Lys Asp Leu Cys Asn Gly Ala
                100                 105                 110

Ser Val Ala Gly Arg Ser Pro Trp Ala Leu Ala Gly Gly Leu Leu Leu
            115                 120                 125

Ser Leu Gly Pro Ala Leu Leu Trp Ala Gly Pro
        130                 135
```